(12) United States Patent
Verma et al.

(10) Patent No.: US 12,667,464 B2
(45) Date of Patent: Jun. 30, 2026

(54) ADVANCED TRIAL SPACERS, HEIGHT MEASURING TOOL, AND INSERTER AND EXTRACTOR HANDLE

(71) Applicant: Howmedica Osteonics Corp., Mahwah, NJ (US)

(72) Inventors: Shashank Verma, Agra (IN); Rajan Yadav, New Delhi (IN); Roy Philip Splieth, Central Valley, NY (US); Matt Kartholl, Fort Wayne, IN (US); Travis Geels, Fort Wayne, IN (US); Brad Parker, Warsaw, IN (US); Doug Garman, Fort Wayne, IN (US); Anthony Andreas, Columbia City, IN (US); Amith Nayak, Great Meadows, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 640 days.

(21) Appl. No.: 18/189,261

(22) Filed: Mar. 24, 2023

(65) Prior Publication Data

US 2023/0310167 A1 Oct. 5, 2023

Related U.S. Application Data

(60) Provisional application No. 63/325,691, filed on Mar. 31, 2022.

(51) Int. Cl.
*A61F 2/40* (2006.01)
*A61F 2/30* (2006.01)
*A61F 2/46* (2006.01)

(52) U.S. Cl.
CPC .......... *A61F 2/4059* (2013.01); *A61F 2/4612* (2013.01); *A61F 2/4657* (2013.01);
(Continued)

(58) Field of Classification Search
CPC .... A61F 2/4059; A61F 2/4612; A61F 2/4657; A61F 2002/30492; A61F 2002/30672;
(Continued)

(56) References Cited

U.S. PATENT DOCUMENTS

| | | | | | |
|---|---|---|---|---|---|
| 2,181,746 | A | | 11/1939 | Siebrandt | |
| 3,846,846 | A | * | 11/1974 | Fischer | ................. A61F 2/3662 |
| | | | | | 411/33 |

(Continued)

FOREIGN PATENT DOCUMENTS

| | | |
|---|---|---|
| EP | 3539512 A1 | 9/2019 |
| EP | 3539513 A1 | 9/2019 |

(Continued)

OTHER PUBLICATIONS

Exactech, Equinoxe Shoulder System Operative Technique, Copyright 2021.

(Continued)

*Primary Examiner* — Yashita Sharma
(74) *Attorney, Agent, or Firm* — SLEMAN & LUND LLP

(57) ABSTRACT

A trial humeral prosthesis may include a trial stem for implantation into a humerus, and a trial proximal body configured to couple to a trial articulating component. A plurality of trial spacers may be configured to couple the trial stem to the trial proximal body, the plurality of trial spacers including a first trial spacer and a second trial spacer. The first and second trial spacers may each include a proximal post and a tab extending radially outward from the proximal post, and a distal body having a larger outer diameter than an outer diameter of the proximal post, a slot being formed in the distal body. The slot of the distal body of the first trial spacer may be configured to receive the tab of the second (Continued)

trial spacer when the proximal post of the second trial spacer is received within the distal body of the first trial spacer.

12 Claims, 101 Drawing Sheets

(52) U.S. Cl.
CPC .............. *A61F 2002/30492* (2013.01); *A61F 2002/30672* (2013.01)

(58) Field of Classification Search
CPC .......... A61F 2/4637; A61F 2002/30505; A61F 2002/30507; A61F 2002/30604; A61F 2002/30616; A61F 2002/4062; A61F 2002/407; A61F 2002/4074; A61F 2002/4077; A61F 2002/4658; A61F 2/4684; A61F 2/40; A61F 2/32; A61F 2/3609; A61F 2/3672; A61F 2/3676; A61F 2002/3674

See application file for complete search history.

(56) References Cited

U.S. PATENT DOCUMENTS

| | | | |
|---|---|---|---|
| 4,135,517 A * | 1/1979 | Reale | A61F 2/4684 |
| | | | 606/86 R |
| 4,335,427 A | 6/1982 | Hunt | |
| 4,633,862 A | 1/1987 | Petersen | |
| 5,147,365 A | 9/1992 | Whitlock | |
| 5,314,479 A | 5/1994 | Rockwood, Jr. | |
| 5,542,947 A | 8/1996 | Treacy | |
| 5,643,272 A | 7/1997 | Haines | |
| 5,888,245 A | 3/1999 | Meulink | |
| 6,010,509 A | 1/2000 | Delgado | |
| 6,102,956 A * | 8/2000 | Kranz | A61F 2/3662 |
| | | | 623/23.15 |
| 6,165,177 A | 12/2000 | Wilson | |
| 6,277,123 B1 | 8/2001 | Maroney | |
| 6,334,874 B1 | 1/2002 | Tornier | |
| 6,494,913 B1 | 12/2002 | Huebner | |
| 6,520,994 B2 | 2/2003 | Nogarin | |
| 6,702,824 B2 | 3/2004 | Maroney | |
| 6,712,823 B2 | 3/2004 | Kelley | |
| 6,719,799 B1 | 4/2004 | Kropf | |
| 6,821,300 B2 | 11/2004 | Masini | |
| 6,899,736 B1 | 5/2005 | Rauscher | |
| 7,044,973 B2 | 5/2006 | Rockwood, Jr. | |
| 7,070,622 B1 | 7/2006 | Brown | |
| 7,125,423 B2 | 10/2006 | Hazebrouck | |
| 7,175,663 B1 | 2/2007 | Stone | |
| 7,175,664 B1 | 2/2007 | Lakin | |
| 7,198,642 B2 | 4/2007 | Hazebrouck | |
| 7,435,263 B2 | 10/2008 | Barnett | |
| 7,662,189 B2 | 2/2010 | Meswania | |
| 7,699,853 B2 | 4/2010 | Durand-Allen | |
| 7,831,292 B2 | 11/2010 | Quaid | |
| 7,854,768 B2 | 12/2010 | Wiley | |
| 7,998,218 B1 | 8/2011 | Brown | |
| 8,021,433 B2 | 9/2011 | Meswania | |
| 8,062,376 B2 | 11/2011 | Shultz | |
| 8,118,875 B2 | 2/2012 | Rollet | |
| 8,177,849 B2 | 5/2012 | Meyers | |
| 8,236,059 B2 | 8/2012 | Stone | |

| | | | |
|---|---|---|---|
| 8,257,359 B2 | 9/2012 | Burkhart | |
| 8,435,244 B2 | 5/2013 | Meek | |
| 8,728,087 B2 | 5/2014 | Soliman | |
| 8,795,379 B2 | 8/2014 | Smith | |
| 8,906,103 B2 | 12/2014 | Stone | |
| 8,992,539 B2 | 3/2015 | Iannotti | |
| 9,005,305 B2 | 4/2015 | Meyers | |
| 9,011,549 B2 | 4/2015 | Splieth | |
| 9,241,803 B2 | 1/2016 | Stone | |
| 9,283,075 B2 | 3/2016 | Wiley | |
| 9,326,862 B2 | 5/2016 | Smith | |
| 9,463,090 B2 | 10/2016 | Meswania | |
| 9,566,172 B2 | 2/2017 | Endsley | |
| 9,572,687 B2 | 2/2017 | Ross | |
| 9,597,191 B2 | 3/2017 | Muir | |
| 9,597,203 B2 | 3/2017 | Emerick | |
| 9,615,941 B2 | 4/2017 | Meek | |
| 9,750,515 B2 | 9/2017 | Soliman | |
| 10,080,664 B2 | 9/2018 | Emerick | |
| 10,172,627 B2 | 1/2019 | Haberman | |
| 10,806,472 B2 | 10/2020 | Bettenga | |
| 10,905,561 B2 | 2/2021 | Roche | |
| 11,197,764 B2 | 12/2021 | Mutchler | |
| 11,350,952 B2 | 6/2022 | Bettenga | |
| 11,654,029 B2 | 5/2023 | Link | |
| 11,672,668 B2 | 6/2023 | Iannotti | |
| 11,723,777 B2 | 8/2023 | Roche | |
| 11,857,428 B2 | 1/2024 | Nerot | |
| 11,931,264 B2 | 3/2024 | Knox | |
| 11,974,926 B2 | 5/2024 | Maale | |
| 12,310,839 B2 * | 5/2025 | Kam | A61F 2/0811 |
| 2002/0156534 A1 | 10/2002 | Grusin | |
| 2003/0204267 A1 | 10/2003 | Hazebrouck | |
| 2004/0193268 A1 | 9/2004 | Hazebrouck | |
| 2005/0107794 A1 | 5/2005 | Hazebrouck | |
| 2005/0278030 A1 | 12/2005 | Tornier | |
| 2005/0278032 A1 | 12/2005 | Tornier | |
| 2006/0155292 A1 | 7/2006 | Krishnan | |
| 2016/0193049 A1 | 7/2016 | Mctigue | |
| 2016/0278945 A1 | 9/2016 | Emerick | |
| 2017/0202685 A1 | 7/2017 | Rao | |
| 2021/0085474 A1 | 3/2021 | Courtney, Jr. | |
| 2021/0228372 A1 | 7/2021 | Knox | |
| 2023/0000633 A1 | 1/2023 | Dalla Pria | |
| 2023/0093485 A1 | 3/2023 | Hodorek | |
| 2023/0190480 A1 | 6/2023 | Wolfe | |
| 2023/0310167 A1 | 10/2023 | Verma | |
| 2024/0065848 A1 | 2/2024 | Clevett | |

FOREIGN PATENT DOCUMENTS

| | | | |
|---|---|---|---|
| FR | 2848099 A1 | 6/2004 | |
| FR | 3047889 B1 | 2/2018 | |
| GB | 2406277 B | 12/2007 | |
| WO | 1997027828 A1 | 8/1997 | |
| WO | 2020072465 A2 | 4/2020 | |
| WO | 2021242842 A1 | 12/2021 | |
| WO | 2022120060 A1 | 6/2022 | |
| WO | 2023212242 A1 | 11/2023 | |
| WO | 2024019364 A1 | 1/2024 | |
| WO | 2024054324 A1 | 3/2024 | |

OTHER PUBLICATIONS

Stryker, Tournier Humeral Reconstruction System Operative Technique, Copyright 2023.

* cited by examiner

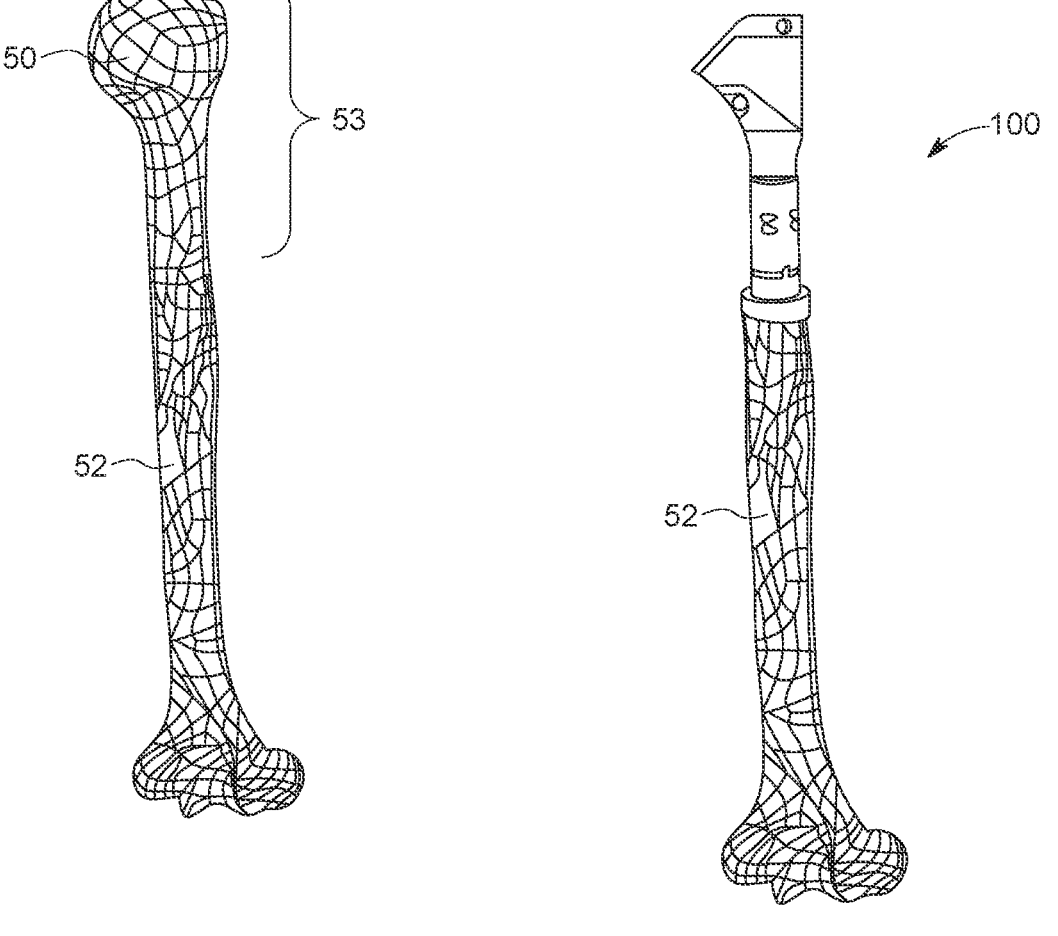
FIG. 2A                    FIG. 2B

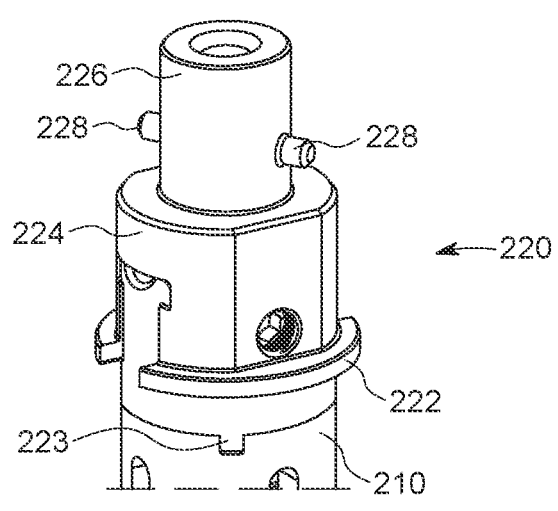
FIG. 4B
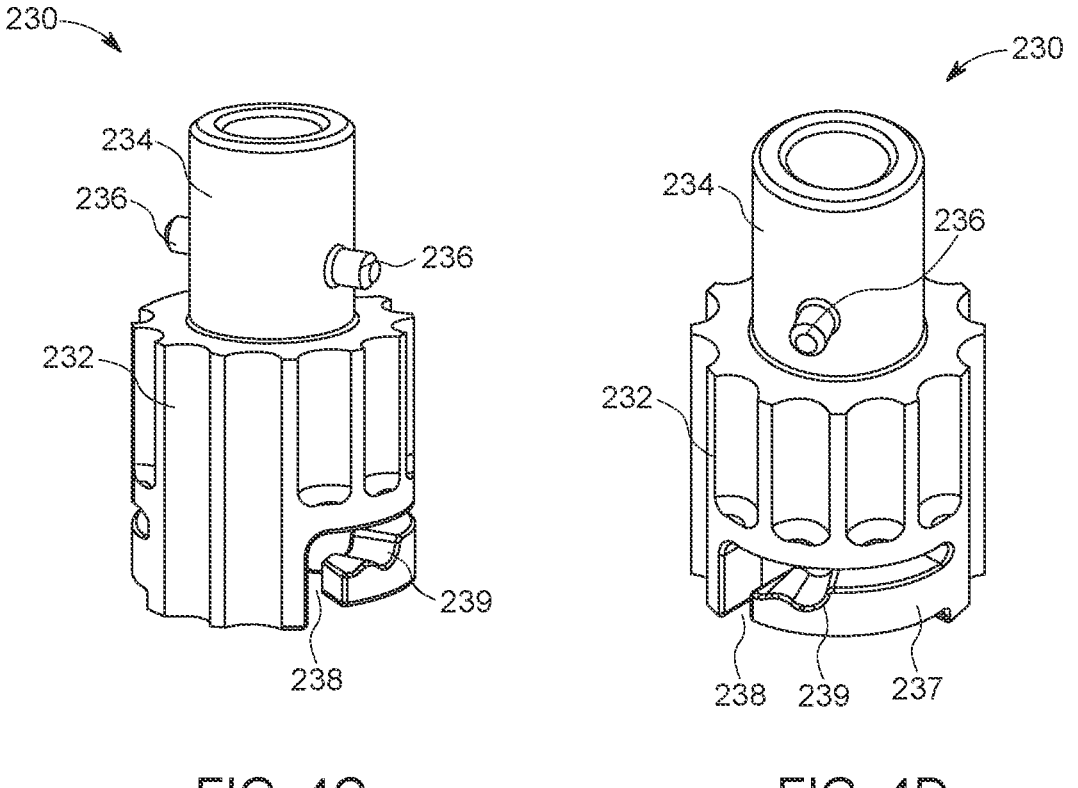
FIG. 4C                    FIG. 4D

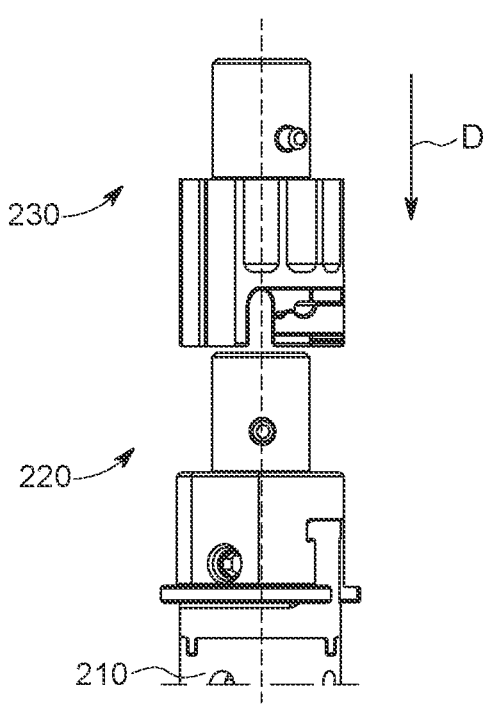
FIG. 4E
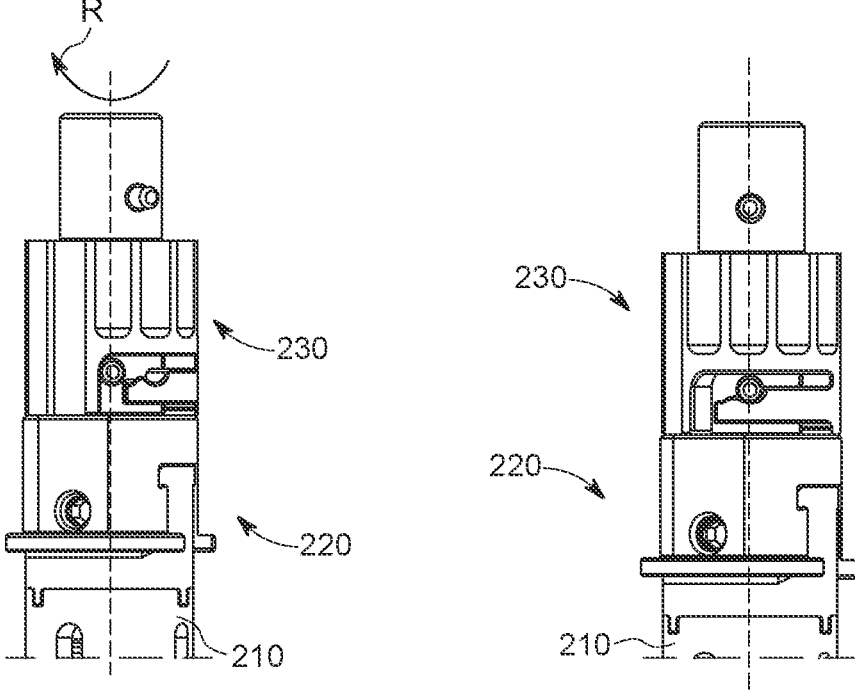
FIG. 4F
FIG. 4G

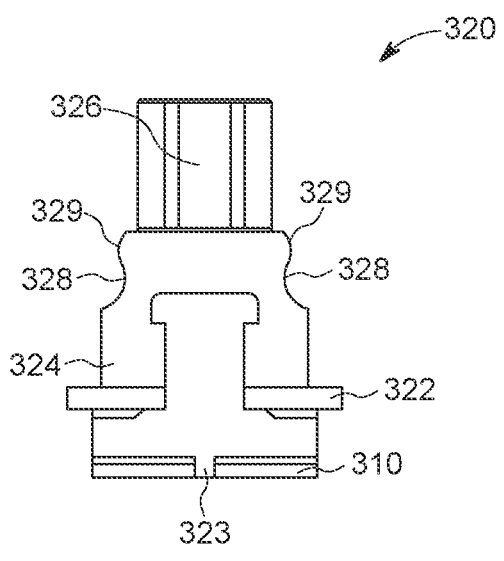
FIG. 6B
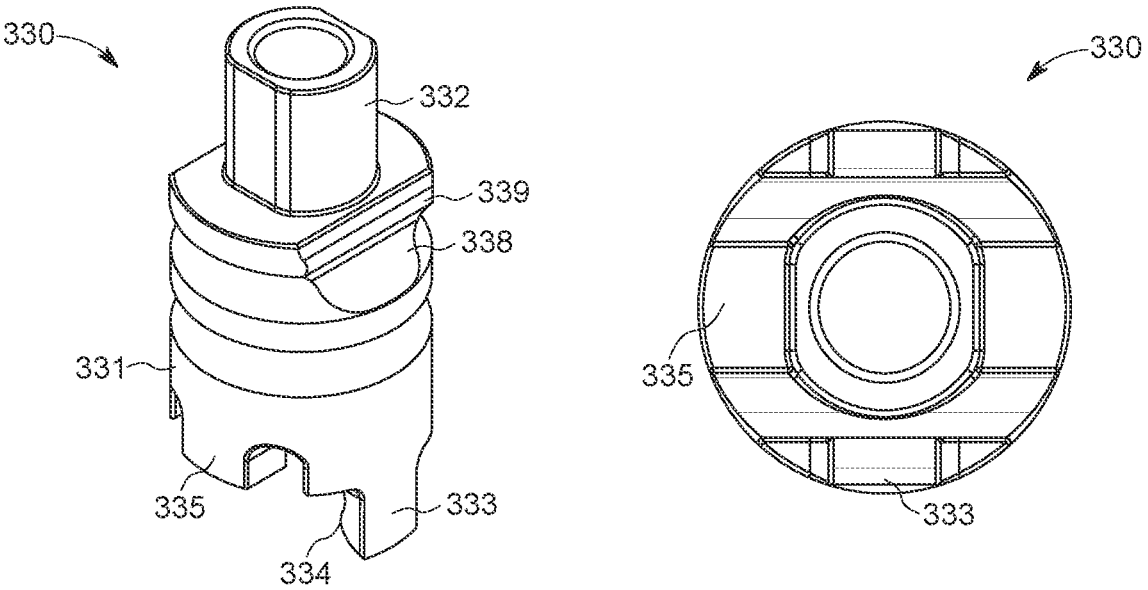
FIG. 6C                    FIG. 6D

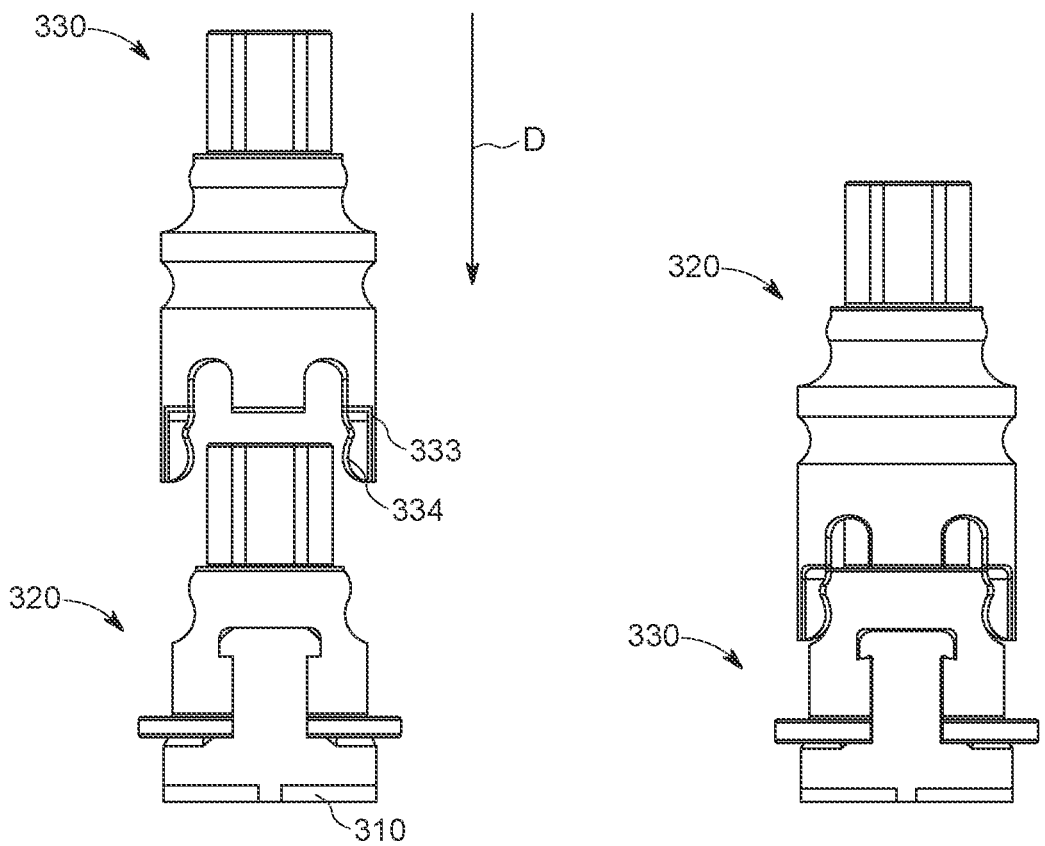
FIG. 6E                    FIG. 6F

400

450

430

420

410

632'

639'

636'

635'

612

638'

610

637'

639'

636'

635'

638'

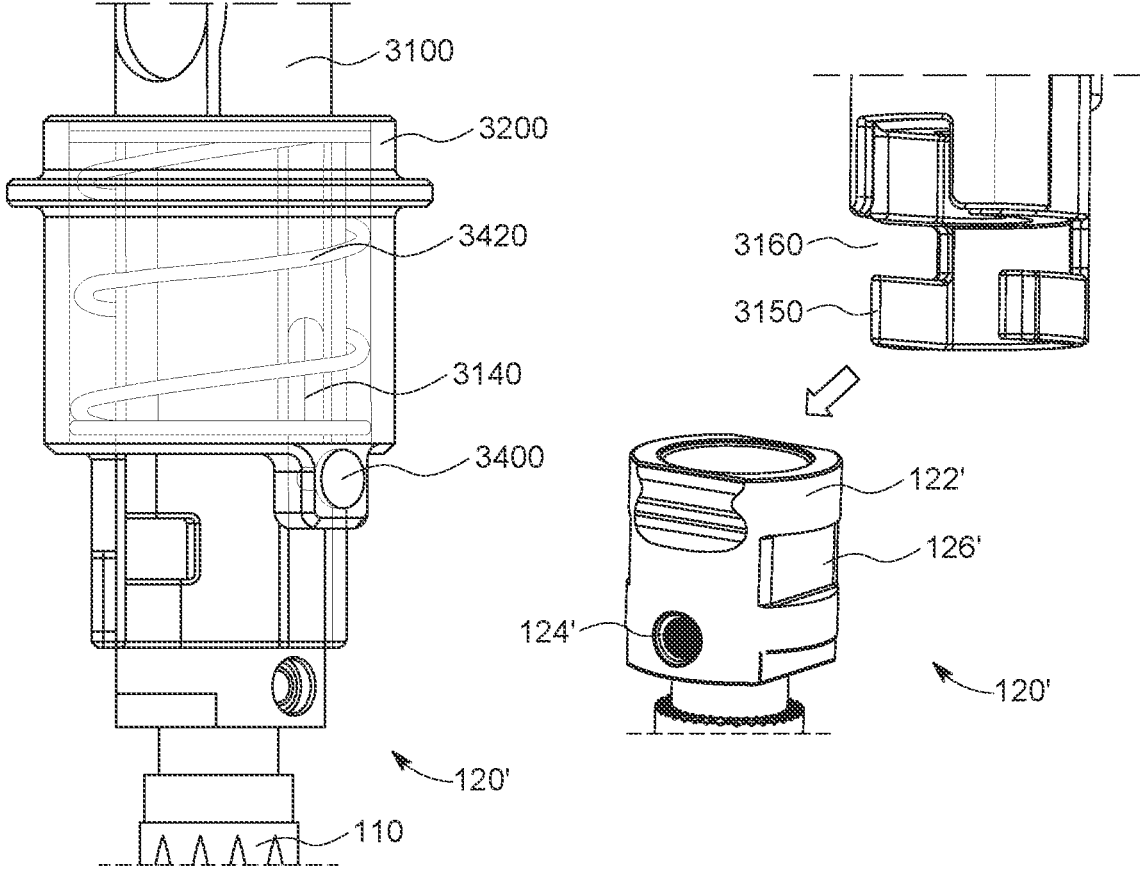
FIG. 22E                              FIG. 22F

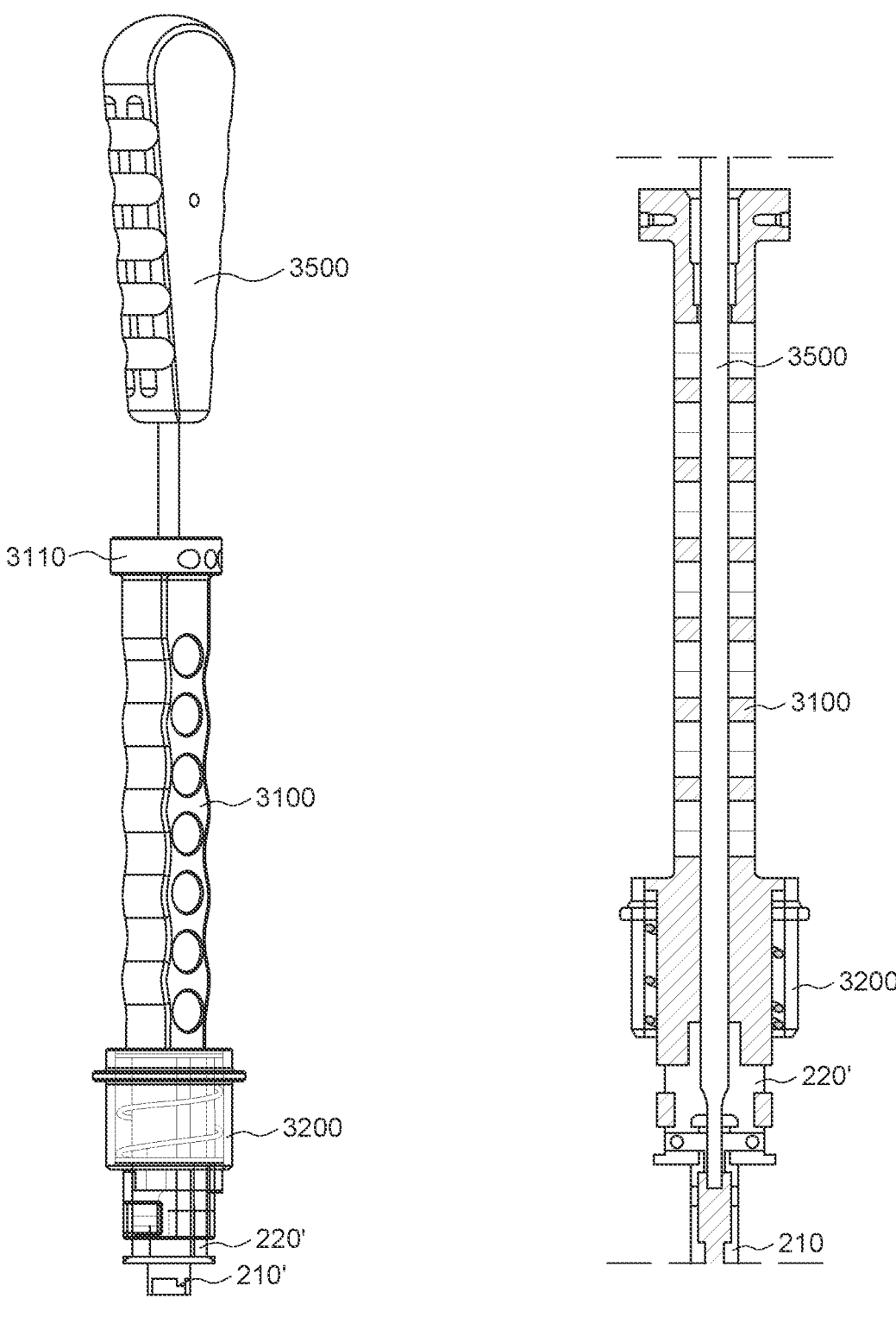
FIG. 22I                    FIG. 22J

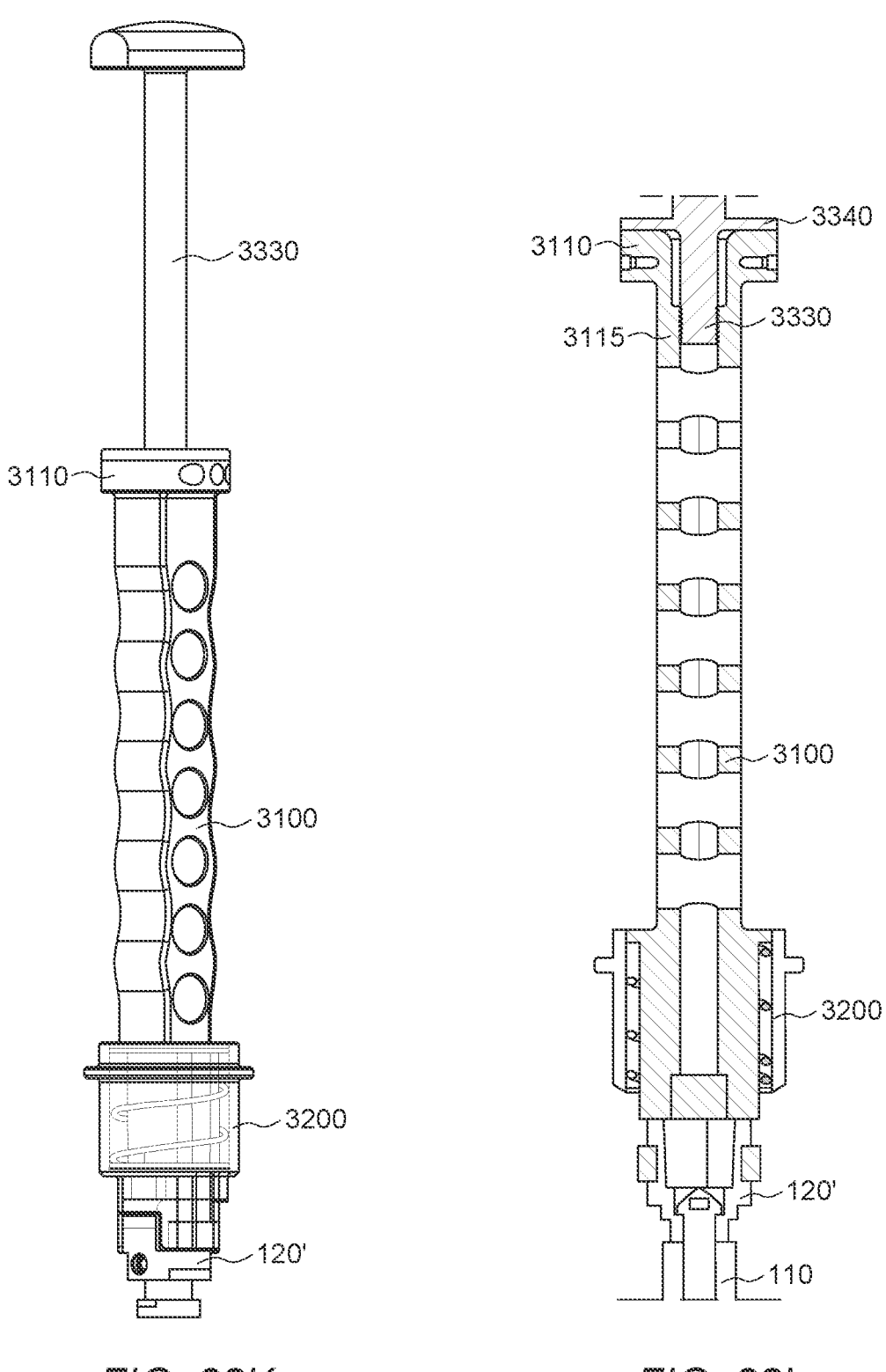
FIG. 22K                    FIG. 22L

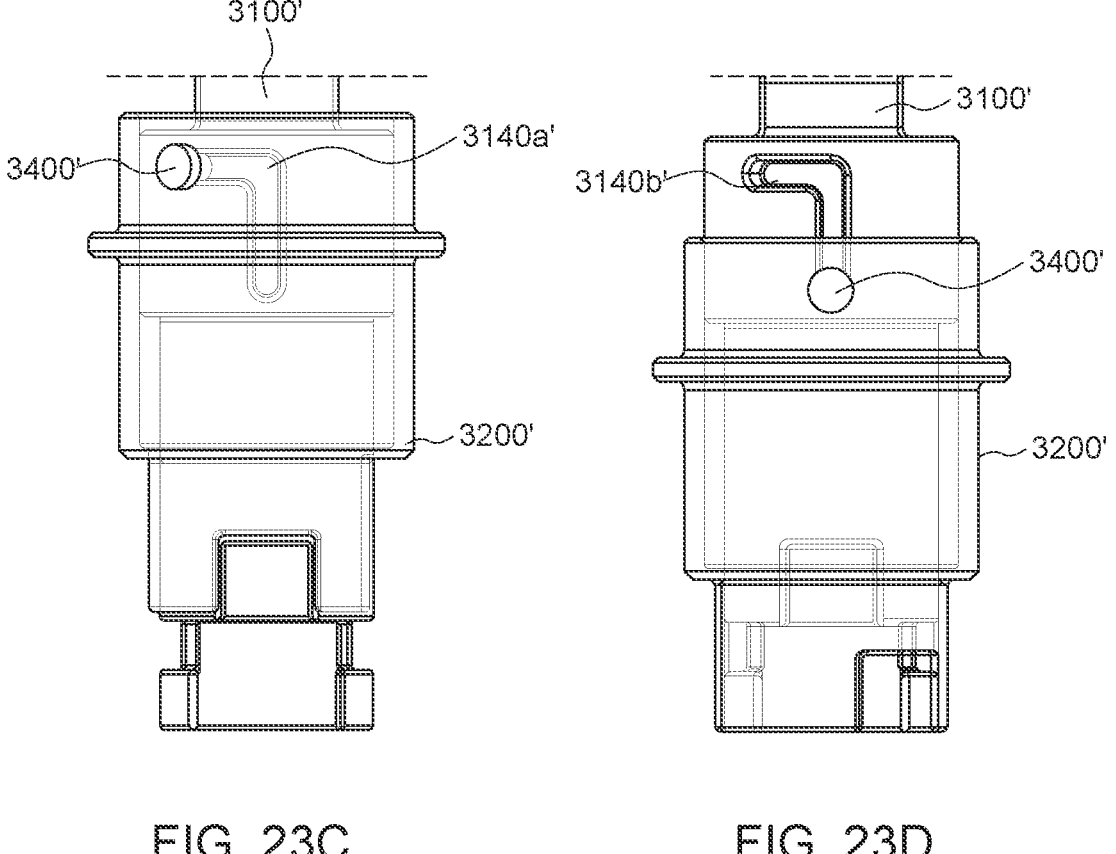
FIG. 23C                    FIG. 23D

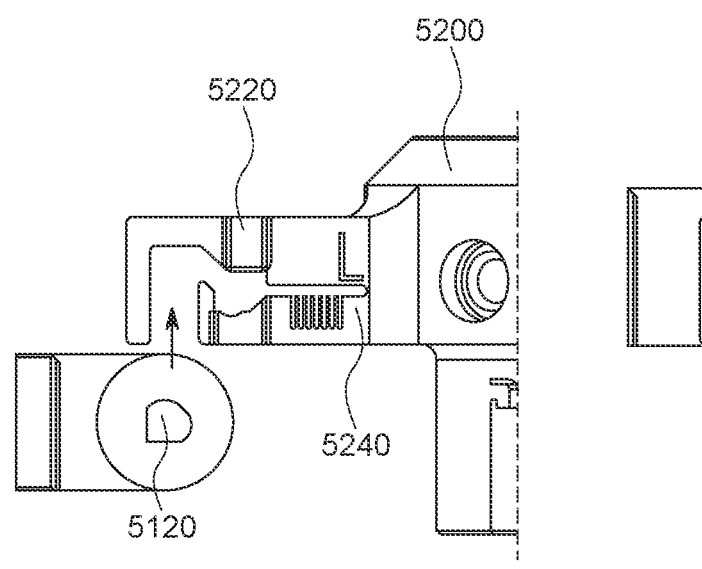
FIG. 27E
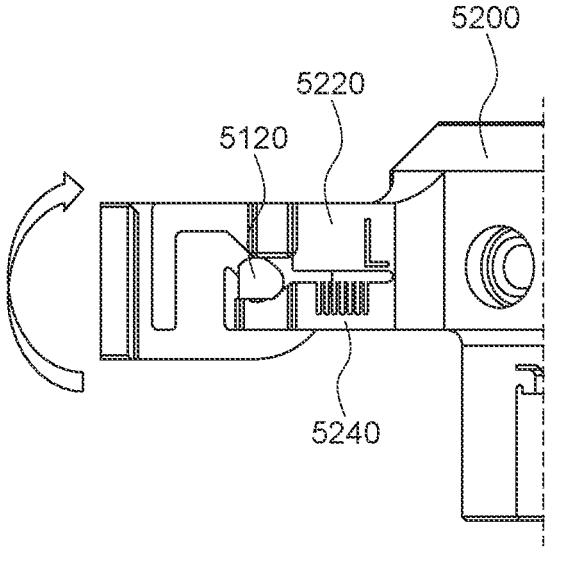
FIG. 27G
FIG. 27F
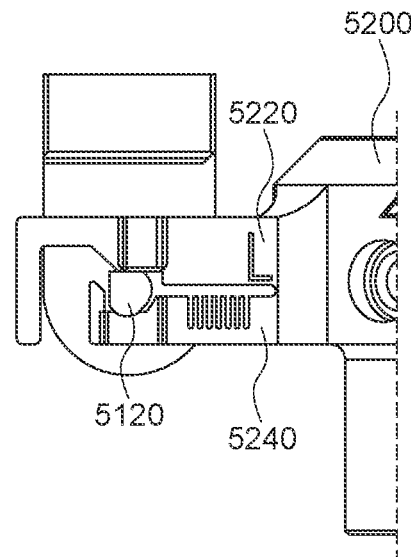
FIG. 27H

5110'

5120'

5300'

5310'

5400'

5410'

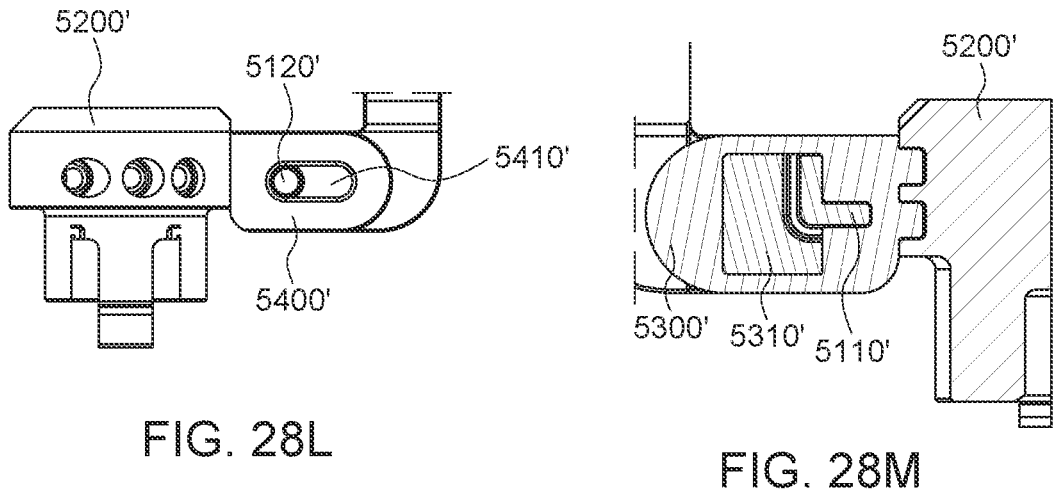
FIG. 28L
FIG. 28M
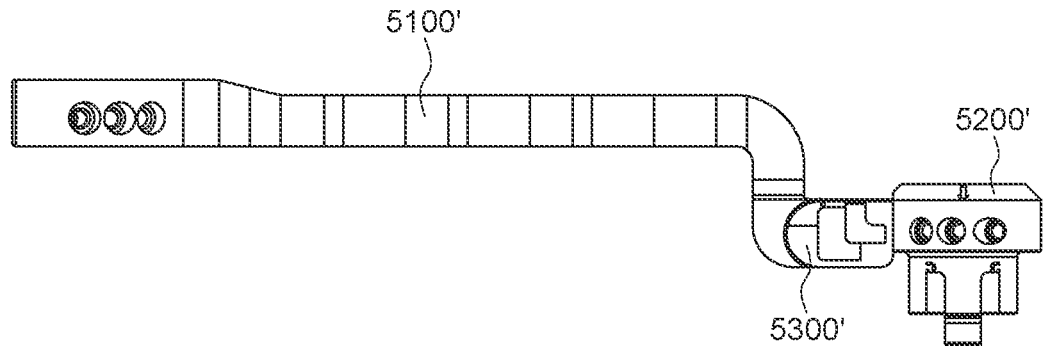
FIG. 28N

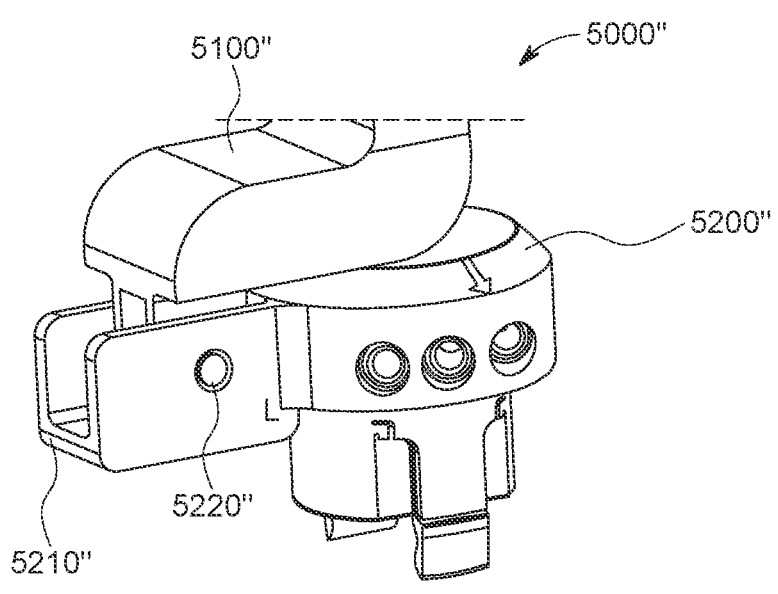
FIG. 29A
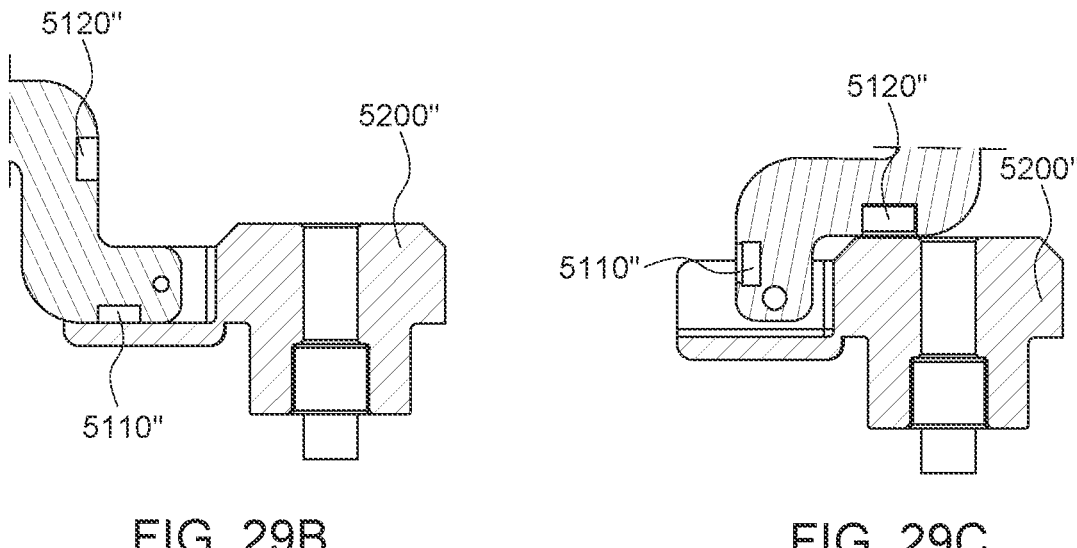
FIG. 29B                    FIG. 29C

5200'''

5210''''  5220''''  5230'''

5232'''  5238'''  5236'''  5230''''

5234''''

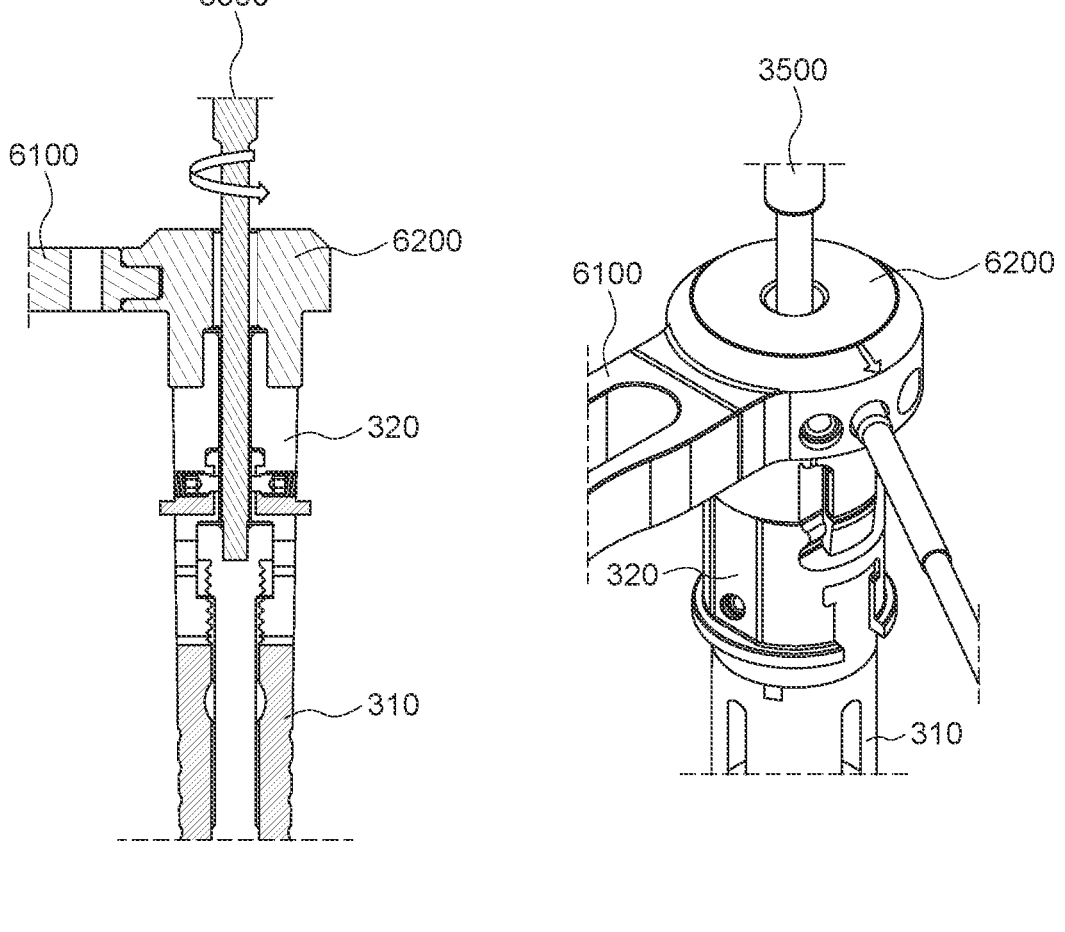
FIG. 31D                    FIG. 31E

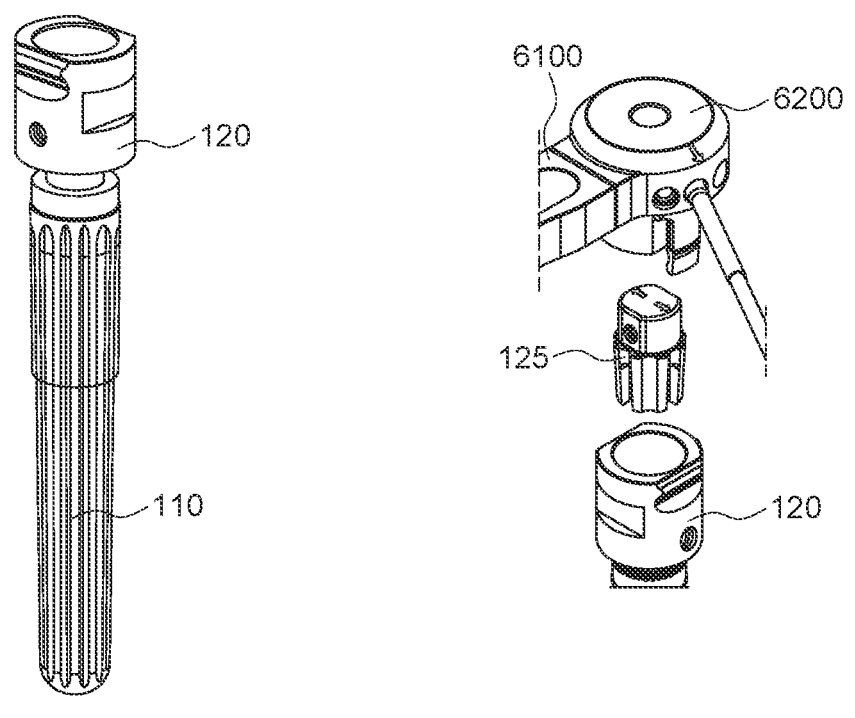
FIG. 31I                    FIG. 31J
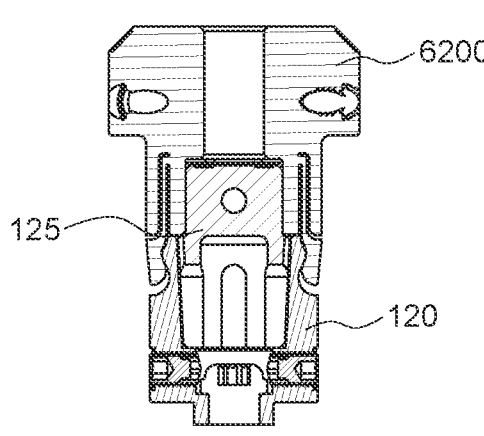
FIG. 31K

8100

8440

8200

8100

8440

8200

ADVANCED TRIAL SPACERS, HEIGHT MEASURING TOOL, AND INSERTER AND EXTRACTOR HANDLE

CROSS-REFERENCE TO RELATED APPLICATIONS

This application claims the benefit of the filing date of U.S. Provisional Patent Application No. 63/325,691, filed Mar. 31, 2022, the disclosure of which is hereby incorporated by reference herein.

FIELD OF THE DISCLOSURE

The present disclosure generally relates to components of a shoulder prosthesis system and a method of using a shoulder prosthesis system.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause the cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in (or adjacent to) the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is shoulder arthroplasty, in which a damaged shoulder joint may be replaced with one or more prosthetic implants. The shoulder joint may have been damaged by, for example, arthritis (e.g., severe osteoarthritis or degenerative arthritis), trauma, or a destructive joint disease.

A typical anatomical shoulder joint replacement attempts to mimic anatomic conditions. For example, a humeral stem and a humeral head replacement are attached to the humerus of the arm and replace the humeral side of a shoulder joint that is arthritic, has suffered trauma or otherwise requires replacement to improve the condition of the patient. The humeral head replacement can articulate with the native glenoid socket or with an opposing prosthetic glenoid implant.

For more severe cases, a reverse reconstruction can be performed, which includes reversing the kinematics of the shoulder joint. A reverse shoulder prosthesis can be provided by securing a semi-spherical device (sometimes called a glenosphere) to the glenoid and implanting a humeral stem with a cavity capable of receiving the glenosphere.

Before implanting the humeral implant, it may be desirable to trial the humeral implant to determine the appropriate length of the stem, the appropriate inclination angle of the articulating head, and/or the size of the articulating head, or other characteristics of the implant. The trial humeral implant can be assembled and then inserted into the humerus. Afterward, the entire trial implant can be removed, and the definitive humeral implant can be chosen and implanted in the bone. In order to determine the desired height for the prosthesis, it may be desirable to have tools to help measure the height between the proximal humeral resection and the center of the glenoid, even before beginning to assemble the trial prosthesis.

BRIEF SUMMARY OF THE DISCLOSURE

According to one aspect of the disclosure, a trial humeral prosthesis includes a trial stem configured for implantation into a humerus, a trial proximal body configured to couple to a trial articulating component of the trial humeral prosthesis, and a plurality of trial spacers configured to couple the trial stem to the trial proximal body, the plurality of trial spacers including a first trial spacer and a second trial spacer. The first and second trial spacers may each include a proximal post and a tab extending radially outward from the proximal post, and a distal body having a larger outer diameter than an outer diameter of the proximal post, a slot being formed in the distal body. The slot of the distal body of the first trial spacer may be configured to receive the tab of the second trial spacer when the proximal post of the second trial spacer is received within the distal body of the first trial spacer. The distal body of the first trial spacer may include a flexure arm with a divot, the divot configured to receive the tab of the second trial spacer, so that rotation of the first trial spacer relative to the second trial spacer advances the tab of the second trial spacer through the slot of the first trial spacer and into the divot to secure the first trial spacer relative to the second trial spacer.

According to another aspect of the disclosure, a trial humeral prosthesis may include a trial stem configured for implantation into a humerus, a trial proximal body configured to couple to a trial articulating component of the trial humeral prosthesis, and a plurality of trial spacers configured to couple the trial stem to the trial proximal body, the plurality of trial spacers including a first trial spacer and a second trial spacer. The first and second trial spacers may each include a proximal post and a divot and a shoulder adjacent the proximal post, and a distal body having a prong extending distally therefrom, the prong including an interior protrusion. The distal body of the first trial spacer may be configured to receive the proximal post of the second trial spacer therein, so that the interior protrusion of the prong is received within the divot of the second trial spacer and in abutment with the shoulder of the second trial spacer. The proximal post of the second trial spacer may include two opposing flats, and an interior surface of the distal body of the first trial spacer may include two opposing flats, the two opposing flats of the second trial spacer being in contact with corresponding ones of the two opposing flats of the first trial spacer when proximal post of the second trial spacer is received within the distal body of the first trial spacer.

According to a further aspect of the disclosure, a trial humeral prosthesis may include a trial stem configured for implantation into a humerus, the trial stem including a proximally extending plate with an oblong aperture extending therethrough. A trial spacer may have a pair of distally extending plates defining a void therebetween, each of the pair of distally extending plates having an oblong aperture extending therethrough, so that when the trial spacer is coupled to the trial stem so that the proximally extending plate is received within the void, the oblong aperture of the proximally extending plate and the oblong apertures of the pair of distally extending plates align with each other. A locking pin may include a trailing end, a leading end, and a shaft extending between the trailing end and the leading end, the leading end having an oblong shape configured to pass through the oblong aperture of the proximally extending plate and the oblong apertures of the pair of distally extending plates when the proximally extending plate is received within the void. The shaft may be split so that the leading end of the locking pin is formed of two members capable of flexing toward and away from each other.

According to still another aspect of the disclosure, a trial humeral prosthesis may include a trial stem configured for implantation into a humerus, the trial stem including a sphere at a proximal end thereof. A trial spacer may have an outer housing, a sphere extending from a proximal end thereof, and a locking mechanism positioned at least partially within the outer housing. The locking mechanism may include a flexure member defining a plurality of arcuate fingers that, in the aggregate, define a spherical void configured to receive the sphere of the trial stem therein. The flexure member may be configured to be transitioned between an unlocked condition in which the plurality of arcuate fingers can snap onto of off of the sphere of the trial stem, and a locked condition in which the plurality of arcuate fingers are locked on the sphere of the trial stem. The locking mechanism may include a sleeve that is threadedly coupled to the outer housing. The sleeve may be translatable relative to the arcuate fingers. The flexure member may be in the unlocked condition when the sleeve is in a first translational position and in the locked condition when the sleeve is in a second translational position.

According to yet another aspect of the disclosure, a trial humeral prosthesis may include a trial stem configured for implantation into a humerus, a trial proximal body configured to couple to a trial articulating component of the trial humeral prosthesis, and a plurality of trial spacers configured to couple the trial stem to the trial proximal body, the plurality of trial spacers including a first trial spacer and a second trial spacer. The first and second trial spacers may each include a plunger within an outer housing and a spring biasing the plunger to a retracted condition. The plunger may include a distal tapered end with a ramped surface, the outer housing including at a distal end thereof a plurality of balls axially retained by a retaining member, the plunger being configured to advance distally upon compression of the spring. As the plunger retracts proximally, the ramped surface of the distal tapered end of the plunger may force the plurality of balls to move radially outwardly with respect to the plunger. The distal tapered end of the plunger of the first trial spacer may be configured to be received within an enlarged proximal cavity of the second trial spacer. When the plunger of the first trial spacer is advanced distally, the plurality of balls of the first trial spacer may be positioned so that the distal end of the first trial spacer can pass into the enlarged proximal cavity of the second trial spacer. When the plunger of the first trial spacer is retracted proximally, the plurality of balls of the first trial spacer may be positioned so that the distal end of the first trial spacer cannot pass out of the enlarged proximal cavity of the second trial spacer.

According to another aspect of the disclosure, a trial humeral prosthesis may include a trial stem configured for implantation into a humerus, the trial stem including a protrusion at a proximal end thereof. A trial proximal body may be configured to couple to a trial articulating component of the trial humeral prosthesis, the trial proximal body including a recess at a distal end thereof. A first trial spacer may have a recess at a distal end thereof sized and shaped to mate with the protrusion at the proximal end of the trial stem. A second trial spacer may have a recess at a distal end thereof sized and shaped to mate with a protrusion at a proximal end of the first trial spacer, and a protrusion at a proximal end thereof sized and shaped to mate with the recess at the distal end of the trial proximal body. A locking button may include a first peg configured to be received within an aperture on the first trial spacer, and a second peg configured to be received within an aperture on the second trial spacer. The first trial spacer may include a first recess at the proximal end thereof, and the second trial spacer may include a second recess at the distal end thereof, so that when the first trial spacer is coupled to the second trial spacer, the first recess and the second recess form a combined recess configured to receive the locking button therein so that outer surfaces of the locking button, the first trial spacer, and the second trial spacer are substantially flush with each other.

According to a further aspect of the disclosure, a height measuring tool is for measuring a distance between a proximal humeral resection and a center of a glenoid. The tool may include an axially extending housing having a distal end with a mating feature configured to mate with a proximal end of a trial stem of a trial humeral prosthesis, the housing including indicia formed thereon corresponding to distances along the axial extent of the housing. A sliding clamp may be received over the housing and configured to slide along the axial extent of the housing. A pointer may be coupled to the sliding clamp, the sliding clamp configured to maintain an axial position relative to the axial extent of the housing in the absence of applied force to the sliding clamp. The housing may include a slot extending axially therethrough, and the sliding clamp may include a flexure tab with an aperture, the pointer extending through the slot and through the aperture of the flexure tab. The sliding clamp may include a slider with an aperture configured to receive the housing therethrough, and an arm with an elliptical aperture configured to receive the housing therethrough, the sliding clamp being slidable along the axial extent of the housing when the arm is depressed toward the slider. The housing may be an outer housing, and the tool may also include an axially extending inner housing received at least partially within the outer housing, the inner housing being translatable into and out of the outer housing, the inner housing including indicia formed thereon corresponding to distances along the axial extent of the inner housing. The pointer may be removably coupled to the sliding clamp, and may include an aperture. A proximal end of the inner housing may include a post sized and shaped to pass into the aperture of the pointer to removably couple the pointer to the inner housing.

According to still another aspect of the disclosure, a height measuring tool is for measuring a distance between a proximal humeral resection and a center of a glenoid. The tool may include a housing including a handle extending therefrom, the housing including a platform extending from a leading end of the housing. A scale may extend through the housing, the scale including indicia formed thereon corresponding to distances along the axial extent of the scale, a plurality of linear teeth being formed on the scale. A pinion may be maintained by the housing, the pinion having a plurality of gear teeth configured to intermesh with the linear teeth, so that rotation of the pinion advances the scale through the housing. A trigger may be operably coupled to the pinion so that depressing the trigger rotates the pinion, while releasing the trigger does not cause rotation of the pinion.

According to yet another aspect of the disclosure, a height measuring tool is for measuring a distance between a proximal humeral resection and a center of a glenoid. The tool may include an "L"-shaped outer housing, a pointer slidably received within a first end of the "L"-shaped housing, the pointer configured to contact a glenoid center. An "L"-shaped bracket may have a first end slidably received within a second end of the "L"-shaped housing. A humeral locator may be positioned on a second end of the "L"-shaped bracket, the humeral locator forming an inverse cup shape configured to receive a proximal end of a humerus therein. A connector may be positioned over the second end of the "L"-shaped bracket, the connector being translatable along the second end of the "L"-shaped bracket. A scale may have a first end slidably coupled to the first end of the "L"-shaped housing, and a second end slidably coupled to the connector, the scale including indicia formed thereon corresponding to distances along an axial extent of the scale.

According to another aspect of the disclosure, a height measuring tool is for measuring a distance between a proximal humeral resection and a center of a glenoid. The tool may include an "L"-shaped outer housing and a pointer slidably received within a first end of the "L"-shaped housing. The pointer may be configured to contact a glenoid center. A scale may form a second end of the "L"-shaped housing. The scale may include indicia formed thereon corresponding to distances along an axial extent of the scale. The scale may include an axially extending enclosed slot. A connector may be coupled to the scale via the slot, the connector being slideable along the slot. A shaft may be slidably received within the connector. A humeral locator may be positioned on an end of the shaft. The humeral locator may form an inverse cup shape configured to receive a proximal end of a humerus therein.

According to another aspect of the disclosure, a trial humeral prosthesis may include a trial stem configured for implantation into a humerus, and a trial proximal body configured to couple to a trial articulating component of the trial humeral prosthesis. The prosthesis may include a plurality of trial spacers configured to couple the trial stem to the trial proximal body, the plurality of trial spacers including a first trial spacer and a second trial spacer. The first and second trial spacers may each include a proximal post, a divot, a shoulder adjacent to the proximal post, and a distal body having a prong extending distally therefrom, the prong including an interior protrusion. The distal body of the first trial spacer may be configured to receive the proximal post of the second trial spacer therein, so that the interior protrusion of the prong of the first trial spacer is received within the divot of the second trial spacer and is in abutment with the shoulder of the second trial spacer. The first trial spacer may have a height that is different than a height of the second trial spacer. The proximal post of the second trial spacer may include two opposing flats, and an interior surface of the distal body of the first trial spacer may include two opposing flats, the two opposing flats of the proximal post of the second trial spacer being in contact with corresponding ones of the two opposing flats of the distal body of the first trial spacer when the proximal post of the second trial spacer is received within the distal body of the first trial spacer. The prosthesis may include a trial stem adaptor configured to be fastened to a proximal end of the trial stem by at least one screw. The trial stem adaptor may include a distally-extending protrusion configured to mate with a corresponding proximal recess in the trial stem to prevent rotational movement of the trial stem adaptor relative to the trial stem. The trial stem adaptor may include a proximal post, a divot, and a shoulder adjacent to the proximal post. The proximal post of the trial stem adaptor may include two opposing flats, and an interior surface of the distal body of the second trial spacer may include two opposing flats, the two opposing flats of the trial stem adaptor being in contact with corresponding ones of the two opposing flats of the distal body of the second trial spacer when the proximal post of the trial stem adaptor is received within the distal body of the second trial spacer.

According to a further aspect of the disclosure, a height measuring tool is for measuring a distance between a proximal humeral resection and a center of a glenoid. The tool may include an axially extending housing having a distal end with a mating feature configured to mate with a proximal end of a trial stem of a trial humeral prosthesis. The housing may include indicia formed thereon corresponding to distances along the axial extent of the housing. A sliding clamp may be received over the housing and may be configured to slide along the axial extent of the housing. A pointer may be coupled to the sliding clamp, and the sliding clamp may be configured to maintain an axial position relative to the axial extent of the housing in the absence of applied force to the sliding clamp. The housing may include a slot extending axially therethrough, and the sliding clamp may include a flexure tab with an aperture, the pointer extending through the slot and through the aperture of the flexure tab. The sliding clamp may include a slider with an aperture configured to receive the housing therethrough, and an arm with an elliptical aperture configured to receive the housing therethrough, the sliding clamp being slidable along the axial extent of the housing when the arm is depressed toward the slider. The clamp may include a proximal extension and a receiver on the proximal extension, the receiver including an aperture configured to receive the pointer therethrough. The receiver may include a flexure finger that terminates in an upwardly projecting protrusion configured to press against the pointer when the pointer is received through the receiver so that, in the absence of additional forces applied on the pointer, the upwardly projecting protrusion is configured to maintain the pointer in a stable position relative to the receiver. The housing may be an outer housing, and the tool may also include an axially extending inner housing received at least partially within the outer housing, the inner housing being translatable into and out of the outer housing, the inner housing including indicia formed thereon corresponding to distances along the axial extent of the inner housing. The pointer may be removably coupled to the sliding clamp, the pointer including an aperture, and a proximal end of the inner housing including a post sized and shaped to pass into the aperture of the pointer to removably couple the pointer to the inner housing.

According to still another aspect of the disclosure, a shoulder prosthesis implant system may include an implant stem adapted to be implanted into a humerus, a trial stem adapted to be temporarily implanted into the humerus during trialing of the shoulder prosthesis implant system, and a handle system. The handle system may be adapted to separately couple to the implant stem and the trial stem to assist with inserting the trial stem and the implant stem into the humerus and extracting the trial stem and the implant stem from the humerus. The handle system may include a handle and a sleeve receiving at least a portion of the handle therethrough. The sleeve may have a first unlocked position in which the implant stem and trial stem can be coupled to the handle, and a second locked position in which the sleeve prevents the implant stem and trial stem from disconnecting from the handle. The handle system may include a spring operatively coupled to the sleeve, the spring biasing the sleeve to the locked position. The handle system may include a pin coupled to the sleeve, and the handle may include an axial slot receiving the pin, engagement between the pin and the axial slot limiting an axial range of motion between the handle and the axial slot, and preventing rotational motion of the sleeve relative to the handle. The handle may include a proximal collar, and an axial bore extending through the proximal collar and through the handle so that the handle is cannulated. The handle system may include a rod having a proximal impaction surface and a distal flange, the distal flange configured to abut the proximal collar when the rod is coupled to the handle. The rod may include a threaded distal tip, and the handle may include interior threading configured to mate with the threaded distal tip of the rod.

BRIEF DESCRIPTION OF THE DRAWINGS

FIG. 2A is a schematic view of a humerus with a significant portion thereof removed.

FIG. 2B is a schematic view of a humeral prosthesis implanted into the humerus of FIG. 2A.

FIG. 4B is a perspective view of a trial adaptor of the trial humeral prosthesis of FIG. 4A.

FIGS. 4C-D are perspective views of a trial spacer of the trial humeral prosthesis of FIG. 4A.

FIGS. 4E-G illustrate different stages of a sequence of coupling the trial spacer of FIGS. 4C-D to the trial adaptor of FIG. 4B.

FIG. 6B is a side view of a trial adaptor of the trial humeral prosthesis of FIG. 6A.

FIGS. 6C-D are perspective and bottom views, respectively, of a trial spacer of the trial humeral prosthesis of FIG. 6A.

FIGS. 6E-F illustrate different stages of a sequence of coupling the trial spacer of FIGS. 6C-D to the trial adaptor of FIG. 6B.

FIG. 22E illustrates the sleeve of FIG. 22C assembled to the handle of FIG. 22B, with the sleeve shown with partial transparency.

FIG. 22F illustrates the handle system of FIG. 22A just prior to engagement with an implant stem.

FIGS. 22I-J are side and cross-section views, respectively, of the handle system of FIG. 22A coupled to a trial stem in a use condition.

FIGS. 22K-L are side and cross-section views, respectively, of the handle system of FIG. 22A coupled to an implant stem in a use condition.

FIGS. 23A-D illustrate a handle system similar to that shown in FIG. 22A, with an alternate mechanism for coupling to implant and trial stems.

FIGS. 27A-H illustrate various views of a rotatable handle assembly according to another aspect of the disclosure.

FIGS. 28J-L show the handle of the handle system of FIG. 28A in a vertical orientation.

FIGS. 28M-N show the handle of the handle system of FIG. 28A in a horizontal orientation.

FIGS. 29A-C illustrate a portion of a handle system that is a variant of those shown in FIGS. 27-28.

FIGS. 31D-G are views of the handle system of FIG. 31A coupled to a trial stem.

FIGS. 31H-K are views of an implant stem and the handle system of FIG. 31A being used therewith.

DETAILED DESCRIPTION

As used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner. As used herein, the term "medial" refers to a location closer to the midline of an individual, while the term "lateral" refers to a location farther away from the midline of the individual.

Figure 1:
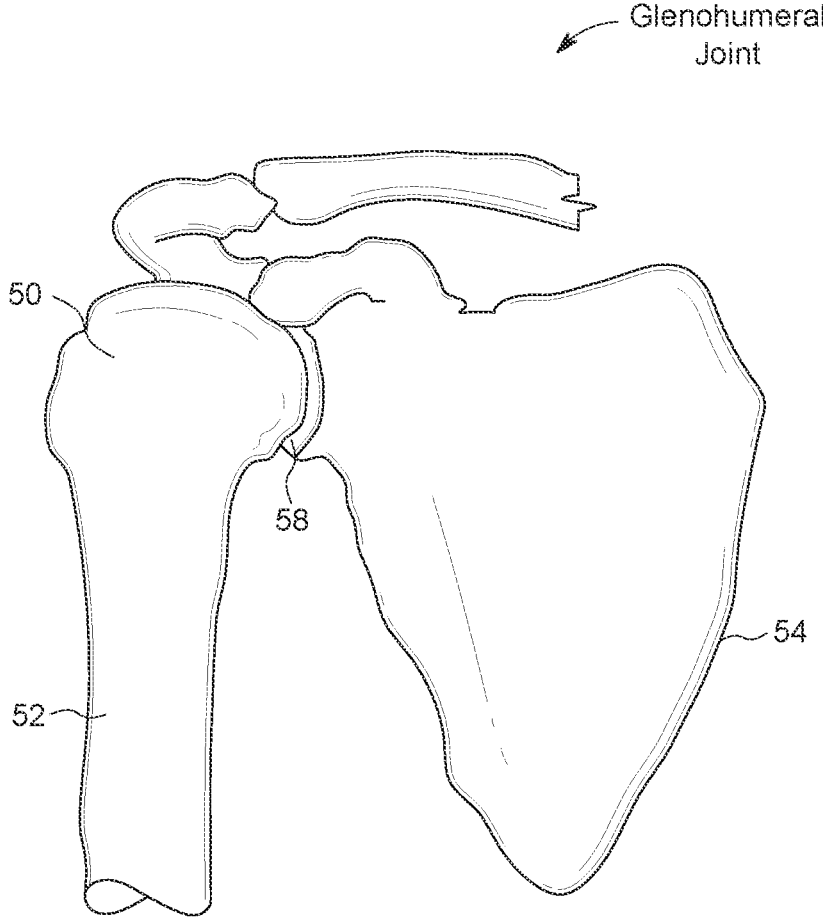
FIG. 1 is a schematic view of a human shoulder joint showing the bones thereof.

FIG. 1 shows the anatomy of a typical glenohumeral joint. The joint is formed in part by a head 50 of a humerus 52 and a glenoid 58 of a scapula 54. The head 50 is a convex structure that is generally spherical. The glenoid 58 includes a concave articular surface upon which the head 50 moves. The humerus has a proximal portion which is the portion of the humerus adjacent to the glenoid 58 and forming part of the shoulder joint. The proximal humerus may sometimes be referred to herein as the superior humerus. When the glenohumeral joint is arthritic, diseased, or damaged, therapy can include forming an incision over the joint to provide access to the head 50 of the humerus 52 and the glenoid 58 of the scapula 54. Once the head 50 is accessible the head can be separated from the rest of the humerus 52 as an early part of a method of placing an implant.

In some situations, a significant portion of the proximal or superior humerus 52 may need to be removed or otherwise may be unavailable to support a humeral implant as part of an arthroplasty procedure. For example, in a revision procedure, in which a previously implanted humeral prosthesis must be removed and replaced with a new humeral prosthesis, a significant portion of the proximal humerus 52 may not be available to support the new humeral prosthesis. In another example, major trauma or disease may require a significant portion of the proximal humerus 52 to be removed prior to implanting a humeral prosthesis. FIG. 2A illustrates a humerus 52 with a significant proximal portion 53 thereof, including humeral head 50, in phantom, providing an example of the remaining humeral bone that may be available to receive a humeral implant. In other words, the phantom proximal portion 53 of humerus 52 is removed and is thus unavailable to support a prosthesis. FIG. 2B shows one such humeral prosthesis 100 that has been implanted into the humerus 52 after the proximal portion 53 thereof has been removed. It should be understood that humeral prosthesis 100 may include other components that are not illustrated, such as a prosthetic humeral head, which would be coupled to the humeral prosthesis 100 as part of the implant procedure.

Figures 3A, 3B:
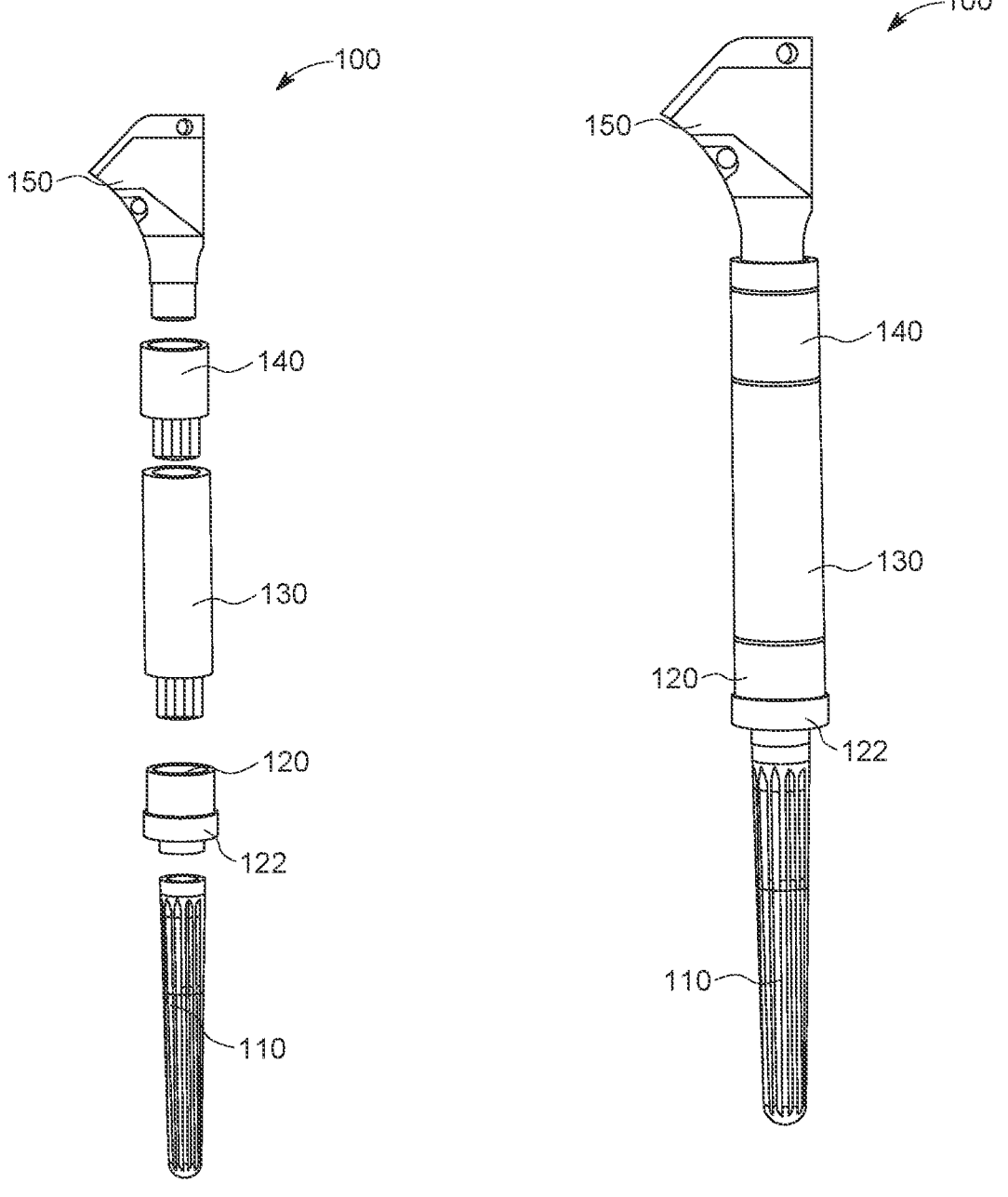
FIGS. 3A-B are exploded and assembled side views, respectively, of the humeral prosthesis of FIG. 2B.

FIGS. 3A-B are exploded and assembled views, respectively, of the humeral prosthesis 100 of FIG. 2B. The humeral prosthesis may include a stem 110 configured to be inserted into the distal (or remaining) portion of the humerus 52. The stem 110 may be configured to mate with cancellous bone of the humerus 52. For example, the stem 110 may include a plurality of channels, ridges, flutes, pores, or other structures that enhance engagement with the bone. These and other structures can enhance the ingrowth of bone into these structures as a way to reduce, minimize, or eliminate rotation or proximal motion of the stem 110 relative to the cancellous bone matter in the humerus 52 in which the stem 110 is positioned. The proximal end of the stem 110 may include a first plurality of proximally facing teeth, for example, to engage complementary distally facing teeth on a spacer or adaptor 120. The stem 110, including proximally facing teeth and their interaction with distally facing teeth of a coupling component, may be similar or identical to that described in U.S. Patent Application Publication No. 2021/0085474, the disclosure of which is hereby incorporated by reference here. In use, the stem 110 may be positioned within the humerus 52 so that the proximal end of the stem 110 is positioned at or adjacent to the proximal end of the remaining bone stock of the humerus 52.

Still referring to FIGS. 3A-B, the stem 110 may be configured for use with other shoulder implant systems, and thus adaptor 120 may be provided to allow for easy connection of the remainder of the shoulder prosthesis 100 to the stem 110. In the illustrated embodiment, the adaptor 120 may be a generally cylindrical member with a radially protruding collar 122 configured to abut the proximal end of the humerus 52, as shown in FIG. 2B. The distal end of the adaptor 120 may couple to the stem 110 by any suitable mechanism, for example via a taper lock that is inserted into the proximal end of the stem 110, via a fastener that fixes the adaptor 120 to the stem 110, etc. Because a large amount of bone is missing or has been removed from the proximal humerus 52, the humeral prosthesis 100 may need to be "built up" to a desired level to allow for proper positioning of the prosthetic articulating surface that is eventually coupled to the shoulder prosthesis.

In order to build up the humeral prosthesis 100, a plurality of spacers may be provided in a number of different sizes or heights. For example, the humeral prosthesis 100 shown in FIGS. 3A-B includes a first relatively large spacer 130, and a second relatively small spacer 140. Each spacer may include a distal connecting feature, such as a taper, configured to mate with a tapered recess in either another spacer or in the adaptor 120. The desired number and lengths of spacers may be stacked up so that, when the proximal body 150 is coupled to the proximal-most spacer, the proximal body 150 is at the desired height to receive the prosthetic articulation member (e.g. a prosthetic humeral head or a prosthetic cup or socket). The proximal body 150 may include a distal connection feature, such as a taper, to couple to the proximal-most spacer in the prosthesis 100. The proximal body may also include an aperture on a proximal portion thereof to receive a prosthetic articulation member, such as a prosthetic humeral head configured to articulate with a native or prosthetic glenoid. Although one particular shape of the proximal body 150 is shown in FIGS. 3A-B, it should be understood that other shapes may be appropriate, including more spherical shapes that help better approximate the native proximal humeral shape.

During an implantation procedure that intends to implant humeral prosthesis 100 or a similar device, it is typically desirable to first implant "trial" components that represent the functionality of the humeral prosthesis 100. With the trial implant in place, range of motion, joint positioning, and other parameters that may be predictive of success may be tested or otherwise determined. When the surgeon determines that a particular trial implant is indicative of desirable surgical outcomes, the actual humeral prosthesis 100 may be implanted in a configuration that strives to match the successful trial configuration, so that the final permanent implant has the desirable parameters tested or identified with the corresponding trial configuration. Although the general use of trialing is well known in joint replacement procedures, humeral prosthesis 100 may result in challenges not found in other joint implants, in part because of the amount of bone stock that is removed. In other words, in many typical shoulder arthroplasty procedures, only the native humeral head is removed, which may provide the surgeon with a relatively clear understanding of where the prosthesis components must be positioned to lead a desired positioning of the prosthetic articulation components. However, with humeral prosthesis 100, in order to account for the large amount of missing bone stock 53, the humeral prosthesis 100 must be "built up" to the desired height through the use of spacers 130, 140. Although only two spacers 130, 140 are illustrated and described in connection with FIGS. 3A-B, a typical kit may include a larger number of spacers and a larger range of spacer sizes in order to afford the surgeon the ability to build the humeral prosthesis 100 up to the desired height for the specific patient. While the relatively large number and size options of spacers are beneficial to allow the surgeon to achieve the best patient outcome, it may also mean that the surgeon needs more of a "trial and error" process when determining which spacers to use to build the humeral prosthesis 100 up to the desired height. For example, if a system included exactly four spacers, with each spacer being a different height, those four spacers will provide for up to twenty-four different heights since the spacers can stack on each other. In order to assist the surgeon in this process, various embodiments of trial spacers are described below that may make the process of trialing more efficient and lead to better outcomes for the patient and fewer difficulties for the surgeon during the procedure. It should also be understood that, in addition to providing an ability to determine which prosthesis components should be used to achieve the desired height, the trial components should also be able to suitably withstand loads that are placed on the trial implant that occur during trialing (including, but not limited to, loads that are applied during range of motion testing).

As should be understood from the description provided herein, when trial spacers are described, the heights of those trial spacers may be substantially equal to the heights of the actual implant spacers (e.g. spacers 130, 140) that will be used to build up the humeral prosthesis 100. So, if four implant spacers are provided having heights of 20 mm, 30 mm, 60 mm, and 100 mm, the trial spacers typically would be provided having heights of 20 mm, 30 mm, 60 mm, and 100 mm. This may be true for each embodiment of the trial spacers described below.

Figure 4A:
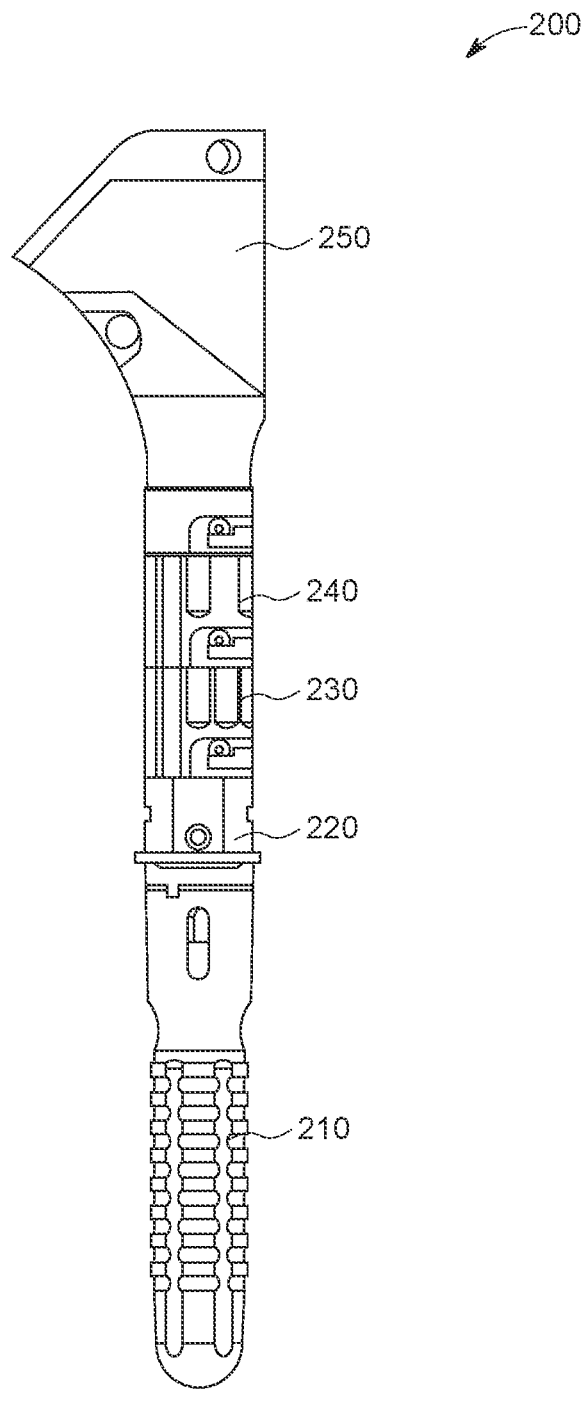
FIG. 4A is a side view of an assembled trial humeral prosthesis.

FIG. 4A illustrates a trial humeral prosthesis 200 (in one particular configuration of a trial) that may be used when performing trialing to determine the desired positioning and configuration of humeral prosthesis 100 (or similar prostheses). Generally, trial humeral prosthesis 200 may include a trial proximal body 250 and a trial stem 210 that have sizes and shapes that generally correspond to proximal body 150 and distal stem 110.

Figure 6A:
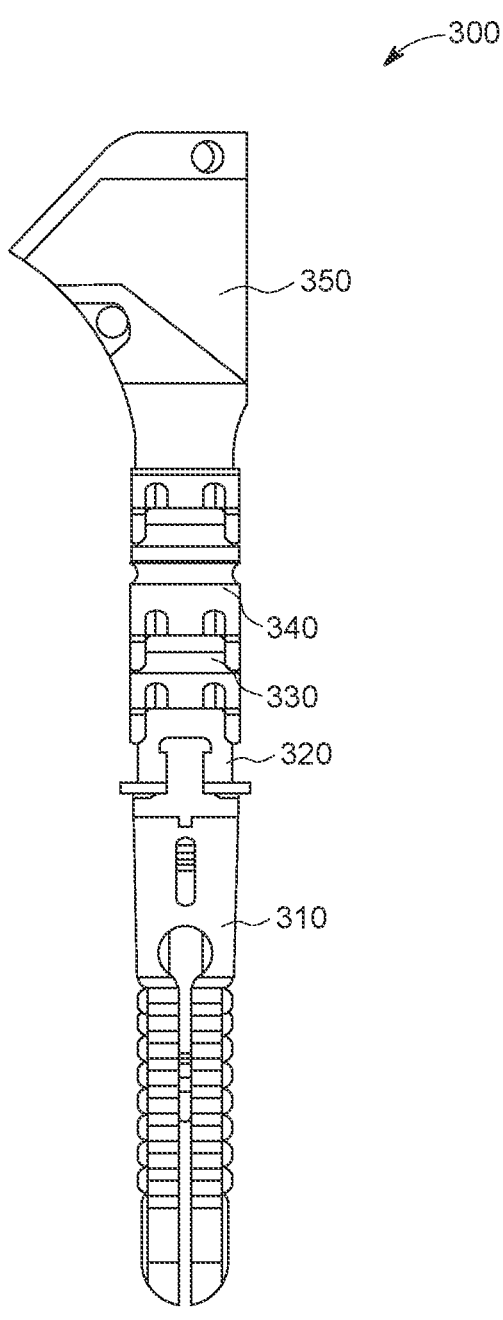
FIG. 6A is a side view of an assembled trial humeral prosthesis according to another aspect of the disclosure.

FIG. 4B shows a trial adaptor 220 that generally corresponds in shape and size to adaptor 120, and which may include a collar 222 corresponding to collar 122. Trial adaptor 220 is shown coupled to trial stem 210, for example via a fastener such as a screw, although other connections may be provided. In this particular example, the trial adaptor 220 may include one or more protrusions 223 configured to mate with a corresponding recess in the trial stem 210, which may for example provide for, or enhance, rotational stability of the trial adaptor 220 relative to the trial stem 210. The one or more protrusions 223 may also help ensure correct rotational alignment of the trial adaptor 220 to the trial stem 210, for example to align screw holes that allow for a screw to pass through and stabilize trial adaptor 220 to trial stem 210. The trial adaptor 220 may include a relatively large diameter base portion 224, and a relatively small diameter post 226 extending proximally therefrom. The outer diameter of the base portion 224 may generally correspond to the outer diameter of the adaptor 120 that may be part of the humeral prosthesis 100. The post 226 is preferably cylindrical to allow for rotation of other components about the post 226, and preferably includes one or more tabs 228 extending radially outward therefrom (e.g. substantially orthogonal to the longitudinal axis of the trial stem 210). In the illustrated embodiment, post 226 includes two tabs 228 spaced about 180 degrees apart from each other, but more or fewer tabs may be used, and while the spacing between two or more tabs is preferably at equal intervals around the circumference of the post 226, other spacing may be suitable. The proximal end of post 226 may also include an opening, and the trial spacers described below may also have a similar opening so that a screw driver may pass through the openings to drive a screw element within trial stem 210 to cause expansion of the trial stem 210 to temporarily fix the trial stem 210 within the humerus 52. Although not labeled, such a screw is illustrated in FIG. 6A in connection with trial stem 310, which may have a split configuration that can be temporarily expanded.

FIGS. 4C-D illustrate a trial spacer 230 in different rotational views. Spacer 230 may include a relatively large diameter base 232 that has an at least partially hollow interior, and a relatively small diameter post 234 extending proximally therefrom. The base 232 may have an outer diameter that substantially matches the outer diameter of base 224 and of the outer diameter of the spacers 130, 140 of the humeral prosthesis 100. In the illustrated embodiment, base 232 may include texture features, such as longitudinal ribs, to assist a user in gripping and rotating the spacer 230 to connect to other devices, as described in greater detail below. Trial spacer 230 may include two tabs 236 extending radially outwardly from the post 234 in substantially the same way as tabs 228 of trial adaptor 220. And while two tabs 236 are shown, more or fewer tabs may be provided in different positions as described in connection with tabs 228 of trial adaptor 220. The proximal end of trial spacer 230 may include two flexure fingers 237 that generally follow the circumferential contour of the outer diameter of base 232. Each flexure finger 237 may have a first end that is integral with the base 232, and extend to a second end that is spaced apart from the base 232 so as to define a slot 238. The slot 238 may have a first slot portion extending parallel to the longitudinal axis of the trial spacer 230, with the first slot portion forming a discontinuity or opening in the proximal end of the base 232. The first slot portion may transition into a second slot portion that extends along a portion of the circumference of the base 232, so that the slot 238 in totality forms a general "L" shape. The end of the flexure finger 237 nearest the first slot portion may have a smaller height (in the longitudinal direction of the trial spacer 230) and may include a recessed portion or divot 239 before transitioning into an opposite end of the flexure finger 237 that has a larger height. It should be understood that although one trial spacer 230 is described and shown in connection with FIGS. 4C-D, and two trial spacers 230, 240 having equal heights are shown in FIG. 4A, more trial spacers may be provided. For example, in order to build up the trial prosthesis 200, a kit may be provided having a number of trial spacers having heights that generally match the number of implant spacers and the heights of those implant spacers. Also, although two flexure fingers 237 are shown about 180 degrees apart, more or fewer flexure fingers may be provided, at equal spacing interval or at other spacing interval. However, the number and relative spacing of the flexure fingers 237 preferably matches the number and spacing of tabs 236 (which, in turn, preferably matches the number and spacing of tabs 228).

Referring briefly back to FIG. 4A, the trial proximal body 250 may have a distal end that includes flexure fingers in substantially the same shape, number, and orientation as flexure fingers 237.

FIGS. 4E-G illustrate different stages in coupling a trial spacer 230 to trial adaptor 220. Referring to FIG. 4E, the trial stem 210 has already been implanted in the remaining bone stock of the humerus 52, and the trial adaptor 220 has already been fixed to the trial stem 210. A first desired height trial spacer 230 is selected and the base 232 of the trial spacer 230 is axially aligned with the post 226 of the trial adaptor 220, with the first slot portion of each slot 238 axially aligned with a corresponding tab 228. The trial spacer 230 is advanced in a distal direction D until the tabs 228 pass through the first slot portion and contact the base 232 of the trial spacer 230, as shown in FIG. 4F. Once the tabs 228 are received within the first slot portions, the trial spacer 230 may be rotated in a rotational direction R, in this example clockwise, to cause the tabs 228 to begin to traverse the second slot portion. While it is preferable for clockwise direction to cause locking, and anticlockwise rotation to cause disconnection, the components may be configured to provide locking via anticlockwise rotation, and unlocking via clockwise rotation. Preferably, the tabs 228 have a larger diameter than the width of the slot 238 at the free end of the flexure finger 237. With this configuration, as the trial spacer 230 is rotated clockwise, the size of the tabs 228 forces the flexure finger 237 to flex away from the tabs 228, until the tabs 228 reach the divots 239. Upon the tabs 228 reaching the divots 239, the flexure fingers 237 may "snap" back with the divots 239 securely but reversibly receiving the tabs 228. Preferably, the height of the slot 238 between the divots 239 and the connected ends of the flexure fingers 237 is small enough relative to the diameter of the tabs 228 that additional clockwise rotation of the trial spacer 230 will not cause the tabs 228 to exit the divots 239 and begin traversing the remainder of the second slot portion. This configuration may provide audible and/or tactile feedback as the flexure fingers 237 "snap" onto the tabs 228, helping make clear to the user that the trial spacer 230 is locked onto the trial adaptor 220. If the trial spacer 230 needs to be disconnected from the trial adaptor 220, the user simply rotates the trial spacer 230 in a direction opposite the initial rotational direction R, in this embodiment anti-clockwise. With enough torquing force, the tabs 228 will be forced out of the divots 239 as the flexure fingers 237 flex, and effectively the steps shown in FIGS. 4E-G may be performed in the opposite order to disconnect the trial spacer 230. However, it should be understood that, under typical loads expected during trialing, the tabs 228 will not be subjected to enough force to move them out of the divots 239, thus maintaining the desired rotational positions unless intentional torquing is used to decouple the components.

It should be understood that the description of the connection and disconnection of the trial spacer 230 to the trial adaptor 220 applies with substantially equal force to stacking of trial spacers, and connecting the trial proximal body 250 to the trial spacer (or the final trial spacer in a stack if multiple trial spacers are stacked). In other words, after achieving the configuration shown in FIG. 4G, another trial spacer 240, of a different height or the same height, may be coupled to the trial spacer 230 to begin stacking the trial spacers to achieve the desired height of the trial prosthesis 200. To complete the assembly of the trial prosthesis 200, the trial proximal body 250 may be coupled to the proximal-most trial spacer, again in substantially the same manner shown and described in connection with FIGS. 4E-G. With the trial prosthesis 200 fully assembled, a trial articulating component such as a trial cup or trial humeral head may be coupled to the trial proximal body 250, and trialing performed and completed. If trialing is successful, the surgeon may note which trial spacers (e.g. which height or combination of heights) provided the successful results, and plan to use the correspondingly sized (or combination of correspondingly sized) implant spacers 130, 140 when performing the implantation of humeral prosthesis 100. The disassembly of the trial prosthesis 200 may generally follow the opposite order of FIGS. 4E-G for disconnection of the trial proximal body 250 and the trial spacers 230, 240.

Figure 5A:
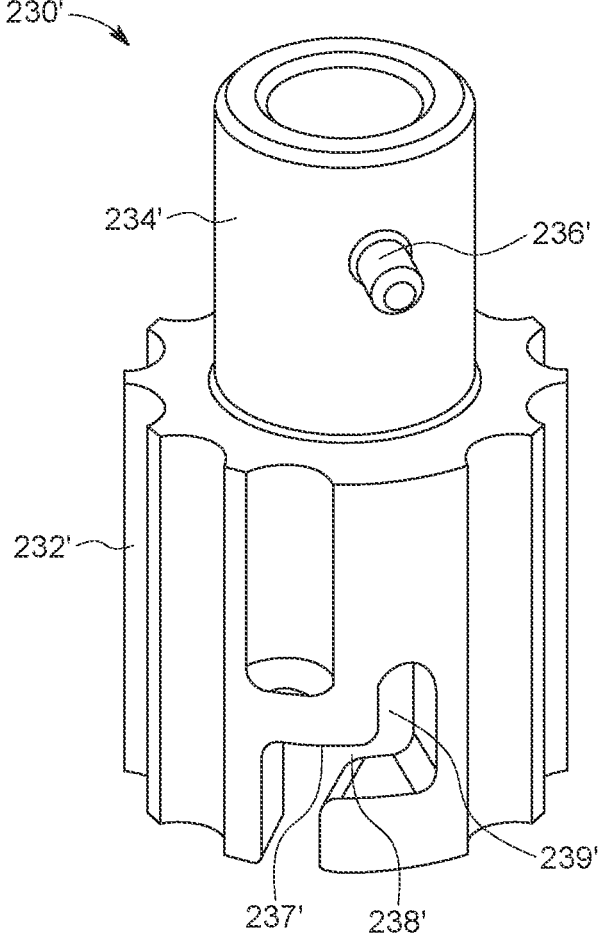
FIG. 5A is a perspective view of an alternate trial spacer of the trial humeral prosthesis of FIG. 4A.

FIG. 5A illustrates a trial spacer 230' substantially similar to trial spacer 230, with a different locking mechanism (and different structure to provide that locking mechanism). Trial spacer 230' may include a post 234' and tabs 236' that are similar or identical to post 234 and tabs 236. The base 232' of trial spacer 230' may be similar or identical to base 232 of trial spacer 230, with the exception of the configuration of the slot that receives the tabs of other spacers or the trial adaptor 220. In particular, base 232' may be formed with two slots, each slot having a first slot portion 237', second slot portion 238', and third slot portion 239'. The first slot portion 237' may extend to the proximal end of the body 232' to allow for access to the slot. The first slot portion 237' may extend parallel to the longitudinal axis of the spacer 230', and lead to the second slot portion 238' extending in a circumferential direction (e.g. substantially orthogonal to the first slot portion 237'). The second slot portion 238' may transition to the third slot portion 239', which may extend proximally from the second slot portion 238' substantially parallel to the longitudinal axis of the spacer 230' and to the first slot portion 237'. If this configuration is used, it should be understood that trial proximal body 250' may also include a similar slot configuration.

Figures 5B, 5C:
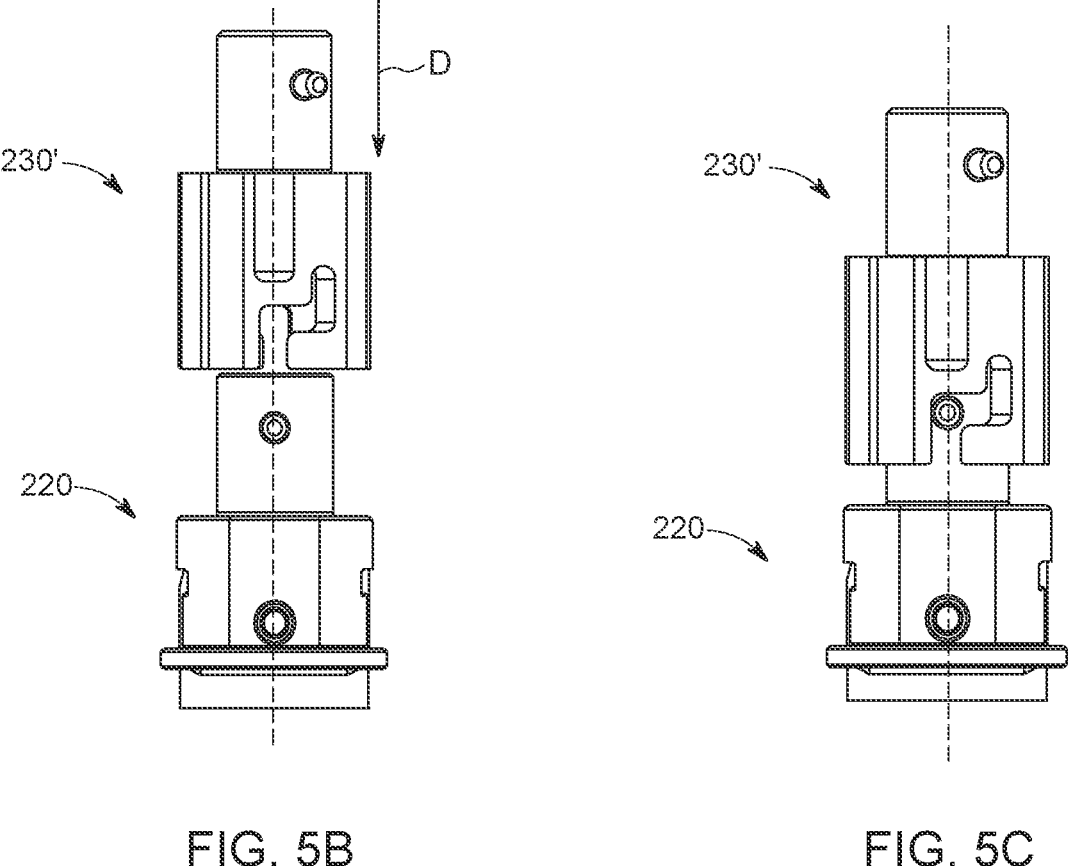
FIGS. 5B-E illustrate different stages of a sequence of coupling the trial spacer of FIG. 5A to the trial adaptor of FIG. 4B.
Figures 5D, 5E:
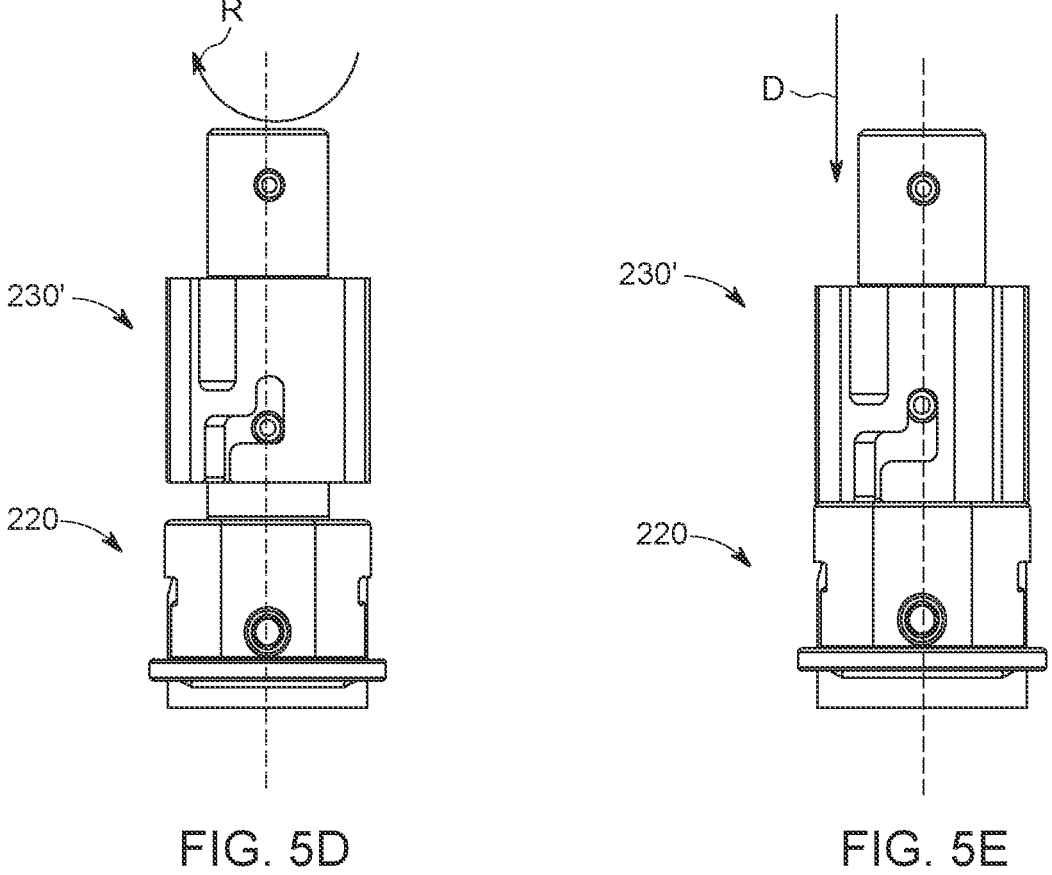

FIGS. 5B-E illustrate different steps in coupling trial spacer 230' to trial adaptor 220 (which is already coupled to trial distal stem 210 in the same manner described for trial spacer 230). With the first slot portion 237' aligned with the tabs 228 of trial adaptor 220, as shown in FIG. 5B, the trial spacer 230' is advanced in the distal direction D until the tabs 228 reach the end of the first slot portion 237'. Then, the trial spacer 230' may be rotated in a first rotational direction R (e.g. clockwise) until the tabs 228 reach the end of the second slot portion 238', as shown in FIG. 5D. Then, the trial spacer 230' may again be advanced in the distal direction D until the tabs 228 reach the end of the third slot portion 239', as shown in FIG. 5E. The process may be repeated to stack one or more additional trial spacers onto trial spacer 230', and then again to couple the trial proximal body 250 to the proximal-most trial spacer. To disconnect the components, the steps shown in FIGS. 5B-5E may be performed in reverse order. It should be understood that, during trialing of trial prosthesis 200, the assembly and in particular the trial spacers are essentially always under compression. This compression helps to ensure that the tabs of the various components remain at the proximal end of the third slot portions 239' during use, without any likelihood of the connection decoupling unintentionally. The widths of the various slot portions 237'-239' are preferably just large enough relative to the diameter of the tabs 228 to allow for the tabs to move through the slots. In other words, while the tabs 228 are at the proximal end of the third slot portions 239', there is not enough clearance to allow for any substantial rotational motion of the trial spacer 230' relative to the trial adaptor 220.

While trial humeral prosthesis 200 includes "twist-to-lock" or "twist-and-push-to-lock" style assembly of spacers (and optionally the trial proximal body), trial humeral prosthesis 300, shown in FIG. 6A, include "push-to-lock" style assembly. As shown in FIG. 6A, trial humeral prosthesis 300 includes a trial stem 310 that may be substantially similar or identical to trial stem 210, and a proximal body 350 that may be substantially similar or identical to proximal body 250, but for the distal end connection mechanism of proximal body 350. Thus, these same components will not be described in detail here again.

FIG. 6B shows a trial adaptor 320 that generally corresponds in shape and size to adaptor 120, and which may include a collar 322 corresponding to collar 122. Trial adaptor 320 is shown coupled to trial stem 310, for example via a fastener such as a screw, although other connections may be provided. In this particular example, trial adaptor 320 may include one or more protrusions 323 configured to mate with a corresponding recess in the trial stem 310, which may for example provide for, or enhance, rotational stability of the trial adaptor 320 relative to the trial stem 310. The one or more protrusions 323 may also help ensure correct rotational alignment of the trial adaptor 320 to the trial stem 310, for example to align screw holes that allow for a screw to pass through and stabilize trial adaptor 320 to trial stem 310. The trial adaptor 320 may include a relatively large diameter base portion 324, and a relatively small diameter post 326 extending proximally therefrom. The largest outer diameter of the base portion 324 may generally correspond to the outer diameter of the adaptor 120 that may be part of the humeral prosthesis 100.

Still referring to FIG. 6B, the post 326 is preferably cylindrical but for two flats extending axially along the post, the flats preferably being parallel to one another. This configuration may prevent rotation of components that slide over post 326, and may also limit the possible rotational orientations of other components relative to the post 326, which may help align different features among different components. As will be described below, other components in the system may include two prongs spaced about 180 degrees, and thus the configuration of two flats may force the two prongs into a desired position. In other embodiments, other shapes for post 326 may be used. For example, if three prongs were used in the other components, it may be preferable to have a post with a triangular profile, if four posts were used, it may be preferable to have a post with a square profile, etc. In addition, the body or base 324 may have near its proximal end two divots 328, with each divot being bound on its proximal end by a shoulder or protrusion 329. The two divots 328 may extend in a known orientation relative to the flats of the post 326. In the illustrated embodiment, the two flats of the post 326 are offset by about 90 degrees from the extent of the divots 328, but in other embodiments, other relative orientations may be suitable. Although only a side view of trial adaptor 320 is shown in FIG. 6B, the shapes of the corresponding features of trial spacer 330, shown and described in connection with FIG. 6C, may generally apply to trial adaptor 320 and vice versa.

One trial spacer 330 is shown in FIGS. 6C-D, although as with other embodiments, it should be understood that multiple trial spacers may be provided with a general similar shape but of different heights. Trial spacer 330 includes a main body 331 having a relatively large diameter and a post 332 having a relatively small diameter extending proximally from the main base or body 331. Post 332 may have substantially the same shape as post 326, including two flats on opposite sides of an otherwise cylindrical profile. An interior of the body 331, best shown in FIG. 6D, may include a cavity that has a shape that corresponds to post 326 (and post 332), including two flats on opposite sides of an otherwise cylindrical profile. In the illustrated embodiment, the flats of the internal cavity are aligned with the flats of the post 332, although this relationship is not necessarily required. The two opposing flats on post 332 and within the cavity may help to align and/or guide the spacer while assembling and/or to restrict the rotation of the spacers when the trial construct is subjected to forces during trialing.

Still referring to FIGS. 6C-D, the trial spacer 330 may include two prongs 333 extending distally from the base 331, with the prongs 333 being spaced about 180 degrees apart and generally aligned with the cylindrical (non-flat) portions of post 332. Each prong 333 may have an outer surface that forms a portion of a cylinder along with the base 331, and a distal end portion of each prong 333 may include an inwardly extending protrusion 334. Two additional extensions 335 may extend distally from the base 331, the extensions 335 being spaced about 180 degrees from each other, and about 90 degrees from the prongs 333. The extensions 335 may extend a distance distally from the base 331 less than the distance which the prongs 333 extend distally. At or near a proximal end of the base 331, two divots 338 and shoulders or protrusions 339 may be provided, in substantially the same manner as described above in connection with divots 328 and shoulders or protrusions 339. In the embodiment of trial spacer 330 shown, each divot 338 aligns with a prong 333.

Figure 6G:
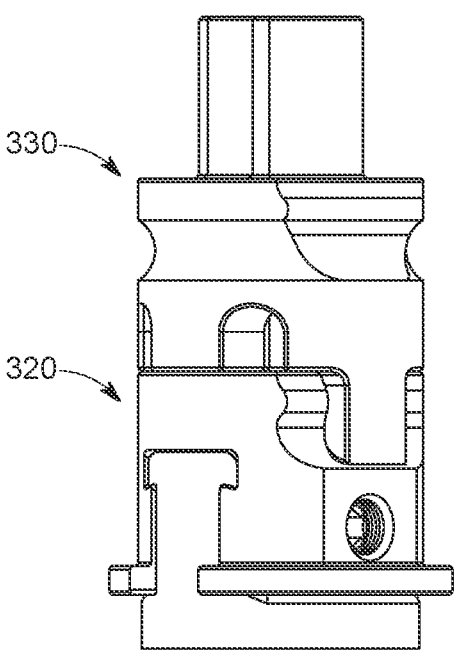
FIGS. 6G-H are perspective and cross-sectional views, respectively, of the trial spacer of FIGS. 6C-D assembled to the trial adaptor of FIG. 6B.
Figure 6H:
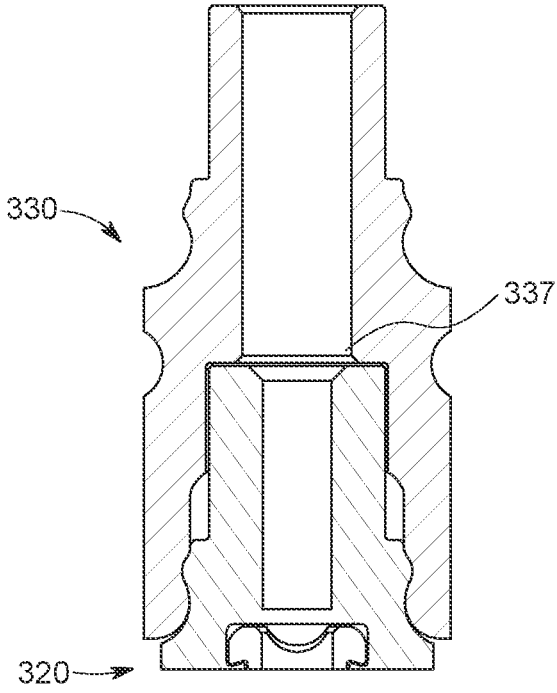

FIGS. 6E-F illustrate stages in coupling the trial spacer 330 the trial adaptor 320 in a "push-to-connect" style. In particular, as shown in FIG. 6E, the trial spacer 330 is positioned adjacent to the post 326 of trial adaptor 320 with the flats of the internal cavity of trial spacer 330 aligned with the flats of the post 326. With this configuration, there are only two rotational orientations in which trial spacer 330 may be coupled to trial adaptor 320. In either rotational configuration, as the trial spacer 330 is advanced in the distal direction D, as shown in FIG. 6E, each prong 333 will align with a respective divot 328 of the trial adaptor 320. The trial spacer 330, upon complete advancement as shown in FIGS. 6F-G, is positioned relative to the trial adaptor 320 so that the prongs 333, and particularly the inwardly extending protrusions 334 of the prongs 333, nest within the divots 328 of the trial adaptor 320. As shown best in FIG. 6H, the prongs 333 and their inward protrusions 334 are shaped and positioned so that, as the trial spacer 330 is connected to the trial adaptor 320, the shoulders or protrusions 329 first force the prongs 333 to flex outwardly. Then, when the inward protrusions 334 clear the shoulders or protrusions 329, the prongs 333 may "snap" back into place. This snap fit may provide audible and/or tactile feedback to confirm the connection. Although the prongs 333 may provide some resistance to the trial spacer 330 being pulled proximally to disconnect from the trial adaptor 320, because the trial spacers 330 are typically under compression during trialing, there is not a significant concern that the trial spacer 330 would unintentionally disconnect from the trial adaptor 320 during use. In order to disconnect the trial spacer 330 from the trial adaptor 320, it merely needs to be pulled proximally away from the trial adaptor 320. Further, as should be understood from the above description, the engagement between the flats of post 326 and the flats of the internal cavity of trial spacer 330 prevent any rotation between the two components once connected. Still referring to FIG. 6H, when the trial spacer 330 is coupled to the trial adaptor 320, a proximal end of the post 326 may abut an internal shoulder 337 of the trial spacer 330.

As with other components described herein, although a single trial spacer 330 is shown, it should be understood that a plurality of trial spacers may be provided in a kit, of the same or differing heights, and the different trial spacers may couple to (or decouple from) each other in essentially the same way that trial spacer 330 couples to (or decouples from) the trial adaptor 320. The proximal body 350 may also include a distal end having prongs substantially similar to those described in connection with trial spacer 330, with the proximal body 350 being coupled to the proximal-most spacer 340 in the assembly. It should be understood that spacer 330 shown in FIG. 6G may be overall similar to that shown in FIGS. 6E-F, with the exception that the spacer 330 of FIG. 6G is a different size (e.g. a 20 mm spacer) versus the size of the spacer 330 of FIGS. 6E-F (e.g. a 30 mm spacer). As with other spacers described herein, spacer 330 may be provided in different sizes, and the larger the spacer 330, the more circumferential grooves that may be provided, which may assist a user in gripping the spacer. For example, spacer 330 of FIGS. 6E-F have two circumferential grooves, whereas spacer 330 of FIG. 6G has a single circumferential groove.

Figure 7A:
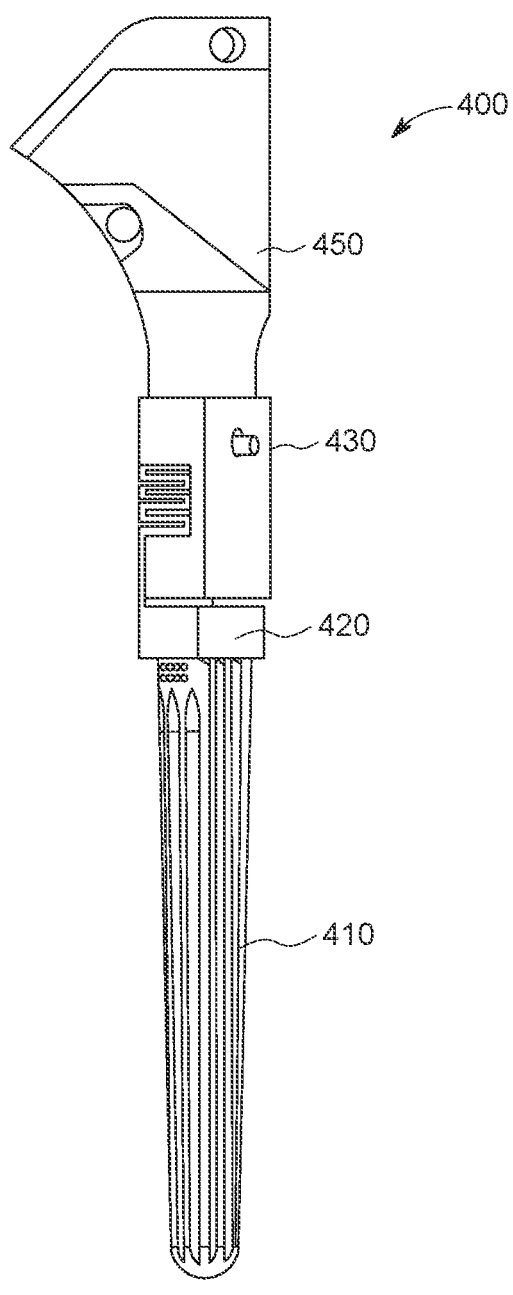
FIG. 7A is a side view of an assembled trial humeral prosthesis according to another aspect of the disclosure, with certain components omitted from the drawing.

FIG. 7A illustrates a trial humeral prosthesis 400 according to another aspect of the disclosure, including a trial stem 410 which may be similar or identical to other trial stems disclosed here, a trial stem adaptor 420, and a trial spacer 430. It should be understood that the trial adaptor 420 and trial spacer 430 are shown in highly schematic form to illustrate the working mechanisms of the components, but the components may take other forms in use and have additional features, for example to allow the trial spacer 430 to couple to a trial proximal body, which is not illustrate in FIG. 7A. For example, as shown in FIG. 7A, trial spacer 430 may be directly coupled to a trial proximal body 450.

Figure 7B:
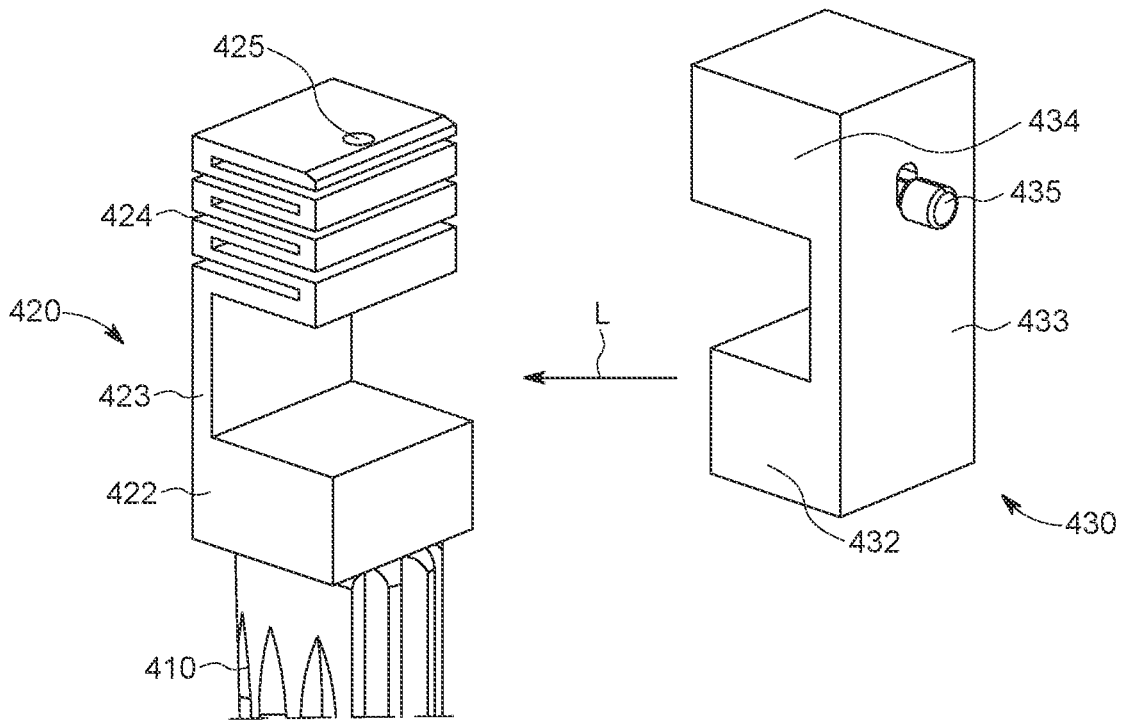
FIG. 7B is a perspective view of a trial spacer and a trial adaptor of the trial humeral prosthesis of FIG. 7A being assembled.

FIG. 7B shows the trial stem adaptor 420, which may be formed integrally with trial stem 410, even though referred to as an "adaptor" herein. In other embodiments, trial stem adaptor 420 may be formed separately from the trial stem 410 and later coupled to the trial stem 410. The trial adaptor 420 may be generally "C"- or "U"-shaped, with a distal platform 422, a proximal platform 424, and a side wall 423 coupling the distal platform 422 and proximal platform 424 so that a recess is formed bounded by these three components. The distal platform 422 and side wall 423 may be substantially solid members, but the proximal platform 424 may be formed as a flexure member. In particular, the proximal platform 424 may include a plurality of smaller platforms stacked adjacent each other, with adjacent platforms being coupled by a side wall, but the position of the side wall alternating in a zig-zag configuration along the height of the proximal platform 424. With this configuration, each smaller platform of the proximal platform 424 has a space between an adjacent smaller platform in the absence of applied forces. Upon compression of the proximal platform 424, the size of the spaces between each individual platform of the proximal platform 424 decreases, decreasing the overall height of the proximal platform 424. The proximal end of the proximal platform 424 may include an aperture 425, which is preferably oval-shaped, although other shapes such as circular could be suitable. The aperture 425 may assist in locking the trial spacer 430 to the trial adaptor 420, as described in greater detail below.

Still referring to FIG. 7B, the trial spacer 430 may have a generally complementary shape to the trial adaptor 420. For example, trial spacer 430 may have a distal platform 432, a side wall 433, and a proximal platform 434 that together form a general "C"- or "U"-shape so that a recess is formed bounded by these three component. In order to couple the trial spacer 430 to the trial adaptor 420, as shown in FIG. 7B, the trial spacer 430 manipulated to slide it in a lateral direction L so that the distal platform 432 of the trial spacer 430 is received in the recess of the trial adaptor 420. Similarly, the proximal platform 424 of the trial adaptor 420 is received within the recess of the trial spacer 430. Although the figures show a small gap between the distal face of the distal platform 432 and the proximal face of the distal platform 422, in practice, this gap would be eliminated upon coupling of the trial spacer 430 and trial adaptor 420, described in greater detail below.

Figure 7C:
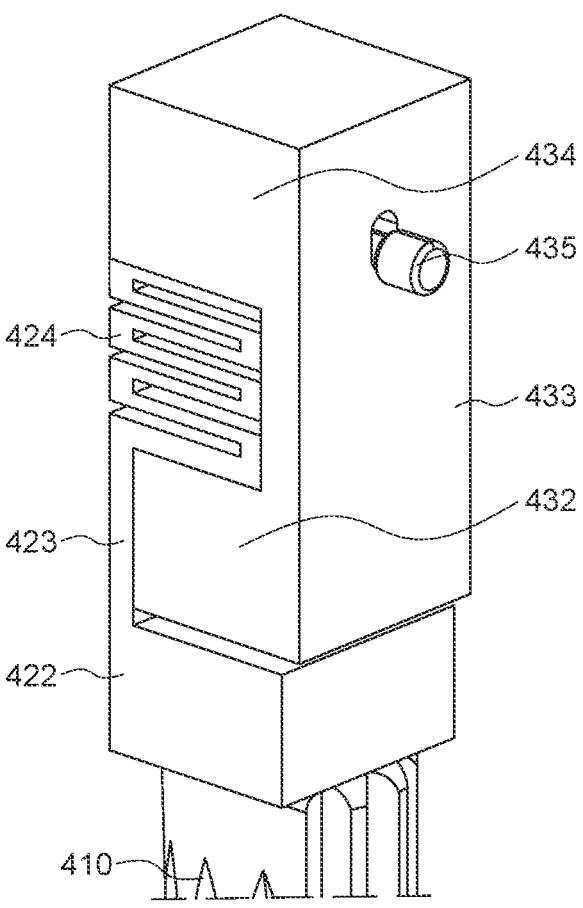
FIG. 7C illustrates the trial spacer and trial adaptor of FIG. 7B assembled together.
Figure 7D:
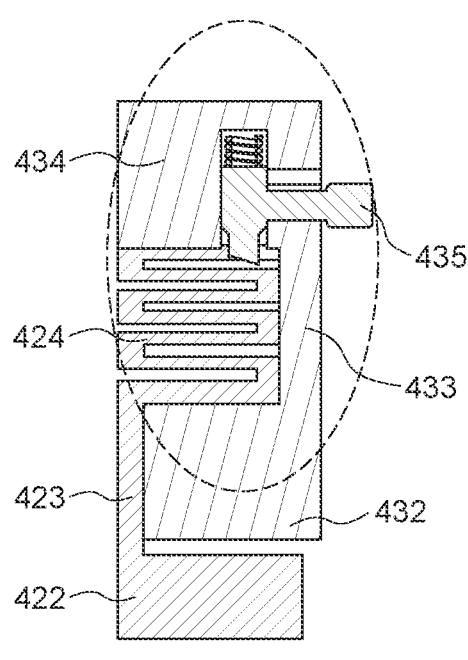
FIG. 7D is a cross-section of the assembly of FIG. 7C.
Figure 7E:
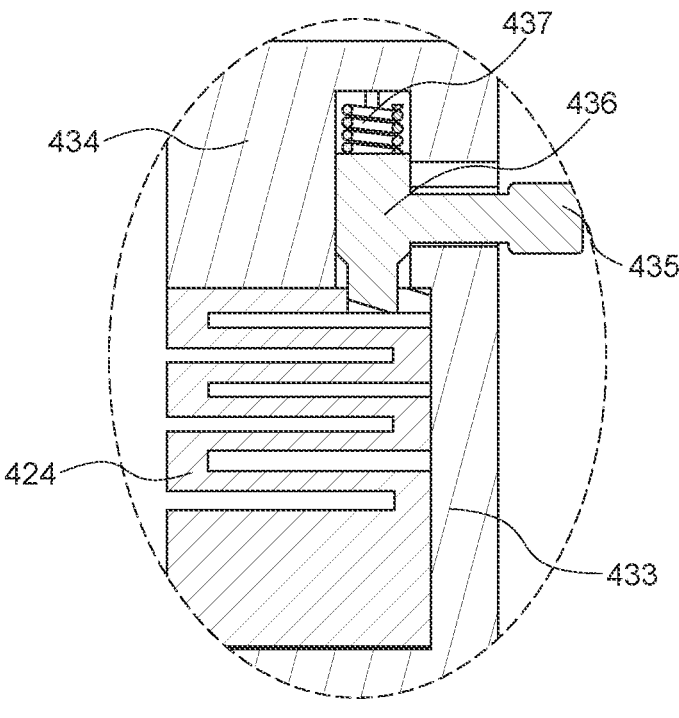
FIG. 7E is an enlarged view of a portion of FIG. 7D.

FIGS. 7D-E are cross-sections of the assembled trial spacer 430 and trial adaptor 420. The trial spacer 430 may include a locking button 435 extending into the proximal platform 434. The portion of the locking button 435 constrained within the proximal platform 434 may include a pin 436 with a distal end that protrudes distally through an opening in proximal platform 434. A biasing element, such as a spring 437, may be compressed between a proximal surface of pin 436 and an internal surface of the proximal platform 434 to bias the distal end of the pin 436 through the opening of the proximal platform 434. As best shown in FIG. 7E, the distal end of the pin 436 may include a ramped surface, and the proximal-most face of proximal platform 424 may include a corresponding ramped surface. As the trial spacer 430 is advanced in the lateral direction L onto the trial adaptor 420, the ramped surfaces interact and the pin 436 is forced upward to compress spring 437. After advancement is complete, the distal end of pin 436 is aligned with the aperture 425, and the pin 436 may "snap" into the aperture 425 due to the prior compression of the spring 437.

As the trial component 430 couples to the trial adaptor 420, the flexure mechanism in the proximal platform 424 compresses distally, such that the distal face of the distal platform 432 contacts (e.g. with zero clearance) the proximal face of the distal platform 422, reducing or eliminating the gap that is shown in the figures. Further, although aperture 425 is preferably oval, the axis of the oval shape is oriented so that, as the top small platforms of the proximal platform 424 begin to compress downward, it matches with the pin 436 of the locking button 435. It should be understood that, to decouple the trial spacer 430 and trial adaptor 420, the locking button 435 may be manually pulled proximally to compress the spring 437, and then the trial spacer 430 may be retracted in the opposite lateral direction away from the trial adaptor 420.

Referring again to FIGS. 7B-C, it should be understood that the proximal platform 434 of trial spacer 430 may include additional components including an additional proximal platform that forms a gap with proximal platform 434, and that additional proximal platform may include a flexure mechanism similar to proximal platform 424. With this configuration, multiple trial spacers 430 may be stacked on one another to achieve a desired height. The proximal body may also include a similar configuration as trial spacer 430 in order to couple to the proximal most trial spacer in the stack-up.

Figure 8A:
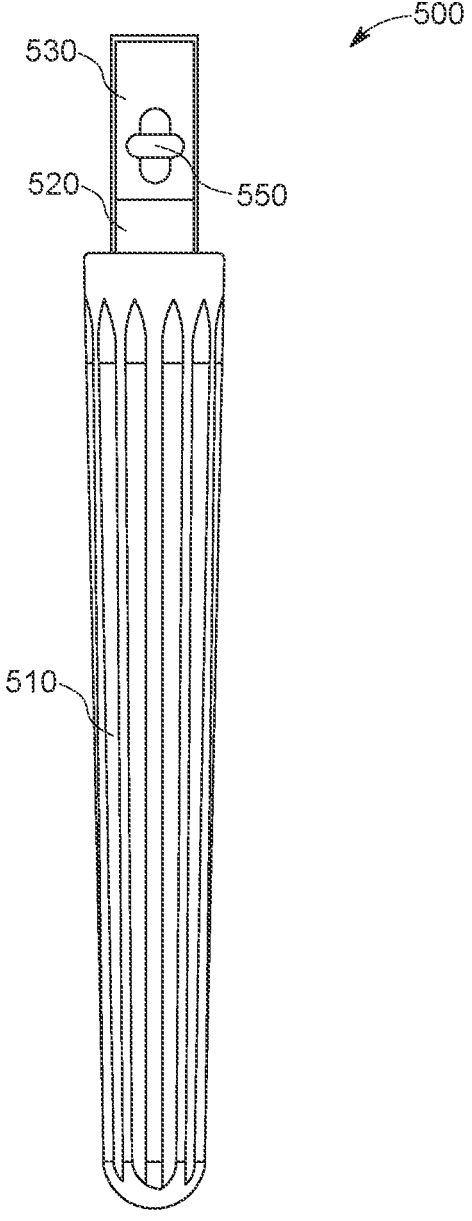
FIG. 8A illustrates a side view of an assembled trial humeral prosthesis according to still another aspect of the disclosure, with certain components omitted form the drawing.

FIG. 8A illustrates a trial humeral prosthesis 500 according to another aspect of the disclosure, including a trial stem 510 which may be similar or identical to other trial stems disclosed here, with the exception of a stem extension 520, and a trial spacer 530.

Figure 8B:
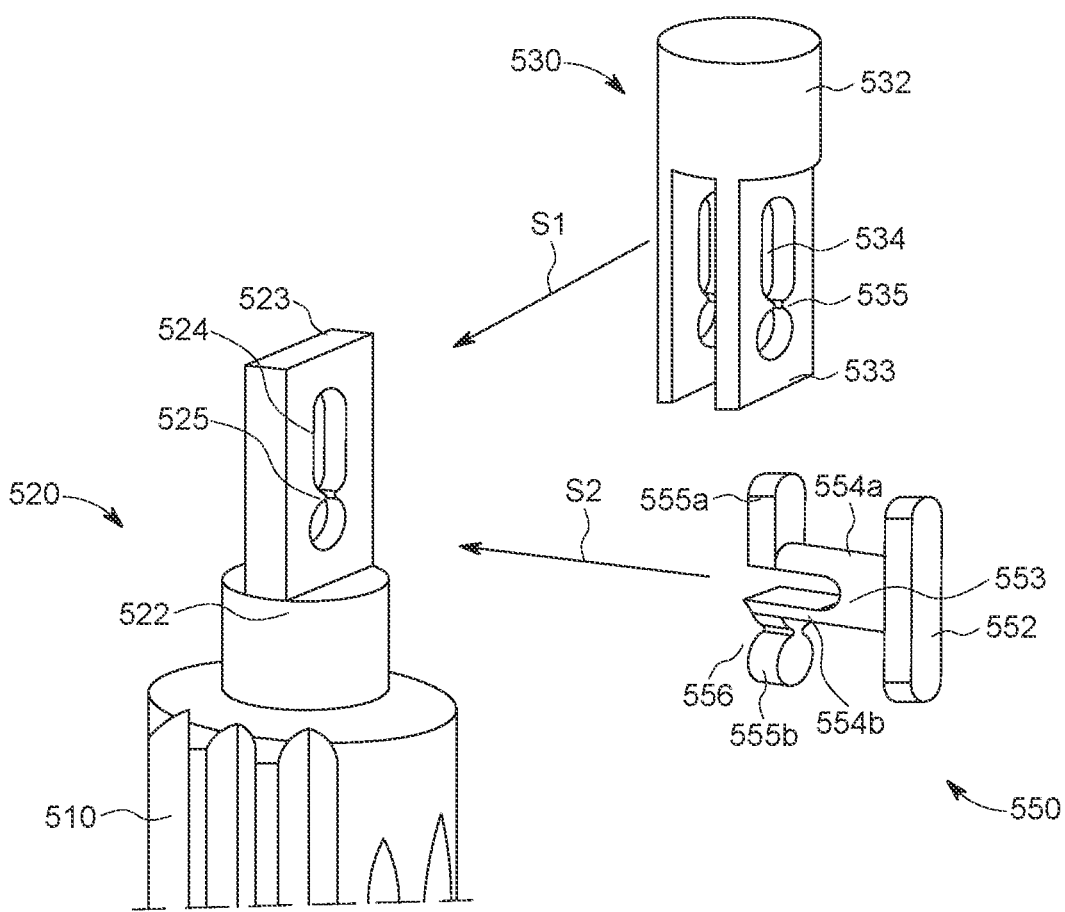
FIG. 8B illustrates steps of coupling a trial spacer and locking pin to the trial stem of FIG. 8A.

The proximal end of trial stem 510, including extension 520, is illustrated in FIG. 8B. The extension 520 may be integral with the trial stem 510 and extend proximally therefrom. It may include a cylindrical base 522 extending proximally from the proximal end of the trial stem 510, and a rectangular plate 523 extending proximally from the cylindrical base 522. The plate 523 may include an oblong aperture 524 with an undercut 525 formed therein. The undercut 525 may be portions of the plate 523 that extend into the oblong aperture 524 to interrupt the contour defining the otherwise smooth oblong shape of the aperture 524. Although extension 520 is described and shown as being integral with the trial stem 510, in other embodiments, it may instead be part of an adaptor that is coupled to the proximal end of the trial stem 510.

Figure 8C:
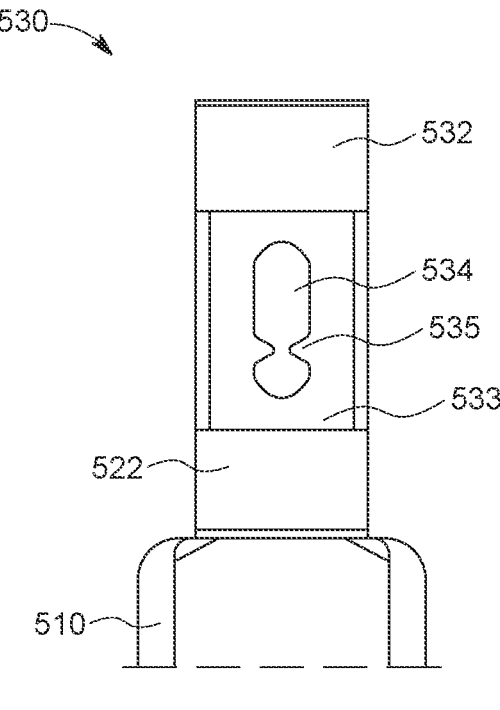
FIG. 8C illustrates the trial spacer of FIG. 8B coupled to the trial stem.

Referring still to FIG. 8B, the trial spacer 530 may include a base portion 532, which in this embodiment is illustrated as a generally solid cylindrical member. Two plates 533, which may each be rectangular and have a generally similar shape as plate 523, may extend distally from the base 532. Each plate 533 may include an oblong aperture 534 with an undercut 535 that substantially matches the shape of the oblong aperture 524 and undercut 525. The plates 533 may be substantially parallel to each other and spaced a distance from each other that generally corresponds to the width of plate 523. In a first step of assembly S1, after the trial stem 510 has been implanted, the trial spacer may be slid over the plate 523 so that Plate 523 is sandwiched between the two plates 533 of trial spacer 530, as shown in FIG. 8C. As can be seen in FIG. 8C, after this first step of assembly S1, the oblong apertures 524, 534 all align with each other.

Figure 8D:
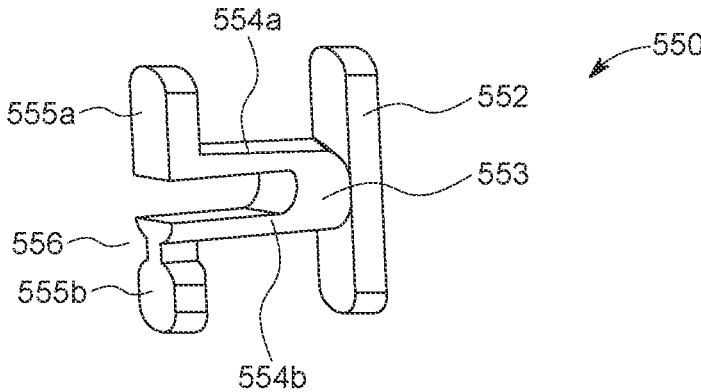
FIG. 8D illustrates the locking pin of FIG. 8B.

Referring back to FIG. 8B, in a second step of assembly S2, a locking pin 550 may be aligned with, and advanced toward, the aligned oblong apertures 524, 534. Referring now to FIGS. 8B and 8D, the locking pin 550 may include a trailing end 552 that is formed as a substantially solid and uninterrupted oblong piece. A central rod 553 may extend in a leading direction from the trailing end 552, the central rod having a diameter about equal to the width of the smaller side of the oblong trailing end 552. The central rod 553 may split into two fingers 554a, 554b so that a space is formed between the fingers 554a, 554b, allowing the fingers 554a, 554b to flex a small amount toward or away from each other. A first extension 555a extends from the end of the first finger 554a radially outwardly from a central axis of the center rod 553, and a second extension 555b extends radially outwardly from the central axis of the center rod 553, such that the two extensions 555a, 555b extend in opposite directions. The first extension 555a may have a generally truncated oblong shape that is sized and shaped to pass through the oblong apertures 524, 534 above the undercuts 525, 535. The second extension 555b may have a shape that generally corresponds to the bottom portion of the oblong apertures 524, 534 including the undercuts 525, 535. In other words, the second extension 555b may have a generally truncated oblong shape with an undercut 556. When the locking pin 550 is not subject to applied forces, the distance between the opposite ends of the first extension 555a and second extension 555b may be slightly greater than the length of the larger dimension (e.g. the height) of oblong apertures 525, 535.

Figure 8E:
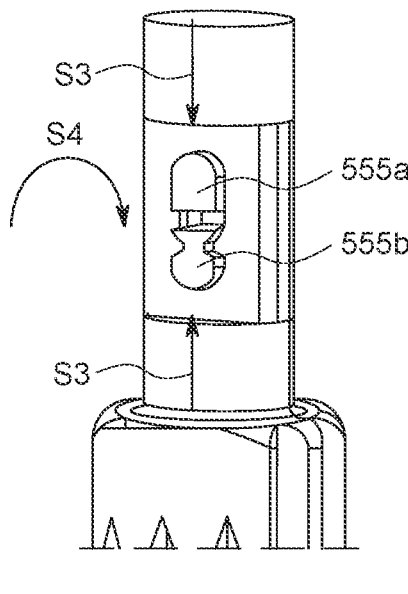
FIGS. 8E-F illustrate different steps of coupling the trial spacer of FIG. 8B to the trial stem of FIG. 8B.
Figure 8F:
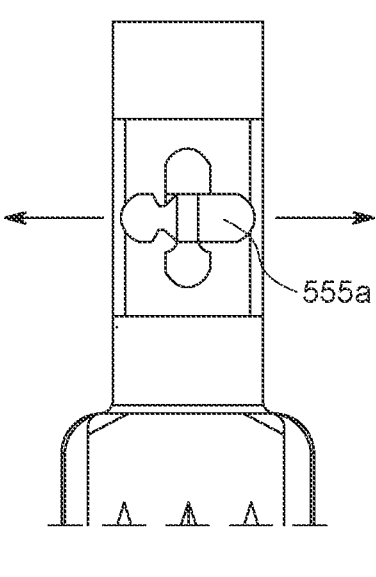
Figure 8G:
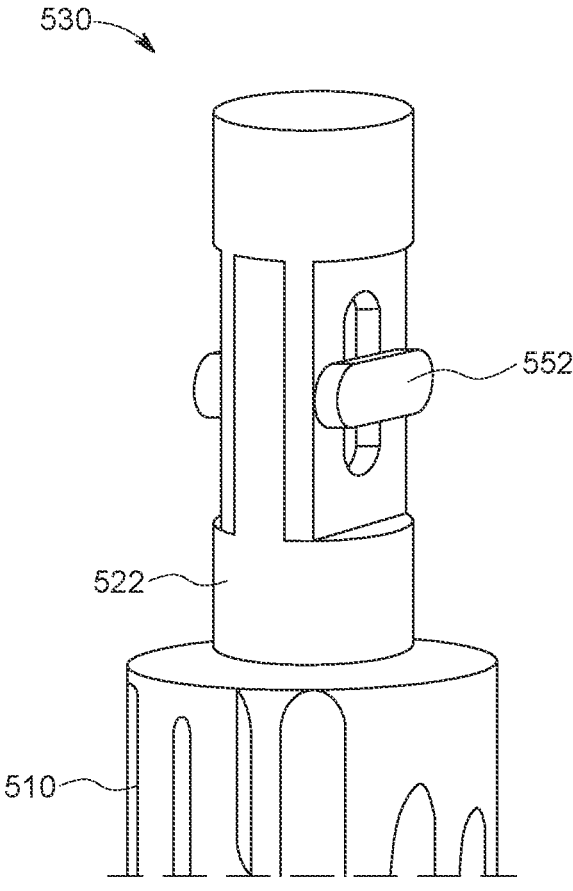
FIG. 8G is an enlarged perspective view of the proximal end of the assembled trial humeral prosthesis of FIG. 8A.

With the configuration described above, as the locking pin 550 is advanced toward the oblong apertures 524, 534, the two fingers 554a, 554b may be compressed toward each other in a third step S3, as shown in FIG. 8E, in order for the leading end of the locking pin 550 to be able to pass through the oblong apertures 525, 535. As can be seen in FIG. 8E, the undercut 556 aligns with the undercuts 525, 535 as the locking pin 550 passes though the oblong apertures 524, 534 in the compressed condition. Once the extensions 555a, 555b of the locking pin 550 both clear the second plate 533, in a fourth step S4 the locking pin 550 may be rotated about 90 degrees. As the extensions 555a, 555b of the locking pin 550 clear the second plate 533, the fingers 554a, 554b may spring back to their relaxed condition, as shown in FIG. 8F. In the final locked condition, best illustrated in FIG. 8G, the locking pin 550 maintains the trial spacer 530 coupled to the trial stem 510, and the undercuts 525, 535 prevent the locking pin 530 from sliding down the oblong apertures 524, 534.

It should be understood that, although the proximal end of trial spacer 530 is shown as a cylindrical base 532, another extension similar to plate 523 may extend proximally from base 532, so that another trial spacer could interact with that proximally extending plate the same way in which trial spacer 530 interacts with stem extension 520. With that configuration, multiple trial spacers 530 may be stacked and locked together (with another locking pin for each additional spacer) to build up the trial prosthesis. Similarly, although not shown here, the trial proximal body can couple to the proximal-most trial spacer in the same way that the trial spacer 530 connects to the stem extension 520.

Figure 9A:
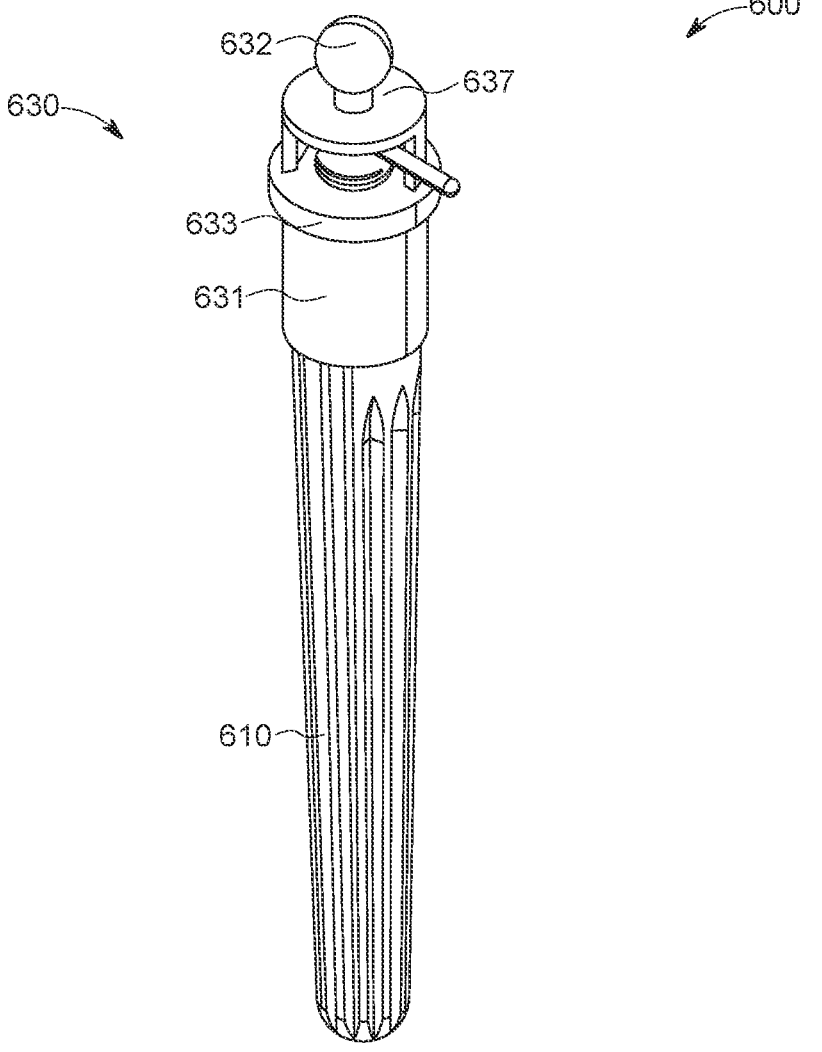
FIG. 9A is a perspective view of a trial humeral prosthesis according to a further embodiment of the disclosure.

FIG. 9A is a perspective view of a trial humeral prosthesis 600 according to a further aspect of the disclosure. Trial humeral prosthesis 600 includes a trial stem 610 that may be generally similar to other trial stems described herein, although trial stem 610 may not be expandable, and as is described below, may include a proximal sphere 612. A trial spacer 630 is illustrated coupled to the proximal end of the trial stem 610.

Figure 9B:
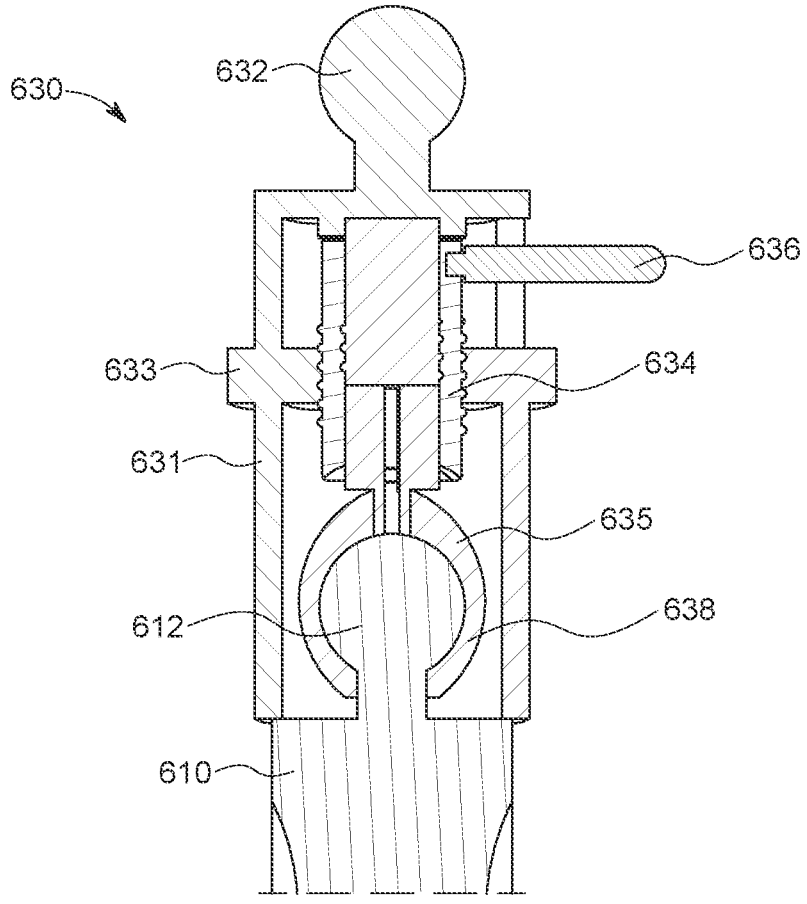
FIG. 9B is a cross-section of the trial spacer of FIG. 9A coupled to the proximal trial stem of FIG. 9A.
Figure 9C:
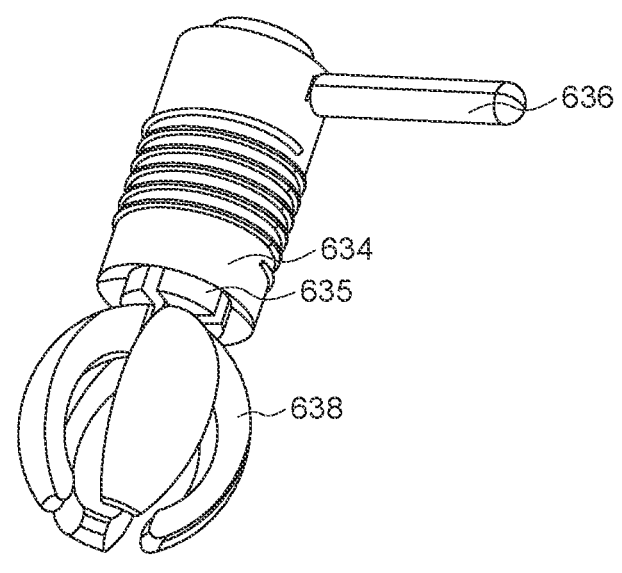
FIG. 9C is a perspective view of an internal locking component of the trial spacer of FIGS. 9A-B.

FIG. 9B is a cross-section of the trial spacer 630 coupled to the proximal end of trial stem 610. One difference between trial stem 610 and other stems described herein is that the trial stem 610 may include a sphere 612 extending proximally therefrom. Although the sphere 612 may be formed integrally with the trial stem 610, in other embodiments the sphere 612 may be provided as part of an adaptor that is coupled to the trial stem 610. Referring to FIGS. 9A and 9B, the trial spacer 630 may include an outer housing that may include a main cylindrical portion 631 and a proximal sphere 632. At the proximal end of the cylindrical portion 631 may be a flange 633, and the flange 633 may include a central aperture for receiving a portion of an inner locking mechanism. The inner locking mechanism of the trial spacer 630 is shown in FIG. 9B, and isolated from other components of the trial spacer 630 in FIG. 9C. The inner locking mechanism may include a sleeve 634 that may be generally cylindrical, and may include outer threads that engage complementary inner threads of the flange 633. The inner locking mechanism may also include an inner flexure member 635 extending through the interior of sleeve 634. The inner flexure member 635 may have a proximal end attached to the distal end of a top platform 637 of the outer housing. The distal end of the inner flexure member 635 may include a plurality of arcuate fingers 638 that, in the aggregate, generally create a spherical void sized to receive sphere 612 therein. The arcuate fingers 638 may not be directly connected to one another at the distal end of the flexure member 635 to allow for the fingers 638 to flex toward or away from each other. The sleeve 634 may also include an actuator 636 fixed to the sleeve 634, so that rotating the actuator 636 rotates the sleeve 634. As the actuator 636 (and thus the sleeve 634) rotates, the threaded connection between the sleeve 634 and the flange 633 causes the sleeve 634 to translate distally toward the fingers 638. As the sleeve 634 translates distally, the sleeve 634 compresses the fingers 638, reducing the size of the void formed between the fingers 638 in the aggregate. It should be understood that the actuator 636 may be only temporarily fixed to the sleeve 634, so that it may be removed after actuation (and later re-attached for actuation in the opposite direction).

Figure 9D:
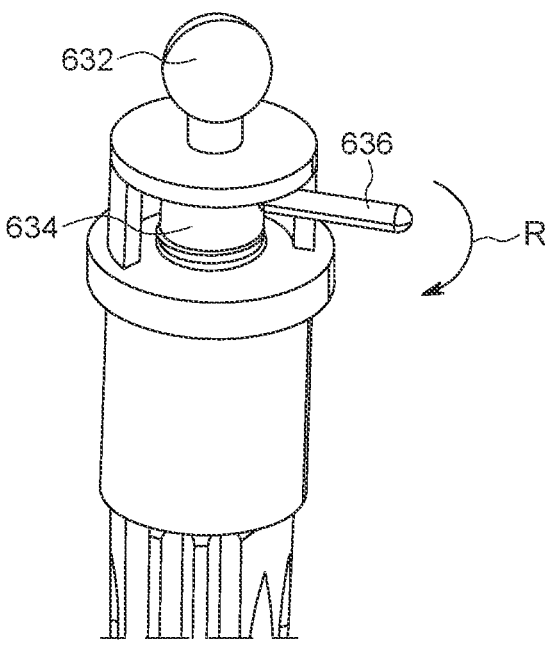
FIG. 9D is an enlarged perspective view of the proximal end of the trial humeral prosthesis of FIG. 9A.

In use, the trial spacer 630 starts with the actuator 636 in the non-actuated position with the sleeve 634 in a proximal-most position. The trial spacer 630 may be pressed over the sphere 612 of the trial stem 610. The fingers 638 may flex away from each other enough so that the sphere 612 snaps into the void between the fingers 638. Once the trial spacer 630 is coupled, but not locked, to the sphere 612, as shown in FIG. 9D, the actuator 636 may be rotated in a direction R, for example clockwise. As the rotation of the sleeve 634 forces the sleeve 634 to translate distally, the sleeve 634 compresses the fingers 638 of flexure member 635, causing the fingers 638 to firmly grip the sphere 612 in a locked condition.

As should be understood from FIGS. 9A-D, the trial spacer 630 includes a sphere 632 that is substantially similar or identical to the sphere 612 of trial stem 610 so that another trial spacer may be coupled and then locked to sphere 632 to build up the trial humeral prosthesis 600. Finally, although not shown, a proximal body similar to those described above may be provided with a similar locking mechanism so that the proximal body may be coupled and then locked to the proximal-most trial spacer in the stack up. Finally, it should be understood that the locking mechanism may be unlocked by rotating the actuator 636 in the opposite rotational direction, unlocking the components so that they may easily be uncoupled from each other.

Figure 10A:
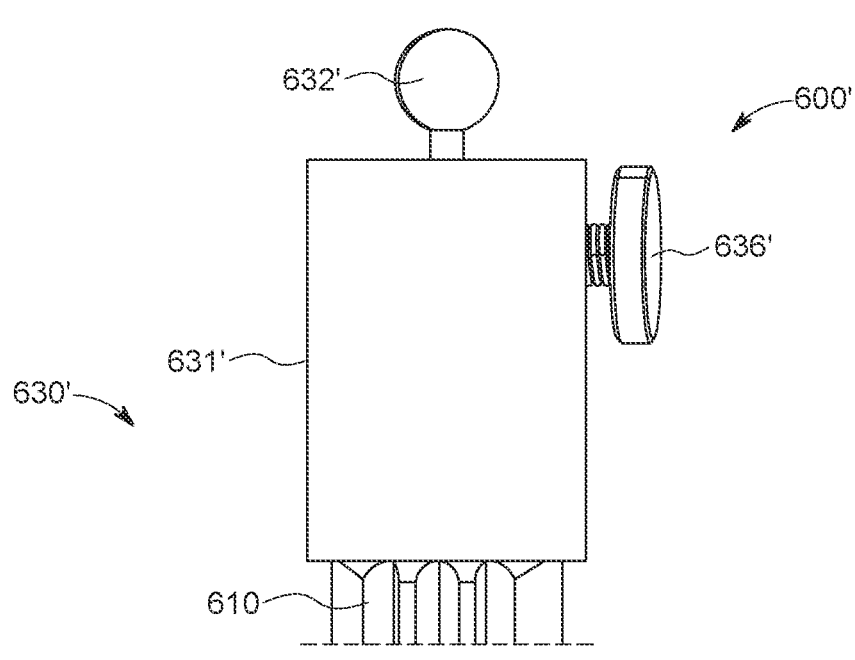
FIG. 10A is a side view of an alternate version of the trial spacer of FIG. 9A coupled to the trial stem of FIG. 9A.

FIG. 10A illustrates a trial humeral prosthesis 600' that includes a trial spacer 630' that is an alternate version of trial spacer 630, coupled to trial stem 610. Trial spacer 630' may include a generally cylindrical outer housing 631' and a sphere 632' extending from the proximal end thereof.

Figure 10B:
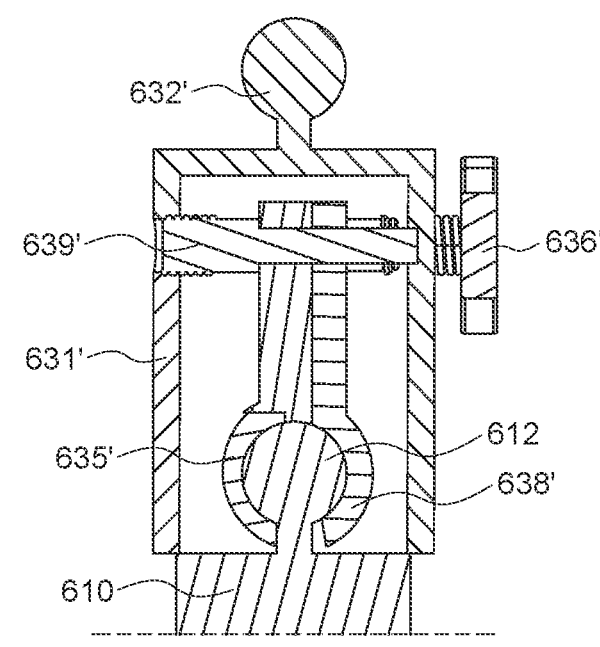
FIGS. 10B-C are cross sections of the configuration of FIG. 10A.
Figure 10C:
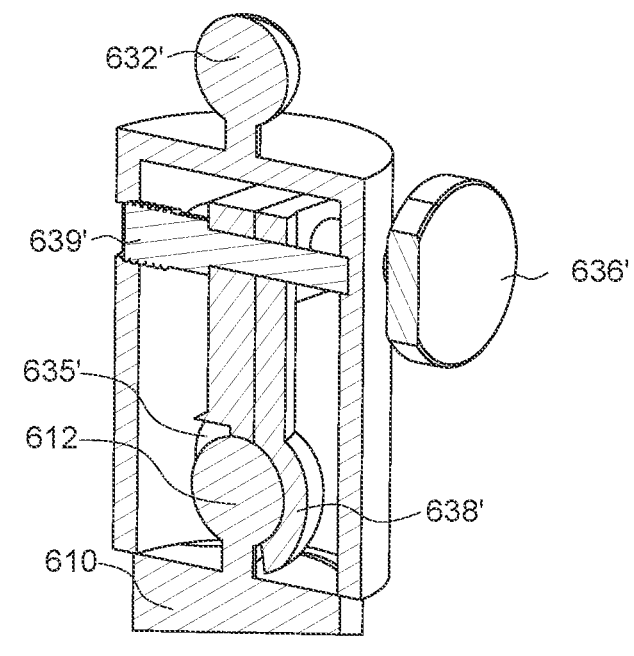
Figure 10D:
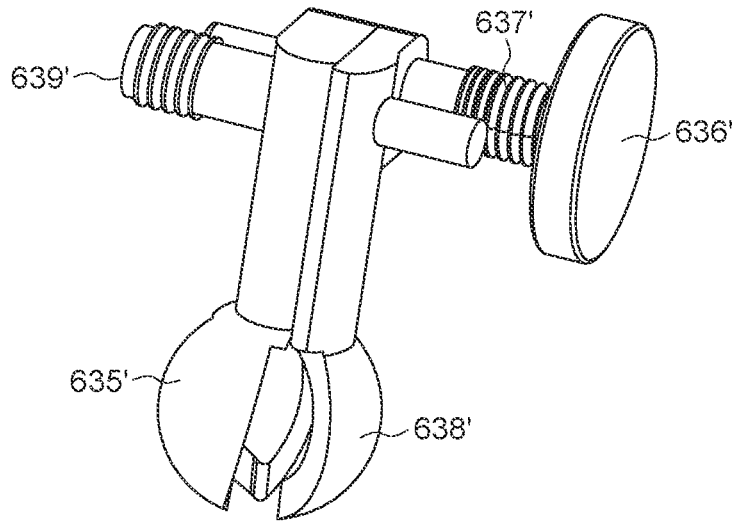
FIG. 10D is a perspective view of an internal locking component of the trial spacer of FIG. 10A.

Referring to FIGS. 10B-D, the trial spacer 630' may include an internal locking mechanism that includes a fixed flange 635' and a moving flange 638'. The fixed flange 635' and moving flange 638' may each include proximal extensions and distal fingers, the distal fingers in the aggregate forming a generally spherical shaped void. A fixation screw 639' may have a threaded trailing end that threads into the cylindrical outer housing 631' to fix the fixation screw 639' to the outer housing 631'. The fixation screw 639' may have an unthreaded shaft that passes through apertures in the proximal extension of the fixed flange 635' and the moving flange 638'. The fixed flange 635' may be securely fixed to the unthreaded shaft of the fixation screw 639', for example by adhesives. An actuator 636' may include a proximal knob and a threaded portion 637' immediately next to the knob 636'. The threaded portion 637' may engage internal threads of an aperture of the outer housing 631' through which the shaft of the actuator 636' passes. With this configuration, rotating the proximal knob of the actuator 636' drives the actuator 636' and its shaft into or away from the outer housing 631'. The shaft of the actuator 636' may pass through the proximal extensions of the fixed flange 635' and the moving flange 638'. The shaft of the actuator 636' is preferably free to move relative to the proximal extension of the fixed flange 635', but translationally fixed to the proximal extension of the moving flange 638'. For example, the shaft of actuator 636' may have a stepped down diameter that forms a shoulder or collar that is too large to pass through the proximal extension of the moving flange 638', so that as the shaft of actuator 636' translates distally, the collar presses against the proximal extension of moving flange 638' to drive it toward the fixed flange 635' With this configuration, rotating the proximal knob of actuator 636' moves the moving flange 638' toward or away from the fixed flange 635', depending on the direction of rotation.

In order to couple the trial spacer 630' to the trial stem 610, the proximal knob of actuator 636' is rotated to move the moving flange 638' away from the fixed flange 635', creating a relatively large void between the distal fingers of the moving flange 638' and the fixed flange 635'. The trial spacer 630' may then be placed over the sphere 612 of the trial stem 610, and the proximal knob of the actuator 636' rotated in the opposite direction to drive the moving flange 638' back toward the fixed flange 635' As the distal fingers of the moving flange 638' and the fixed flange 635' move toward one another, they compress on the sphere 612 to lock the trial spacer 630' to the trial stem 610. As with trial spacer 630, trial spacer 630' includes a proximal sphere 632' substantially similar to sphere 612 so that multiple trial spacers may be coupled and locked to one another in a stack to achieve the desired height of the trial humeral prosthesis 600'. The proximal body, not shown in FIGS. 10A-D, may include a similar fixation mechanism to trial spacer 630' to couple and lock the proximal body to proximal-most trial spacer 630' in the stack up.

Figure 11A:
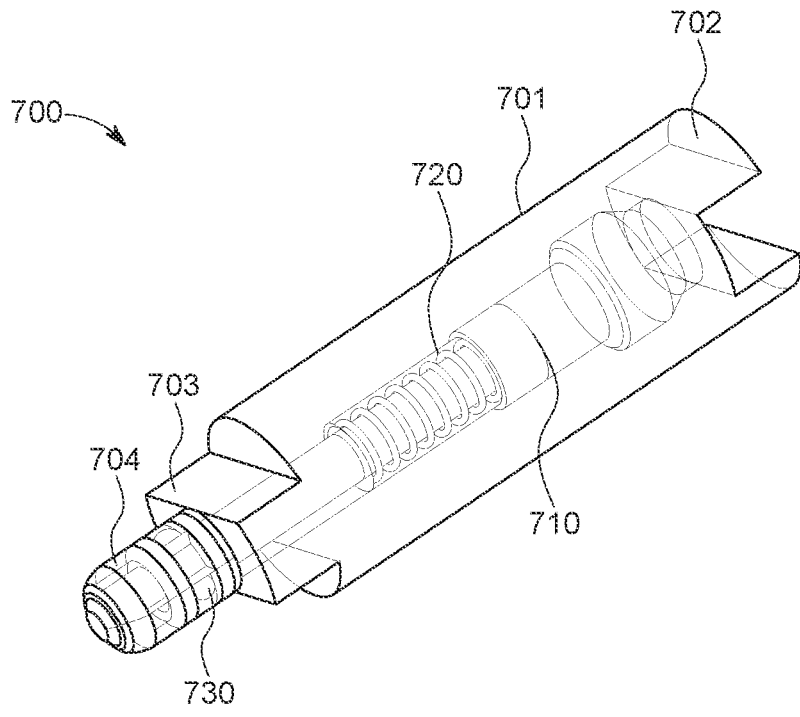
FIGS. 11A-B are transparent, perspective views of a trial spacer according to another aspect of the disclosure in unlocked and locked states, respectively.
Figure 11B:
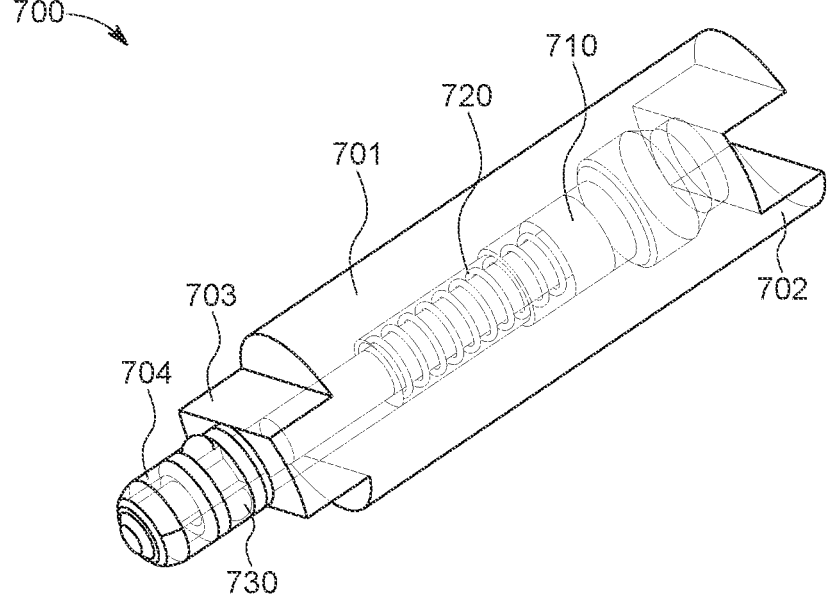

FIGS. 11A-B are perspective views of trial spacer 700 according to another aspect of the disclosure. Trial spacer 700 is shown in an unlocked state in FIG. 11A, and a locked state in FIG. 11B, with both figures showing an outer housing as partially transparent to show internal components. It should be understood that trial spacer 700 may be used in a trial humeral prosthesis in much the same way as described for other trial spacers herein. In other words, although not shown, a trial stem (or an adaptor component coupled to the trial stem) may include features at a proximal end that generally match features at the proximal end of trial spacer 700, and a trial proximal body may include features at a distal end that generally match features at the distal end of trial spacer 700. With this configuration different numbers and sizes of trial spacers 700 may be coupled to each other and to the other components of the trial humeral prosthesis to quickly and stably build up the trial prosthesis to the desired height.

Referring still to FIGS. 11A-B, trial spacer 700 may include generally cylindrical outer housing 701 that is at least partially hollow to receive the internal working components of the trial spacer 700. Certain components of trial spacer 700 are introduced here prior to going into greater detail about their functionality below. The outer housing 701 may include two proximal extensions 702 that together form a portion of a cylinder with a generally rectangular slot cut out between the two proximal extensions 702. A distal end portion of the outer housing 701 may include a rectangular extension 703 that generally matches the size, shape, and orientation of the rectangular slot defined by the proximal extensions 702. As should become clear from the description below, this configuration allows for the distal end of one trial spacer 700 to couple to the proximal end of another trial spacer 700 in a way that prevents rotation, about the longitudinal axis, of one trial spacer 700 relative to another. In other words, when the distal rectangular extension 703 of one trial spacer 700 is received in the rectangular cavity between two proximal extensions 702 of another trial spacer 700, a cylindrical shape is formed in the aggregate and neither trial spacer 700 can rotate about their common longitudinal axis relative to the other trial spacer 700.

Still referring to FIGS. 11A-B, the trial spacer may include a plunger 710 maintained within the outer housing 701, the plunger 710 having a proximal button 712 that interacts with a biasing mechanism, such as spring 720, with the main shaft of the plunger 710 traversing through a center of the spring 720. The outer housing 701 may have a distalmost tip 704 which houses certain components that comprise the locking mechanism, including one or more retention members, which in the illustrated embodiment comprise three or four axisymmetric balls 730. As described below, these components may interact so that, upon engaging the distal end of one trial spacer 700 into the proximal end of another trial spacer 700, the balls 730 may be activated to lock the two trial spacers together.

Figure 11C:
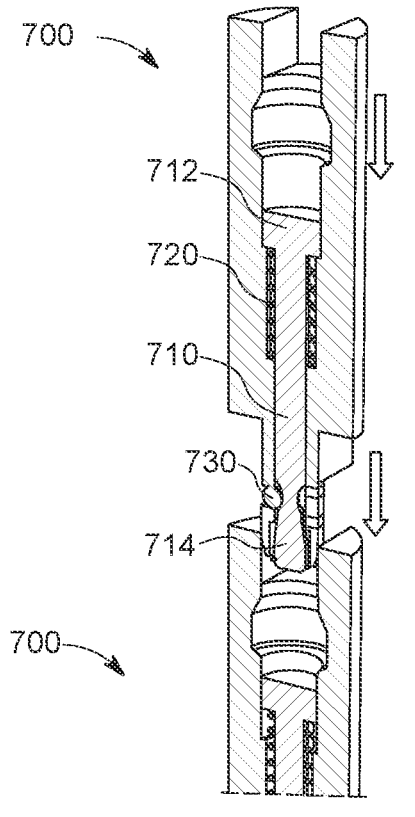
FIG. 11C is a cross-section showing two of the trial spacers of FIGS. 11A-B just prior to coupling.
Figure 11D:
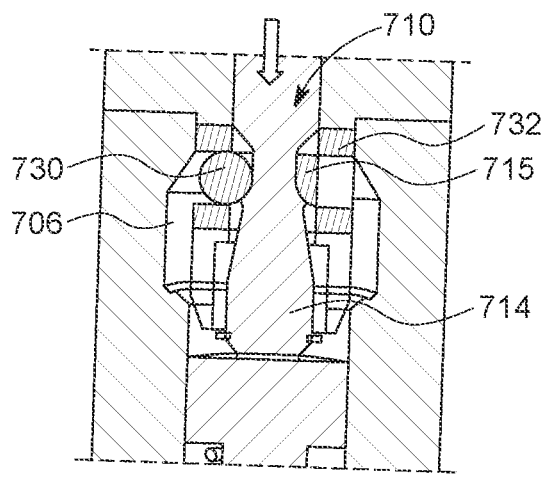
FIG. 11D is a cross-section of two of the trial spacers of FIGS. 11A-B after being coupled but prior to locking.

FIGS. 11C-D illustrate the distal end of one trial spacer 700 being inserted into the proximal end of another trial spacer 700 prior to the locking mechanism being activated. As shown in the figures, the outer housing 701 includes an internal shoulder, with one end of the spring 720 resting on the shoulder, and the opposite end of the spring in contact with the distal face of the proximal button 712 of the plunger 710. The outer housing 701 may include a second internal shoulder proximal to the first internal shoulder to limit the distance which the proximal button 712 may travel distally before contacting the second internal shoulder. The plunger 710 may include a main shaft that extends from the proximal button 712 to a tapered distal end 714. The tapered distal end 714 may include a first generally concave transition 715 at the distal end of the main shaft, and then may taper outwardly (e.g. increase in diameter) from the transition 715 to the terminal distal end of the plunger 710.

Figure 11E:
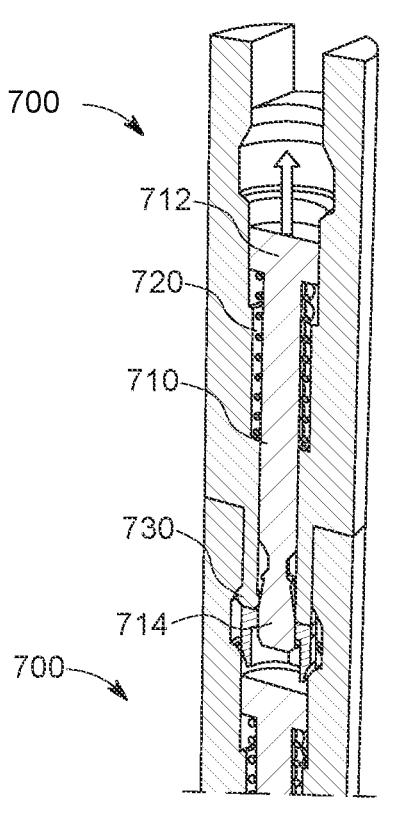
FIGS. 11E-G are cross-sections of two of the trial spacers of FIGS. 11A-B after being coupled and locked together.

Still referring to FIGS. 11C-D, the proximal end of the outer housing 701 may include an enlarged cavity 706 just distal to the proximal extensions 702, and just proximal to the main channel that receives the spring 720 and the proximal button 712. As best shown in FIG. 11E, the enlarged cavity 706 may have a main portion with a diameter larger than the proximal button 712, with the diameter tapering to a smaller interior diameter at the proximal and distal ends of the enlarged cavity 706, forming ramped surfaces along the taper.

Still referring to FIG. 11D, the three axisymmetric balls 730 may be maintained axially between two retention members such as retention housing 732. In the unlocked condition shown in FIGS. 11C-D, the balls 730 are aligned with the small-diameter transition 715 of the tapered distal end 714 of the plunger 710. To build up the stack of trial spacers

730, the distal end of one trial spacer 700 is inserted into the proximal end of another trial spacer 700, as shown in FIGS. 11C-D. As this insertion is performed, the user may apply distally-directed force to the proximal button 712 to maintain the balls 730 within the small-diameter transition 715, as best shown in FIG. 11D. The first trial spacer 700 is inserted into the second trial spacer 700 so that the rectangular extensions 703 of the first trial spacer 700 mates with the rectangular recess defined by the proximal extensions 702 of the second trial spacer 700. This alignment, just prior to insertion, is shown in FIG. 11J.

Figure 11F:
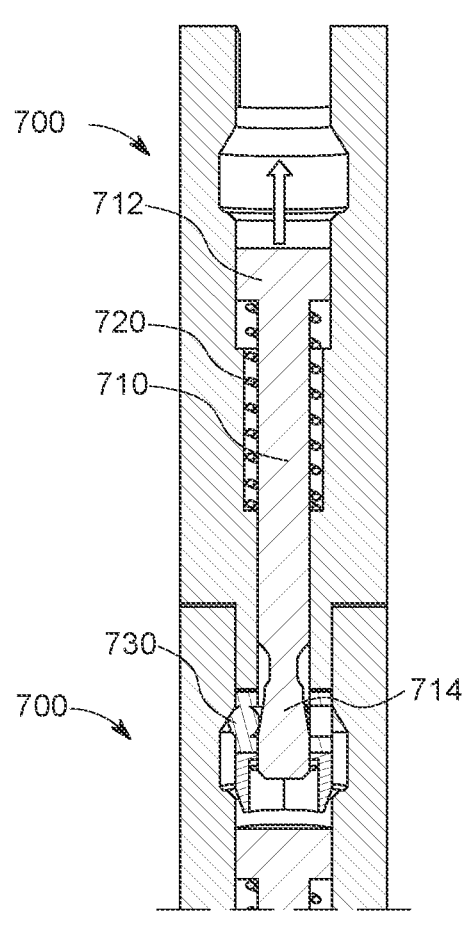
Figure 11G:
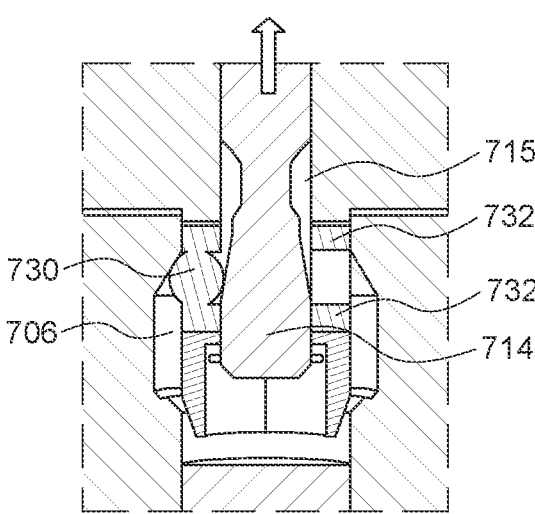

In order to lock the two trial spacers 700 together after having being coupled, the user may release the distally applied force on the plunger 710, allowing the spring 720 to start to decompress so that the spring 720 applies a proximally-directed force onto the plunger 710 via interaction with proximal button 712, as shown in FIGS. 11E-G. As best shown in FIG. 11G, the distal end of the tapered distal portion 714 of plunger 710 may include a ring or stopper that limits the extent that the plunger may move proximally relative to outer housing 701. As the plunger 710 is pushed proximally from the force of spring 720, the tapered portion 714 of the distal plunger 710 moves proximally relative to the balls 730, the taper causing the balls 730 to move radially outwardly so that they protrude outside of the distalmost tip 704 and into engagement with a ramped surface of the enlarged cavity 706. In this condition, the balls 730 prevent disengagement of the first trial spacer 700 from the second trial spacer 700, resulting in the locked condition. As described above, these mechanisms may be provided on the trial stem (or an adaptor coupled thereto), and the proximal body, so that the same mechanism may be used to assemble the trial humeral prosthesis with the desired number and height of spacers 700, resulting in the desired trialing height and stability of the assembly under trialing loads.

Figures 11H, 11I:
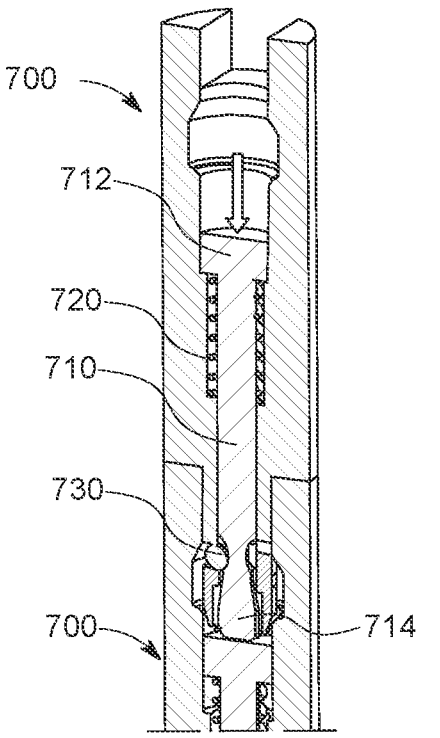
FIGS. 11H-I are cross-sections of two of the trial spacers of FIGS. 11A-B in the stage of being unlocked and uncoupled from each other.
Figure 11J:
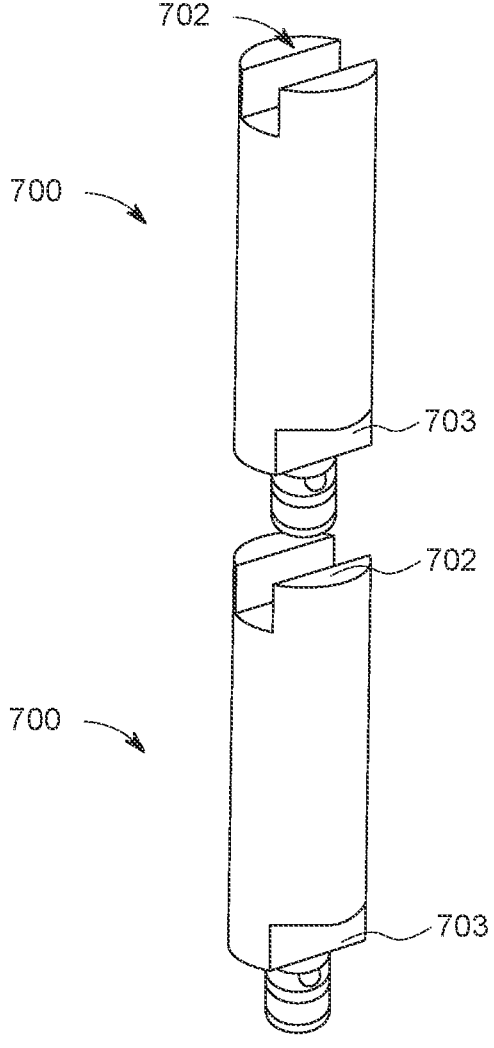
FIG. 11J is a perspective view of two of the trial spacers of FIGS. 11A-B just prior to coupling.

To disassemble the components, for example two coupled and locked trial spacers 700, the process may be generally reversed. For example, as shown in FIG. 11H, the user may depress plunger 712 with a distally directed force, causing the tapered distal tip 714 to advance distally, allowing the balls 730 to reside within the small-diameter transition portion 715 of tapered distal tip 714. Then, with this distal force applied to the plunger 710, the proximal trial spacer 700 may be pulled proximally relative to the distal trial spacer 700. The ramped surface of the enlarged cavity 706 will force the balls 730 radially inwardly, and the increased clearance at the small-diameter transition zone 715 allows the balls 730 to move radially inwardly, providing clearance for the first trial spacer 700 to be decoupled from the second trial spacer 700. The distal force applied to the plunger 710 in the description above may be achieved via any suitable mechanism, including manually using a finger, for example, or a separate tool sized to pass into the proximal opening of the trial spacer 700 and contact the proximal button 712.

Figure 12A:
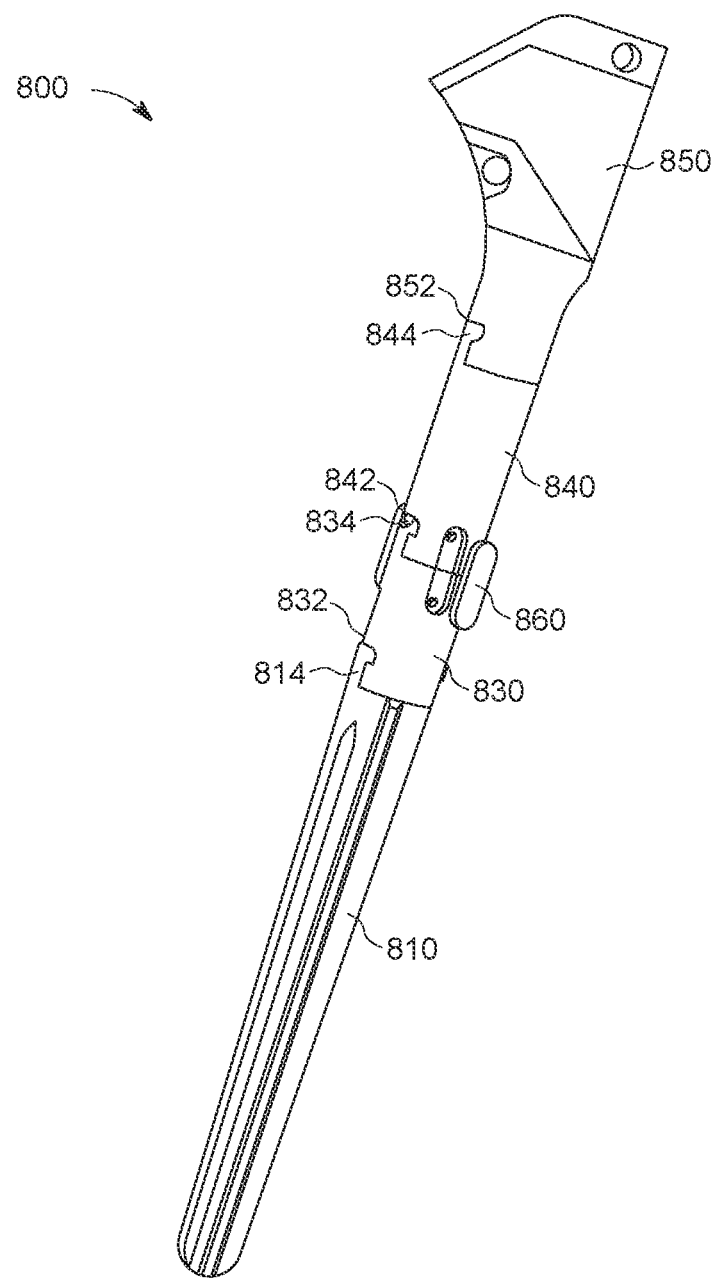
FIG. 12A is a perspective view of an assembled trial humeral prosthesis according to still another aspect of the disclosure.

FIG. 12A shows another embodiment of a trial humeral prosthesis 800 in an assembled condition, including a trial proximal body 850, first and second trial spacers 830, 840, and a trial stem 810. The general principal of assembling trial humeral prosthesis 800 includes the use of male mating member and corresponding female mating members, which may have a dovetail type of configuration, with a separate plug later attached that spans two coupled members to prevent unintentional decoupling of those members.

Figures 12B, 12C:
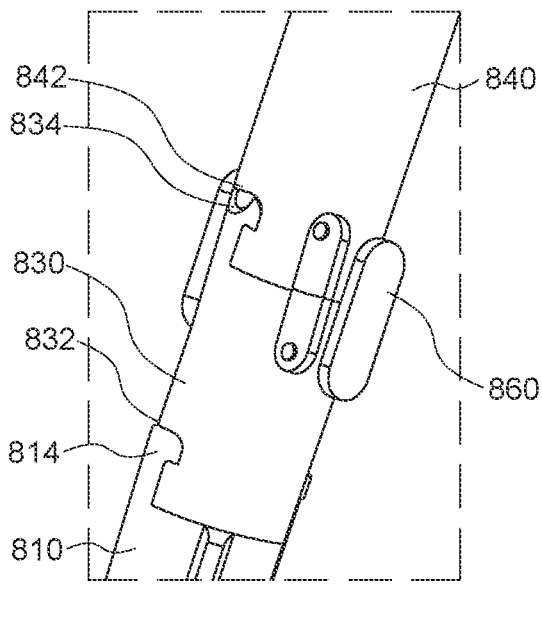
FIGS. 12B-D are enlarged views of a portion of the trial humeral prosthesis of FIG. 12A in different stages of assembly.
Figure 12D:
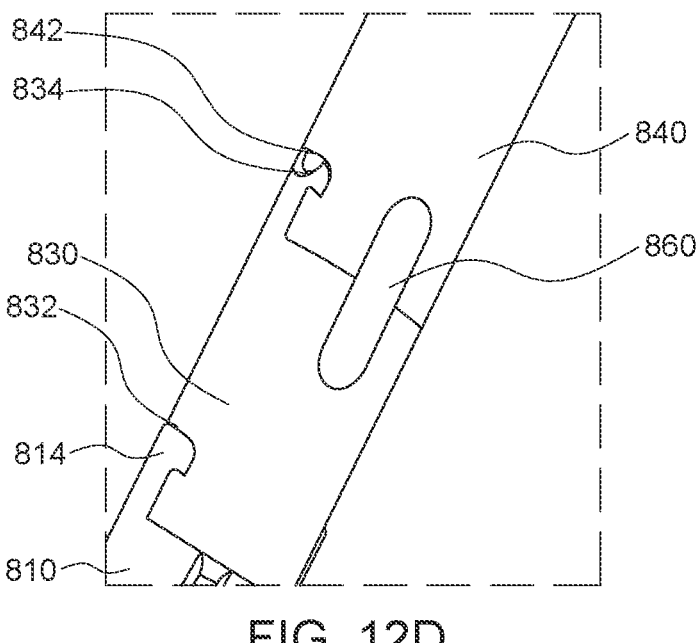

FIG. 12B is an enlarged view of a proximal portion of trial stem 810 coupled to a first trial spacer 830, with the first trial spacer 830 coupled to second trial spacer 840, and a locking plug 860 spaced apart from the spacers 830, 840. FIG. 12C is a similar view with the locking plug 860 omitted, and FIG. 12D is a similar view with the locking plug 860 coupled to the two spacers 830, 840.

Referring generally to FIGS. 12A-D, each spacer 830, 840 may include a female portion 832, 842 at a distal end thereof, and a male portion 834, 844 at a proximal end thereof, the male and female portions have complementary shape. Although two trial spacers 830, 840 are shown, additional trial spacers in the same or different sizes may be provided to help assemble the trial humeral prosthesis 800 to the desired height. A proximal end of the trial stem 810 (or an adaptor coupled thereto) may include a male portion 814 that has the same shape as male portions 834, 844, and a distal end of the trial proximal body 850 may include a female portion 852 that has the same shape as female portions 832, 842.

To begin assembling the trial humeral prosthesis 800, the female portion of one component may be slide laterally over the male portion of another component to couple the two pieces together. For example, as shown in the cross-section of FIG. 12F, the male portions 834 of trial spacer 830 may be inserted into the female portions 842 of trial spacer 840 to couple the two components together. In the illustrated embodiment, the male portions have a generally "T"-shape or dovetail shape, to help prevent axial disengagement.

As best shown in FIG. 12C, the spacers 830, 840 may each include a pair of partially-oblong shaped recesses 836, 846 that, when the spacers are coupled, form a continuous oblong recess. It is preferably that each spacer include a pair of these recesses spaced on opposite sides of the spacer, about 90 degrees offset from the pair of male protrusions or female recesses, although more or fewer such recesses may be provided in the same or other spacing. And although each spacer is illustrated with such a partial recess on only one terminal end of the spacer, such recesses may be provided on both terminal ends of the spacers (as well as the proximal terminal end of the trial stem 810 and on the distal terminal end of the trial proximal body 850) to allow for more than two spacers to stack up. Each partial recess 836, 846 may also include an aperture 838, 848 therein to receive corresponding pegs 864 of locking plug 860, described below.

Figure 12E:
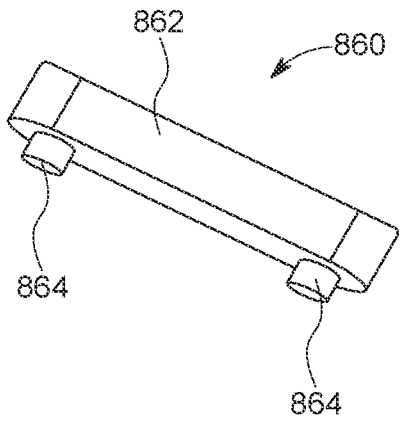
FIG. 12E is a perspective view of a locking plug for use with the trial humeral prosthesis of FIG. 12A.

Referring to FIG. 12E, locking plug 860 may have a main body 862 that has a generally oblong shape that matches the shape of the combined partial recesses 836, 846. An interior face of the locking plug 860 may include two pegs 864 that are sized, shaped, and positioned to be received within corresponding apertures 838, 848 when the trial spacers 830, 840 are coupled together. The exterior face of locking plug 860 may have a curvature so that, when the locking plug 860 is coupled to the trial spacers 830, 840, a smooth cylindrical outer surface is formed between the trial spacers 830, 840 and the locking plug 860.

Figure 12F:
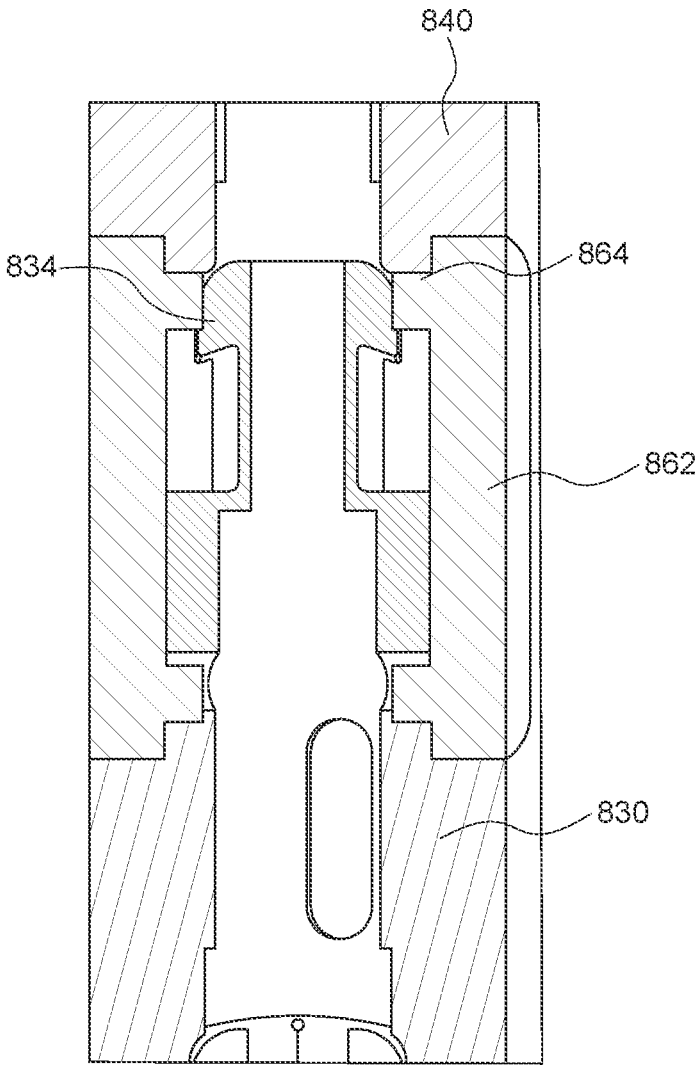
FIG. 12F is a cross-section of the assembled trial humeral prosthesis of FIG. 12A.

As shown in the sequence between FIGS. 12B and 12C, after the trial spacers 830, 840 are coupled, one locking plug 860 may be inserted into each pair of partial recesses 836, 846 with the pegs 854 extending into the corresponding apertures, as shown in FIG. 12F. The result, shown in FIG. 12D, is a smooth outer surface of the assembly. Preferably, the interface between the locking plugs 860 and the partial recesses 836, 846 has a press-fit relationship, and when the locking plugs 860 are put in place onto the coupled trial spacers 830, 840, the locking plugs 860 will prevent any angular or transverse movements of the spacers relative to each other.

In order to decouple the trial spacers 830, 840, the locking plugs 860 may be removed, and then the trial spacer 840 may be slid laterally relative to the trial spacer 830 to remove the male portion 834 of trial spacer 830 from the complementary female portion 842 of trial spacer 840. In some embodiments, gripping features or additional tool-receiving holes may be provided on the outer surface of the locking plug 860 to help with such removal.

Figure 13A:
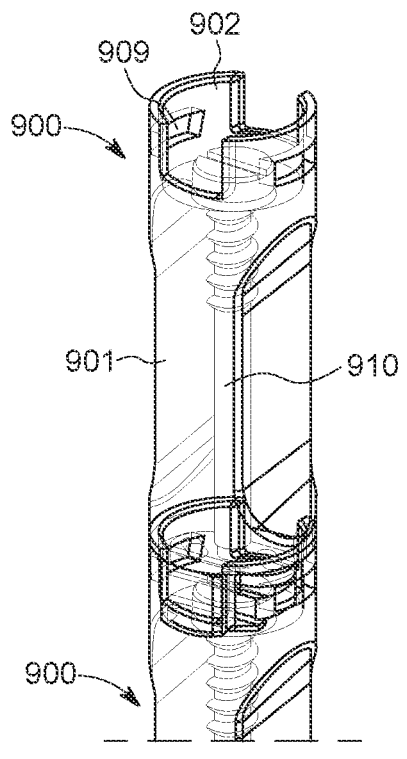
FIGS. 13A-B are transparent, perspective views of a trial spacer according to another aspect of the disclosure in locked and unlocked states, respectively.
Figure 13B:
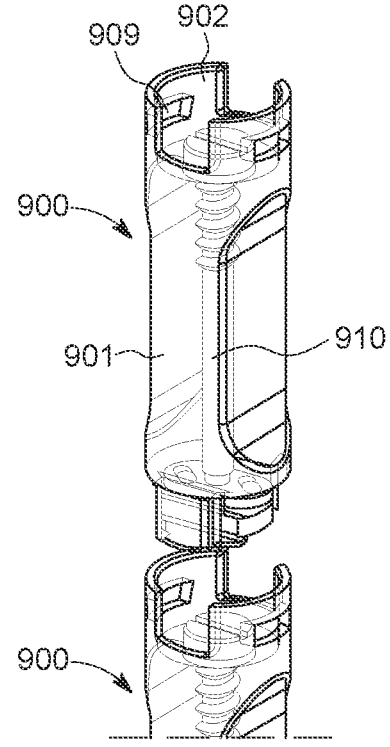

FIGS. 13A-B are perspective views of trial spacers 900 according to another aspect of the disclosure. Trial spacers 900 are shown in a locked state in FIG. 13A, and an unlocked state in FIG. 13B, with both figures showing an outer housing as partially transparent to show internal components. It should be understood that trial spacers 900 may be used in a trial humeral prosthesis in much the same way as described for other trial spacers herein. In other words, although not shown, a trial stem (or an adaptor component coupled to the trial stem) may include features at a proximal end that generally match features at the proximal end of trial spacer 900, and a trial proximal body may include features at a distal end that generally match features at the distal end of trial spacer 900. With this configuration different numbers and sizes of trial spacers 900 may be coupled to each other and to the other components of the trial humeral prosthesis to quickly and stably build up the trial prosthesis to the desired height.

Referring still to FIGS. 13A-B, trial spacer 900 may include generally cylindrical outer housing 901 that is at least partially hollow to receive internal working components of the trial spacer 900. Certain components of trial spacer 900 are introduced here prior to going into greater detail about their functionality below. The outer housing 901 may include two proximal extensions 902 that together form a portion of a cylinder with openings formed therein to receive a distal end portion of another trial spacer 900. Each extension 902 may be a generally thin walled portion of a cylinder with a slot 909 formed therein, the slot extending in a circumferential direction along the extension 902. As should become clear from the description below, this configuration allows for the distal end of one trial spacer 900 to couple to the proximal end of another trial spacer 900 in a way that prevents disconnection as well as rotation, about the longitudinal axis, of one trial spacer 900 relative to another. The distal or male end of trial spacer 900 is shown in detail in FIG. 13C, in a non-activated state, and the proximal or female end of trial spacer 900 is shown in detail in FIG. 13D. Referring still to FIGS. 13A-B, a threaded screw 910 may extend through and along a central longitudinal axis of the outer housing 901, with a proximal head that protrudes beyond a proximal face of the housing 901, and a distal end that engage a cam actuator 960. As shown in FIG. 13D, the proximal head may include a feature (such as a slot or hex feature) to engage with a screwdriver member.

Figure 13C:
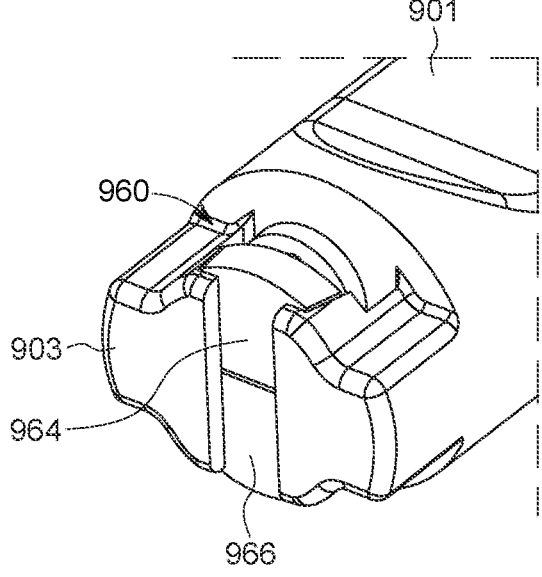
FIG. 13C is a perspective view of a distal or male end of the trial spacer of FIGS. 13A-B.
Figure 13D:
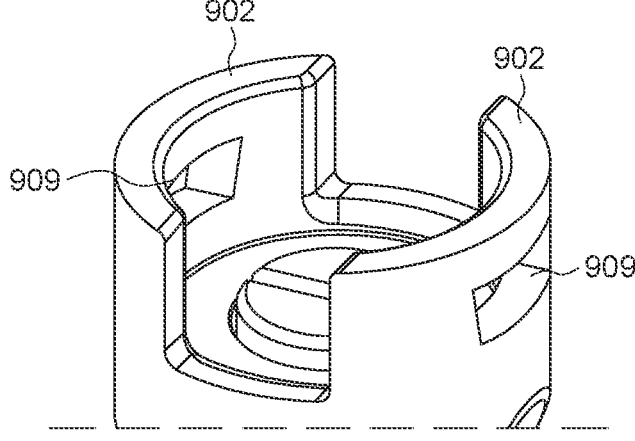
FIG. 13D is a perspective view of a proximal or female end of the trial spacer of FIGS. 13A-B.

Referring now to FIG. 13C, which shows the distal or male end of the trial spacer 900, the distal end of the housing 901 may transition into two distal side extensions 903 that are sized and shaped to fit between the two proximal extensions 902. The actuator 960 is shown in FIG. 13C in an unlocked or non-actuated condition, and is at least partially contained between a distal face of the housing 901 and the distal side extensions 903.

Figures 13E, 13F, 13G:
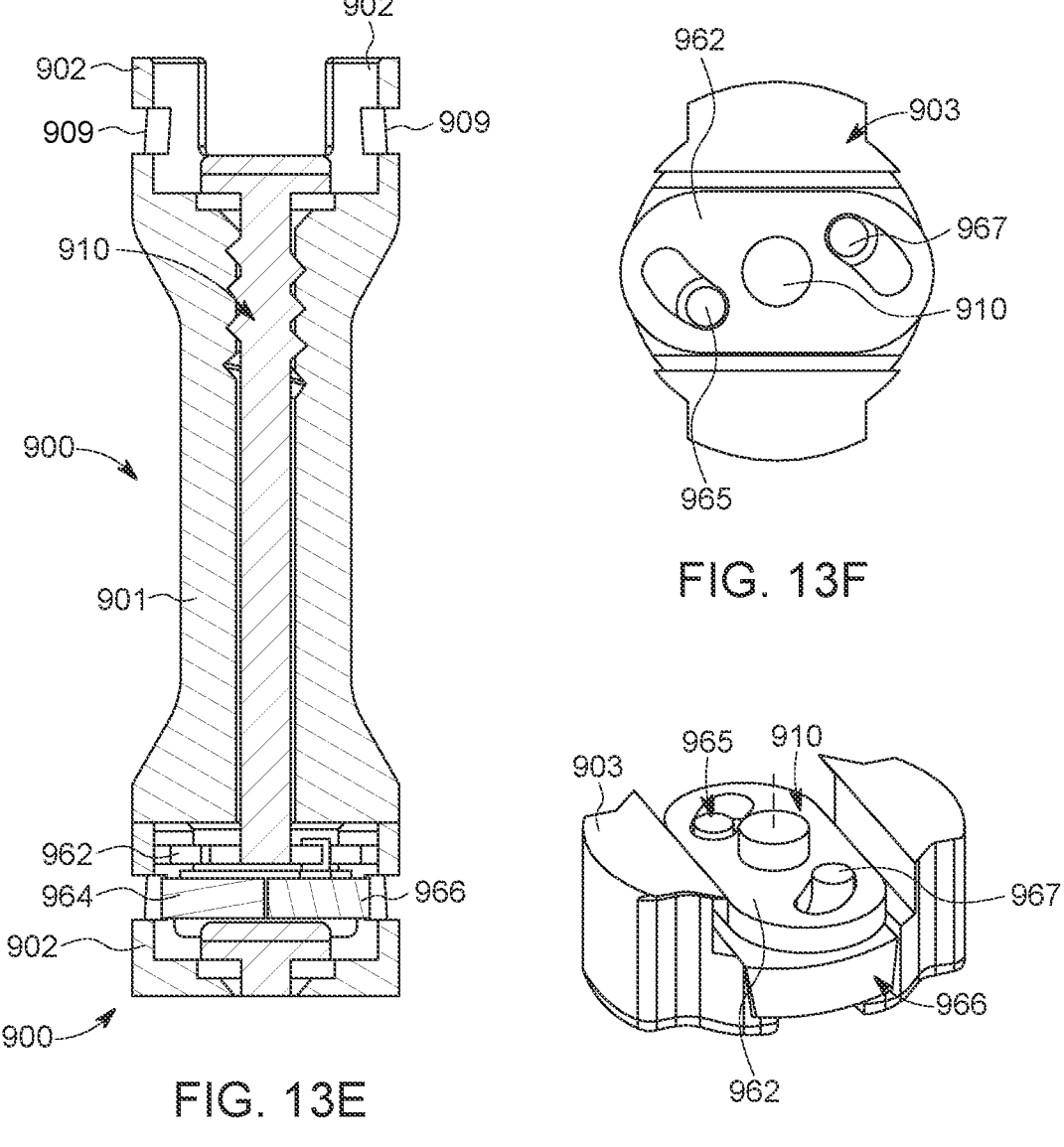
FIG. 13E is a cross-section of two of the trial spacers of FIGS. 13A-B connected to each other in an unlocked condition.
FIGS. 13F-G are top and perspective views of the distal end of the trial spacer of FIGS. 13A-B in an unlocked condition, with proximal portions of the trial spacers omitted for clarity.

FIG. 13E is a cross-section of one spacer 900 positioned adjacent to another spacer 900, but in an unlocked condition. As shown in FIG. 13E, the threaded screw 910 may extend through a central channel in the outer housing 901, and may include threads that engage corresponding internal threads of the portion of housing 901 forming the channel through which the screw 910 passes. The distal end of threaded screw 910 may couple to a rotating link 962 of the cam actuator 960. FIGS. 13F-G illustrate top views of the cam actuator 960, with most of the outer housing 901 omitted from the view for purposes of clarity. As shown in FIGS. 13F-G, the rotating link 962 may have an oval-type shape, with two parallel sides that are each connected by rounded ends. The rotating link 962 may include a central aperture through which a distal end portion of screw 910 passes, and two curved channels or slots on either side of the central aperture. The size of the rotating link 962 relative to the space between the distal side extensions 903 may be such that rotating link 962 has enough clearance for a small amount of rotation, for example approximately 45 degrees. The distal end portion of screw 910 may be fixed to rotating link 962 so that, upon rotation of screw 910, the rotating link 962 begins to rotate.

Referring to FIGS. 13E-G, the cam actuator 960 may include two jaws or locking platforms 964, 966 positioned distal to the rotating link 962. Each locking platform 964, 966 may be shaped to be generally rectangular, except that a radially outer surface of each locking platform 964, 966 may be rounded. The width of each locking platform 964, 966 is small enough to be able to pass through a respective slot 909 in proximal extensions 902. Each locking platform 964, 966 may include a protrusion 965, 967 sized and shaped to pass through a corresponding curved channel in the rotating link 962, as best shown in FIGS. 13F-G. In the unlocked condition shown in FIGS. 13C and 13E-G, the two locking platforms may be directly adjacent to each other.

Figure 13H:
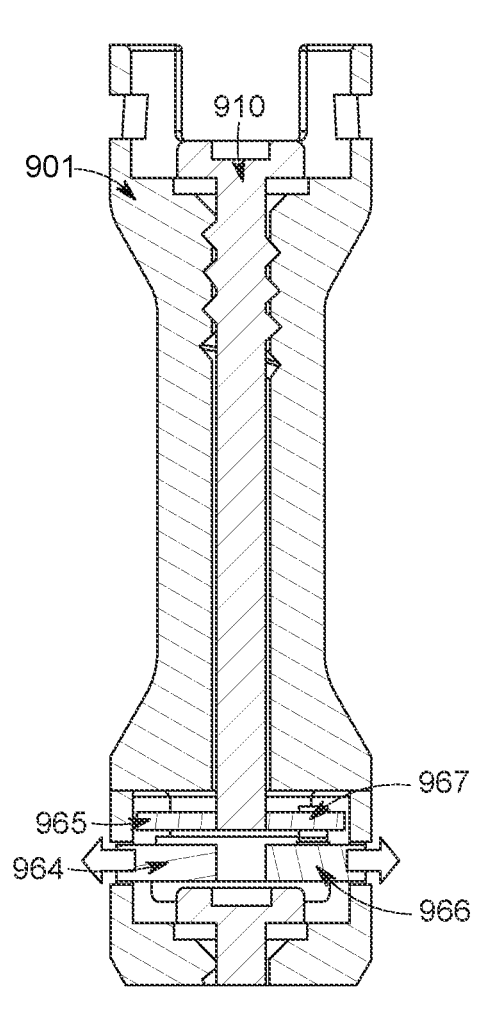
FIG. 13H is a cross-section of two of the trial spacers of FIGS. 13A-B connected to each other in a locked condition.
Figure 13I:
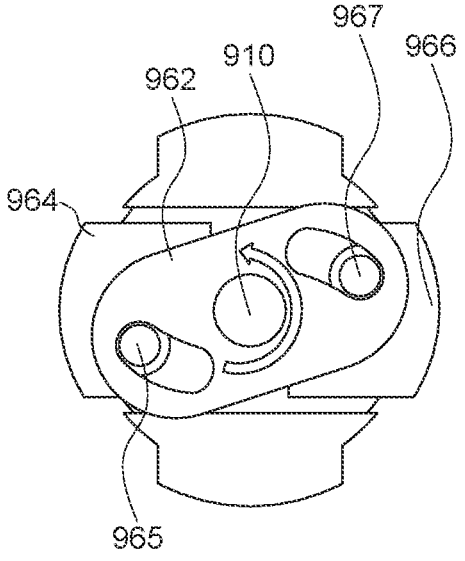
FIGS. 13I-J are top and perspective views of the distal end of the trial spacer of FIGS. 13A-B in a locked condition, with proximal portions of the trial spacers omitted for clarity.
Figure 13J:
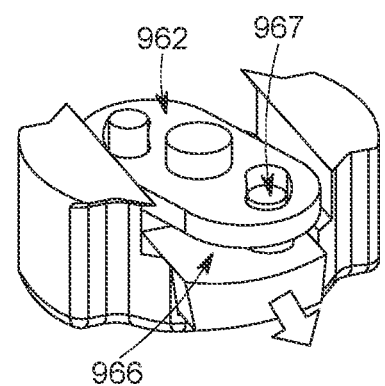

FIGS. 13H-J show views of trial spacer 900 that correspond to FIGS. 13E-G, except that the cam actuator 960 is in the (or being transitioned into) the locked condition. As best shown in FIGS. 13I-J, as the screw 910 is rotated, it causes the rotating link 962 to rotate. The curved channels within rotating link 962 are cam channels, so that as the rotating link 962 rotates, the protrusions 965, 967 ride along the cam channels, in order to drive the jaws or locking platforms 964, 966 away from each other to protrude radially outwardly from the distal end of housing 901. When this actuation is performed, and when the distal end of one trial spacer 900 is received within the proximal end of another trial spacer 900, the jaws or locking platforms 964, 966 bass into and at least partially though the slots 909 formed in the proximal extensions 902. This results in one trial spacer 900 being locked to the other 900 from axial movement, with the engagement between distal side walls 903 and the proximal extensions 902 preventing relative rotational movement. Although cam actuator 960 is shown with two jaws or locking platforms, more can be included, preferably with a similar number of slots 909.

While the above disclosure has generally focused on the use of trial spacers to assist in building up the trial humeral prosthesis, as part of the trialing process, it may be desirable to determine the distance between the humeral resection plane and the center of the glenoid. Various embodiments of tools to assist with measuring this distance, including via connection to one of the trial components above, are described below.

Figure 14A:
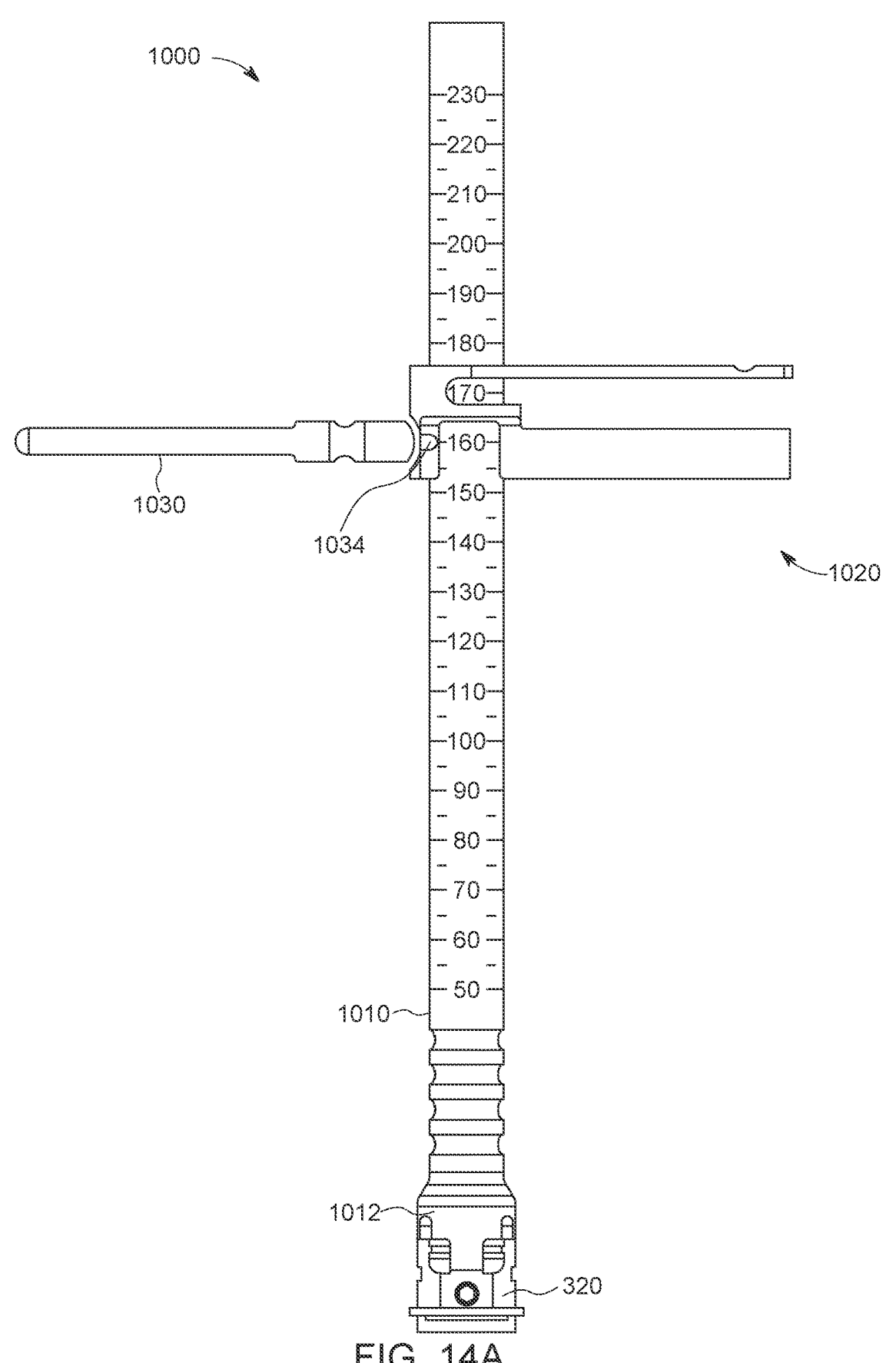
FIG. 14A is a side view of a height measuring gauge assembled to a trial stem according to one aspect of the disclosure.

FIG. 14A is a side view of a distance or height measuring gauge 1000. Gauge 1000 may include a main body or scale 1010 which may be a generally cylindrical member. The scale 1010 may include indicia provided thereon (e.g. hash marks with millimeter markings). The scale 1010 may have a distal end configured to couple to any of the trial stems (or adaptors used therewith), and may include coupling features of any of the embodiments of the trial spacers described above. In this particular example, the distal end of the scale includes a mating member 1012 that corresponds to the coupling features described in connection with trial spacers 330, 340 of FIG. 6A, and is shown coupled to adaptor 320. However, it should be understood that this is merely exemplary, and any suitable coupling mechanism may be used to couple the scale 1010 to the trial stem, including any of the mechanisms described above.

Figure 14B:
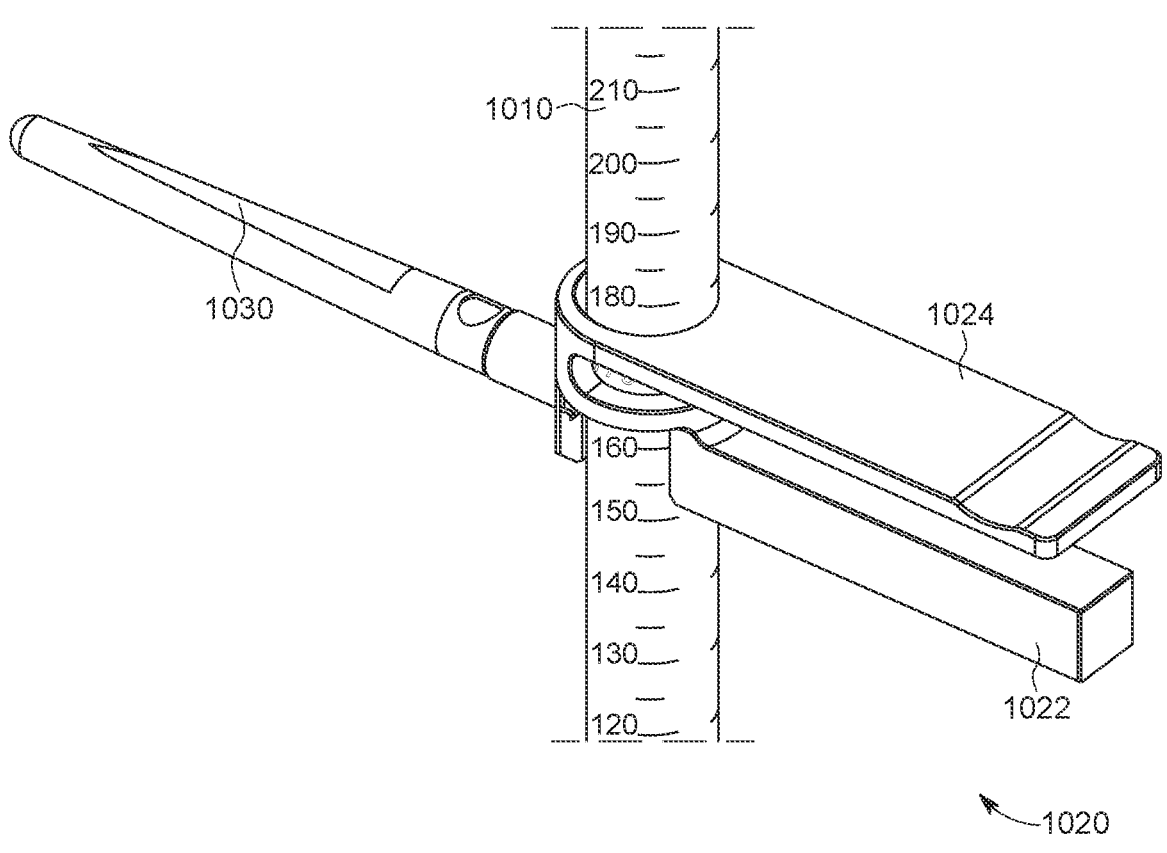
FIG. 14B is an enlarged perspective view of the measuring gauge of FIG. 14B.
Figure 14C:
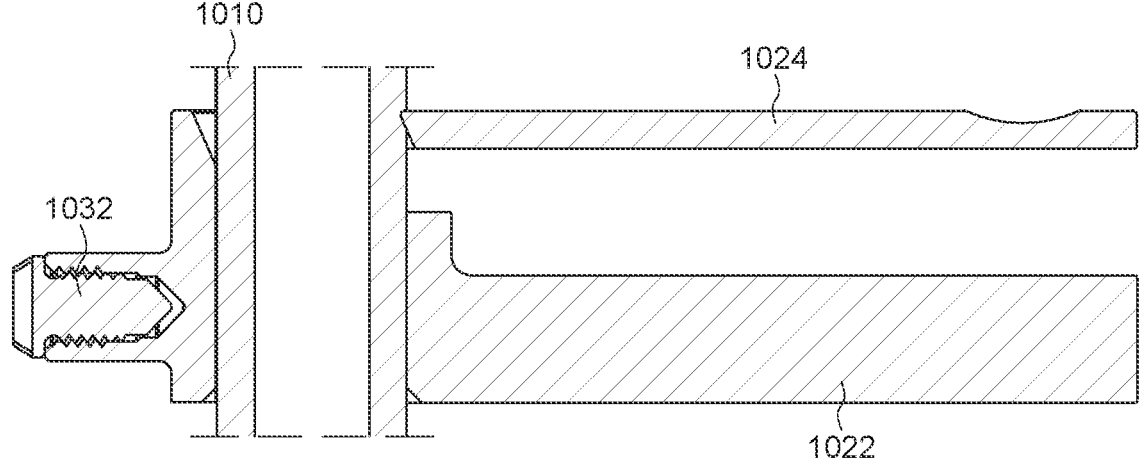
FIG. 14C is a cross-section of a portion of the measuring gauge of FIG. 14A.

The measuring gauge 1000 may also include an indicator member coupled to the scale 1010. The indicator member may include a clamp 1020 and a pointer 1030. FIG. 14B shows an enlarged perspective view of the clamp 1020 and pointer 1030 coupled to the scale 1010, with FIG. 14C showing a cross-section of the assembly. A trailing end of the pointer 1030 may have a threaded connector 1032 so that the pointer 1030 may be screwed into the clamp 1020 to couple the two members. This may be useful because there is typically limited space in and around the surgical site, and it may be desirable to only couple the pointer 1030 to the clamp 1020 when the clamp 1020 is close to is final position, described in greater detail below.

The clamp 1020 may include an aperture through which the scale 1010 extends, a slider 1022, and an arm 1024 spaced from the slider 1022. Referring to FIGS. 14B-C, the slider 1022 may include a generally cylindrical aperture that receives the scale 1010 therethrough. The arm 1024, which is positioned proximally but otherwise aligned with the slider 1022, may also include an aperture that receives the scale 1010, with the apertures of the slider 1022 and the arm 1024 being generally aligned. However, as shown in FIG. 14C, the aperture in the arm may be elliptical. With this configuration, when there is no forced applied to the arm 1024 relative to the slider 1022, the elliptical shape of the aperture of the arm 1024 maintains the clamp 1020 at the current height. In order to slide the clamp 1020 proximally or distally relative to the scale 1010, the arm 1024 may be depressed toward the slider 1022, causing the elliptical hole to change orientation relative to the scale 1010 and allow sliding of the clamp 1020 proximally or distally relative to the scale 1010. As soon as the force on the arm 1024 is released, it returns to the orientation shown in FIG. 14C to fix the clamp 1020 at the current height. It should be understood that, while the arm 1024 is depressed toward the slider 1022, the clamp 1020 may also be rotated around the scale 1010. Referring again to FIG. 14A, a portion of the slider 1022 positioned on the side with the pointer 1030 may include an arrow 1034 or another indicator that helps a user read exactly what height or distance is being indicated by the position of the clamp 1020 relative to the scale 1010.

In use, after implanting a trial stem (e.g. trial stem 310) into the humerus, with adaptor 320 coupled to the trial stem 310, the measuring gauge 1000, and specifically the mating member 1012 of scale 1010, may be pressed onto the adaptor 320 in the same way described in connection with trial spacer 330. At this point, the pointer 1030 may be, but is preferably not, coupled to the clamp 1020. With the scale 1010 coupled to the trial stem, the user may depress arm 1024 toward slider 1022 and, while depressed, slide the clamp 1020 to a position (height and/or angle) that is near the patient's glenoid. If not already attached, the pointer 1030 may be screwed into the clamp 1020, and the position of the pointer 1030 may be fine-tuned until it points to the center of the patient's glenoid. At this point, the arm 1024 may be released to temporarily re-lock the clamp 1020 in its position, and the height or distance measurement may be read by comparing the position of the arrow 1034 to the indicia on the scale. This distance may be used for any desired purpose, including for example to get a better idea of what combination of number and heights of trial spacers should be used to build up the trial humeral prosthesis, minimizing the amount of trial and error necessary, and thus reducing surgery time and increasing patient outcomes.

It should be understood that, although pointer 1030 is generally illustrated as a static component, in some embodiments it may be a dynamic component in the sense that it may change lengths. For example, in one embodiment, the pointer 1030 may be formed of two or more components that may have a telescopic relationship such that the pointer 1030 may be advanced to extend the tip of the pointer farther from the scale 1010, or retracted to move the tip of the pointer closer to the scale 1010. Other mechanisms may be provided to achieve variable length of the pointer 1030. For example, the pointer 1030 may be formed of two components that threadedly engage each other, such that rotation of one component allows that component to translate farther away from, or closer to, the scale 1010 as it rotates. Still other mechanisms may be suitable to achieve a variable length of the pointer 1030. In some embodiments, the pointer 1030 may be formed as a single length component, but allowed to move laterally toward or away from the scale 1010 even if the actual length of the pointer component itself does not change. One of the benefits of this ability for the tip of the pointer 1030 to move laterally relative to the scale 1010, whether by forming the pointer 1030 as a variable length component or allowing sliding or other similar motion relative to the scale 1010, is that different patients may have different distances that the pointer 1030 will need to extend in order to make contact with the center of the glenoid. It should be understood that the features described in this paragraph relative to pointer 1030 may apply to all other similar pointer devices described below, including pointer 1130, pointer 1230, platform 1308, and platform 1308', all described below. Pointers 1430, 1530, and 1630, all described below, include mechanisms for lateral movement, but other mechanisms such as those described in this paragraph may be suitable for use with those embodiments as well for similar purposes.

Figures 15A, 15B:
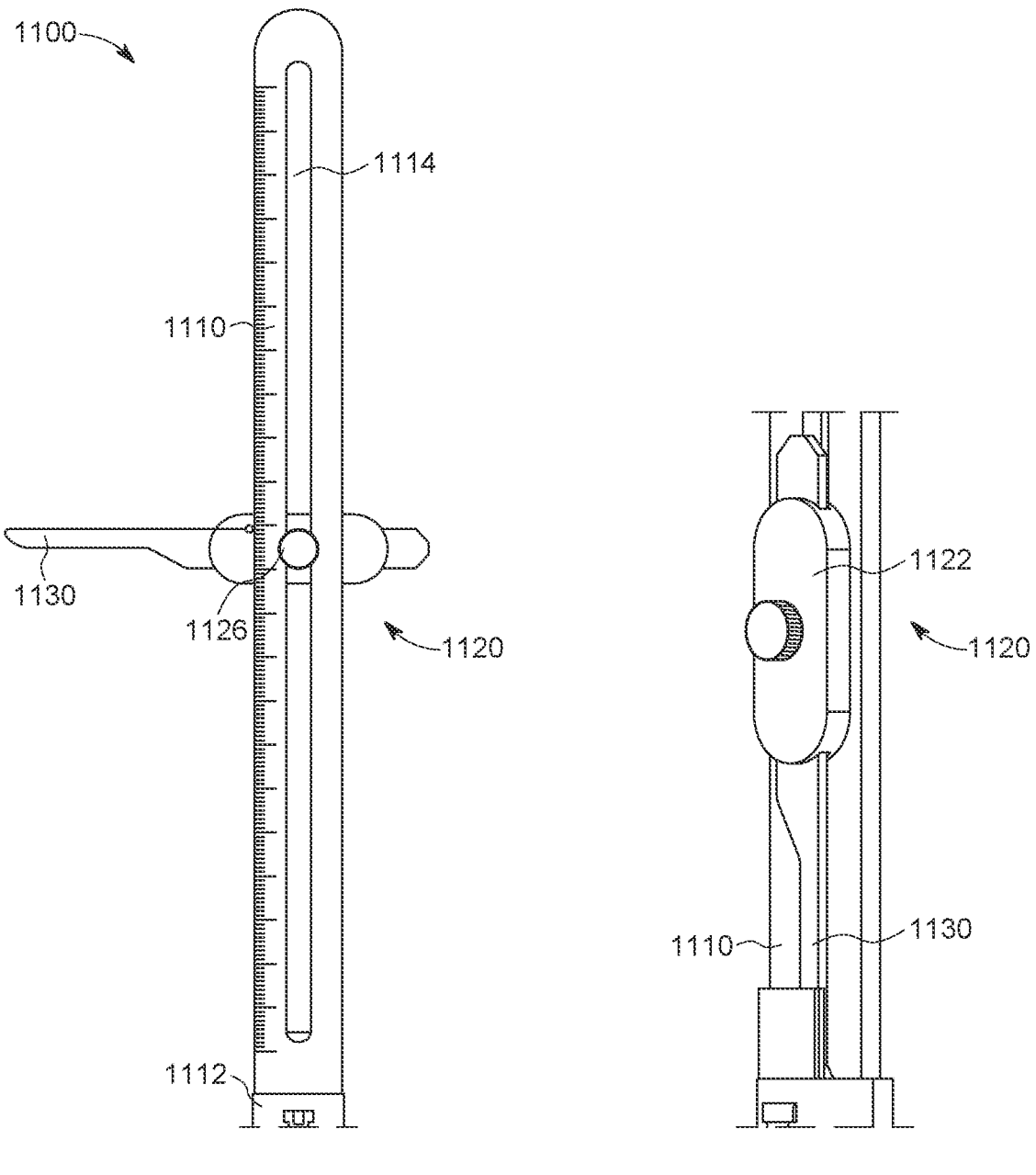
FIG. 15A is a side view of a height measuring gauge according to another aspect of the disclosure.
FIG. 15B is a side view of the height measuring gauge of FIG. 15A with a pointer in stowed condition.

FIG. 15A is a side view of a distance or height measuring gauge 1100 according to another aspect of the disclosure. Gauge 1100 may include a main body or scale 1110 which may be a generally oblong member with an enclosed slot 1114 extending along much of the axial length of the scale 1110. The scale 1110 may include indicia provided thereon (e.g. hash marks with millimeter markings). The scale 1110 may have a distal end configured to couple to any of the trial stems (or adaptors used therewith), and may include coupling features of any of the embodiments of the trial spacers described above. For example, the distal end of the scale 1110 may include a mating member 1112 similar to mating member 1012, including the variations described therewith. In other words, it should be understood that mating member 1112 may be any suitable coupling mechanism to couple the scale 1110 to the trial stem, including any of the mechanisms described above.

The gauge 1100 may include a slider 1120, which may include a main body 1122. The main body 1122 may be generally oblong, and have a width (the smaller dimension of the oblong shape) that is about equal to or smaller than the medial-to-lateral width of the scale 1110. The main body 1122 may include a slot traversing the length of the main body 1122 that is sized and shaped to snugly receive a pointer 1130 with a friction fit. In other words, the pointer 1130 may be translated through the slot of the main body 1122 by applying force, but in the absence of an intentional application of force, the pointer 1130 will remain in its current position relative to the main body 1122. This allows for a user to slide the pointer 1130 within the main body 1122 to move the tip of the pointer 1130 closer to or farther away from the center of the glenoid.

Figure 15C:
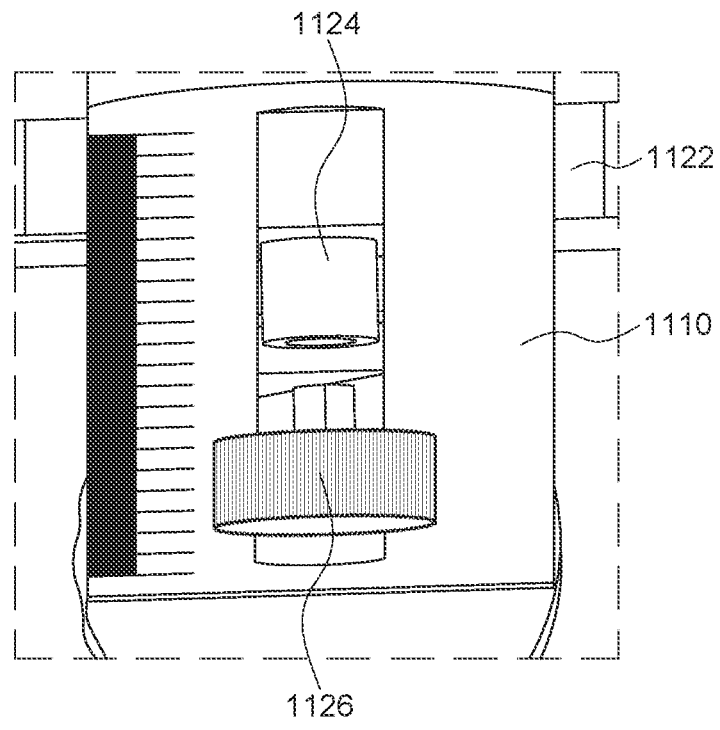
FIG. 15C is a top view of a portion of the slider and a rotating knob in an exploded condition relative to the scale of the height measuring gauge of FIG. 15A.
Figure 15D:
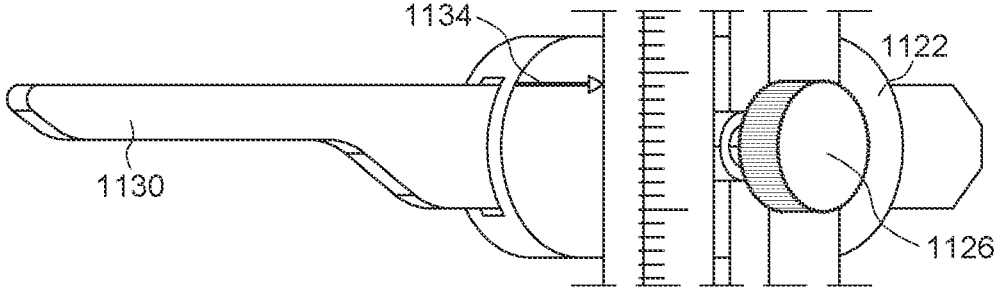
FIG. 15D is an enlarged side view of the pointer of FIG. 15B in a use condition.

Referring to FIGS. 15C-D, the main body 1122 of slider 1120 may include a protrusion 1124, which may be internally threaded. A rotating knob 1126 may have a threaded member that threads into the protrusion 1124 to connect the rotating knob 1126 to the main body 1122. The protrusion 1124 may extend through the slot 1114 of the scale 1110. With this configuration, as the rotating knob 1126 is snugly connected to the protrusion 1124, the main body 1122 becomes positionally fixed to the scale 1110. In other words, by loosening the rotating knob 1126, the slider 1120 may be slid proximally or distally along the scale 1110, and may also be rotated about the central longitudinal axis of the protrusion 1124. Referring to FIG. 15D, the main body 1122 may include an indicator, such as arrow 1134, to help the user read the height position (e.g. via hash marks on the scale 1110), similar to height measurement gauge 1000.

In use, after implanting a trial stem into the humerus, the measuring gauge 1100, and specifically the mating member 1112 of scale 1110, may be coupled to the trial stem. As noted above, any coupling mechanisms may be used, including the connection mechanism between trial spacer 330 and adaptor 320. With the scale 1110 coupled to the trial stem, the user may loosen knob 1126 (if necessary), and slide the slider 1120 up or down until the pointer 1130 points to the glenoid center. If required, the pointer 1130 may be advanced medially or laterally through the main body 1122 of slider 1120 to provide more accurate positioning of the tip of the pointer 1130 relative to the glenoid center. Once at the desired position, the knob 1126 may be tightened to secure the slider 1120 to the scale 1110, and the height reading may be taken by comparing the position of arrow 1134 to indicia on scale 1110. Once the reading is taken, the knob 1126 may be loosened, and the slider 1120 (and pointer 1130) may be rotated to align with the axis of the scale 1110, as shown in FIG. 15B. This may be referred to as a stowed condition, and may provide efficiency of space, for example for storage before/after use. In another embodiment, instead of a connection via rotating knob 1126, a ratchet mechanism may be provided so that the slider 1120 may be adjusted in known increments to reach the final measurement position.

Figure 16A:
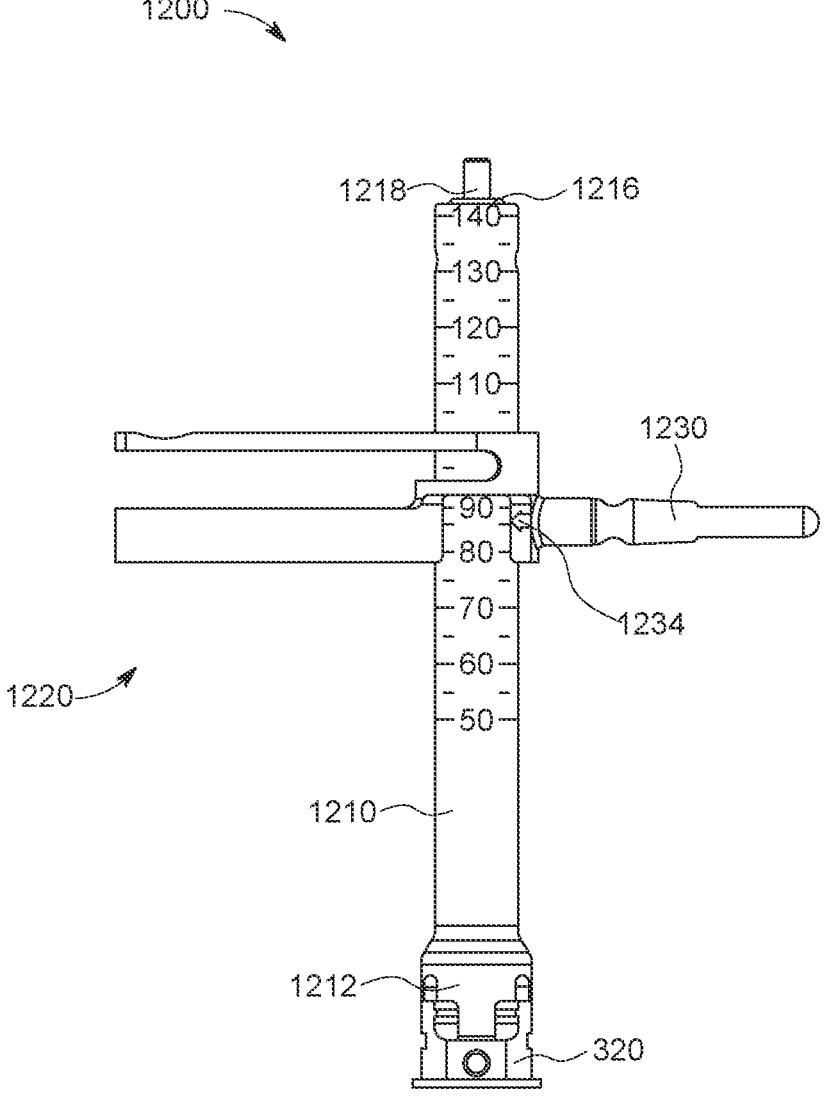
FIG. 16A is a side view of a height measuring gauge according to another aspect of the disclosure in a collapsed condition.

FIG. 16A is a side view of a height measuring gauge 1200 according to a further aspect of the disclosure. Gauge 1200 may have certain components that are identical to those of gauge 1000 and thus are not described in detail again here. For example, gauge 1200 includes a mating member 1212 that mates to a trial stem (e.g. an adaptor 320 of the trial stem). The gauge 1200 may include an outer scale 1210 that is substantially similar, but shorter, than the scale 1010, and may include a clamp 1220 and pointer 1230 that are identical to clamp 1020 and pointer 1030. The main difference between gauge 1200 and gauge 1000 is that gauge 1200 includes a telescoping inner scale 1216 that may slide into or out of outer scale 1210.

Figure 16B:
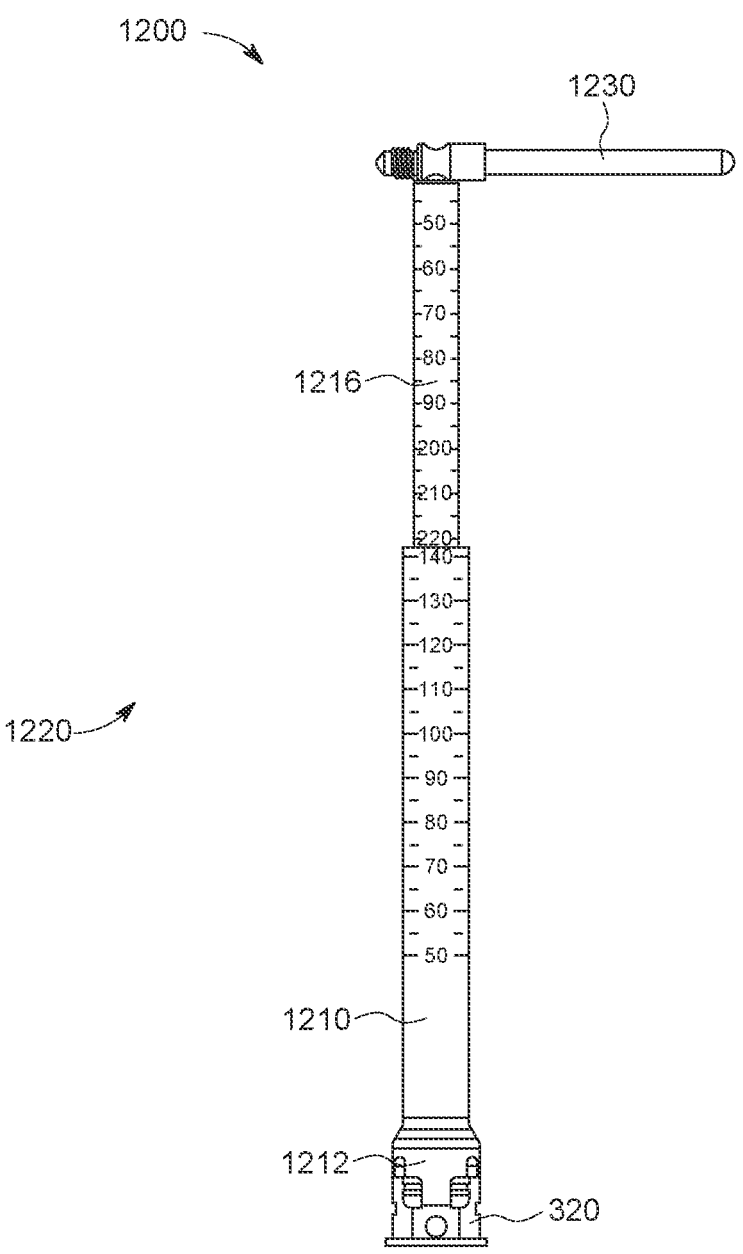
FIG. 16B is a side view of the height measuring gauge of FIG. 16A in an extended condition.

FIG. 16B shows the gauge 1200 with the clamp 1220 removed, and the inner scale 1216 extended out from the outer scale 1210, and the pointer 1230 removed from the clamp 1220 and coupled to the top of the inner scale 1216. The inner scale 1216 may also include measurement indicia, such as hash marks with millimeter markings. Those marking may be provided in increasing number from top to bottom, with the reading based on the measurement of the indicia on inner scale 1216 where it meets outer scale 1210 (assuming inner scale 1216 is used), as described in greater detail below.

Figures 16C, 16D, 16E:
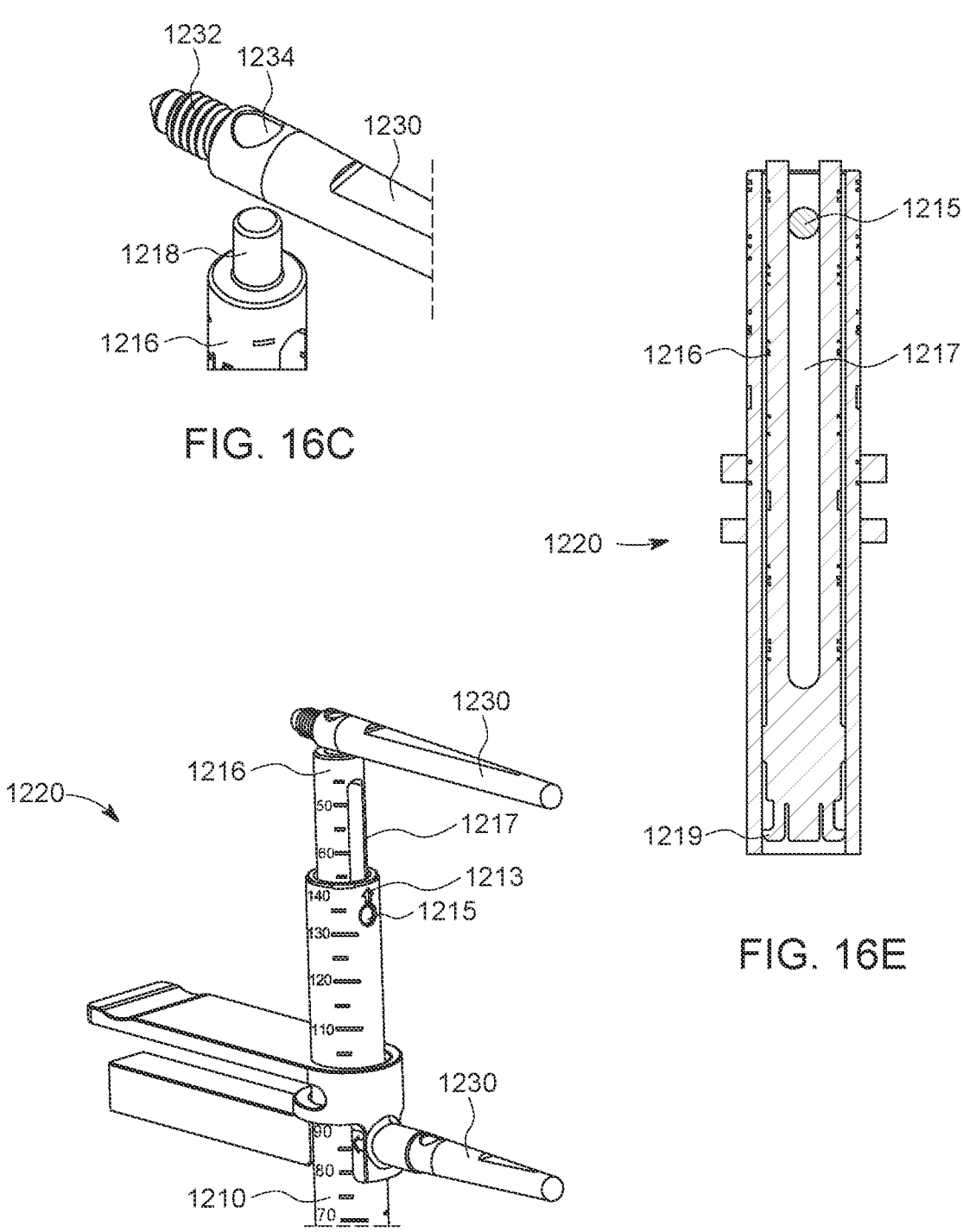
FIG. 16C is an enlarged perspective view of a pointer positioned adjacent to an inner scale of the height measuring gauge of FIG. 16A.
FIG. 16D is a perspective view of a top portion of the height measuring gauge of FIG. 16A.
FIG. 16E is a cross-section of the height measuring gauge of FIG. 16A.

FIG. 16C is an enlarged view of the pointer 1230 prior to connection to the top of inner scale 1216. In FIG. 16C, the threaded connector 1232 is illustrated, although the threaded connector 1232 only has use when coupling the pointer 1230 to the clamp 1220. The pointer 1230 may include an aperture 1234 sized and shaped to receive a proximal post 1218 extending from the inner scale 1216. When coupled in this fashion, the pointer 1230 may rotate about the axis of the post 1218. Although a single pointer 1230 may be provided, in other embodiments two pointers 1230 may be provided, one for use with clamp 1220 on outer housing 1210, and one for use with the post 1218 of inner housing 1216.

FIGS. 16D-E illustrate mechanisms that assist with the sliding of the inner scale 1216 relative to outer scale 1210. The outer scale 1210 may have a cylindrical channel extending axially therethrough sized to receive the cylindrical inner scale 1216 therein. The inner scale 1216 may include an enclosed slot 1217 extending axially along a length of the inner scale 1216, and a pin 1215 may traverse both sides of the slot 1217 and be secured (e.g., by welding) on diametrically opposite sides of the outer scale 1210 near a proximal end of the outer scale 1210. This pin 1215 and slot 1217 assembly allows the inner scale 1216 to telescope into or out of the outer scale 1210 without the ability for the scales to rotate relative to each other. The pin 1215 may also limit the total amount of extension possible, ensuring the inner scale 1216 cannot disconnect from the outer scale 1210. A distal end of the inner scale 1216 may include flexure members 1219 that may press against the interior of outer scale 1210 to create a friction fit. In the absence of applied forces, the flexure members 1219 maintain the axial positioning of the inner scale 1216 relative to the outer scale 1210, but application of manual pushing or pulling force overcomes the friction to allow the inner scale 1216 to slide.

In use, after implanting a trial stem (e.g. trial stem 310) into the humerus, with adaptor 320 coupled to the trial stem 310, the measuring gauge 1200, and specifically the mating member 1212 of outer scale 1210, may be pressed onto the adaptor 320 in the same way described in connection with trial spacer 330. At this point, the inner scale 1216 may be fully collapsed in the outer scale 1210. The user may use the clamp 1220 and pointer 1230 in the same fashion as described in connection with gauge 1000. However, if additional height is needed, the pointer 1230 may be removed from clamp 1220 and placed on the post 1218. As noted above, a separate pointer 1230 may be provided instead if desired. Also if desired, the clamp 1220 may be slid off the top of the outer scale 1210 and beyond the inner scale 1216 to fully remove the clamp 1220 from the system and operating field. With the pointer 1230 coupled to the top of inner housing 1216, the inner housing 1216 may be extended proximally until the pointer 1230 reaches the desired height. As noted above, the pointer 1230 may also rotate relative to the post 1218 for enhanced positioning. When the pointer 1230 is at the desired height, the user may refer to an indicator, for example arrow 1213 at the top of outer scale 1210 shown in FIG. 16D, to take the reading of the height on the inner scale 1216. As noted above, the measurements on the outer scale 1210 may increase in the proximal direction (e.g. in 10 mm increments up to 140 mm at the proximal end of the outer scale 1210). The measurement on the inner scale 1216, however, may increase in the distal direction (e.g. in 10 mm increments starting at 140 mm and increasing towards the distal end of the inner scale 1216).

Figure 17A:
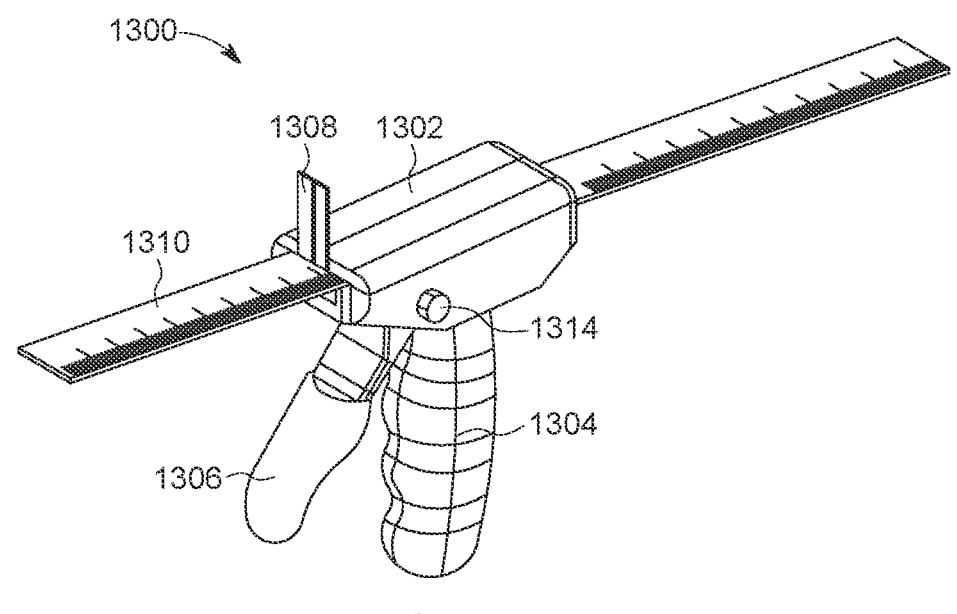
FIG. 17A is a perspective view of a height measurement gauge according to another aspect of the disclosure.
Figure 17B:
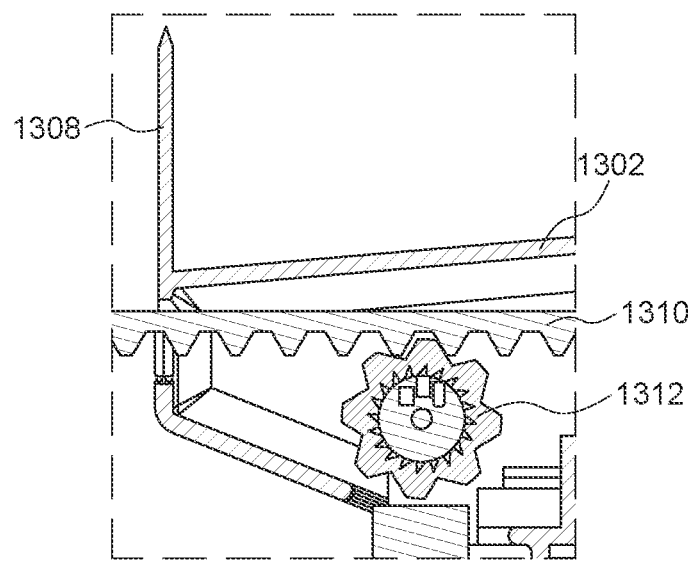
FIG. 17B is a cross-section of a portion of the gauge of FIG. 17A.

FIG. 17A illustrates a height measuring gauge 1300 according to yet another aspect of the disclosure. Height measuring gauge 1300 may be used for the same purpose as gauges 1000, 1100, and 1200, but does not involve any connection with any trial component. Rather, gauge 1300 has a pistol configuration with a main housing 1302, handle 1304, and trigger 1306. A scale 1310 is received through a slot extending through the main housing 1302 generally transverse the handle 1304. The scale 1310 may include indicia, such as hash marks with millimeter markings. As shown in FIG. 17B, an underside of the scale 1310 may have a rack configuration that engages with a pinion 1312. For example, the underside of the scale 1310 may include linear teeth while the pinion 1312 may include gear teeth configured to engage the spacing between linear teeth of the scale 1310. The trigger 1306 may be coupled to the housing 1302 via torsion spring (or other biasing member) and may be coupled to the pinion 1312 via a one way clutch. With this configuration, each squeeze of the trigger 1306 will rotate the pinion 1312 anticlockwise (in the view of FIG. 17B) to drive the scale 1310 distally (to the left in the view of FIG. 17B), and upon releasing the trigger 1306, the trigger 1306 will spring back to its initial condition without causing any rotation of the pinion 1312 until the trigger 1306 is squeezed again. A button 1314 may be provided on the outside of housing 1302, which may be pressed to disengage the pinion 1312 from the rack of the scale 1310 to allow for quick sliding of the scale 1310 relative to the housing 1302.

The housing 1302 may include an extrusion or substantially planar platform 1308 extending in a direction away from the scale 1310 substantially orthogonal to the scale 1310. Preferably, the platform 1308 is positioned at the distalmost end of the housing 1302.

In use, after the humeral resection is made, and preferably before (or possibly after) the trial stem is implanted, the height measurement gauge 1300 may be used. In particular, the free end of the platform 1308 may be aligned with the patient's glenoid with the front end (the left in the view of FIGS. 17A-B) of the gauge housing 1302 pointing toward the proximal humeral resection. The user may squeeze the trigger 1306 as many times as necessary to advance the distal end of the scale 1310 toward the proximal humeral resection until it makes contact. At this point, the user may read the indicia on the scale 1310 to determine the height between the proximal humeral resection and the glenoid center. In some embodiments, each squeeze of the trigger 1306 may correspond to a distance of advancement of the scale 1310. The scale 1310 may begin with its front end aligned with the extension 1308, and the trigger 1306 may be activated a certain number of times until the scale 1310 contacts the proximal humerus. At that point, the total number of activations of trigger 1306 may be multiplied by the travel distance per activation to determine the distance between the proximal humerus and glenoid center. Then, the scale 1310 may be referred to, if desired, to confirm the height measurement determined using the number of activations of trigger 1306. For example, one complete activation of the trigger 1306 may correspond to 30 degrees of rotation of the pinion 1312 and 5 cm of movement of the scale 1310, although those numbers are merely exemplary. Once complete, button 1314 may be depressed to disengage the scale 1310 from the pinion 1312 and the scale 1310 can be pulled proximally and removed from the gauge 1300.

Figures 17C, 17D:
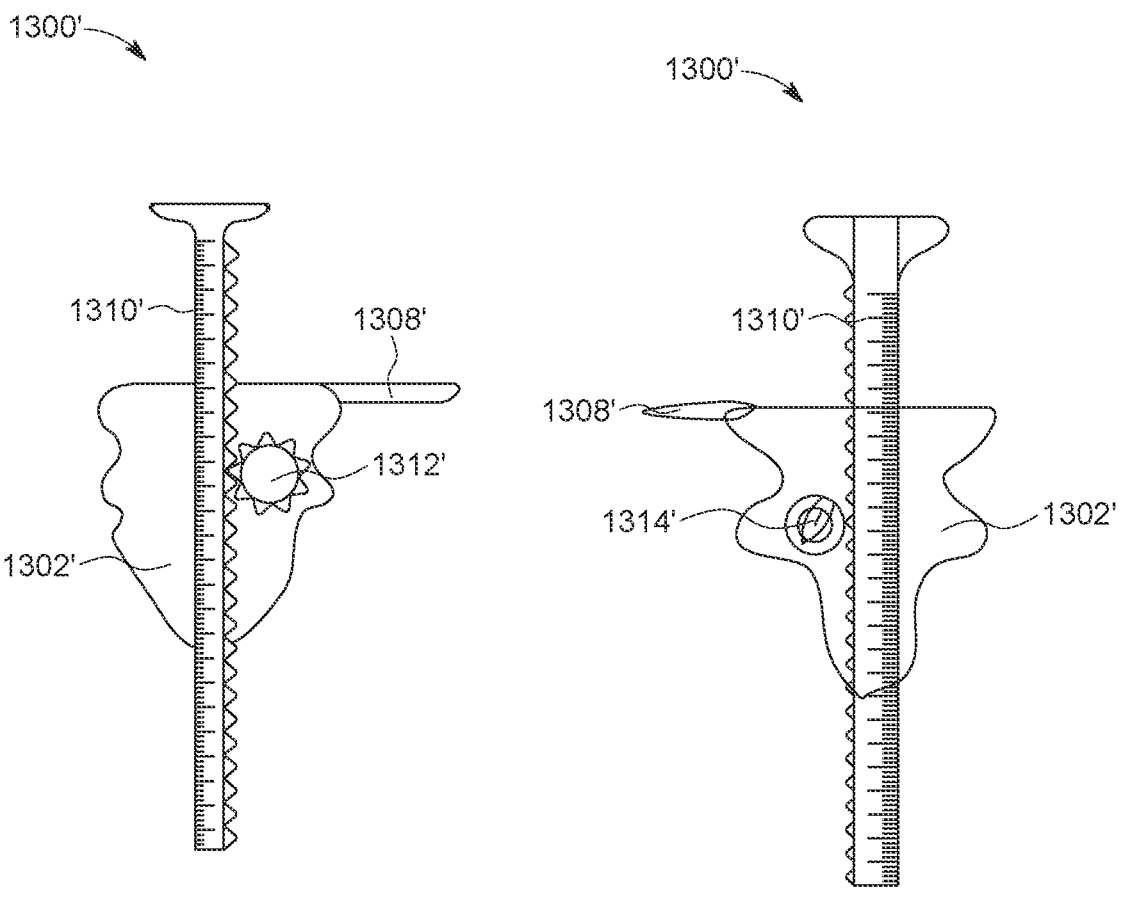
FIGS. 17C-D are front and rear views of an alternate version of the gauge of FIG. 17A.

FIGS. 17C-D show front and rear views of a height measurement gauge 1300' that is similar to gauge 1300. Gauge 1300' may include a scale 1310' similar or identical to scale 1310, which works with a rack and pinion 1312' system in substantially the same way as gauge 1300. The housing 1302' may have a different shape that is not the pistol-style of gauge 1300. The housing 1302' may include an extrusion of platform 1308' substantially similar or identical to platform 1308. The pinion 1312' may be disengaged via a button 1314' in the same was as described above for gauge 1300. In order to advance scale 1310', a user may manually operate the gauge 1300'. For example, the user may hold housing 1302' (which may include grips or other features to create an ergonomic design), align the platform 1308' with the center of the glenoid, and then gradually start pushing (or pulling) the scale 1310' with his or her hand, until the distal end of the scale 1310' reaches the intended target. At that point, the user may note down the measurement using scale 1310', activate the button 1314' to disengage the pinion 1312', and pull the scale 1310' back so it is back in an initial position for subsequent use.

Figure 18A:
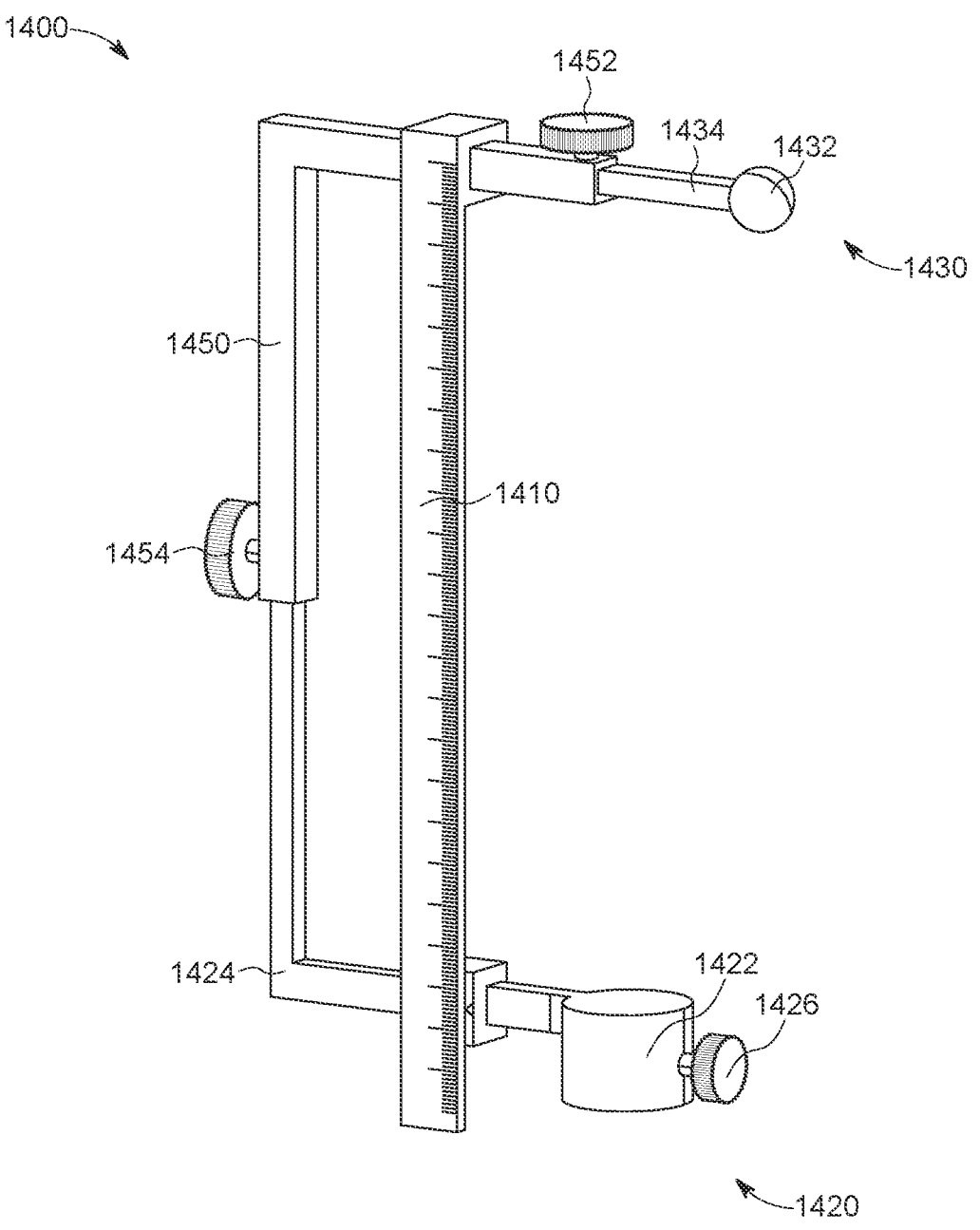
FIGS. 18A-C are various views of a height measurement gauge according to a further aspect of the disclosure.
Figure 18B:
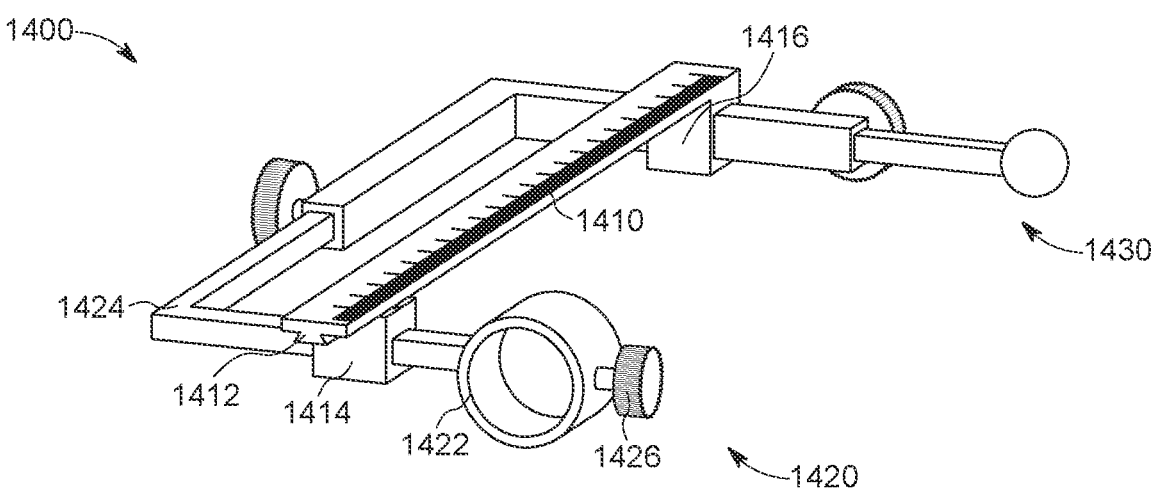
Figure 18C:
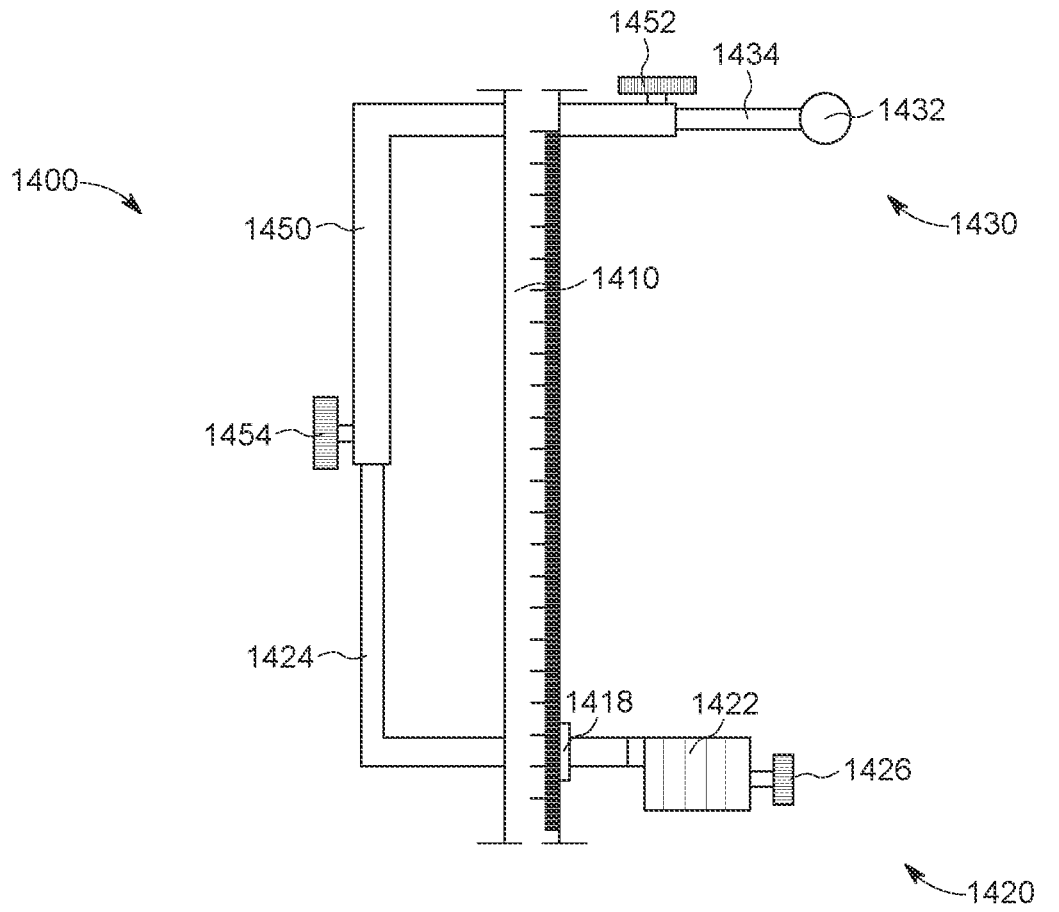

FIGS. 18A-C illustrate a height measurement gauge 1400 according to still another aspect of the disclosure. Generally, gauge 1400 may include a scale 1410, a humeral support 1420, and a pointer 1430.

The pointer 1430 may include a tip 1432, which may be round or spherical, and a shaft 1434 received within an outer housing 1450, which may be generally "L"-shaped. In the illustrated embodiment, the shaft 1434 may have a rectangular or square profile and the outer housing 1450 may define a first channel having a corresponding shape. With this configuration, shaft 1434 may slide into or out of the outer housing 1450, to bring the tip 1432 closer to the glenoid center, without rotation of the shaft 1434. A knob 1452 may be provided on housing 1450 that may be rotated to frictionally engage shaft 1434 to lock the shaft 1434 (and thus tip 1432) in a desired translational position relative to housing 1450.

The humeral support 1420 may include a generally "L"-shaped bracket 1424, which may have a square or rectangular profile. One portion of the "L"-shaped bracket 1424 may be sized to be received within a second channel of outer housing 1450, the second channel being substantially perpendicular to the first housing so that a "C"-shape is formed between outer housing 1450 and bracket 1424. The "L"-shaped bracket 1424 may telescope into or out of the outer housing 1450 to move the humeral support 1420 toward or away from the pointer 1430, and the position may be locked using knob 1454. Referring to FIG. 18B, the humeral support 1420 may include a humeral locator 1422 that has a generally hollow cylindrical shape, with a distal end being open and a proximal end being closed so that the proximal end may be positioned and sit on the proximal humerus, with the remainder of humeral locator 1422 at least partially surrounding the humerus. A knob 1426 may be coupled to the humeral locator 1422, with rotation of the knob driving a shaft into the interior cavity of the humeral locator 1422. This shaft may contact the humerus to help secure the humeral locator 1422 to the humerus.

Referring to FIGS. 18B-C, the scale 1410 may include indicia such as hash markings with millimeter indicators. A first end of the scale 1410 may include a connector 1416 which may define a channel through which outer housing 1450 passes. With this configuration, the scale 1410 may translate along the outer housing 1450. A connector 1412 may be provided on a surface of the scale 1410, for example a dovetail shape on a rear surface of the scale 1410. A second connector 1414 may include a channel that the bracket 1424 passes through, allowing the scale 1410 to translate relative to the bracket 1424. The connector 1414 may include a recess, such as a dovetail recess, to receive connector 1412 therein so that the connector 1414 may translate relative to scale 1410 without decoupling from the scale 1410. The connector 1414 may also include an indicator, such as an arrow 1418, to help read an indicator (e.g. a height measurement) on the scale 1410.

In an exemplary use of height measurement gauge 1400, after the proximal humeral resection has been made, the humeral locator 1422 may be placed over the proximal end of the resected humerus. In other words, the end of the humerus may be placed within the inverted cup shape of the humeral locator 1422. The knob 1426 may then be rotated to secure the humeral locator 1422 to the humerus. Then, the knobs 1452 and/or 1454 may be loosened to allow for telescoping of the pointer 1430 relative to outer housing 1450, as well as outer housing 1450 relative to bracket 1424. The outer bracket 1450 and pointer may be adjusted until the tip 1432 of the pointer 1430 contacts the glenoid center. Then, the knobs 1452, 1454 may be tightened to lock the relative positions of the components of the height measurement gauge 1400. As the various telescoping actions are occurring, the scale 1410 does not interfere with such telescoping action, and the scale 1410 itself may be moved side to side if such positioning is desirable. Once the components are locked, the user may review arrow 1418 and where on the scale 1410 that the arrow 1418 points to determine the height between the glenoid center and the proximal humerus.

Figure 19A:
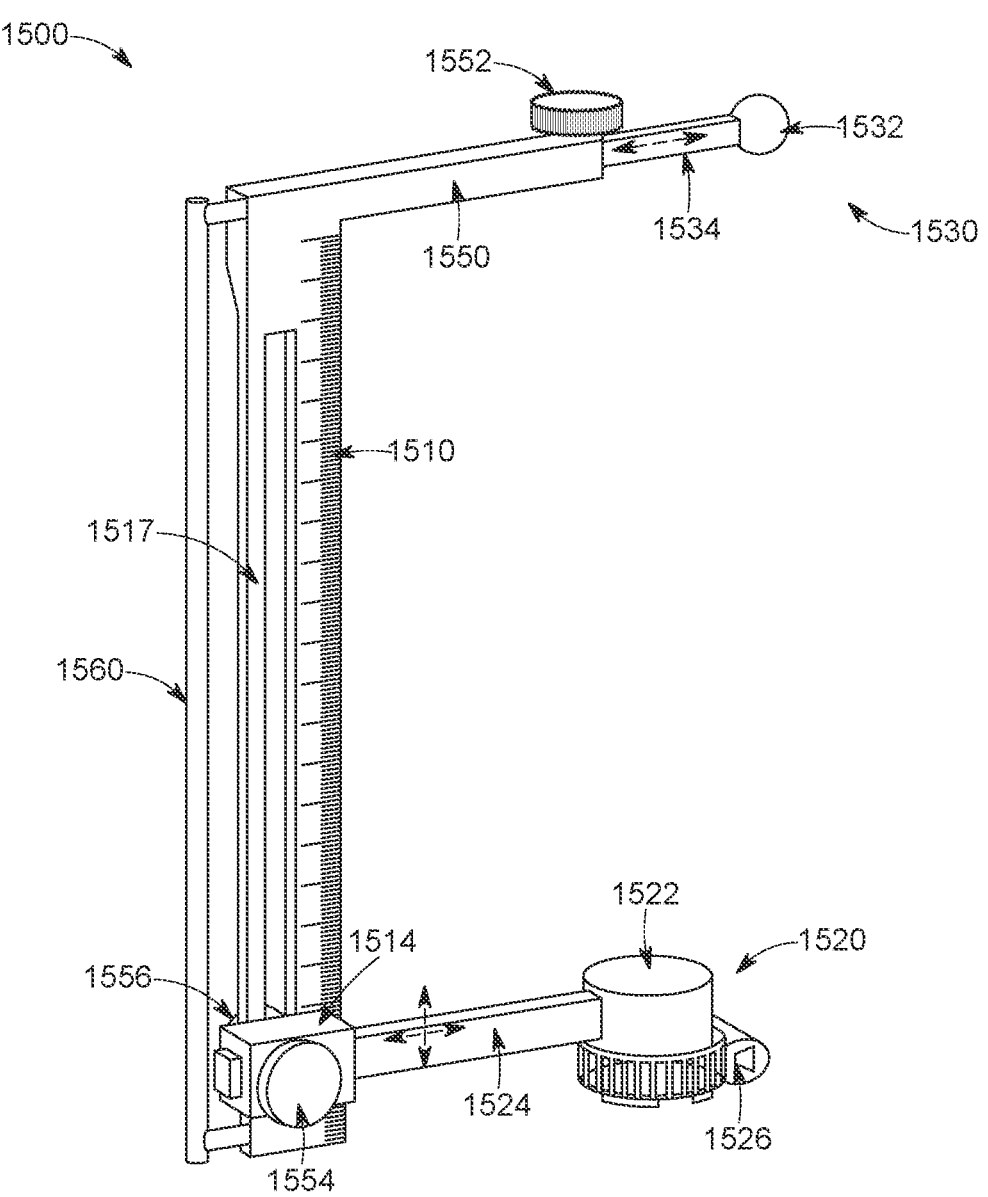
FIG. 19A is a perspective view of a height measurement gauge according to another aspect of the disclosure.

FIG. 19A illustrates a height measurement gauge 1500 according to still another aspect of the disclosure that has significant similarities to gauge 1400. For example, gauge 1500 may include a pointer 1530 with a distal tip 1532, which may be spherical, and a rectangular shaft 1534 that can telescope into or out of housing 1550, in substantially the same way described in connection with gauge 1400. A locking knob 1552 may be provided to lock the pointer 1530 in the desired translational position. Similarly, gauge 1500 may include a humeral support 1520 that includes a humeral locator 1522 that may have the shape of an inverted cup. The humeral locator 1522 may include a shaft 1524, which may have a rectangular profile that can translate into or out of connector 1514, which may have a rectangular channel therein. The humeral locator 1522 may include flexure members at a bottom end thereof, and a clamp 1526 may encircle the flexure members. In use, the humeral locator 1522 may be positioned over the top of the resected humerus, and the clamp 1526 tightened to compress the flexure members toward the bone to secure the humeral locator 1522 to the proximal humerus. A knob 1554 may be included on connector 1514 to lock a position of the shaft 1524 in a particular point of translation relative to the connector 1514.

A scale 1510 may be provided integral with housing 1550, extending downwardly toward humeral support 1520. The scale 1510 may include indicia, such as hash marks with millimeter markings, and an enclosed slot 1517 extending parallel to the long axis of the scale 1510. The connector 1514 may include a member protruding through the slot 1517, with a knob 1556 that can be used to lock the translational position of the connector 1514 relative to the scale 1510, generally similar to protrusion 1124 and knob 1126 shown and described in connection with FIG. 15C. In some embodiments, a handle 1560 may be provided, for example connecting the top of the scale 1510 near housing 1550 to the bottom of the scale 1510, allowing for easy gripping of the gauge 1500. An indicator, such as an arrow (not shown) may be provided on shaft 1524 or connector 1514 to help indicate the height measurement via indicia on scale 1510.

Figure 19B:
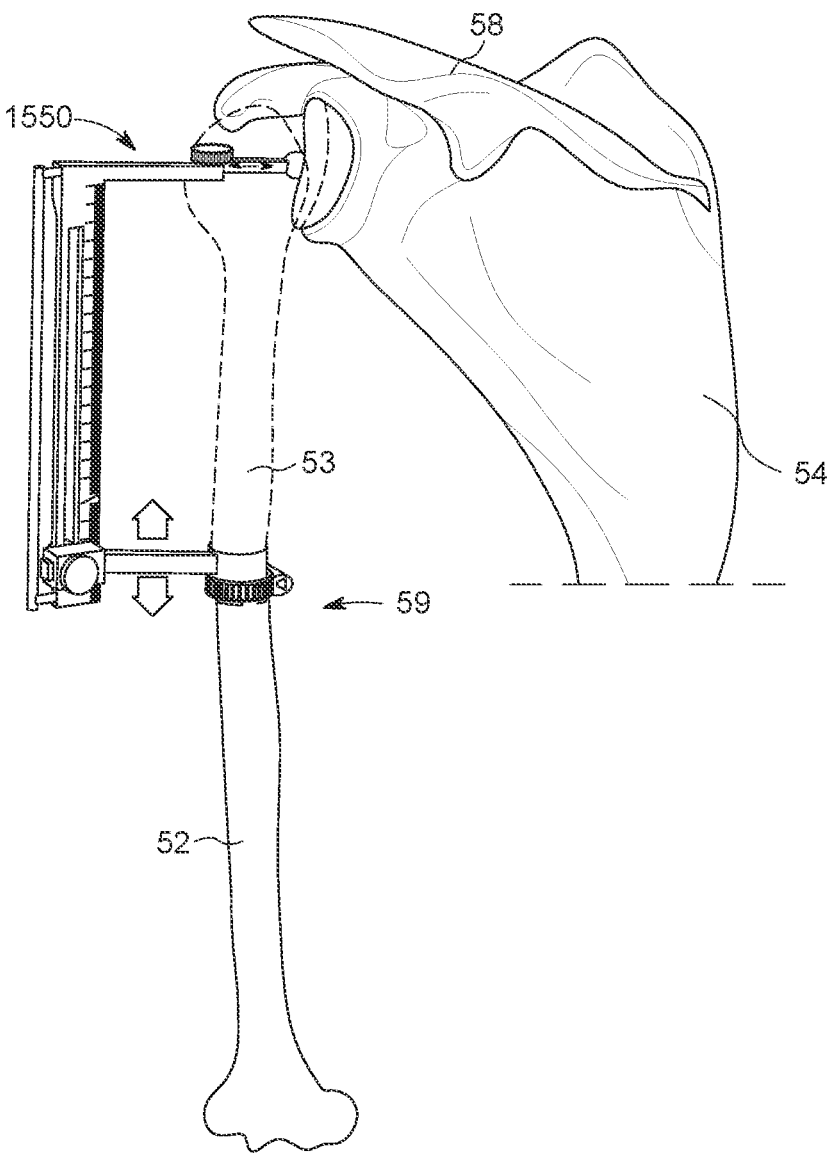
FIG. 19B is a perspective view of the height measurement gauge of FIG. 19A during use.

FIG. 19B illustrates height measurement gauge 1500 during an exemplary use. As shown, the inverted cap style humeral locator 1522 may be positioned over the remaining bone stock of the humerus 52 at the resection plane 59 where the proximal humerus 53 has been removed. The clamp 1526 may be tightened to secure the humeral locator 1522 on the humerus 52. Knobs 1552, 1554, and 1556 may be loosened so that the scale 1510 can be moved up and down and laterally relative to the humeral locator 1522, and so that the pointer 1530 may be moved toward or away from the center of the glenoid 58. When the tip 1532 of the pointer 1530 is in contact with the center of the glenoid 58, the outer housing 1550 may be aligned with the glenoid axis. At this stage, the knobs 1552, 1554, and 1556 can all be tightened to lock the components of the height measurement gauge 1500 in place, and the height reading may be determined from the scale 1510.

Figure 20A:
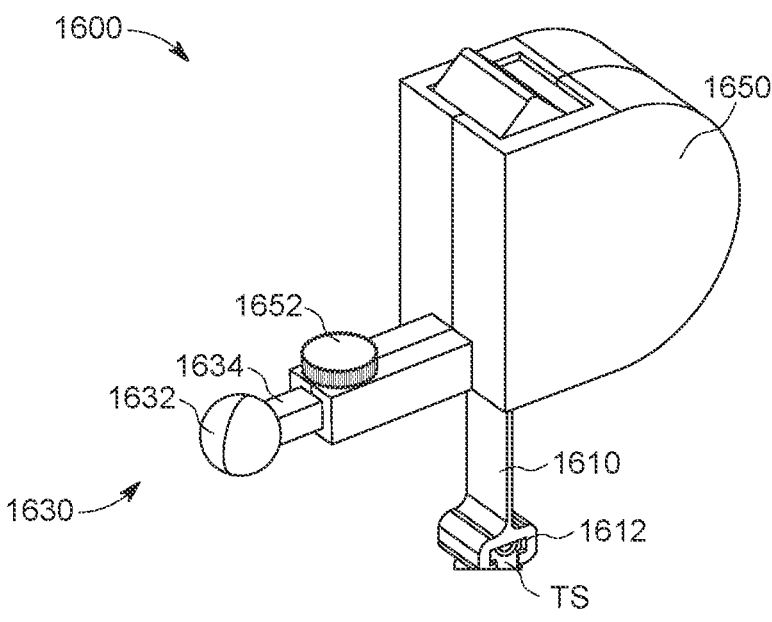
FIGS. 20A-B are perspective and cross-sectional views, respectively, of a height measurement gauge according to a further aspect of the disclosure.

FIG. 20A shows another height measurement gauge 1600 according to still a further aspect of the disclosure. Gauge 1600 may be a tape-measure style device, including a scale 1610 that may roll up into, or extend out of, housing 1650. A distal end of the scale 1610 may include a mating feature 1612, which may have any suitable configuration (e.g. a "T"-slot) to grip or otherwise mate with a proximal end of a trial stem TS (or an adaptor coupled thereto). The housing 1650 may include a main area that houses the rolled-up scale 1610, and an extension member defining a rectangular channel into which the shaft 1634 of pointer 1630 may extend. As in prior embodiments, the pointer 1630 may include a tip 1632, for example a sphere, and the translational position of the pointer 1630 relative to the extension of housing 1650 may be blocked with a knob 1652.

Figure 20B:
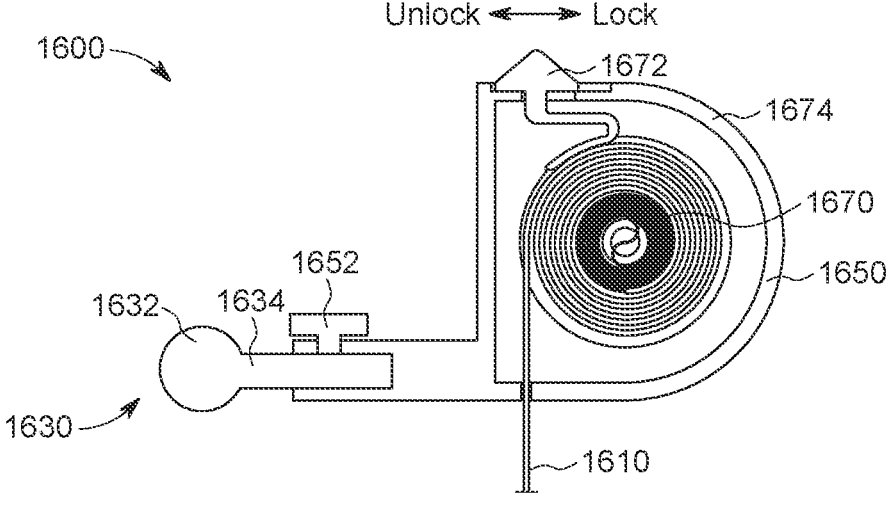

FIG. 20B illustrates a cross-section of the gauge 1600. A rotatable wheel 1670 may be provided within the housing 1650, and one end of the scale 1610 may be coupled to the wheel 1670. A biasing member, such a spring, may be provided with wheel 1670 so that the gauge 1600 is biased to the collapsed condition shown in FIG. 20C. In order to lock the scale 1610 in a desired level of extension, an actuator 1672 may be retracted proximally. The actuator 1672 may include a flexure member 1674 that contacts the rolled up scale 1610. When in the locked condition, the frictional force from flexure member 1674 overcomes the spring force that tends to rotate the wheel 1670 to wind or roll the scale 1610 up into housing 1650.

Figures 20C, 20D:
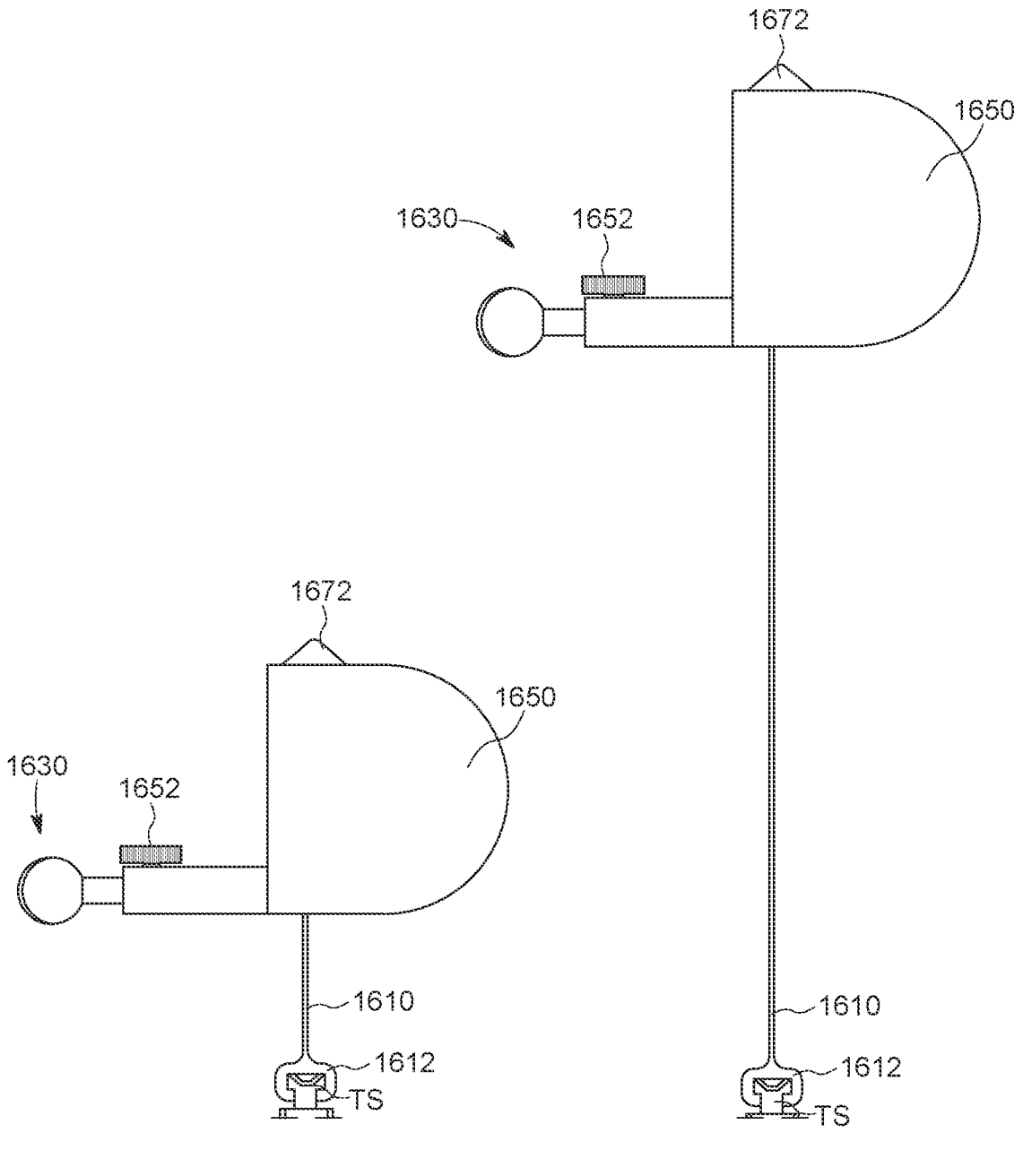
FIGS. 20C-D are side views of the height measurement gauge of FIGS. 20A-B in a contracted and extended state, respectively.

In use, after the trial stem TS is implanted, the mating feature 1612 at the free end of scale 1610 may be clipped or otherwise coupled to the trial stem, as shown in FIG. 20C. The actuator 1672 may be transitioned to the unlocked condition if not already unlocked. The user may also unlock rotating knob 1652 to allow for the pointer 1630 to translate out of the extension of the housing 1650. The user may then bring the tip 1632 of the pointer 1630 into contact with the center of the glenoid, lock the knob 1652, and lock the actuator 1672. At this point, the user may look at the scale 1610 at the point which it exits the housing 1650 to read the height measurement between the proximal humerus and the glenoid center.

FIGS. 21A-D are various views of a height measuring gauge 2000 according to a further aspect of the disclosure. Height measuring gauge 2000 may include a main body or scale 2010 which may be a generally cylindrical member, except that one face of the otherwise cylindrical member is flattened, creating a "D"-shape, as best shown in the top view of FIG. 21D. For example, the flat side of scale 2010 may be positioned on the side of the height measuring gauge 2000 that the tip of the pointer 2030 (described in greater detail below) faces. Thus, in use, the flat side of the scale 2010 may face the patient's glenoid. As described in greater detail below, the flat side of the scale 2010 may help prevent rotation of the clamp 2020 about the scale 2010. The scale 2010 may include indicia provided thereon (e.g. hash marks with millimeter markings), and may include a slot 2017 (which may be enclosed on one or both axial ends) extending along an axial length of the scale 2010, the slot 2017 defining two openings in the perimeter of the scale 2010 positioned about 180 degrees apart. In the illustrated embodiment, one of the openings created by the slot 2017 is along the flat surface of the "D"-shape of the scale 2010.

The scale 2010 may have a distal end configured to couple to any of the trial stems (or adaptors used therewith), and may include coupling features of any of the embodiments of the trial spacers described above. In this particular example, the distal end of the scale 2010 includes a mating member 2012 that corresponds to the coupling features described in connection with trial spacers 330, 340 of FIG. 6A, and is shown coupled to trial stem 310 via adaptor 320. However, it should be understood that this is merely exemplary, and any suitable coupling mechanism may be used to couple the scale 2010 to the trial stem, including any of the mechanisms described above.

The measuring gauge 2000 may also include an indicator member coupled to the scale 2010. The indicator member may include a clamp 2020 and the pointer 2030. The pointer 2030 may be a general pin-shaped member, with a pointed leading end intended to point to and/or contact a center of the patient's glenoid, and a trailing end that has a slightly larger diameter than the main shaft of the pointer 2030. The main shaft of the pointer 2030 may pass through the slot 2017 of the scale 2010. In some embodiments, the enlarged trailing end of the pointer 2030 may have a diameter that is larger than the width of the slot 2017 to ensure that the trailing end of the pointer 2030 does not pass through slot 2017. This size relationship is not necessary however, and any suitable features (including an enlarged diameter) may be provided at the trailing end of the pointer 2030 to facilitate a user gripping and moving the pointer 2030, described below.

Figure 21A:
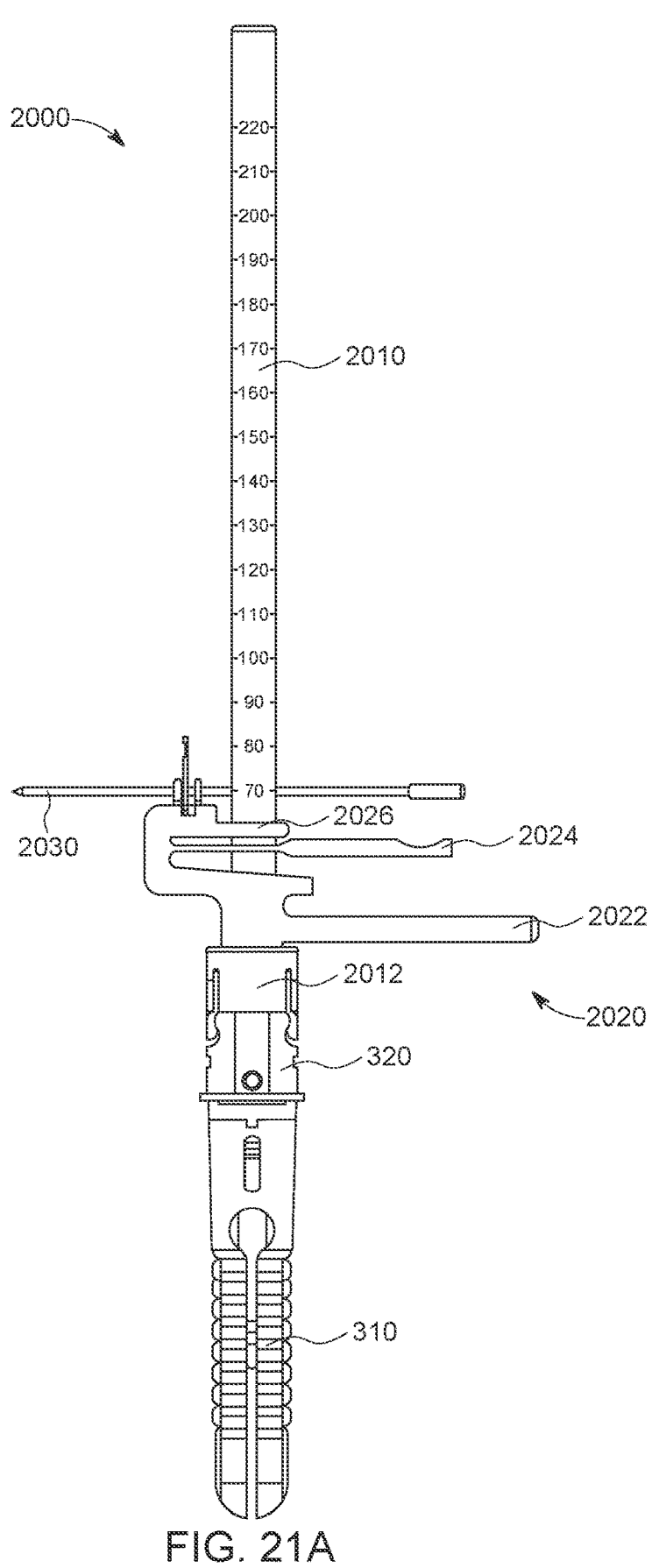
FIGS. 21A-B are side and front views, respectively, of a height measuring gauge, according to another aspect of the disclosure, assembled to a trial stem.
Figure 21B:
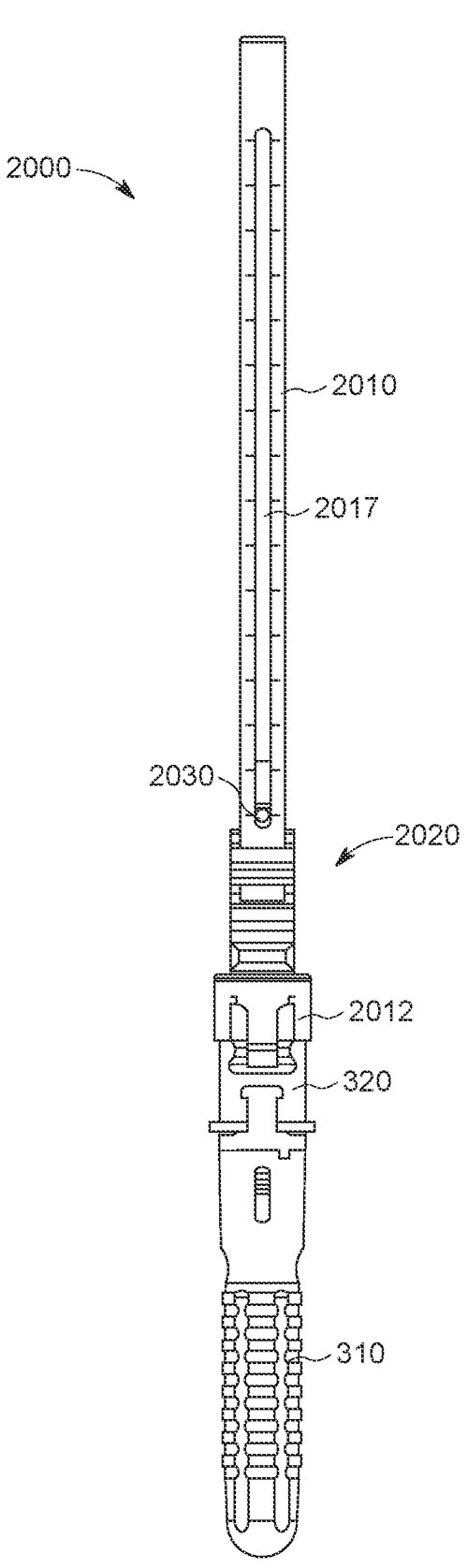
Figure 21C:
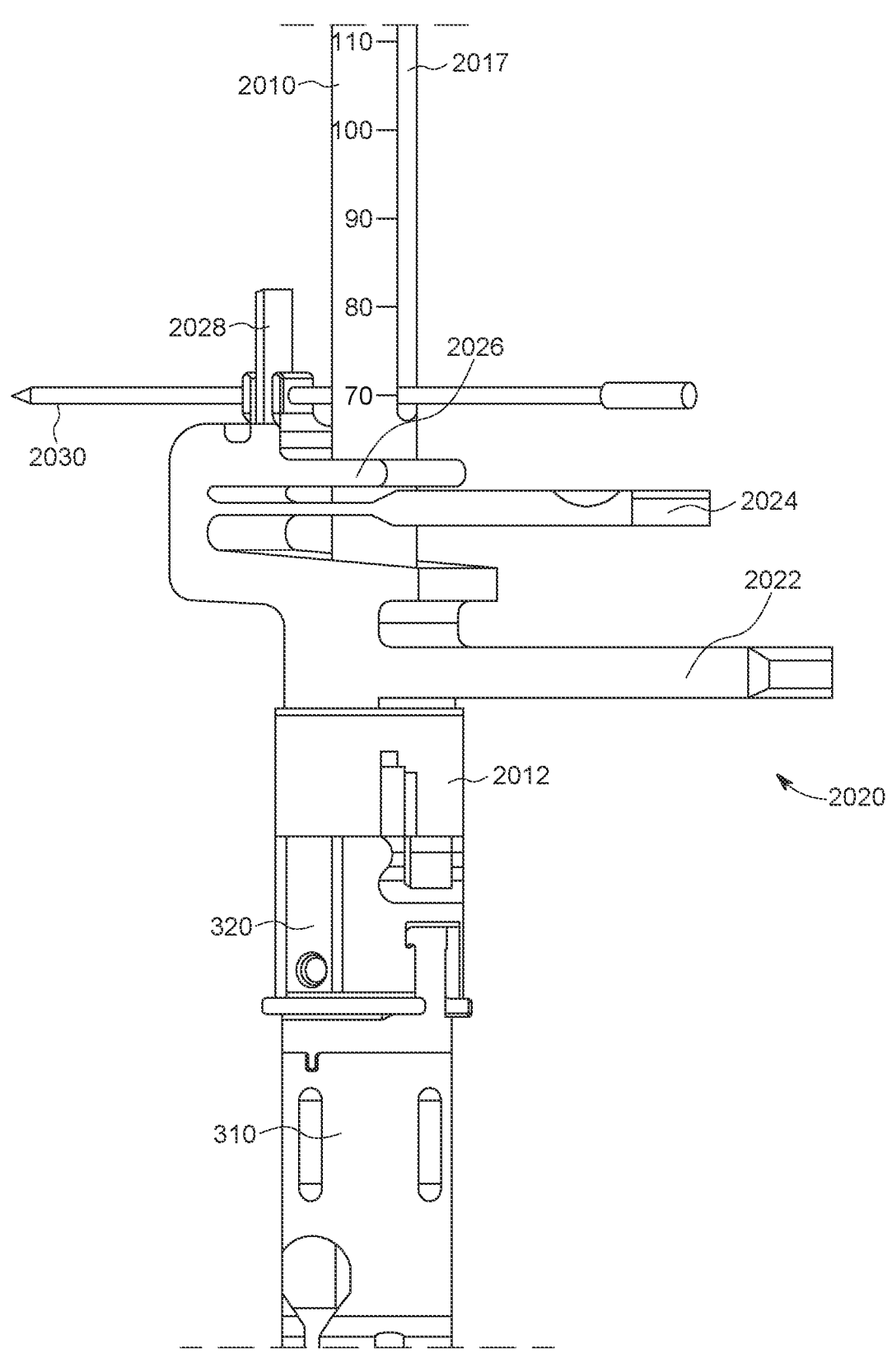
FIG. 21C is an enlarged perspective view of the height measuring gauge assembled to the trial stem of FIGS. 21A-B.
Figure 21D:
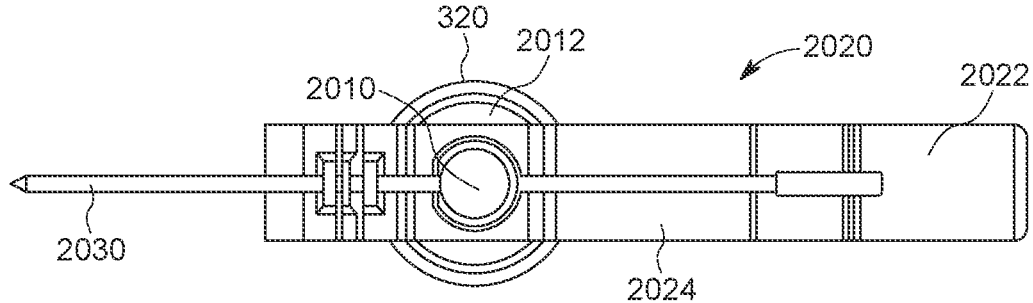
FIG. 21D is a top view of the height measuring gauge assembled to the trial stem of FIGS. 21A-B.

The clamp 2020 may include an aperture through which the scale 2010 extends, a slider 2022, and an arm 2024 spaced from the slider 2022. The slider 2022 may include a generally "D"-shaped aperture that receives the scale 2010 therethrough. The arm 2024, which is positioned proximal but otherwise aligned with the slider 2022, may also include a generally "D"-shaped aperture that receives the scale 2010, with the apertures of the slider 2022 and the arm 2024 being generally aligned. However, the "D"-shaped aperture of the arm 2024 may be slightly angled (similar to the slider 1024 shown in FIG. 14C) so that, when there is no force applied to the arm 2024 relative to the slider 2022, the shape of the aperture of the arm 2024 maintains the clamp 2020 at the current height. In order to slide the clamp 2020 proximally or distally relative to the scale 2010, the arm 2024 may be depressed toward the slider 2022, causing the angled hole to change orientation relative to the scale 2010 and allow sliding of the clamp 2020 proximally or distally relative to the scale 2010. As soon as the force on the arm 2024 is released, it returns to its original orientation to fix the clamp 2020 at the current height. Unlike clamp 1020, clamp 2020 is unable to rotate relative to the scale, whether or not the arm 2024 is depressed, due to corresponding "D"-shapes of the scale 2010 and the apertures in the slider 2022 and arm 2024. It should be also understood that, although an arrow similar to arrow 1034 of clamp 1020 may be provided with clamp 2020 to help indicate the current height (via comparison with the indicia on the scale 2010), such an arrow is not necessary because the main shaft of the pointer 2030 itself may be used to read the height marking of the scale 1020 (as best shown in FIG. 21A).

Clamp 2020 may include a proximal extension 2026 positioned proximal to the arm 2024, and proximal extension 2026 may have a "D"-shaped aperture to receive the scale 2010 therethrough similar to slider 2022. A flexure tab 2028 may extend proximally from the proximal extension 2026, on the opposite side of the scale 2010 from slider 2022. The flexure tab 2028 may include a generally circular hole sized to receive a portion of the pointer 2030 therethrough. The flexure tab 2028 may be positioned between two smaller extensions, each with a generally cylindrical hole aligned with the hole of the flexure tab 2028, so that the pointer 2030 can pass through all three holes. However, similar to the aperture of arm 1024 of clamp 1020, the hole in the flexure tab 2028 may be angled to create friction with the pointer 2030 so that, in the absence of applied forces, the pointer 2030 cannot easily translate through the hole of the flexure tab 2028. However, if a user wants to slide the pointer 2030 toward the user's glenoid so that it makes contact with the glenoid center, the flexure tab 2028 may be pulled to release the friction on the pointer 2030, and the pointer 2030 may be manually advanced. Once the pointer 2030 is in the desired position (e.g. in contact with the glenoid center of the patient), the flexure tab 2028 may be released, and a height reading may be taken, for example by comparing the position of the shaft of the pointer 2030 with the indicia on the scale 2010. It should be understood that height measurement gauge 2000 may be mostly or fully symmetrical, meaning that it may be easily used on either side of a patient's anatomy (e.g. a right or left shoulder arthroplasty), and the configuration of pointer 2030 and scale 2010 may result in the pointer 2030 always being perpendicular to the surface of the glenoid which the tip is intended to contact. Besides the different functionality of pointer 2030 described above, the remaining use of the height measuring gauge 2000 may be substantially similar or identical to height measurement gauge 1000.

Figures 21E, 21F:
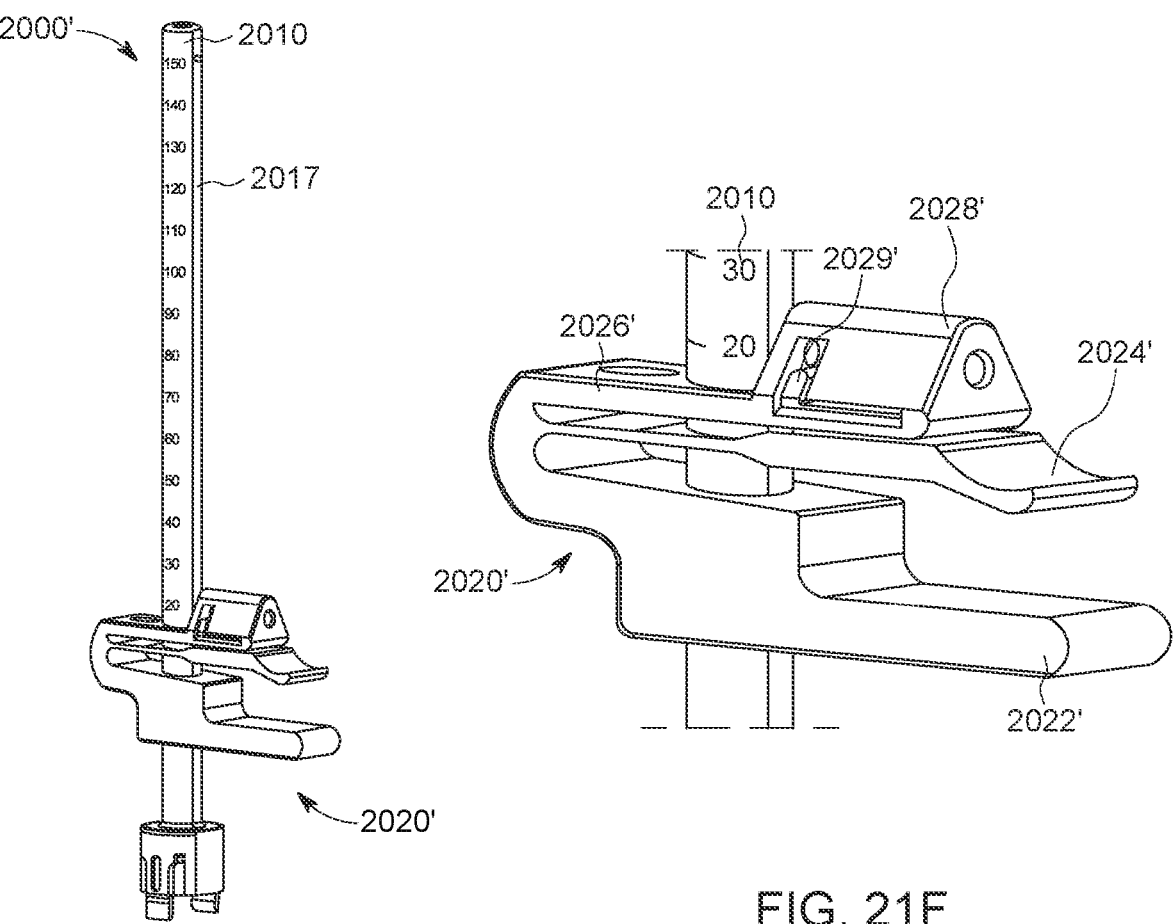
FIG. 21E is a perspective view of a height measurement gauge that is a variant of the gauge of FIG. 21A.
FIG. 21F is an enlarged view of the clamp of the height measurement gauge of FIG. 21E.

FIG. 21E illustrates a height measuring gauge 2000' that is very similar to height measuring gauge 2000, with minor variations. Similar to gauge 2000, gauge 2000' may include a scale 2010 with a slot 2017 which may be identical to the scale 2010 of gauge 2000, and is thus not described again here. Gauge 2000' may include a clamp 2020' that is generally similar to clamp 2020, with certain modifications. Similar to clamp 2020, clamp 2020' includes a slider 2022', an arm 2024', and a proximal extension 2026'. These components may be similar in structure and function to the corresponding slide 2022, arm 2024, and proximal extension 2026 of clamp 2020. The main difference is that clamp 2020' includes a receiver 2028' on the opposite side of the scale 2010 compared to flexure tab 2028. The receiver 2028' may be a generally triangular shape and define a through-hole to receive a pointer (not shown) which may be similar or identical to pointer 2030. Further, whereas flexure tab 2028 locked the pointer 2030 in place, the receiver 2028' holds the pointer in place by friction only. For example, the receiver 2028' may include a flexure finger 2029' that terminates in an upwardly projecting protrusion that presses against the pointer when the pointer is received through the receiver 2028'. The protrusion provides a baseline level of friction against the pointer via the flexure finger 2029' so that the pointer will tend to remain stationary in the absence of applied force (other than the force applied by the flexure finger 2029'). If a user wants to move the pointer, he may simply push or pull the pointer, with the pushing or pulling force overcoming the friction from the protrusion of the flexure finger 2029'. Otherwise, the height measurement gauge 2000' may function identically as described in connection with height measurement gauge 2000.

While the above disclosure generally deals with trial spacers and height measurement gauges, still other instrumentation may be useful in connection with implant systems (including trial components of such implant systems) similar to prosthetic humeral implant 100. For example, it would be desirable to have a handle that could function to assist in inserting and/or extracting an implant stem (e.g. stem 110) and/or a trial stem (e.g. trial stem 210 or 310). Various handles that may be used for this purpose are described in more detail below.

Figure 22A:
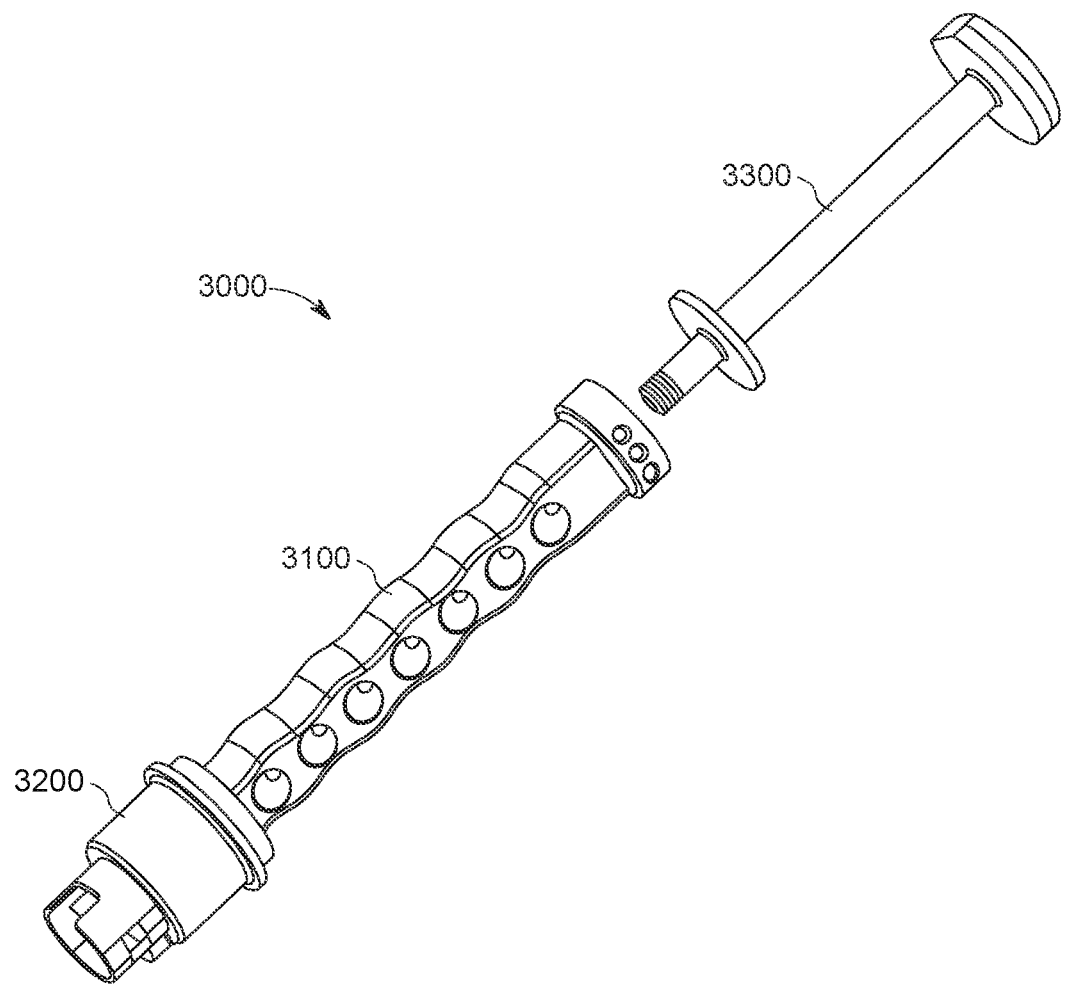
FIG. 22A is a perspective view of a handle system for inserting and extracting trial and implant stems.

FIG. 22A is a perspective view of a first handle system 3000. Generally, handle system 3000 may include a handle 3100 primarily for grasping and transmitting insertion/extraction forces, a sleeve 3200 for coupling an implant/trial stem to the handle system 3000, and a rod 3300 primarily for directly receiving impaction forces for insertion/extraction, as is described in greater detail below.

Figures 22B, 22C, 22D:
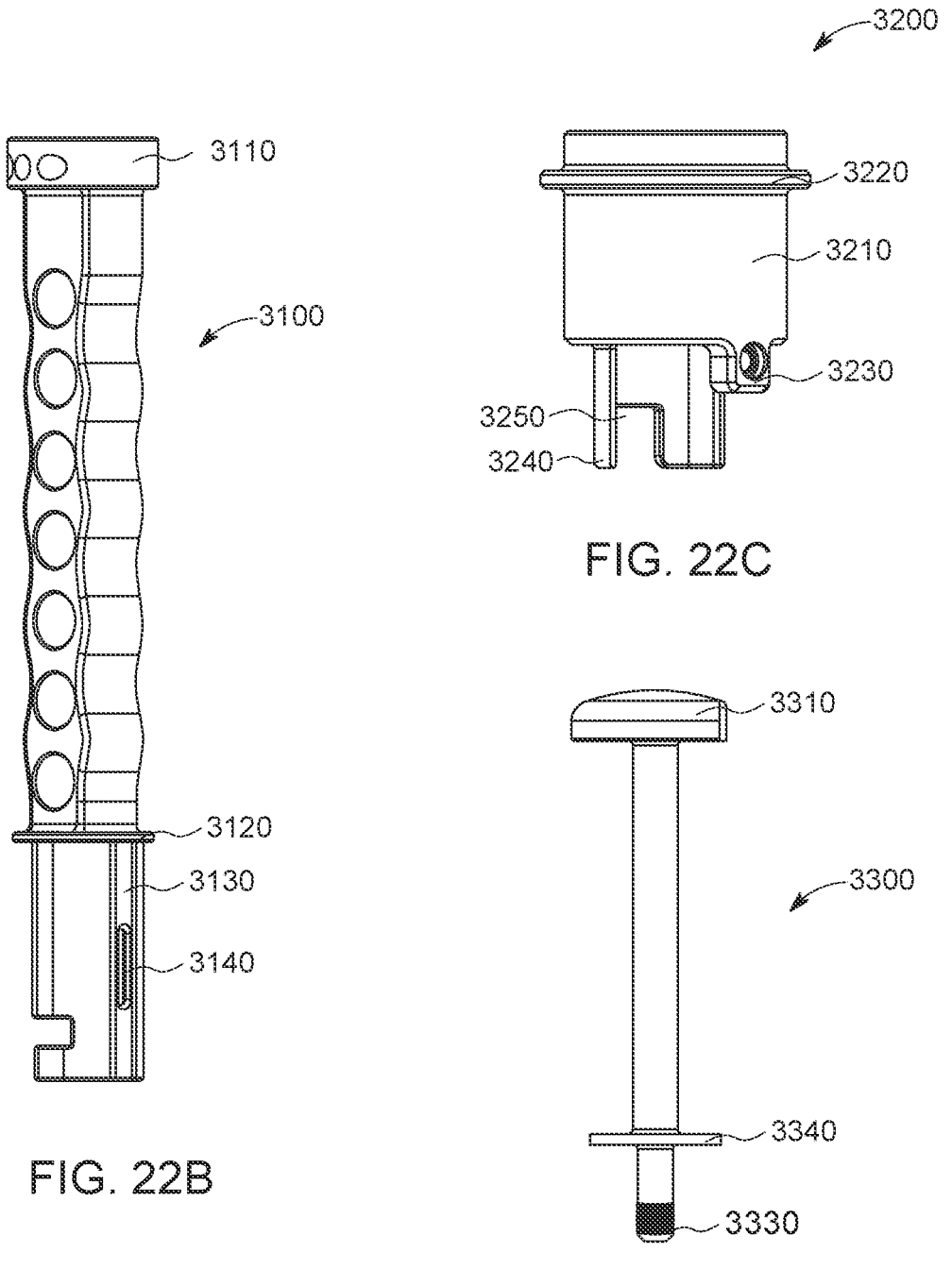
FIG. 22B is a side view of a handle of the handle system of FIG. 22A.
FIG. 22C is a side view of a sleeve of the handle system of FIG. 22A.
FIG. 22D is a side view of a rod of the handle system of FIG. 22A.

FIG. 22B illustrates the handle 3100 isolated from other components of the handle system 3000. The handle 3100 may have an axially extending main body, which may include contouring to assist with easier gripping, and one or more through holes to reduce the weight of the handle 3100. A collar 3110 may be positioned at a proximal end of the main body, which may include one or more version holes into which a version rod may be attached (e.g. via threading), with each version hole corresponding to a pre-set version that is anatomically relevant for a shoulder arthroplasty. A flange 3120, having a diameter larger than the main body, may be positioned at a distal end of the main body of the handle 3100. As described in greater detail below, the flange 3120 may provide a surface for contacting an end of a biasing member, described in greater detail below. The handle 3100 may include a handle sleeve portion 3130 extending distal of the flange 3120. As is described in greater detail below, the handle sleeve portion 3130 may act in cooperation with sleeve 3200 to reversibly attach to a trial stem or implant stem.

FIG. 22C illustrates the sleeve 3200 isolated from other components of the handle system 3000. The sleeve 3200 may have a cylindrical main body 3210 which is hollow and sized to overlie handle sleeve portion 3130. A proximal flange 3220 may extend outward of the main body 3210 and may provide a gripping surface for a user to pull the sleeve 3200 proximally, as described in greater detail below. A protrusion 3230 may extend distally from the main body 3210, and an aperture may be provided in the protrusion 3230 to receive a pin 3400 therethrough, the pin extending into the axial slot 3140 of handle sleeve portion 3130. The interaction of the pin 3400 and the axial slot 3140 is described in greater detail below. Although not visible in the view of FIG. 22C, the main body 3210 may define an inwardly extending shoulder at a distal end thereof, the shoulder providing a surface against which a spring 3420 may rest. Extending distally form the shoulder portion may be a pair of protrusions 3240 defining a recess 3250 therebetween. The protrusions 3240 may be formed along a wall of a cylinder having a smaller diameter (or radius of curvature) than the main body 3210. 340

FIG. 22D illustrates the rod 3300 isolated from other components of the handle system 3200. Rod 3300 may include an impaction surface 3310 at a proximal end of the rod 3300, the impaction surface 3310 having a larger diameter than the rod 3300. The proximal surface of the impaction surface 3310 may be adapted to be impacted in the distal direction for insertion, while the distal surface of the impaction surface 3310 may be adapted to be impacted in the proximal direction for extraction. The distal end of the rod 3300 may include a threaded tip 3330 that may be threaded into a corresponding internally threaded surface 3115 of the interior of the handle 3100, as described in greater detail below. When the rod 3300 is coupled to the handle 3100 via the threaded distal tip 3330, a flange 3340 may abut the proximal surface of collar 3110. With this configuration, impaction of the impaction surface 3310 may be easily transmitted to the handle 3100 via contact between flange 3340 and proximal collar 3110.

FIG. 22E illustrates the sleeve 3200 assembled to the handle 3100, with the sleeve 3200 shown with partial transparency. A pin 3400 may be fixed (e.g. via welding) to the protrusion 3230 of the sleeve 3200, with a leading end of the pin 3400 extending into the axial slot 3140 of the handle 3100. With this configuration, as the sleeve 3200 moves proximally or distally relative to the handle 3100, the sleeve 3200 is unable to rotate relative to the handle 3100 and has a maximum axial extend of translation defined by the proximal end distal ends of the axial slot 3140. Also visible in FIG. 22E is the spring 3420 (although other biasing members besides a spring may be suitable) that is positioned between the sleeve 3200 and the handle 3100. A top or proximal end of the spring 3420 may abut the distal surface of the flange 3120 of the handle 3100, and a bottom or distal end of the spring 3420 may abut the proximal surface of the shoulder of the sleeve 3200. With this configuration, the sleeve 3200 is biased toward the distal (or locked) position relative to the handle 3100. A user may grip the proximal flange 3220 of the sleeve 3200 and pull it proximally relative to the handle 3100 to move the sleeve 3200 to the proximal (or unlocked) position relative to the handle 3100. In this unlocked position, the spring 3420 is more compressed, such that releasing the sleeve 3200 will tend to move the sleeve 3200 back to the distal (or locked) position.

FIG. 22F illustrates the handle system 3000 just before coupling to an adaptor 120' attached to implant stem 110. Adaptor 120' may be generally similar in structure and function to adaptor 120, but may include certain features to assist with mating with handle system 3000. For example, the adaptor 120' may have a main cylindrical body with a tapered proximal opening to receive a spacer such as spacers 130 or 140. Adapter 120' may also have serrated teeth on a distal-facing surface to engage complementary teeth on a proximal-facing surface of the implant stem 110 to help rotationally lock the adaptor 120' to the implant stem 110. Although not shown in FIG. 22F, a screw may be received through the center of the adaptor 120' which may extend into the implant stem 110. That screw may help to secure the adaptor 120' to the implant stem 110. One or more locking screws (not illustrated) may be received through a side aperture 124' to help lock the assembly screw in place. The main cylindrical body of adaptor 120' may be interrupted by a plurality of flats 126'. In the illustrated embodiment, two flats 126' spaced on diametrically opposite sides of the cylindrical body are provided, although other specific numbers and positions of flats may be provided in other embodiments. Each flat 126' is preferably bounded proximally and distally by a cylindrical surface of the main body. The adaptor 120' may include other features described above to help couple spacers to the adapter 120', including for example divots similar to divots 338 of spacer 330 shown in FIG. 6C.

Figure 22G:
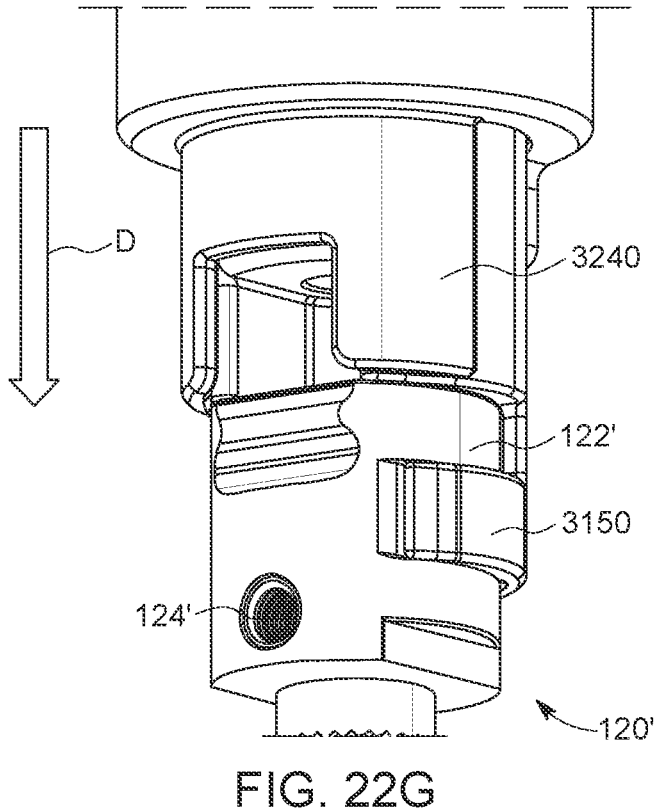
FIG. 22G illustrates the handle system of FIG. 22A just after engagement with the implant stem, while still in an unlocked position.
Figure 22H:
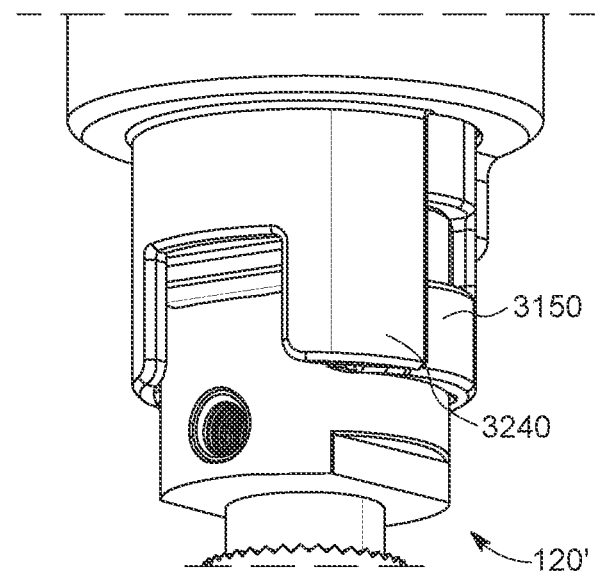
FIG. 22H illustrates the handle system of FIG. 22A just after engagement with the implant stem, after transitioning to a locked position.

Still referring to FIG. 22F, just prior to coupling, the sleeve 3200 has been pulled proximally, and proximal force is maintained on the sleeve 3200, while the spring 3420 is highly compressed. In this proximal or unlocked position, two arms 3150 at the distal end of the handle 3100 are exposed, as are two recesses or slots 3160 proximal to the arms 3150 which help define the arms 3150. The two arms 3150 are sized and shaped to contact the corresponding flats 126' in the adaptor 120', with a proximal collar 122' of the adaptor 120' received within the slots 3160. FIG. 22G illustrates the handle system 3000 after the arms 3150 are slid laterally over flats 126' to engage the handle 3100 to the adaptor 120', but while the sleeve 3200 is maintained in the proximal or unlocked condition. At this point, the user may simply release the force on the sleeve 3200, so that the spring 3420 decompresses, forcing the sleeve 3200 to slide in the distal direction D. FIG. 22H illustrates the sleeve 3200 having transitioned back to the distal or locked position. In this locked position, each protrusion 3240 overlies a portion of the main body of the adaptor 120' as well as a portion of a corresponding arm 3150. In this locked condition, which is maintained by the spring 3240 in the absence of applied forces, lateral, axial, and rotational movement between the adaptor 120' and the handle system 3000 is prevented. Although FIGS. 22F-H illustrate connection of the handle system 3000 to the adapter 120' of implant stem 110, it should be understood that a trial stem (e.g. trial stem 210 or 310) may include an adaptor that has the same mating features to allow the handle system 3000 to connect to the adaptor of the trial stem in the exact same way as described in connection with FIGS. 22F-H.

Exemplary uses of the handle system 3000 for insertion and extraction of a trial stem 210 or an implant stem 110 are described below in connection with FIGS. 22I-L. For insertion of a trial stem 310, the handle system 3000 may be coupled to an adapter 220' of the trial stem 210 in the same way as shown and described in connection with FIGS. 22F-H. With the handle system 3000 coupled to the trial stem, the proximal surface of the handle collar 3110 may be directly impacted to drive the trial stem 310 into the humerus. As shown in FIGS. 22I-J, the handle 3100 is cannulated so that devices, such as driver 3500, may be inserted through the handle 3100 and into the stem coupled to the handle 3100. In the example illustrated in FIGS. 22I-J, a driver (e.g. a T20 driver) is inserted through the cannular of the handle 3100 and into the head of a screw within the trial stem 210. The driver 3500 may be used to advance the screw to force expansion of the trial stem 210 (in the case of an expandable trial stem). The handle 3100 may be provided with contours to aid with gripping the handle 3100 to help prevent rotation of the trial stem 210 while torquing the screw. If the version of the trial stem 210 needs to be adjusted, the driver 3500 may be used to unlock the screw, and the handle 3100 may be manually rotated to align a version rod coupled to the handle collar 3110 as desired. Once the version is adequate, the trial stem 210 may again be expanded using the 3500 to advance the screw. To remove the handle system 3000 from the trial stem 210, the steps of FIGS. 22F-H may be performed in reverse order.

After trialing is complete, the trial stem 210 may be extracted from the patient using the handle system 3000. The handle system 3000 is again coupled to the trial stem 210 in the same manner as described in connection with FIGS. 22D-F, and the driver 3500 is used to unlock the screw in the trial stem 210. After unlocking, the driver 3500 may be removed and the rod 3300 may be coupled to the handle 3100. Briefly referring to FIGS. 22K-L, the distal threaded tip 3330 may be threaded into the internal threaded surface 3115 of the handle 3100, resulting in close contact between the flange 3340 and the collar 3110. Although FIGS. 22K-L illustrate the handle system 3000 coupled to the implant stem 110, the same configuration may apply when the handle system 3000 is instead coupled to the trial stem 210. After the rod 3300 is coupled to the handle 3100, reverse impaction may be performed by impacting the bottom or distal surface of the impaction surface in a proximal or upward direction to remove the trial stem 210 from the bone.

For insertion of the implant stem 110 into the bone, the handle system 3000 may be coupled to the implant stem 110 in the same manner as described in connection with FIGS. 22F-H, and the rod 3300 coupled to the handle 3100 as described above. A version rod may be attached to the collar 3110 at the desired angle. The handle 3100 may be used to align the version of the implant stem 110 by referencing the version rod, and a proximal (or top) portion of the impaction surface 3310 may be impacted in a distal (or downward) direction to insert the implant stem 110 into the bone. If the implant stem 110 needs to be removed from the bone, for example for version adjustment, the same procedure as described above for trial stem 210 may be performed. After the implant stem 110 is confirmed to be in the final desired position, the handle system 3000 may be disconnected from the implant stem 110 as described in connection with FIGS. 22F-H, in reverse order.

One of the benefits of handle system 3000 are that a single instrument (or instrument system) may be used with both a trial stem as well as an implant stem, including for both insertion (impaction) and extraction (reverse impaction). Another benefit is that the handle system 3000 may be rapidly and easily connected to, or disconnected from, the trial or implant stem, with the connection being secure upon engagement.

Figure 23A:
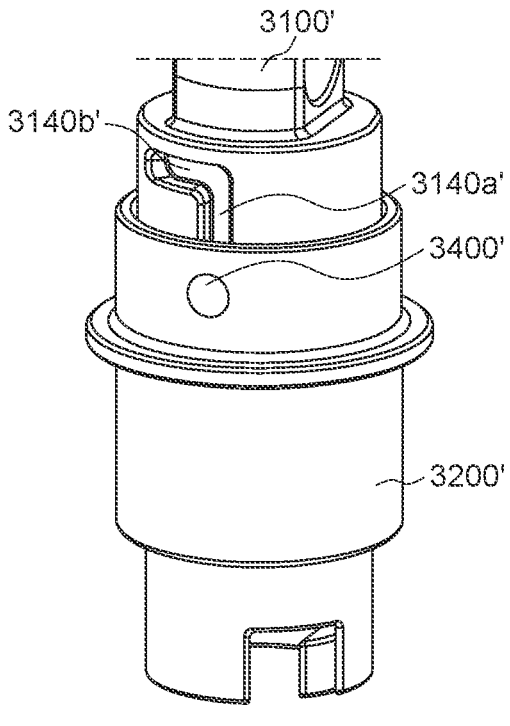
Figure 23B:
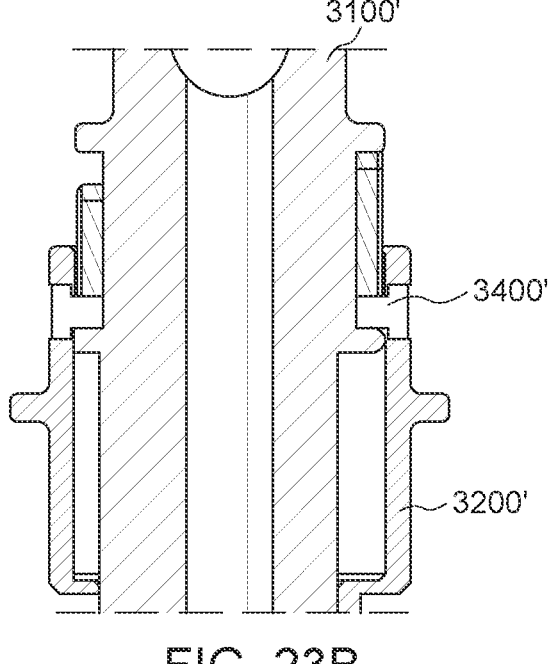

FIGS. 23A-D illustrate a portion of a handle system that is identical to handle system 3000, with certain exceptions on the handle and sleeve, which provide a "twist-to-lock" mechanism compared to the pulling mechanism of handle system 3000. Referring to FIG. 23A, which shows a perspective view of the distal end of the handle 3100' and the sleeve 3200', it can be seen that the sleeve 3200' is highly similar to sleeve 3200. Sleeve 3200' may be a more complete cylinder than sleeve 3200, and may include a pair of pins 3400' fixed to the sleeve 3200'. Each pin 3400' may be received within a corresponding slot 3140' of the handle 3100'. However, instead of the slot being only an axial slot, each slot 3140' includes an axial portion 3140a' and a circumferential portion 3140b' that together form an "L" shape, with the circumferential portion 3140b' being positioned proximal to the axial portion 3140a'. Referring now to FIG. 23B, which is a cross-section of the view of FIG. 23A, it should be understood that a spring (not shown) similar or identical to spring 3420 may be provided between sleeve 3200' and handle 3100'. With this configuration, the top of the spring abuts a flange of the handle 3100', while the bottom of the spring abuts an internal bottom shoulder of the sleeve 3200', so that the spring tends to bias the sleeve 3200' downwardly or distally relative to the handle 3100.

FIGS. 23C-D show the sleeve 3200', in partial transparency, in the open or unlocked, and closed or locked, positions respectively. The operation of sleeve 3200' is generally similar to that described for sleeve 3200', except that after manually pulling the sleeve 3200' proximally (while the pins

3400' travel along the axial slot portion 3140a' as shown in FIG. 23D), the sleeve 3200' may be rotated so that the pins 3400' travel along the circumferential slot portion 3140b' as shown in FIG. 23C. With this configuration, while the pins 3400' are in the circumferential slot portions 3140b', the sleeve 3200' is unable to transition to the locked position of FIG. 23D, even if the user releases his grip on the sleeve 3200'. The main benefit if this embodiment, compared to that of FIGS. 22A-L, is that the user can release his grip on the sleeve 3200' as the handle system is coupled to, or decoupled from, the implant or trial stem while the sleeve 3200' is in the open or unlocked condition. In order to switch back to the closed or locked condition, the user simply rotates the sleeve 3200' until the pins 3400' are in the axial slot portion 3140a', at which point the spring will tend to decompress to advance the sleeve 3200' distally or downwardly relative to the handle 3100. It should be understood that only a single slot and single pin may be provided, or two or more slots and corresponding pins may be provided. The operation and components of the embodiment of FIGS. 23A-D, but for the differences described above, may be identical to that of handle system 3000.

Figure 24A:
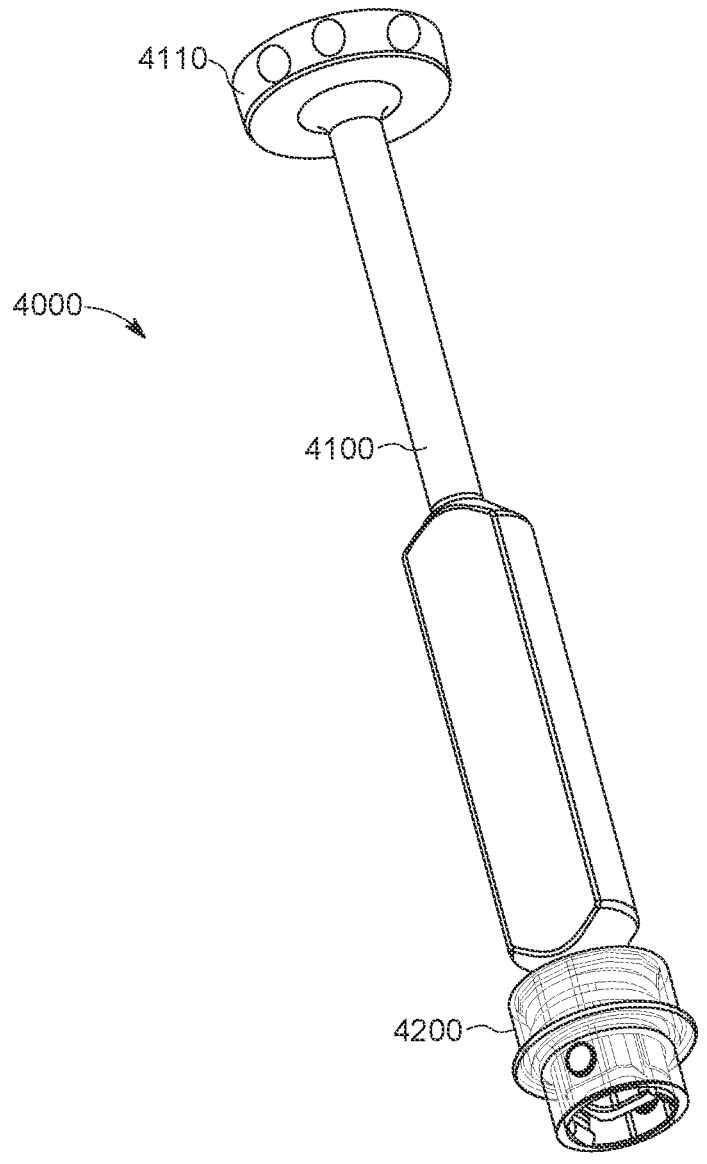
FIGS. 24A-E are various illustrations of a handle system of inserting and extracting trial and implant stems according to another aspect of the disclosure.

FIGS. 24A-E illustrate a handle system 4000 that has generally similar functionality to handle system 3000 described above, but with a number of variations. FIG. 24A illustrates the handle system 4000, which may mainly include a handle 4100, and a sleeve 4200. Handle 4100 may include a proximal impaction surface 4110, a generally cylindrical shaft extending distally from the impaction surface 4110, and an enlarged tripping portion extending distally from the cylindrical shaft. Compared to handle 3100, handle 4100 may be somewhat less complex since handle 4100 is formed as a single member. Although not labeled, impaction surface 4110 may include a plurality of holes or apertures for attaching a version rod at pre-defined angles.

Figures 24B, 24C:
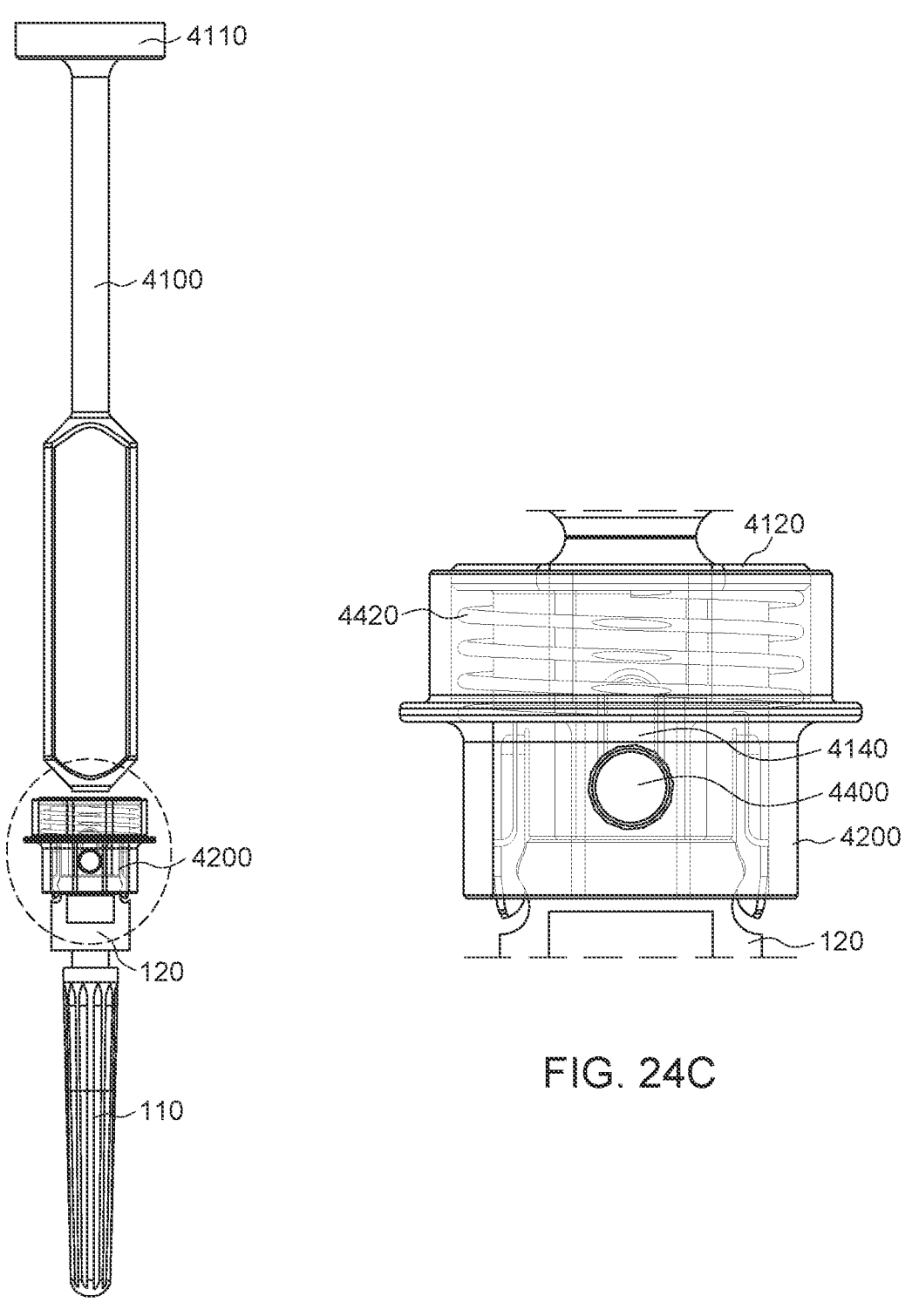

As with handle system 3000, handle system 4000 may be configured to easily couple and decouple with either an implant stem 110 or a trial stem. FIG. 24B shows the handle system 4000 coupled to an implant stem 110, but the description applies with substantially equal force to a trial stem. The coupling between the sleeve 4200 and the implant adaptor 120, outlined in a dashed circle in FIG. 24B, is shown enlarged in FIG. 24C, with the sleeve 4200 having partial transparency. As with handle system 3000, the handle 4100 of handle system 4000 may include a flange 4120 near a distal end, and the sleeve 4200 may include an internal shoulder so that a spring 4420 (or other biasing member) can be received between the sleeve 4200 and the flange 4120 in order to bias the sleeve 4200 distally (or downwardly) relative to the handle 4100. Also similar to handle system 3000, the handle 4100 of handle system 4000 may include an axial slot 4140, and a pin 4400 may be fixed to the sleeve 4200 and extend into the axial slot 4140. The interaction between the pin 4400 and the axial slot 4140 may prevent rotation of the sleeve 4200 relative to the handle 4100, and provide limits for the total axial travel possible for the sleeve 4200 relative to the handle 4100.

Figure 24D:
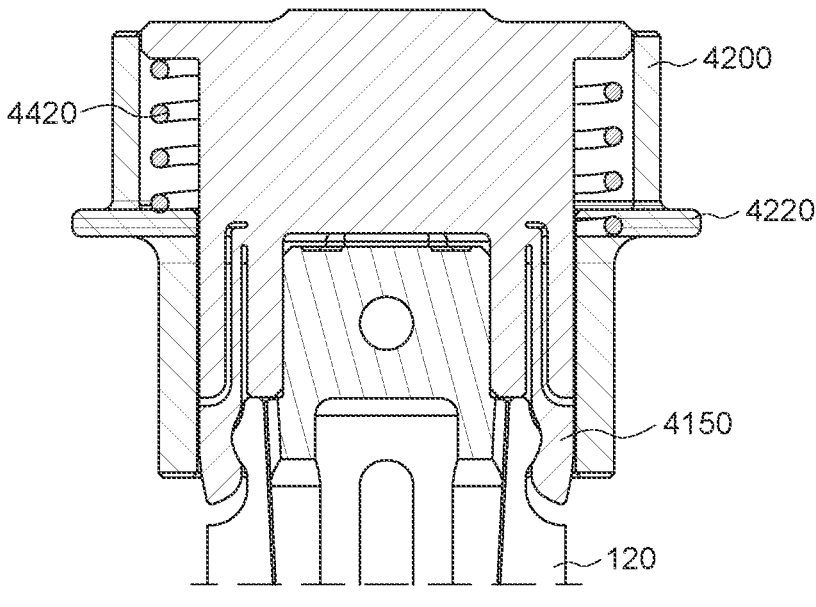
Figure 24E:
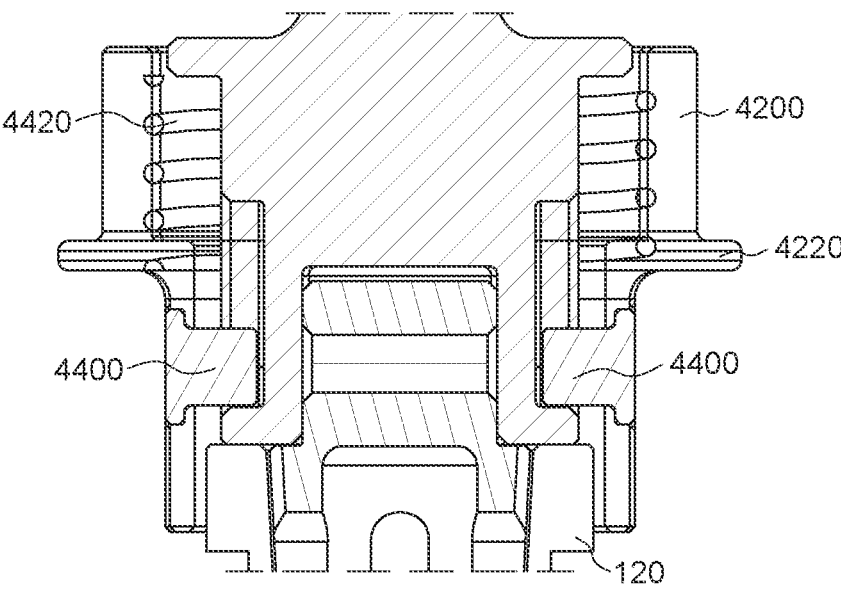

FIGS. 24D-E are cross-sections of the view of FIG. 24C, taken at 90-degree angles relative to each other. First referring to FIG. 24E, the two pins 4400 are shown within the corresponding slots 4140 with the sleeve 4200 in the closed or locked condition (e.g. the spring 4420 at maximum decompression) such that the sleeve 4200 surrounds at least part of the adaptor 120. As with handle system 3000, the sleeve 4200 of handle system 4000 includes a flange 4220 that can be manually pulled proximally to compress the spring 4420 until the sleeve 4200 fully clears the adaptor 120.

Now referring to FIG. 24D, the distal end of the handle 4100 may include flexure arms 4150 extending distally therefrom. In the illustrated example, the handle 4100 includes two flexure arms 4150 that are coupled to the handle 4100 via a thin link such that the flexure arms 4150 are capable of flexing inwardly or outwardly. The flexure arms 4150 may terminate in a contoured tip that has a shape complementary to a groove and/or protrusion in the adaptor 120, much like the spacers 330 of FIGS. 6A-H. The interior of the sleeve 4200 contacts the outside of the flexure arms 4150 when the sleeve 4200 is in the distal or locked position shown in FIG. 24D, such that the flexure arms 4150 are prevented from flexing outwardly. Thus, in order to couple the handle system 4000 to the trial or implant stem 110, the user pulls the sleeve 4200 proximally so that the sleeve 4200 clears the flexure arms 4150. The user may then press the handle system 4000 downwardly over the adapter 120, causing the flexure arms 4150 to flex outwardly, and then "snap" back into the groove(s) of the adaptor 120. Then, the sleeve 4200 is released and the spring 4420 starts to decompress, pushing the sleeve 4200 into the distal or locked position. As noted above, in this position, the flexure arms 4150 are no longer capable of flexing outwardly, and thus the trial or implant stem is locked to the handle system 4000.

Other than the way in which sleeve 4200 locks to the trial or implant stem, and the fact that the handle 4100 is a monolithic member, the use of handle system 4000 may be essentially the same as the handle system 3000, and thus is not described again herein. In some embodiments, the handle 4100 may be cannulated like handle 3100.

Figures 25A, 25B, 25C:
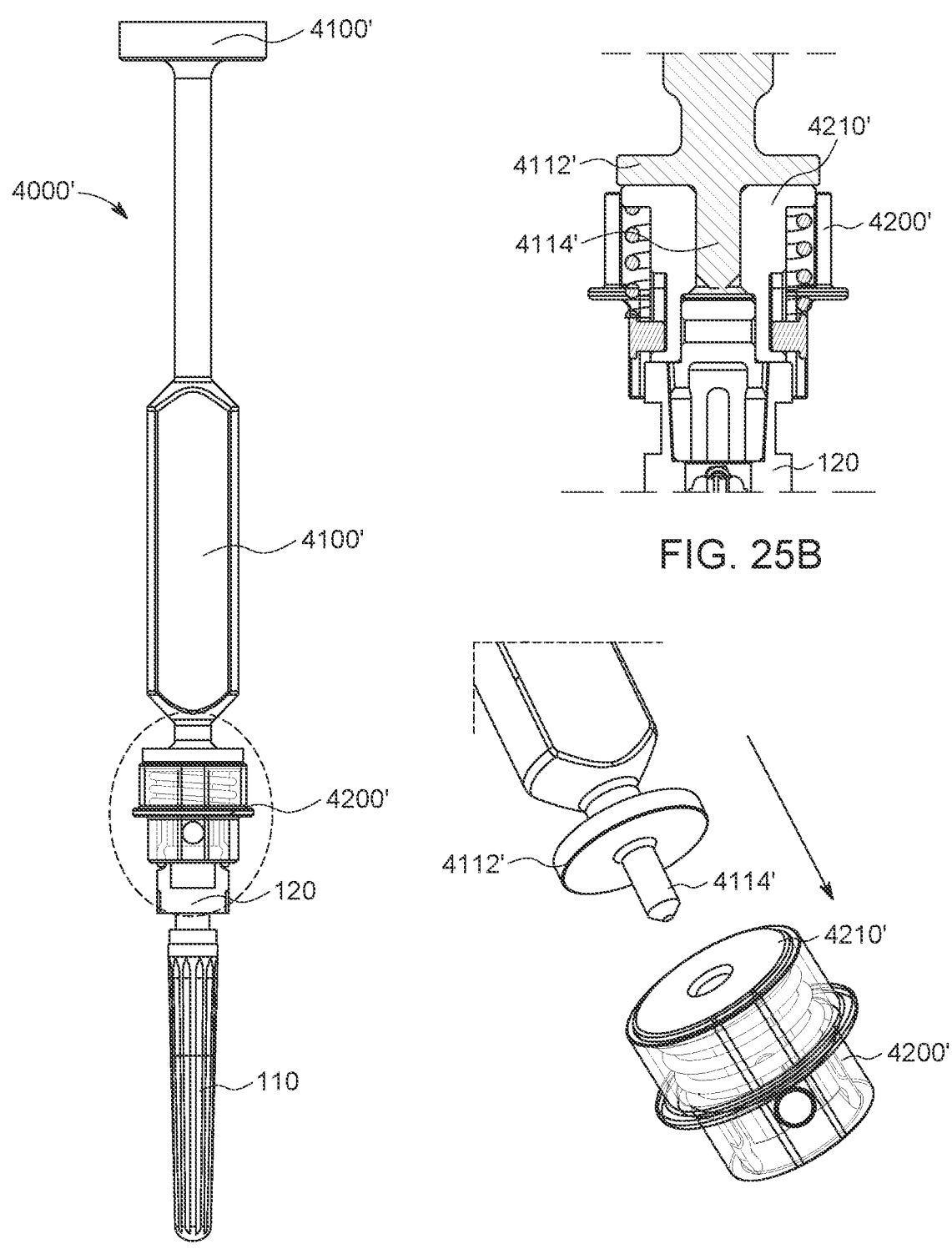
FIGS. 25A-F are various illustrations of a first variation of the handle system of FIGS. 24A-E.
Figure 25D:
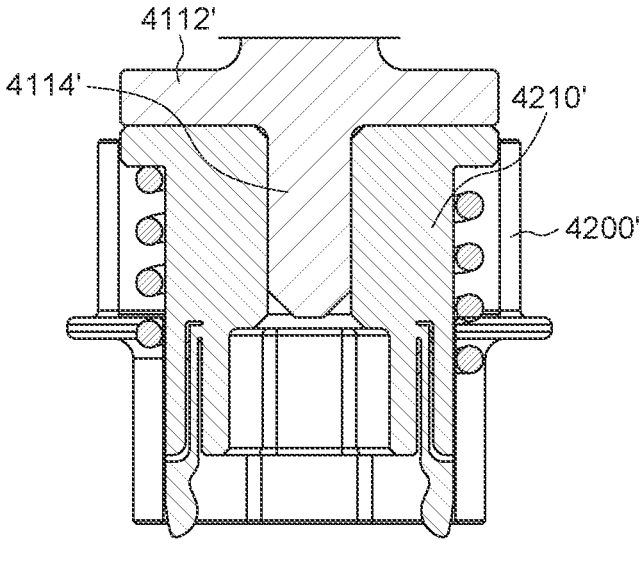

FIGS. 25A-F illustrate a handle system 4000' that is a slight variation of handle system 4000 above. The main difference of handle system 4000' is that the handle 4100' is formed as a piece that separately couples to a sleeve assembly. FIG. 25B is a cross-section of the connection location of FIG. 25A. As shown in FIG. 25B, the handle 4100' includes a distal flange 4112' and a threaded tip 4114' extending distally therefrom. The sleeve assembly includes a sleeve 4200' and an inner sleeve body 4210'. The sleeve assembly is structurally similar or identical to sleeve 4200 and the corresponding portion of handle 4100 within the sleeve 4200, except that the sleeve assembly is provided as a single unit that is attached separately to the handle 4100'. As with handle system 4000, a spring or other biasing member may be provided within the sleeve assembly.

The sleeve assembly of handle system 4000' may couple to an implant or trial stem (e.g. to an adaptor on the stem) in essentially the same fashion as described in connection with handle system 4000. First, the handle 4100' may be coupled to the inner sleeve body 4210', for example by threading the distal tip 4114' of the handle 4100' into a complementary internal threading in the inner sleeve body 4210'. After the handle 4100' is coupled to the inner sleeve body 4210', the remainder of the process for coupling or decoupling the handle system 4100' to an implant or trial stem is essentially identical. For example, the sleeve 4200' may be pulled proximally relative to the inner sleeve body 4210' to compress the spring until the sleeve 4200' clears the flexure arms, which may be snapped over a stem adaptor, in generally the same fashion as described in connection with handle system 4000. After attachment, the user may release the sleeve 4200', causing the spring to decompress and the sleeve to cover the flexure arms of the inner sleeve body 4210', preventing disengagement of the implant or trial stem.

Figure 25E:
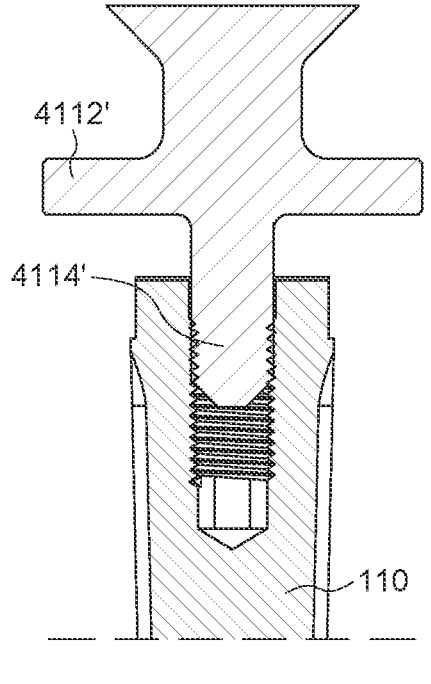
Figure 25F:
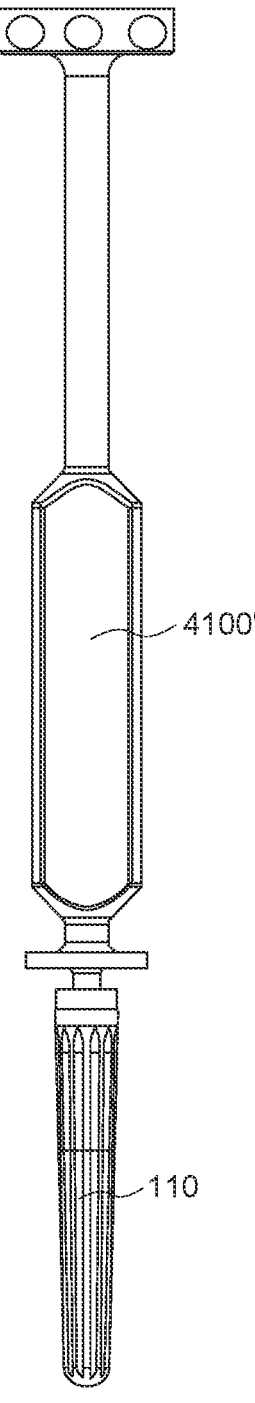

Once coupled, the impaction surface 4110' may be impacted for insertion or extraction. One benefit of the handle system 4000' compared to handle system 4000 is that the modularity may allow for the handle 4100' to act as a separate extractor. For example, as shown in FIGS. 25E-F, the threaded distal tip 4114' may also be configured to thread directly into an implant 110 (as opposed to coupling via the sleeve assembly and adaptor 120), so that the handle 4100' may separately be used as an extractor for a previously-implanted implant stem 110.

Figure 26:
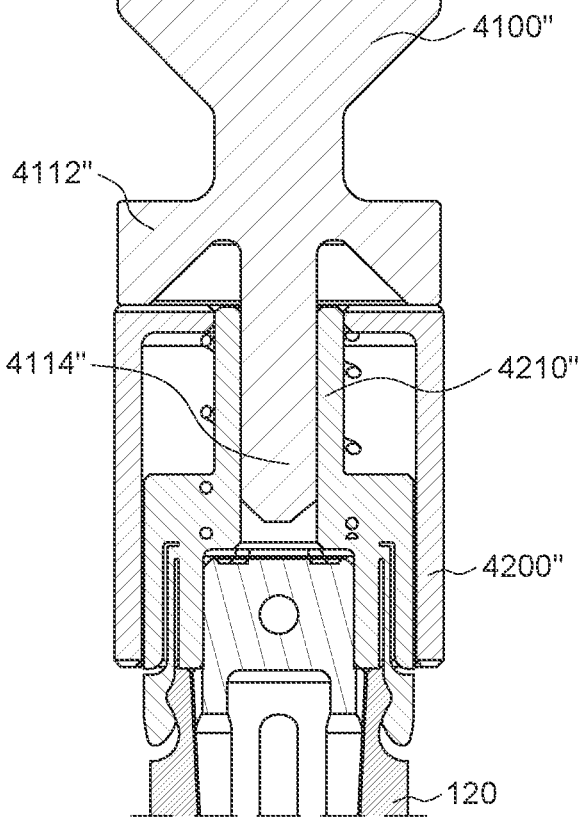
FIG. 26 is a cross-section of a second variation of the handle system of FIGS. 24A-E.

FIG. 26 illustrates a cross-section of a further variant similar to handle system 4000'. The main difference here is that handle 4100" includes a distal flange 4112" that has interior recesses into which a proximal end of the sleeve inner body may extend. With this configuration, the handle 4100" may first be coupled to the sleeve assembly by threading the distal tip 4114" into the complementary threaded interior surface of the inner sleeve body 4210". However, in this embodiment, the spring biases the sleeve 4200" proximally or upwardly relative to the inner sleeve body 4210" so that the sleeve assembly is naturally in the unlocked condition. To transition the sleeve assembly to the locked condition, the user may continue to thread the distal tip 4114" into the inner sleeve body 4210", causing the spring to compress and the sleeve 4200" to move distally. This is possible because the top of the inner sleeve body 4210" can move into the void space of the distal flange 4112" as the relative movement occurs. When the handle 4100" is fully threaded, the sleeve 4200" covers the flexure arms to prevent disengagement between the flexure arms and the adaptor 120. Other than the differences described above, the functionality of the embodiment of FIG. 26 is essentially the same as handle assembly 4000'.

Figures 27A, 27B:
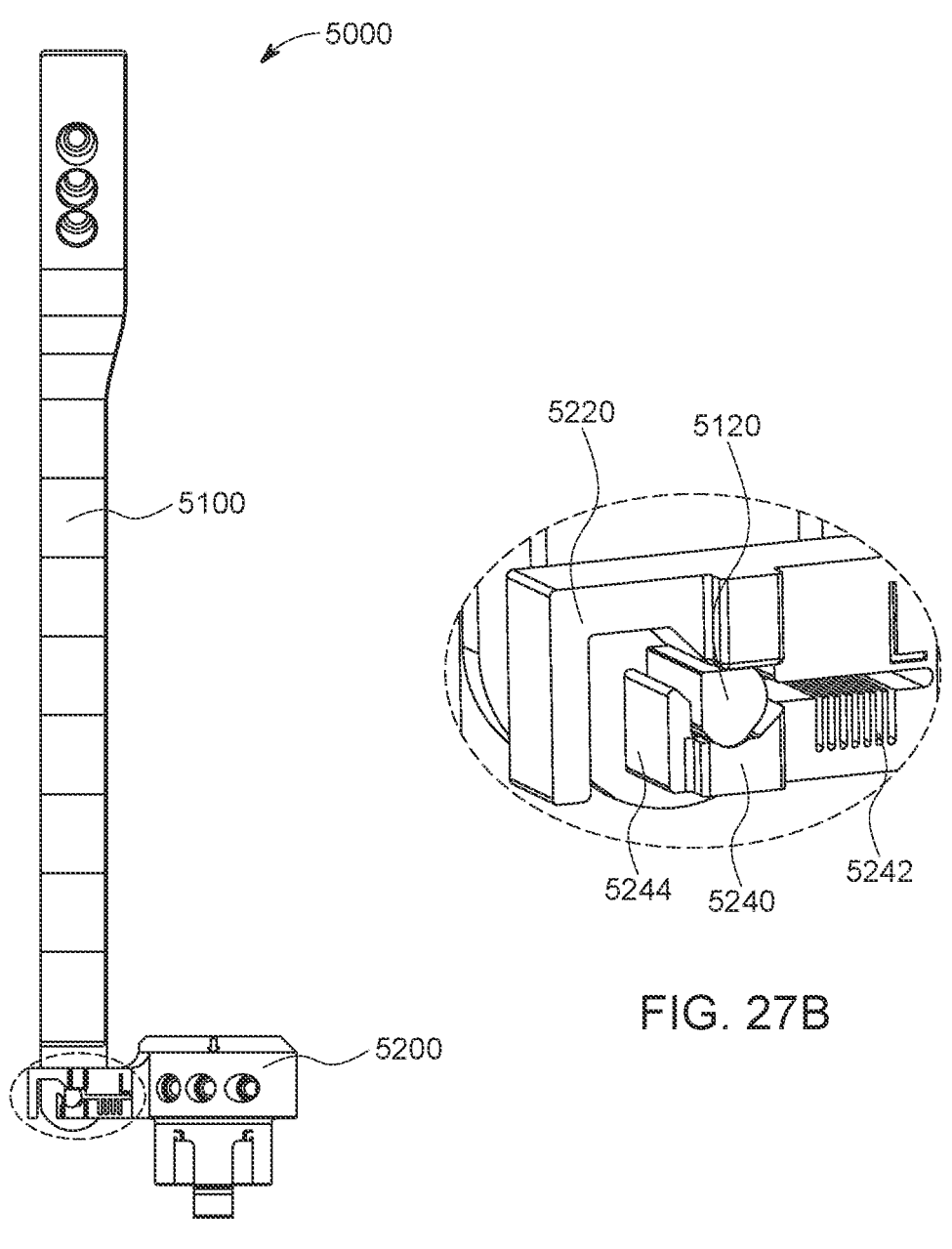

FIGS. 27A-H illustrate a handle assembly 5000 according to another aspect of the disclosure. One distinguishing feature of handle assembly 5000, compared to handle assemblies 3000, 4000, is that handle assembly 5000 has different rotational positions to allow for vertical or horizontal handle positioning. Referring to FIG. 27A, handle assembly 5000 may include a handle 5100 and an impaction member 5200. Handle 5100 may include a main handle body, with a proximal handle end that may include a plurality of holes for coupling with a version rod at different predetermined angles, and a distal handle end that connects to the impaction member 5200. Although not shown in FIGS. 27A-H, the proximal handle end may have a wrench-shape configured to engage an implanted trial to adjust the version of the trial. This feature is separately described in connection with handle assembly 6000 of FIGS. 31A-K, but it should be understood that description also applies to handle assembly 5000. The impaction member 5200 may have a proximal surface for impacting to drive a trial or implant stem coupled thereto into the humerus. The impaction member 5200 may also include holes to accept a version rod at desired pre-determined angles. The distal end of the impaction member 5200 may include features for coupling to adaptors of an implant or trial stem. For example, this particular embodiment of impaction member 5200 may include two prongs that are substantially shaped like the prongs 333 of spacer 330. Although this is one shape that may be used to couple the impaction member 5200 to the trial or implant stem, it should be understood that other connection configurations may be used, including any of those described above. Although not viewable in the figures, the impaction member 5200 may include a central opening to pass devices, such as drivers, therethrough and into the trial or implant stem coupled to the impaction member 5200.

Figure 27C:
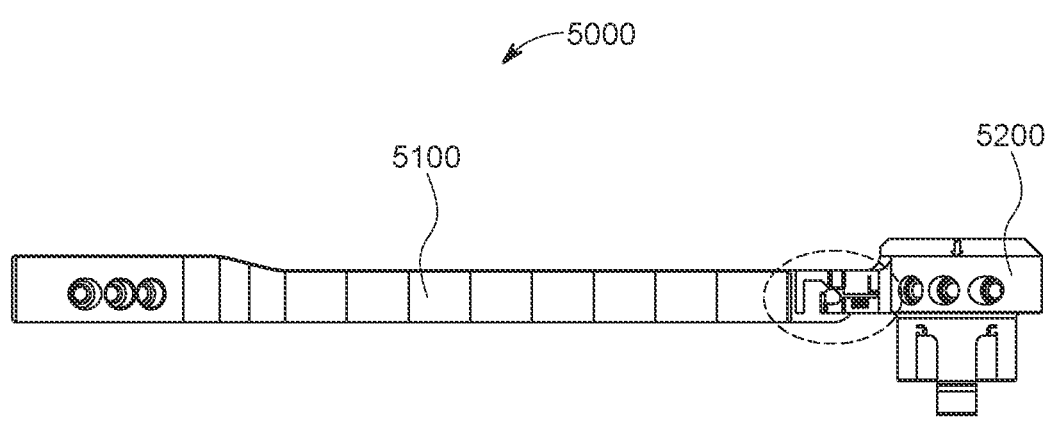

FIG. 27A illustrates the handle 5100 in a vertical orientation relative to the impaction member 5200, which would be substantially parallel to the central longitudinal axis of the implant or trial stem coupled to the impaction member 5200. This orientation may be particularly useful when coupling the impaction member 5200 to the trial or implant stem. FIG. 27C, on the other hand, illustrates the handle 5100 in a horizontal orientation relative to the impaction member 5200. This orientation may be particularly useful when impacting the impaction member 5200. Further, the handle 5100 in the horizontal orientation may assist in providing counter-torque if a screw within the implant or trial stem is being rotated (e.g. using a driver passing through the impaction member 5200). As is described in greater detail below, the vertical and horizontal orientations may be stable orientations, in which the orientation resists changing until and unless a user intentionally applies a rotational force to the handle 5100.

Figure 27D:
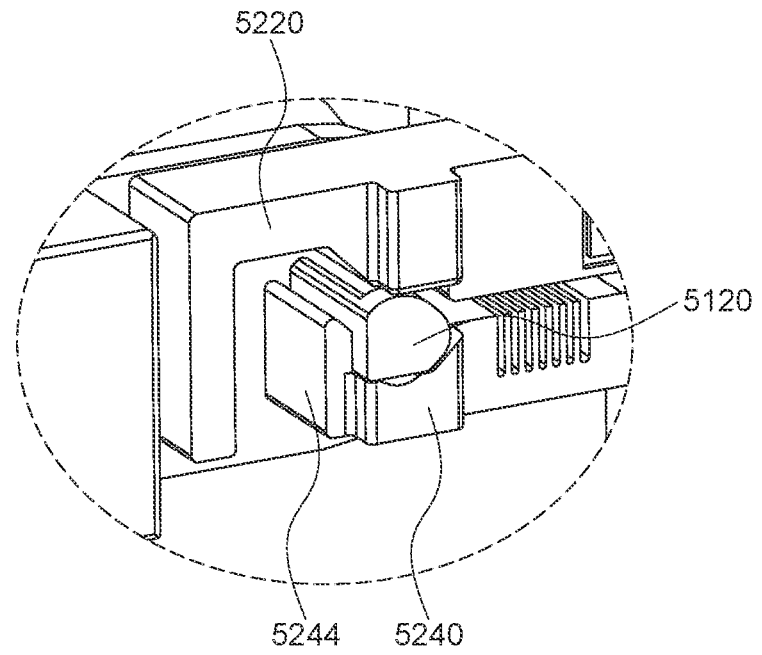

FIG. 27B is an enlarged view of the dashed circle of FIG. 27A, illustrating the connection between the handle 5100 and the impaction member 5200. FIG. 27D corresponds to FIG. 27B, but with the handle 5100 in the horizontal orientation. Referring to FIGS. 27B and 27D, the distal end of the handle 5100 may include a pair of pins 5120 extending outward therefrom, the pins 5120 configured to pivotably couple the handle 5100 to the impaction member 5200. The impaction member 5200 may include a pair of horizontal extensions including an upper arm 5220 and a lower arm 5240 that cooperate to receive the pins 5120 to pivotably couple the handle 5100 to the impaction member 5200. In the illustrated embodiment, the top arm 5220 is generally "L"-shaped and the bottom arm 5240 is a substantially straight member. The bottom arm 5240 may include a plurality of cutouts 5242 so that the bottom arm 5240 is a flexure arm. Each pin 5120 may include two substantially straight edges that form a 90-degree angle, and two cam surfaces, each cam surface adjacent to an end of a corresponding straight edge. The bottom arm 5240 may terminate in an upward projection wall 5244 that ends a spaced distance from the upper arm 5220, and which presents a straight surface toward a cavity between the upper arm 5220 and lower arm 5240. The bottom arm 5240 may also include a curved profile just prior to the wall 5240, the curved profile positioned where the pins 5120 are positioned.

With the configuration described above, the pins 5120 may preferentially lock between the upper arm 5220 and bottom arm 5240 when the handle 5100 is in either the horizontal or vertical position. However, as the handle 5100 transitions between the horizontal and vertical positions, the handle 5100 does not lock into any intermediate position between the horizontal and vertical positions. For example, in the horizontal and vertical positions of the handle 5100, one of the flat surfaces of the pins 5120 contacts the flat surface of wall 5244, while the other flat surface of the pins 5120 contacts a flat surface of the top arm 5220. This flat-to-flat contact helps lock the pin 5120 in that rotational orientation relative to the upper arm 5220 and lower arm 5240. As the handle 5100 rotates between the horizontal and vertical positions, the cam surfaces of the pins 5120 tend to flex the bottom arm 5240 downwardly, until the flats meet again at which point the bottom arm 5240 may "snap" back into place. However, it should be understood that even in the horizontal and vertical positions, the bottom arm 5240 may be flexing to provide compression on the pins 5120, further helping to maintain the horizontal or vertical position.

FIGS. 27E-H illustrate an exemplary use of handle assembly 5000. In a first step, shown in FIG. 27E, the pins 5120 are slide upward through a channel defined between the "L"-shape of the upper arm 5220 and the terminal wall 5244 of the lower arm 5240. Then, as shown in FIG. 27F, the pins 5120 are advanced past the terminal wall 5244 into the cam cavity between the upper arm 5220 and lower arm 5240. Once received in the cam cavity, the bottom arm 5240 is flexing and causing compression on the pins 5240, helping to lock the handle 5100 in the horizontal position, as shown in FIG. 27G. To transition to the vertical orientation, the user may manually rotate the handle 5100 upwardly, with the complementary shape of the pin 5120 and the cam cavity helping the pins 5120 self-align when the handle 5100 is in the vertical orientation. Some of the benefits of handle assembly 5000 are that the handle 5100 can be quickly, easily, and reliably rotated and locked into the desired horizontal or vertical orientation. Also, similar to other handle assemblies described herein, the handle assembly 5000 may be used with both trial and implant stems.

Figure 28A:
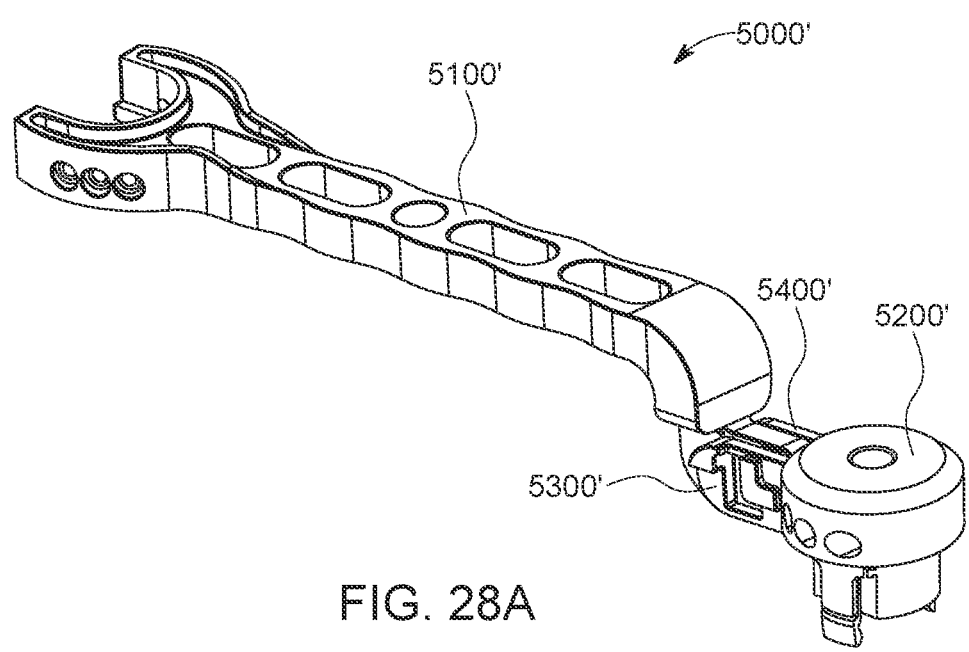
FIG. 28A is a perspective view of a rotatable handle system according to another aspect of the disclosure.
Figure 28B:
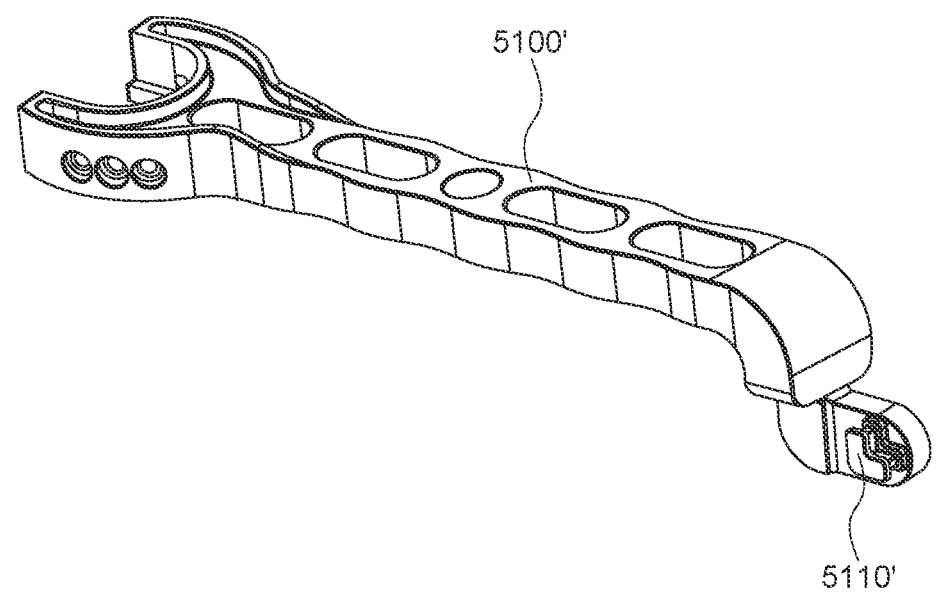
FIG. 28B is a perspective view of the handle of the handle system of FIG. 28A.

FIG. 28A illustrates a handle assembly 5000' that has features in common with handle assembly 5000. Handle assembly 5000' may include a handle 5100' and an impaction member 5200'. Handle 5100' may include a main handle body, with a proximal handle end that may include a plurality of holes for coupling with a version rod at different predetermined angles, and a distal handle end that connects to the impaction member 5200'. As shown in FIGS. 28A-B, the proximal handle end may have a wrench-shape, including two prongs with internal flat surfaces, to engage an implanted trial to adjust the version of the trial. This feature is separately described in connection with handle assembly 6000 of FIGS. 31A-K, but it should be understood that description also applies to handle assembly 5000'. The impaction member 5200' may have a proximal surface for impacting to drive a trial or implant stem coupled thereto into the humerus. The impaction member 5200' may also include holes to accept a version rod at desired pre-determined angles. The distal end of the impaction member 5200' may include features for coupling to adaptors of an implant or trial stem similar to impaction member 5200, and the impaction member 5200' may include a central opening 5205' to pass devices, such as drivers, therethrough and into the trial or implant stem coupled to the impaction member 5200'.

Figure 28C:
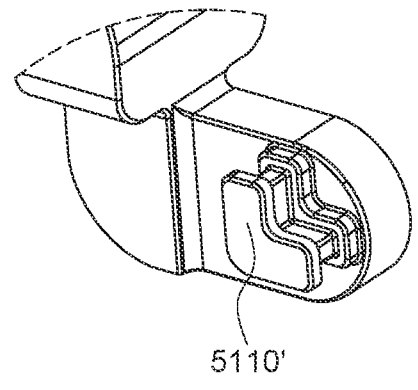
FIGS. 28C-D are enlarged views of a distal end of the handle of FIG. 28B.
Figure 28D:
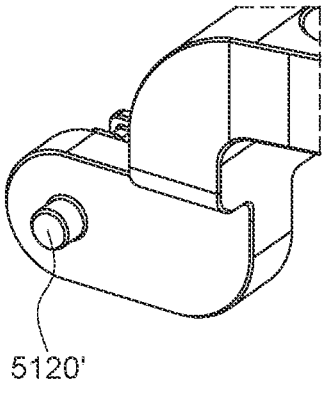

FIGS. 28A and 28N illustrate the handle 5100' in a horizontal orientation relative to the impaction member 5200', which would be substantially perpendicular to the central longitudinal axis of the implant or trial stem coupled to the impaction member 5200'. This orientation may be particularly useful when impacting the impaction member 5200' after the trial or implant stem is connected to the impaction member 5200'. FIG. 28J, on the other hand, illustrates the handle 5100' in a vertical orientation relative to the impaction member 5200'. This orientation may be particularly useful when connecting the impaction member 5200' to the trial or implant stem. As is described in greater detail below, the vertical and horizontal orientations may be stable orientations, in which the orientation resists changing until and unless a user is ready to transition the handle 5100' to a different orientation.

As shown in FIG. 28A, the handle 5100' may be coupled to the impaction member 5200' by a pair of plates, including a first plate 5300' and a second plate 5400'. Referring briefly to FIG. 28G, each plate 5300', 5400' may have one or more prongs or protrusions (two each in the illustrated embodiment) that are received within corresponding holes of the impaction member 5200', and preferably fixed to the impaction member 5200, for example via welding. However, it should be understood that other types of connections between the plates 5300', 5400' and the impaction member 5200' may be suitable. Further, the plates 5300' and 5400' are preferably coupled to the distal end of the handle 5100' before being fixed to the impaction member 5200', so that upon coupling, the handle 5100' cannot be removed from its connection to the impaction member 5200', but rather only change its orientation as described below.

Referring briefly to FIG. 28B, the main body of the handle 5100' may transition to a distal end of the handle 5100', the transition including a first portion extending substantially perpendicular from the main body, and a second terminal portion extending substantially parallel to the main body, so that a "S"- or "Z"-type shape is formed. FIGS. 28C-D are enlarged views of the second terminal portion of the handle 5100' from opposite sides. As shown in FIG. 28C, one side may include an "L"-shaped connector 5110' that may include two larger "L"-shapes sandwiching a smaller "L"-shape. As shown in FIG. 28D, the other side may include a pin 5120' extending outwardly.

Figure 28E:
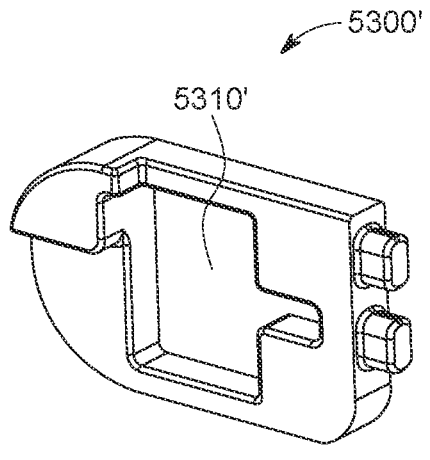
FIGS. 28E-F are perspective views of first and second plates, respectively, of the handle system of FIG. 28A.
Figure 28F:
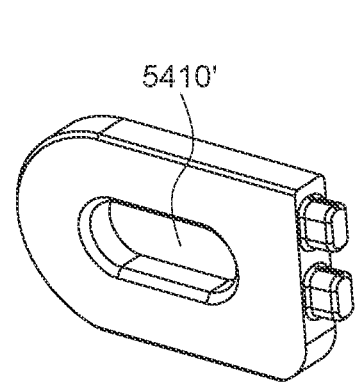
Figure 28G:
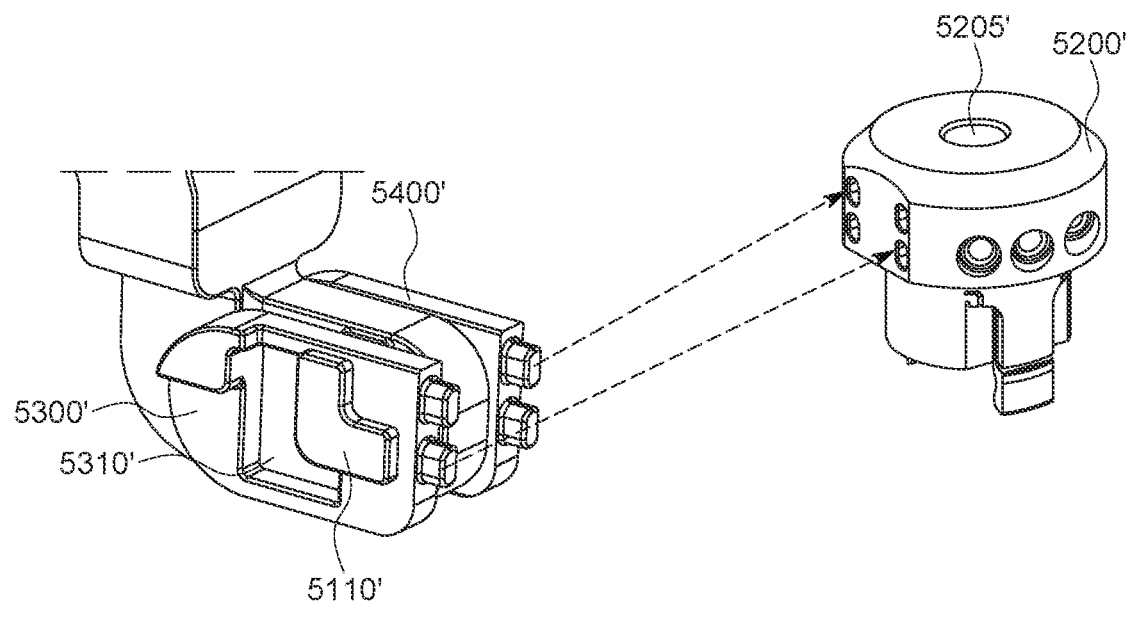
FIGS. 28G-I show the connection of the plates of FIG. 28E-F to the impaction member of the handle system of FIG. 28A.
Figure 28H:
Figure 28I:
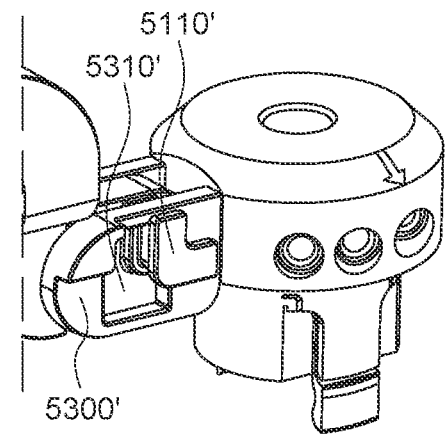
Figures 28J, 28K:
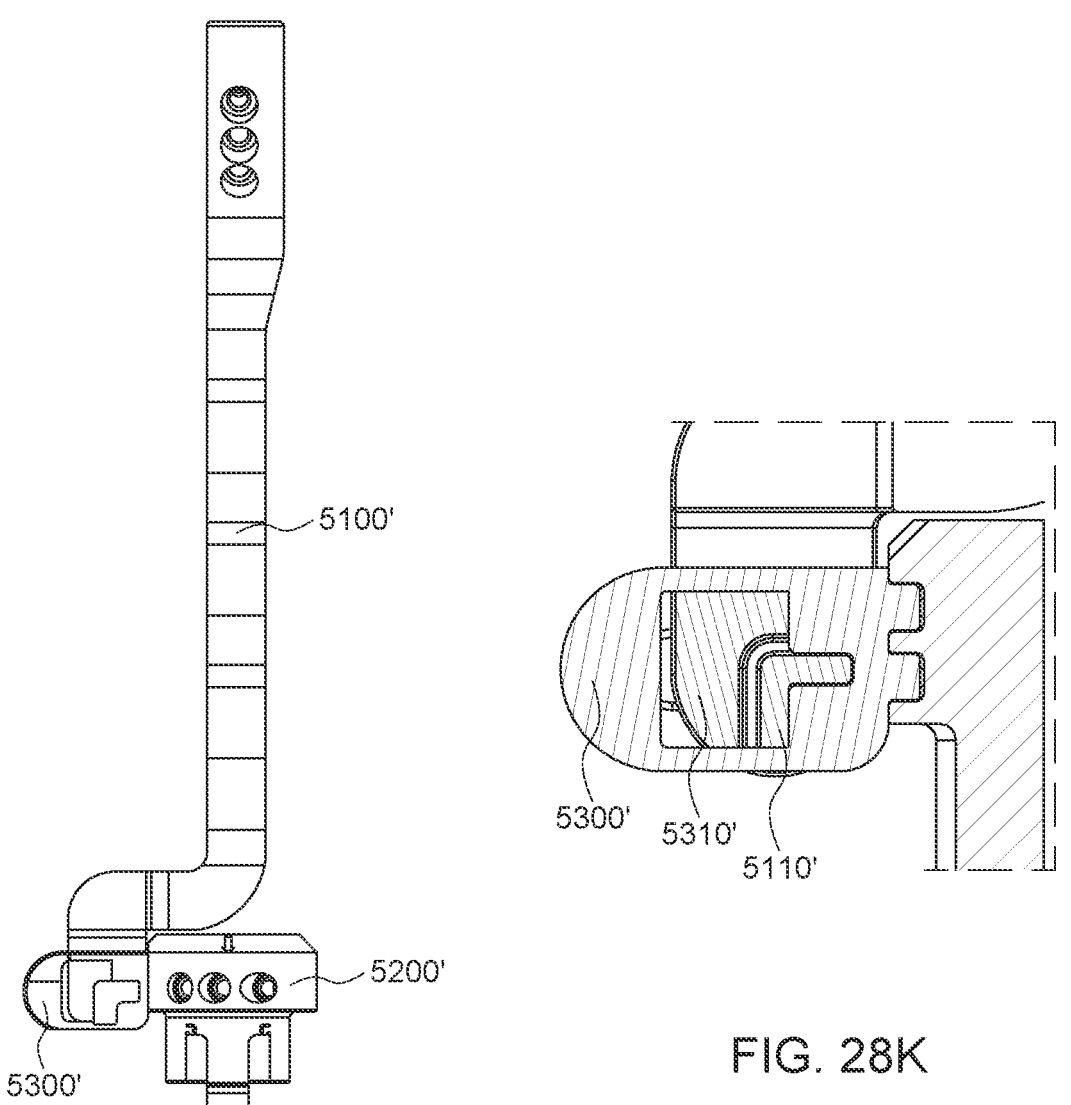

The first plate 5300' is shown in FIG. 28E, and may be a generally rectangular or oval member with a general "T"-shaped recess 5310' including a proximal rectangular recess portion and a narrow slot portion extending distally from a center area of the rectangular recess. The second plate 5400' is shown in FIGS. 28F, and may be a generally rectangular or oval member with an elongated slot 5410' extending in the proximal-to-distal direction along a center portion of the plate 5400', the slot 5410' being generally stadium-shaped. As shown in FIGS. 28G-I, the "L"-shaped connector 5110' is preferably received within the "T"-shaped recess 5310' of the first plate 5300', and the pin 5120' is preferably received within the elongated slot 5410' of the second plate 5400', prior to the plates 5300', 5400' being fixed to the impaction member 5200'. With this configuration, the pin 5120' is able to slide within the elongated slot 5410', but only when the "L"-shaped connector 5110' is backed out of the narrow slot portion of the "T"-shaped recess 5310'.

An example of the movement required to rotate the handle 5100' from the vertical position to the horizontal position is shown in FIGS. 28J-N. For example, As shown in FIGS. 28J-K, one leg of the "L"-shaped connector 5110' is received within the narrow slot portion of the "T"-shaped recess 5310', with the other leg of the "L"-shaped connector 5110' being received within the larger rectangular portion of the "T"-shaped recess 5310'. In this vertical position, as shown in FIG. 28L, the pin 5120' is positioned at the end of the elongated slot 5410' closest to the impaction member 5200'. In order to rotate the handle 5100' to the horizontal orientation, the user may pull the handle 5100' so that the "L"-shaped connector 5110' backs out of the narrow slot of the "T"-shaped recess 5310', while the pin 5420' slides to the opposite end of the elongated slot 5410'. Then, the user may rotate the handle 5100' to the horizontal orientation, and push the handle 5100' distally until the other leg of the "L"-shaped connector 5110' is received within the narrow slot of the "T"-shaped recess 5310' (as shown in FIGS. 28M-N), and the pin 5120' is again positioned at the end of the elongated slot 5410' nearest the impaction member 5200'.

In use, when the handle 5100' is either in the horizontal orientation or the vertical orientation with one of the legs of the "L"-shaped connector 5110' within the narrow slot of the "T"-shaped recess 5310', the handle 5100' is stable and locked in that orientation, with rotation or movement of the handle 5100' being prevented until and unless the user provides an intentional force to back the "L"-shaped connector 5110' out of the narrow slot of the "T"-shaped recess 5310'. The interaction between the pin 5120' and the elongated slot 5410', on the other hand, guides and limits the movement of the handle 5100' relative to the impaction member 5200', and maintains the axis of rotation of the handle 5100'.

In an exemplary use of handle system 5000', the handle 5100' begins in the vertical orientation and the user confirms that the handle 5100' is locked in that vertical orientation. Upon confirmation, the impaction member 5200' is coupled to a trial stem using the particular complementary shapes of the impaction member 5200' and the trial or implant stem (which may be any suitable complementary shape, including those described above). After assembly, the handle 5100' may be slid out of the locking slot of the first plate 5300', rotated 90 degrees to the horizontal orientation, and then re-locked in the narrow slot of the first plate 5300'. The handle 5100' may be torqued to adjust the version of the trial or implant stem to the desired level, and if a trial stem is to be expanded for securement, a driver may be passed through the central longitudinal channel in the impaction member 5200' to access the screw for expansion. While the handle 5100' is in the horizontal orientation, the impaction member 5200' may be impacted to drive the implant (or trial) stem into the bone. Some of the benefits of handle assembly 5000' are similar to those of handle system 5000, including for example the ability to rotate the handle 5100' to the vertical orientation for easy assembly to the trial or implant stem, and to rotate the handle 5100' to the horizontal orientation for impaction and/or torquing, with the handle 5100' being easy to rotate but remaining sturdy and locked in the desired orientation.

FIGS. 29A-C illustrate a handle system 5200" according to another aspect of the disclosure. Handle system 5200" may be identical to handle system 5200', with the exception of the structures which allow for the locking rotation between the horizontal orientation (FIG. 29B) and the vertical orientation (FIG. 29C). Thus, only the differences in handle system 5200", compared to handle system 5200', are described here. The impaction member 5200" may include a bracket 5210" (e.g. a "U"-shaped bracket) which receives a portion of the distal end of the handle 5100". The bracket 5210" may include apertures so that a pin 5220" may pass through the two sides of the bracket 5210", and also through one or more apertures in the handle 5100" when it is received within the bracket 5210". The pin 5220" may be fixed (e.g. welded) to the bracket 5210" so it cannot be removed. With this configuration, the handle 5100" is rotatable about the pin 5220" (compare FIGS. 29B and 29C).

The handle 5100" may have two (or more) magnets 5110", 5120", embedded within the distal end of the handle 5100" to assist with locking the handle 5100" in either the horizontal or vertical orientation. For example, in the horizontal orientation shown in FIG. 29B, a first magnet 5110" abuts a bottom surface of the bracket 5210", so that the first magnet 5110" is attracted to the bracket 5210". In this orientation, the second magnet 5120" is not closely spaced to any metal of the impaction member 5200". To switch orientations of the handle 5100", the user simply applies enough force to the handle 5100" to overcome the magnetic forces between the first magnet 5110" and the bracket 5210", allowing the handle 5100" to rotate about pin 5220". Rotation is continued until the second magnet 5120" abuts the top surface of the impaction member 5200", magnetically locking the handle 5100" in the vertical orientation. As with handle systems 5200 and 5200', handle system 5200" allows for quick and easy re-orientation of the handle 5100", while providing secure locking in either of the two different use conditions.

FIGS. 30A-D illustrate another rotatable handle system 5000'" that is generally similar to handle systems 5000, 5000', 5000". Thus, only the differences will be described relative to handle system 5000". Handle system 5000'" may include an impaction member 5200'", best shown in FIG. 30A, may include two flanges 5210'" spaced apart from each other, instead of the "U"-shaped bracket 5210" described above. A pin 5220'" may be fixed between the two flanges 5210'", for example by welding. Although the impaction member 520'" is shown in isolation in FIG. 30A, it should be understood that, in use, the pin 5220'" extends through an aperture within the handle 5100'" so that the handle may rotate about the pin, in a similar fashion as described in connection with handle system 5000".

Figure 30A:
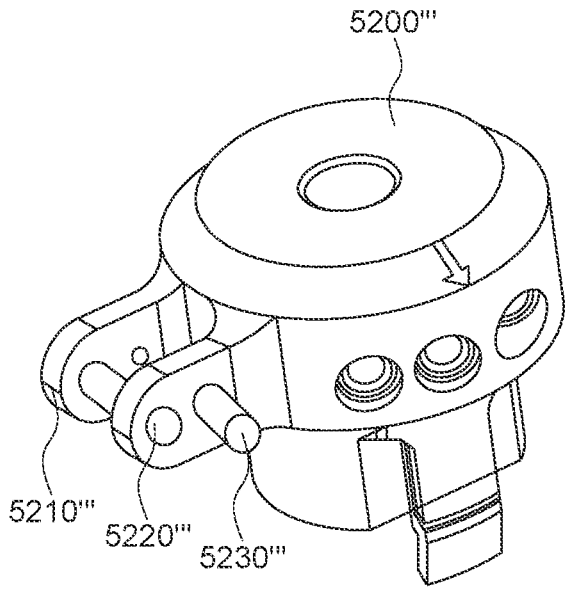
FIGS. 30A-D illustrate a handle system that is a variant of those shown in FIGS. 27-29.
Figure 30B:
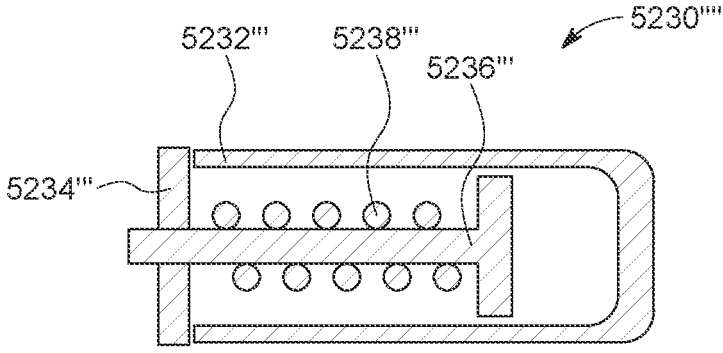

One or both flanges 5210'" may include a spring pin 5230'". However, in FIG. 30A, only a single spring pin 5230'" is visible. A cross-section of spring pin 5230'" is shown in FIG. 30B, although it should be understood that other spring-pin configurations may be used. In this particular example, the spring pin 5230'" includes a casing 5232'" which may be generally cylindrical and closed at one end, with a cap 5234'" covering the open end. The cap 5234'" may be fixed (e.g. welded) to both the case 5232'" and the flange 5210'". A pin 5236'" may be received within the case 5232'" and include a shaft that extends through a center hole of the cap 5234'". A spring 5238'" may be positioned between the cap 5234'" and a head of the pin 5236'", and each end of the spring 5238'" may be fixed to those components. With this configuration, if the pin 5236'" is pressed farther into the case 5232'", the spring 5238'" is put under tension, tending to bias the shaft of the pin 5236'" back through the cap 5234'". However, as noted above, this is just one suitable configuration for a spring pin.

Figure 30C:
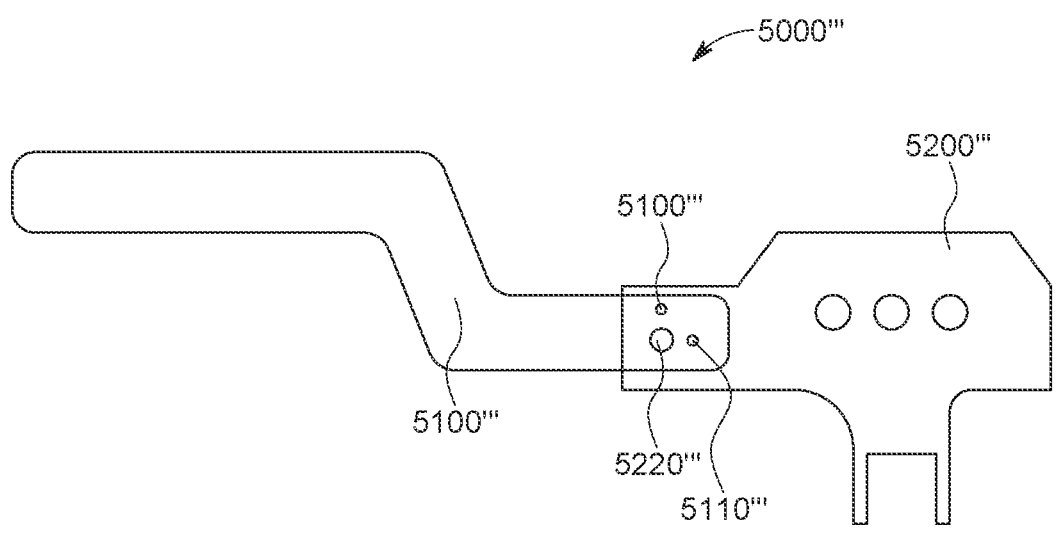
Figure 30D:
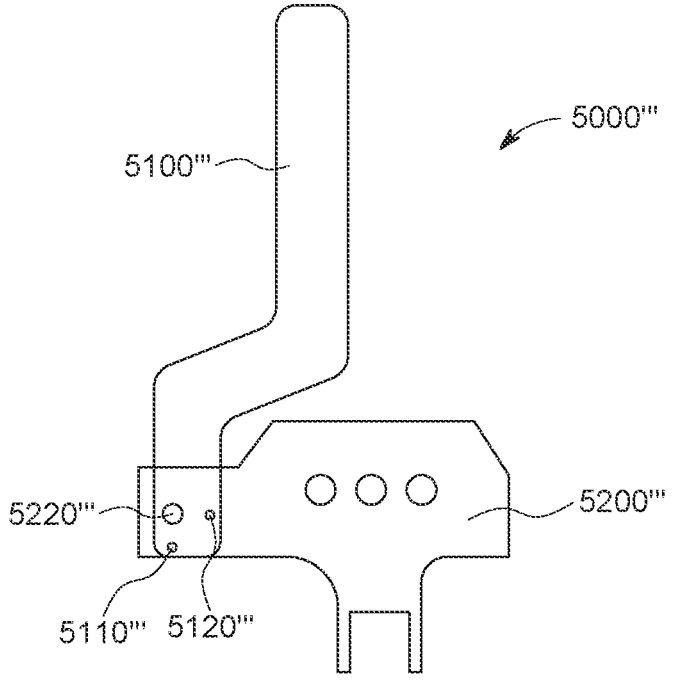

FIGS. 30C-D illustrate the handle system 5000'" in the horizontal and vertical orientations, respectively. Handle 5100'" may be identical to handle 5100", except at the distal end where it connects to the impaction member 5200'". In particular, the distal end of the handle 5100'" may include a pair of spring pin holes 5110'" and 5120'" that are positioned around the hole that receives the pin 5220'". These spring pin holes 5110'" and 5120'" are sized and shaped to receive the shaft of pin 5236'" therein. The end of the pin 5236'" and/or surfaces of the handle 5100'" between the spring pin holes 5110'" and 5120'" may have a ramped surface. In the horizontal orientation shown in FIG. 30C, the spring pin 5236'" is received within spring pin hole 5110'", locking the handle 5100'" in the horizontal orientation. If the user wants to rotate the handle 5100'" to the vertical orientation of FIG. 30D, the user applies rotational force to the handle 5100'". This rotational force will help push the spring pin 5236'" back into the case 5232'", with the help of the one or more ramped surfaces, causing the spring 5238'" to come under tension. Rotation continues until the pin hole 5120'" aligns with the spring pin 5236'", and the spring 5238'" relaxes, moving the pin 5236'" into pine hole 5120'", locking the handle 5100'" in the vertical orientation as shown in FIG. 30D. Other than the mechanisms for rotating the handle 5100'", the handle system 5000'" may be similar or identical in structure and function to handle systems 5000, 5000', and/or 5000".

Figures 31A, 31B, 31C:
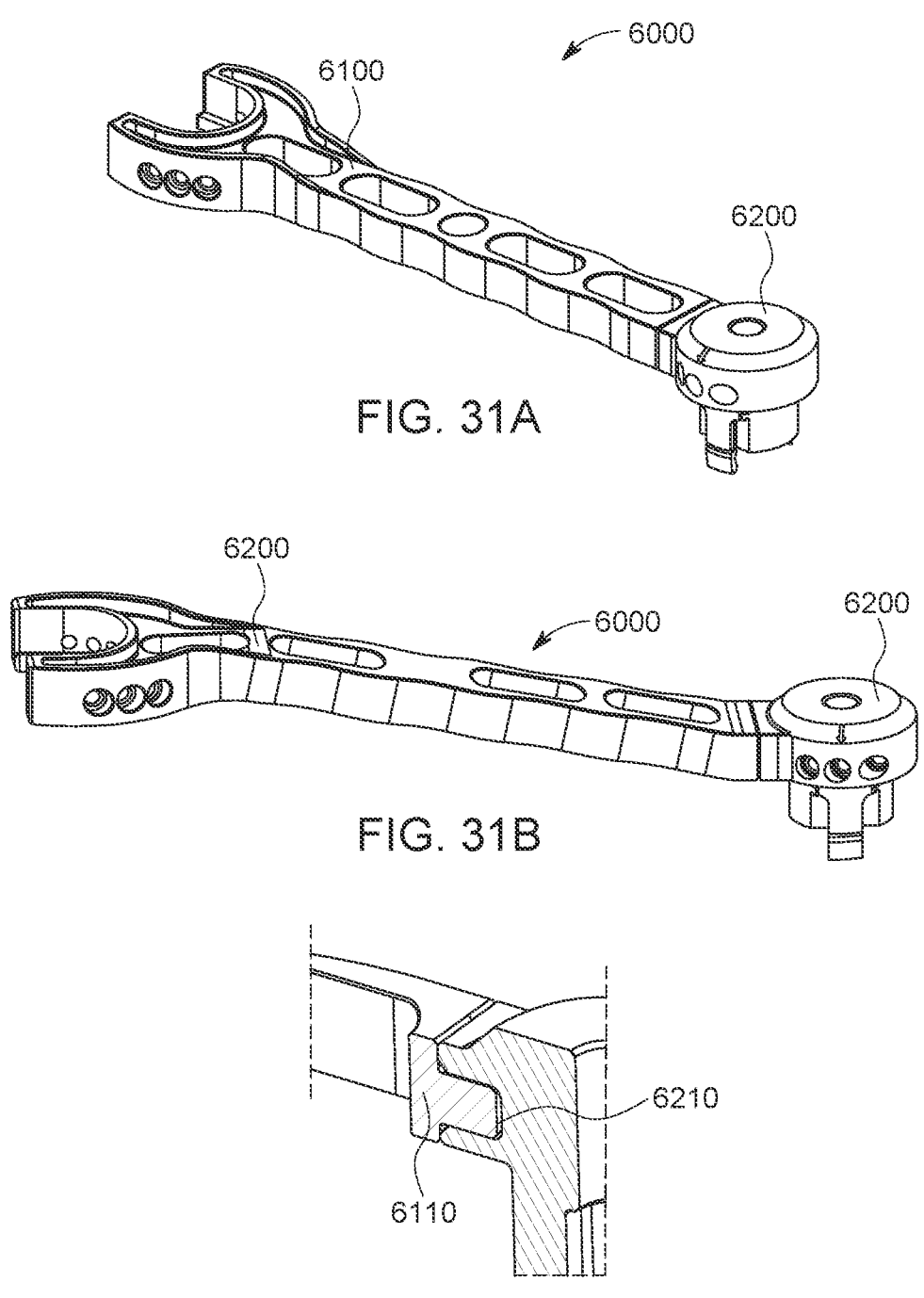
FIGS. 31A-C illustrate a handle system for inserting trial and implant stems according to another aspect of the disclosure.

FIGS. 31A-B are perspective views of a handle system 6000 according to another aspect of the disclosure. Handle system 6000 may have features in common with handle systems 5000, 5000', 5000", 5000'", with one main exception being that the handle 6100 is not rotatable to a vertical condition. Handle system 6000 may include a handle 6100, which may include a first end having a wrench-shape, and a second end fixed to an impaction member 6200. The wrench-shape may be substantially similar to those described above, including for example two arms that include flat surfaces for engagement with a trial or implant stem, as described in greater detail below. As best shown in FIG. 31B, the wrench-shaped end may be contoured or curved with respect to the main body of the handle 6100, which may provide for an ergonomic feel. However, it should be understood that any of the wrench-shaped handles described herein may include or exclude such curvature. In fact, FIG. 31A illustrates a straight version of the handle 6100 of FIG. 31B. Impaction member 6200 may be similar or identical to impaction members 5200, 5200', 5200", and/or 5200'", with the exception of the interface between the handle 6100 and the impaction member 6200. In particular, the distal end of the handle 6100 may include one or more prongs 6110, pins, protrusions, or other features that may be received in and fixed to (e.g. welded to) one or more complementary feature 6210 in the impaction member 6200. However, it should be understood that other types of mating or fixation between the handle 6100 and the impaction member 6200 may be suitable.

Referring now to FIGS. 31D-E, the handle system 6000 is shown with the impaction member 6200 coupled to a trial adaptor 320 on trial stem 310, having the same or similar configuration to that shown in FIGS. 6A-H. As can be seen in FIGS. 31D-E, the trial stem 310 is an expandable trial stem that includes a screw that can be driven to force the expansion of the trail stem 310. Prior to expanding the trial stem 310, the user may impact the impaction member 6200 toward the humerus to drive the trial stem 310 into the bone. Then, to further secure the trial stem 310 in the bone, a driver 3500 may be passed through the central aperture of the impaction member 6200 and into the head of the screw. The handle 6100 may be gripped to prevent rotation of the trial stem 310 as the driver 3500 is torqued, forcing the trial stem 310 to expand.

Figures 31F, 31G:
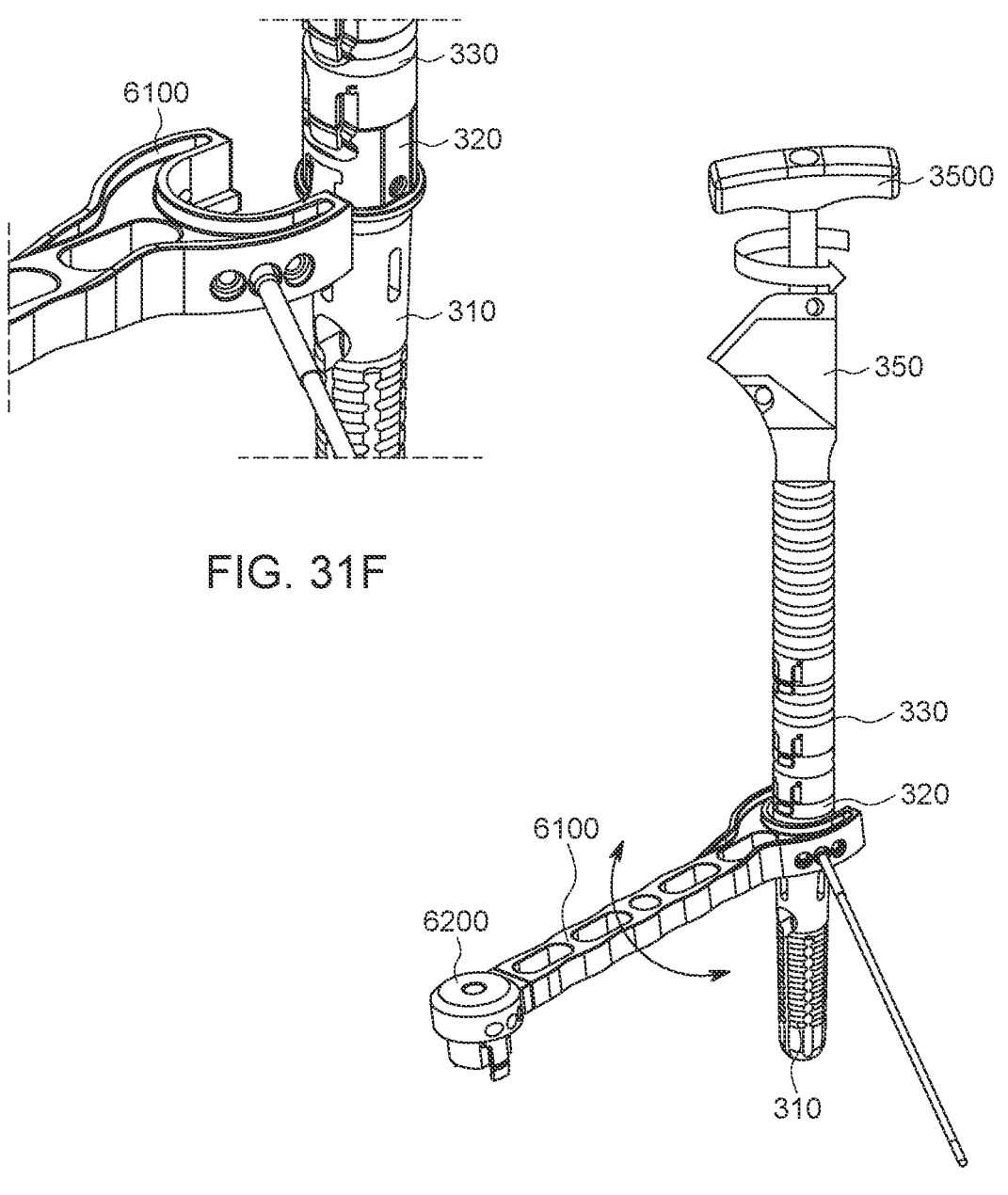

After the expansion of the trial stem 310, the handle system 6000 may be disconnected from the trial stem 310, for example by pulling the impaction member 6200 proximally off of the adaptor 320. At this point, the trial may be built up, as described above, for example by using one or more spacers 330 to increase the height of the trial, and a proximal body 350, as shown in FIGS. 31F-G. If it is desired to change the version of the trial stem 310, the wrench-end of the handle 6100 may be inserted over the adaptor 320, as shown in FIG. 31F, so that two opposing internal flat surfaces of the wrench shape abut two corresponding flat surfaces of the adaptor 320. The driver 3500 may again be used to unlock the expansion of the trial stem 310, and the handle 6100 may be rotated as shown in FIG. 31G to adjust the version, which may be confirmed via a version rod attached to the wrench-end of the handle 6100. After achieving the desired version, the trial stem 310 may again be expanded using driver 3500, and further trialing may be performed.

Figure 31H:
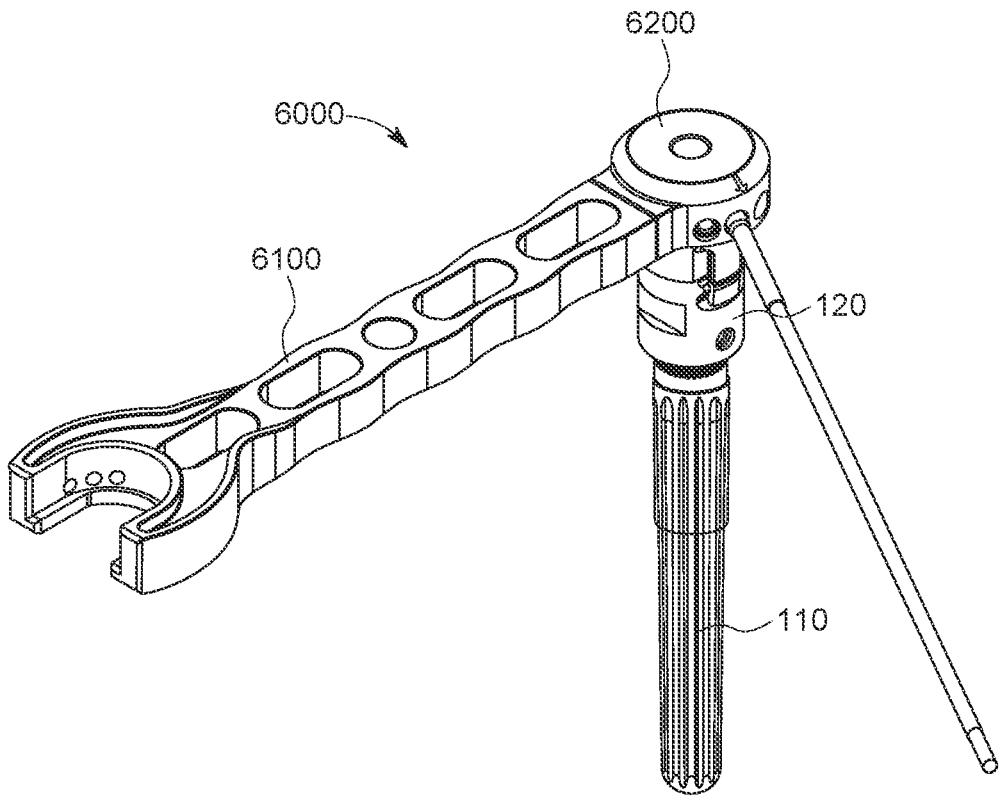

After trialing is complete, the handle system 6000 may be connected to an implant stem 110, as shown in FIG. 31H, for example by pressing the impaction member 6200 over an implant adaptor 120 so that prongs of the impaction member 6200 snap over corresponding recesses of the adaptor 120, for example in a similar configuration as shown in connection with FIGS. 6A-H. Prior to impaction, a version rod attached to the impaction member 6200 may be used to confirm the desired version of the implant stem 110. In some embodiments, as shown in FIGS. 31I-K, the implant adaptor 120 may include a central hole defined by a tapered interior surface, so that spacers (e.g., spacers 130, 140) with tapered surfaces may be secured to the adapter 120 with a Morse taper fit. However, trial adaptors 320, as shown in FIGS. 31D-E, may not include such an interior taper. Instead of having a separate impaction member 6200 that has a specific fit with the implant adaptor 120, a taper protector insert 125 may be used, as shown in FIGS. 31J-K. As shown in FIGS. 31J-K, the taper protector insert 125 may be inserted into the central aperture of the implant adaptor 120 prior to coupling the impaction member 6200 to the implant stem 110. The taper protector insert 125 may have a generally tapered bottom portion, with a non-tapered top portion. As shown in FIG. 31K, the tapered portion of the taper protector insert 125 may be received within the corresponding taper of the stem adaptor 120, and the top non-tapered portion of the taper protector insert 125 may be received within an opening of the impaction member 6200. With this configuration, when the impaction member 6200 is impacted to drive the implant stem 110 into the bone, there is not a large void space between the impaction member 6200 and the implant adaptor 120, helping to ensure that the impaction forces are evenly distributed and that the impaction member 6200 does not damage the implant adaptor 120. After impaction, the impaction member 6200 may be removed from the implant adaptor 120, the taper protector insert 125 may be removed from the implant adaptor 120, and then the implant may be built up using the desired configuration determined from trialing and/or height measurement.

Figure 32A:
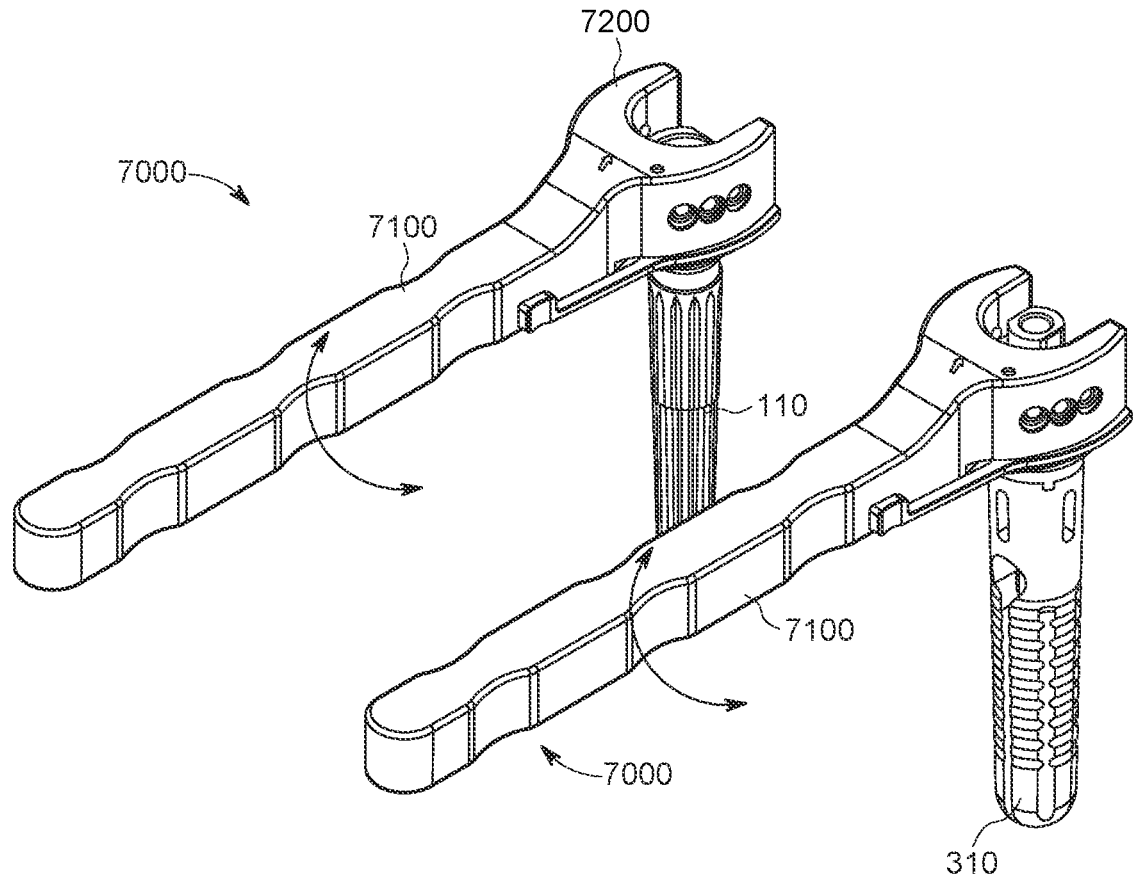
FIG. 32A is a perspective view of a handle system according to another aspect of the disclosure, coupled to an implant stem and trial stem.

FIGS. 32A-E illustrate different views of another embodiment of a handle system 7000. In particular, FIG. 32A illustrates the handle system 7000, showing that it can be used with either an implant stem 110 or a trials stem 310, as is true for other handle systems described herein. The main difference between handle system 7000 and handle system 6000 is that handle system 7000 does not include a separately formed impaction member. Rather, handle system 7000 includes a handle 7100 with a wrench shape at an end, but the wrench shape doubles as an impaction member 7200. In other words, the impaction member 7200 is the wrench shape, and the top surface of the wrench shape may be impacted directly when it is attached to either the implant stem 110 or the trial stem 310.

Figure 32B:
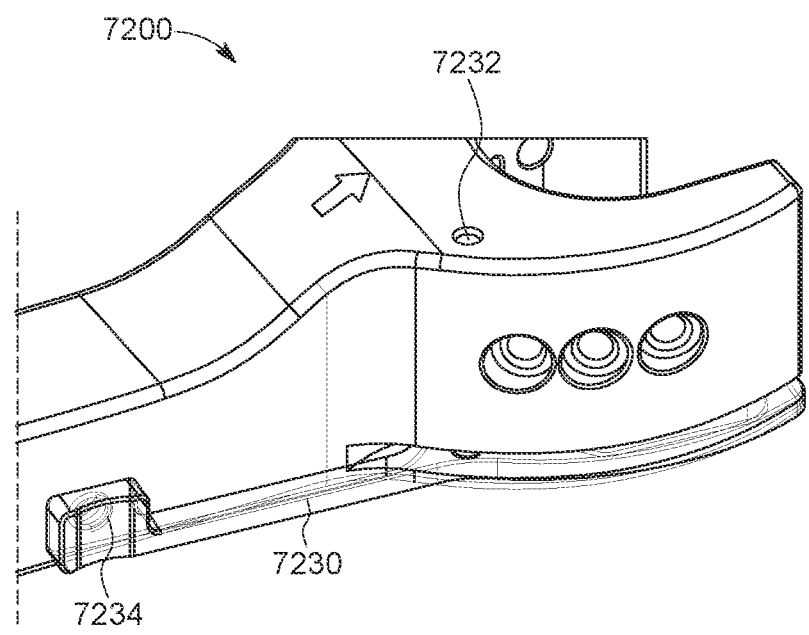
FIGS. 32B-C are views of the handle system of FIG. 32A.
Figure 32C:
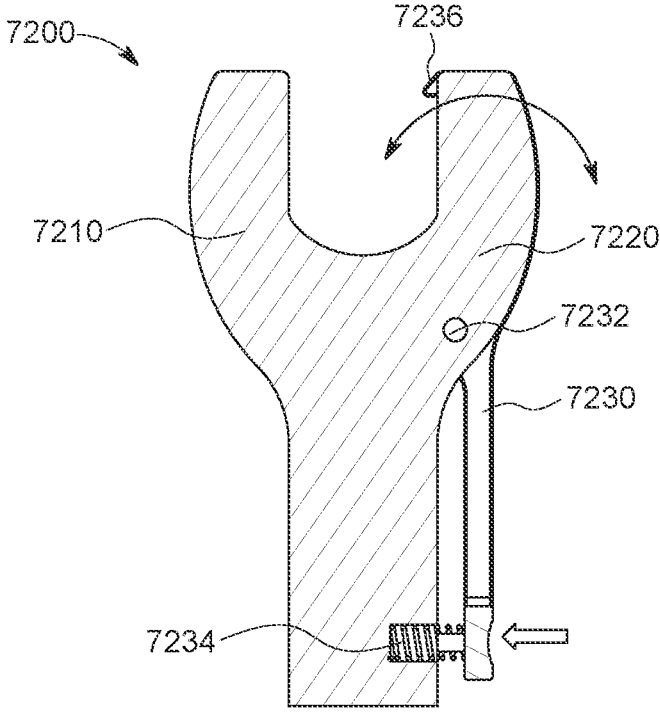

FIGS. 32B-C better illustrate the wrench shaped end impaction member 7200. The impaction member may include two prongs 7210, 7220 that together form the wrench shape, including two flat interior surfaces, as in the other similar embodiments described above. Also, as with other embodiments herein, one or both prongs 7210, 7220 of the wrench shape may include holes for attachment of a version rod at various different pre-determined angles. Unlike other embodiments, however, the impaction member 7200 may include a latch member 7230 that at least partially extends into one of the prongs 7220. The latch member 7230 may include a center portion that includes a hole through which a pin 7232, which may be fixed (e.g. welded) to the impaction member, extends. This pin 7232 may serve as a pivot point around which the latch member 7230 may pivot. A proximal end of the latch member 7230 may include a pin extending into an aperture in the handle 7100, with a spring 7234 surrounding the pin. The proximal end of the latch member 7230 may also present a button-like surface. With this configuration, if the user presses the proximal end of the latch member 7230 inwardly, the spring 7234 will tend to counteract this pressing force. The distal end of the latch member 7230 may include a hook 7236. In the absence of applied forces, the hook 7236 extends inwardly from the prong 7220, near a distal end thereof, so that the hook 7236 extends into the space between the two prongs 7210, 7220 that form the wrench shape. With this configuration, as the user presses the proximal end of the latch member 7230 and compresses the spring 7234, the latch member 7230 pivots about pin 7232 so that the hook 7236 no longer occupies space between the two prongs 7210, 7220. When the user releases the applied force, the spring 7234 will decompress and cause pivoting action that moves the hook 7236 back to the position shown in FIG. 32C. In the illustrated embodiment, the distal end of the hook 7236 may have a ramped surface, while the proximal end of the hook 7236 may be flat and extend at a right angle to the flat interior surface of the prong 7220.

Figure 32D:
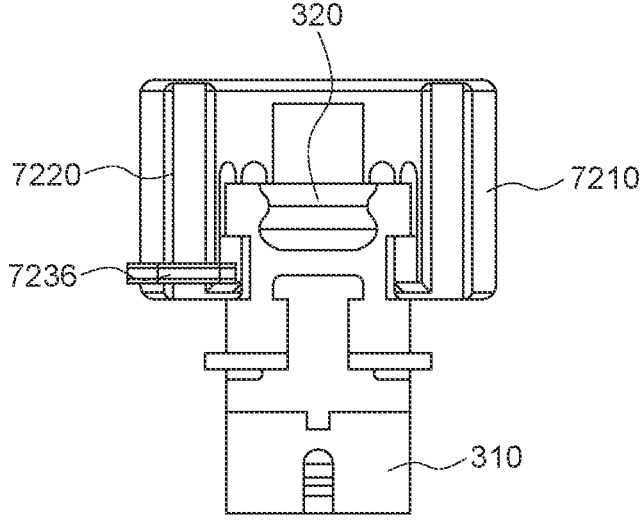
FIGS. 32D-E are views of the handle system of FIG. 32A coupled to a trial stem and implant stem, respectively.
Figure 32E:
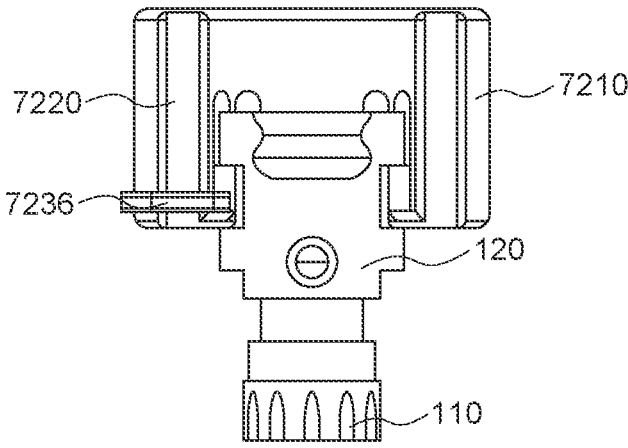

FIGS. 32D-E show the impaction member 7200 coupled to an adaptor 320 of a trial stem 310, and to an adaptor 120 of an implant stem 110, respectively. As shown in these figures, the hook 7236 may be at least partially positioned within a slot of the prong 7220. To couple the impaction member 7200 to either adaptor 120, 320, the user may align the interior flats of the prongs 7210, 7220 with the exterior flats of the adaptor 120, 320, and simply push the impaction member 7200 forward. The distal ramped surface of the hook 7236 will cause the latch member 7230 to pivot without requiring the user to depress the proximal end of the latch member 7230. After the proximal flat surface of the hook 7236 clears the ends of the flats of the adaptor 120, 320, the spring 7234 will decompress, causing the hook 7236 to "snap" back as the latch member 7230 pivots back to the unbiased condition. While connected, the user may rotate the trial stem 310 or implant stem 110 to adjust version, may impact the impaction member 7200 may striking the top surfaces of the prongs 7210, 7220, and may access any interior screws easily since there is no structure obstructing the top of the adaptors 120, 320.

Figure 33A:
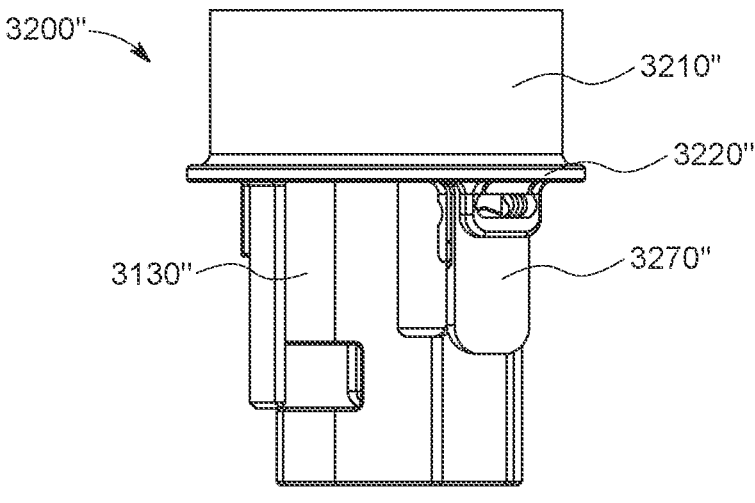
FIG. 33A illustrates a perspective view sleeve assembly similar to that included in the handle assembly of FIGS. 22A-L.
Figure 33B:
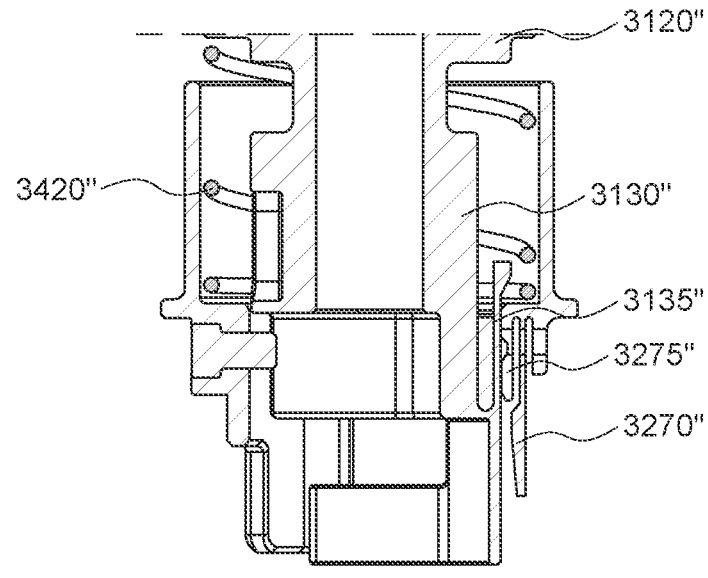
FIG. 33B is a cross-section of the sleeve assembly of FIG. 33A.
Figure 33C:
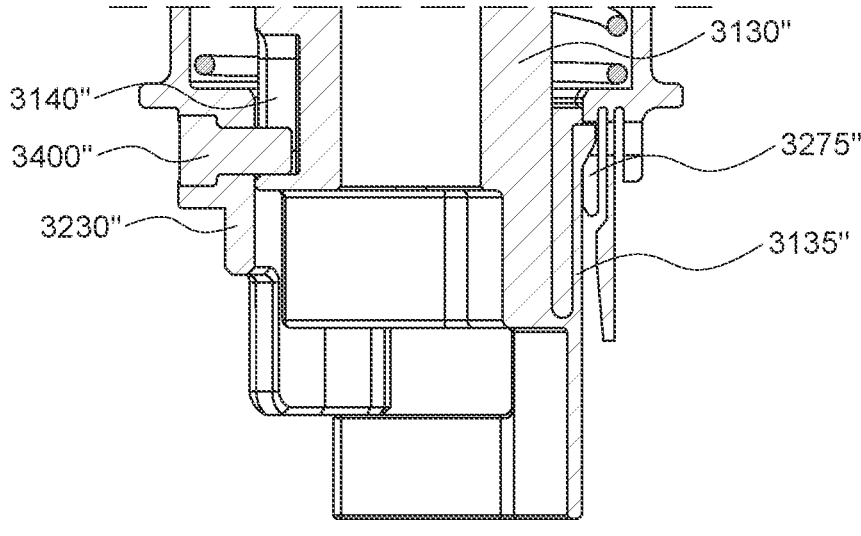
FIGS. 33C-D are cross-sections of the sleeve assembly of FIG. 33A in closed and open conditions, respectively.
Figure 33D:
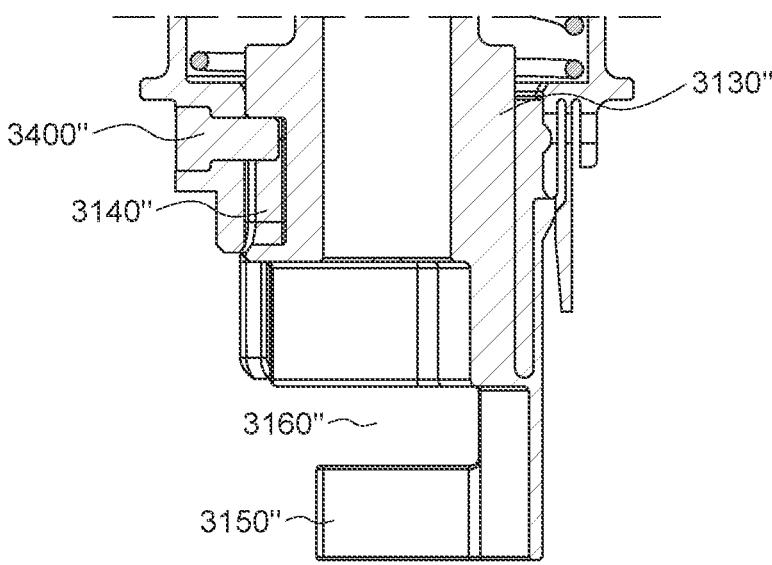

FIGS. 33A-D illustrate an alternate version of the handle system of FIG. 22A. In particular, the handle system of FIGS. 33A-D may be identical to that of FIG. 22A with only certain exceptions. Those exceptions are described below, and it should be understood that any non-described features of the handle system of FIGS. 33A-D may be understood to be similar or identical to those shown and described in connection with FIG. 22A. For example, the handle system of FIGS. 33A-D may include a handle which includes a distal end portion that includes a flange 3120" and a handle sleeve portion 3130". As best shown in FIGS. 33C-D, the handle sleeve portion 3130" may include an axial slot 3140" configured to receive a pin 3400" in substantially the same fashion as described above in connection with the handle system 3000 of FIGS. 22A-L. Although only one arm 3150" and slot 3160" is visible in FIGS. 33A-D, the handle sleeve portion 3130" may include two arms 3150" and slots 3160" in a similar or identical manner as arms 3150 and slots 3160 of handle sleeve portion 3130.

Still referring to FIGS. 33A-D generally, sleeve 3200" may be generally similar to sleeve 3200, and include a cylindrical main body 3210" and a proximal flange 3220". Sleeve 3200" may include a protrusion 3230" with an aperture for receiving the pin 3400" therethrough, for example with the pin 3400" being fixed (e.g., via welding) to the protrusion 3230". Although not separately labeled, the sleeve 3200" may include a pair of protrusions and recesses substantially similar or identical to protrusions 3240 and recesses 3250 of the sleeve 3200 of handle system 3000. As best shown in FIG. 33B, the handle system may include a spring 3420" or similar biasing member with one end abutting flange 3120" and an opposite end abutting an internal shoulder of the sleeve 3200" so that the spring 3420" tends to push the sleeve 3200" downwardly relative to the handle.

The components described above are similar or identical to the corresponding components of handle system 3000. The main difference is the inclusion of a flexure component that can temporarily lock the sleeve 3200" in the "open" condition for assembling to a trial stem or implant stem. For example, referring to FIGS. 33A-B, the sleeve 3200" may include a downwardly projecting tab 3270" and a flexure member 3275" positioned radially inward of the tab 3270". The flexure member 3275" includes a recess or divot (not separately labeled) that faces inwardly toward the handle. It should be understood that void spaces are provided between the tab 3270" and the flexure member 3275" so that each component may have the ability to readily flex inwardly our outwardly. It should also be understood that the tab 3270" nay extend downwardly or distally farther than the flexure member 3275". Referring to FIG. 33B, the handle sleeve portion 3130" may include an upwardly extending flexure member 3135" which terminates in an outwardly extending protrusion (not separately labelled). Flexure member 3135" is spaced radially outwardly from the handle sleeve portion 3130" so that the flexure member 3135" may readily flex inwardly and outwardly. As is described immediately below, the flexure members 3135" and 3275" may engage to temporarily keep the sleeve 3200" in the open condition for assembling, and may be released using the tab 3270" to allow the spring 3420" to force the sleeve 3200" into the closed condition. It should be understood that the position shown in FIG. 33B may not actually be achievable (not how the pin is positioned outside the axial slot), but the figure is intended to help better illustrate the features of the flexure members 3135" and 3275".

FIG. 33C illustrates sleeve 3200" in the closed condition, with the protrusion of flexure member 3135" being received within the recess or divot of flexure member 3275". To temporarily lock the sleeve 3200" in the open condition, the user may manually pull the flange 3220" upwardly, similar to handle system 3000. As shown in FIG. 33D, after this upward movement of sleeve 3200" is achieved, the bottom of the flexure member 3275" sits atop the protrusion at the top of flexure member 3135". This engagement is strong enough to keep the spring 3420" compressed so that the user does not need to manually keep the spring 3420" compressed as the handle system is being engaged or otherwise coupled to a trial stem or implant stem. Once the handle system is engaged to the trial stem or implant stem, the user may release the flexure engagement by pressing tab 3270" inwardly. As shown in FIG. 33D, when the flexure members are temporarily engaged, the tab 3270" is positioned directly adjacent the protrusion of flexure member 3135". As a result, if the tab 3270" is pressed inwardly, it pushes against the protrusion of flexure member 3135", forcing the flexure member 3135" to flex inwardly. This movement disengages the top of flexure member 3135" with the bottom of flexure member 3275", and thus there is nothing stopping the spring 3420" from pressing the sleeve 3200". Thus, once the handle system is assembled to the trial stem or implant stem, the user may press the tab 3270", allowing the sleeve 3200" to snap into the closed position, in which (as shown in FIG. 33C), the pin 3400" is in a maximum position of travel, and the protrusion of flexure member 3135" rests within the divot or recess of flexure member 3275". As explained above, the main benefit of this additional feature is that the user does not need to manually maintain the sleeve 3200" in the open condition during assembly to the trial stem or implant stem.

FIGS. 34A-E illustrate another handle system that is generally similar handle system 3000, with certain differences. Due to the similarity, the differences are described below, but otherwise the system may be similar or identical to handle system 3000. The handle system of FIGS. 34A-E includes a handle 8100 and sleeve 8200. The sleeve 8200 may be identical to sleeve 3200 and is not described further. One of the main differences is that handle 8100 is provided as a two-piece member that is assembled (e.g. via welding) together. The handle proximal portion of handle 8100 may be generally similar to the proximal portion of handle 3100, with some slight size, weight, and/or ergonomic differences. For example, where handle 3100 includes individual apertures extending therethrough, some of the apertures in handle 8100 are joined together to form larger slots to further reduce the weight of the handle 8100. Also, compared to handle 3100, handle 8100 may be shorter in length and smaller in width/diameter, which further reduce weight and may provide a more ergonomic and/or user friendly design compared to handle 3100.

Figure 34A:
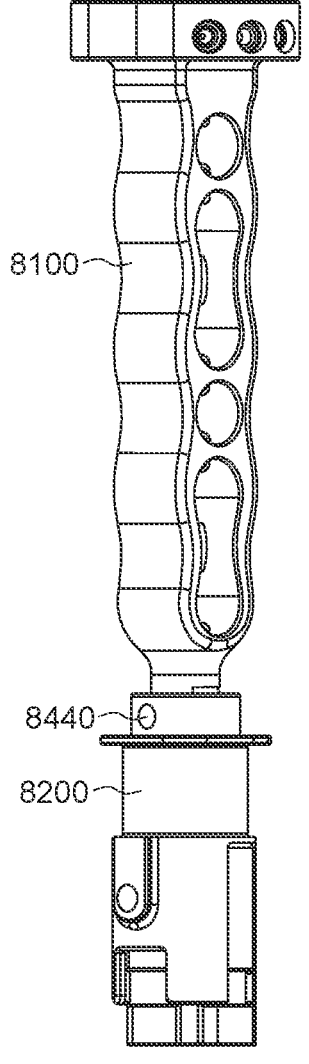
FIGS. 34A-B are perspective and cross-section views, respectively, of a handle assembled to a sleeve according to another aspect of the disclosure.
Figure 34B:
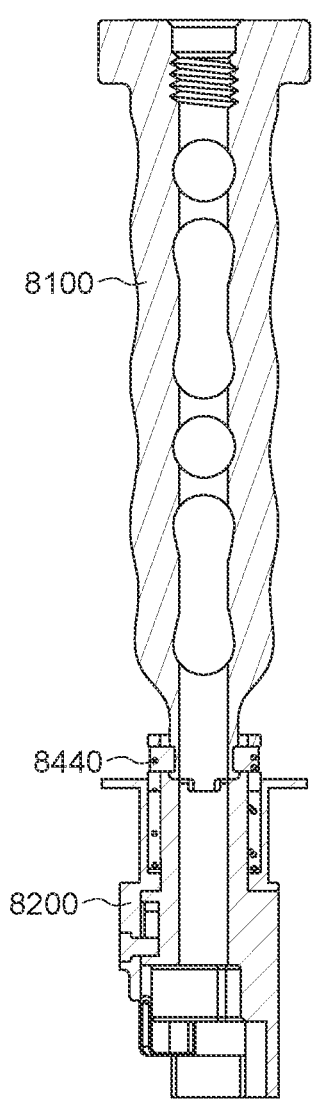
Figure 34C:
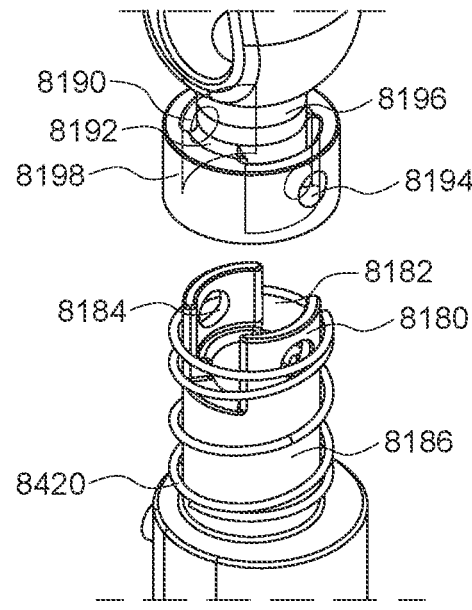
FIG. 34C is a perspective of the handle of FIGS. 34A-B prior to being assembled.
Figure 34D:
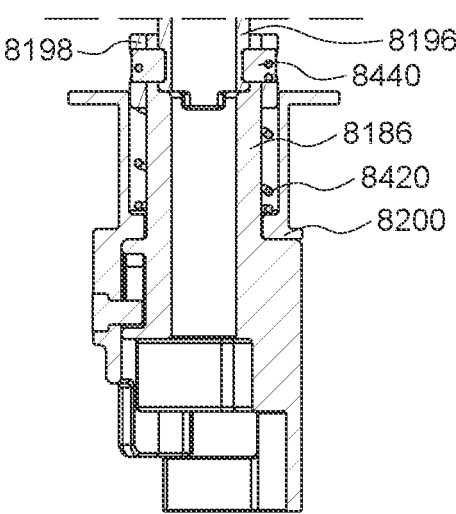
FIGS. 34D-E are enlarged cross-sections and perspective views, respectively, after the handle assembly of FIGS. 34A-B has been assembled.
Figure 34E:
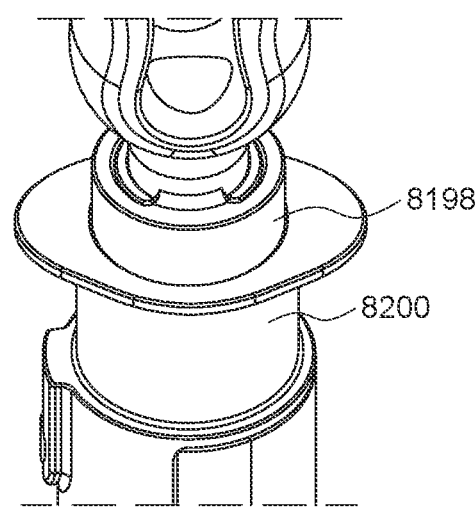

Referring to FIG. 34C, the handle 8100 is shown prior to assembly with the proximal portion being separate from the distal portion. The distal portion (which may include the handle sleeve portion similar or identical to handle sleeve portion 3130) may include two upwardly extending curved tabs 8180. Each of these curved tabs 8180 may extend about one quarter of the circumference of a circle, such that each tab 8180 is separated by a pair of curved recesses 8182. Each tab 8180 may include an aperture 8184 extending therethrough. These tabs 8180 may extend from a shaft 8186 of the distal handle portion. The spring 8420 may be received around this shaft 8186.

Still referring to FIG. 34C, the distal end of the proximal handle portion may include a collar 8199. The collar 8198 may have surround a shaft 8196, with the collar 9189 connected to the shaft 8196 by two links 8192, each link 8192 having a size, shape and position that corresponds to recesses 8182. A pair of recesses 8190 may be positioned between the two links 8192, the recesses 8190 having a size, shape and position that corresponds to tabs 8180. The collar 8198 may be sized to snugly fit around the outside of the shaft 8186, and the shaft 8196 may be sized to snugly fit between the interior of the tabs 8180. The collar 8198 may include a pair of apertures 8194 that are sized and shaped to match apertures 8184.

To assemble the two pieces of the handle 8100 to the sleeve 8200, the sleeve 8200 may first be placed over the shaft 8186, and then the spring 8420 may be placed over the shaft 8186 and within the sleeve 8200. Then, the collar 8198 may be passed over the tabs 8180 until the tabs 8180 are received within the corresponding recesses 8190, and the links 8192 are received within the corresponding recess 8182. As this occurs, the distal end of the collar 8198 will compress the top end of the spring 8420, and the proximal end of the handle 8100 is advanced until the shaft 8196 contacts a top interior surface of the shaft 8186. While the spring 8420 is compressed, pins 8440 may be inserted into apertures 8194 which are aligned with apertures 8184, and the pins 8440 may be fixed (e.g. by laser welding) to fixedly couple the proximal handle portion to the distal handle portion.

Figure 35A:
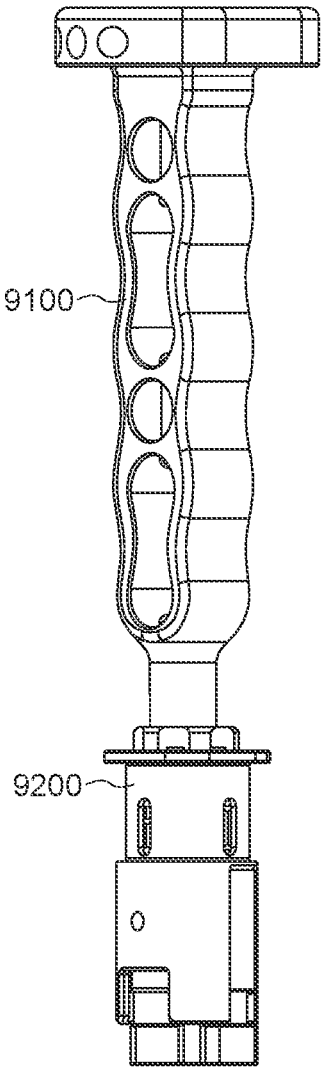
FIGS. 35A-B are perspective and cross-section views, respectively, of a handle assembled to a sleeve according to another aspect of the disclosure similar to FIGS. 34A-B.
Figure 35B:
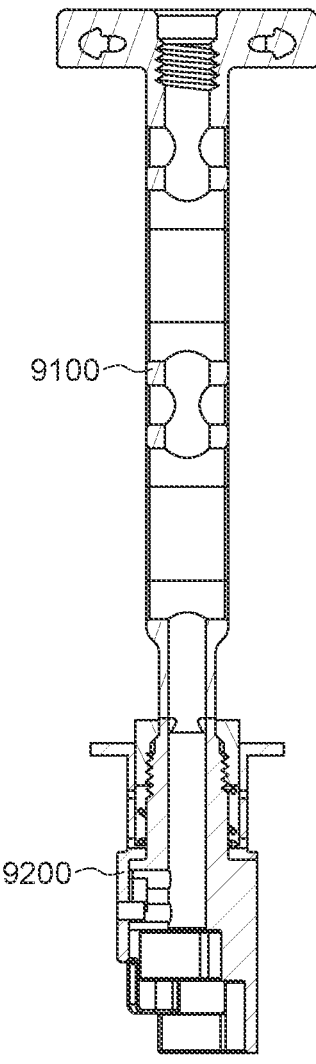

FIGS. 35A-B illustrate another handle system, including a handle 9100 and sleeve 9200 that are generally similar handle 8100 and sleeve 8200. Due to the similarity, the handle 8100 and sleeve 8200. Due to the similarity, the differences are described below, but otherwise the system may be similar or identical to handle system 8100 and sleeve 8200 (and thus similar or identical to handle system 3000).

Figure 35C:
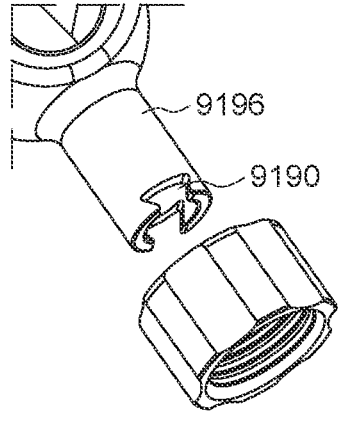
FIGS. 35C-D illustrate initial assembly steps of the proximal handle portion of FIGS. 35A-B.
Figure 35D:
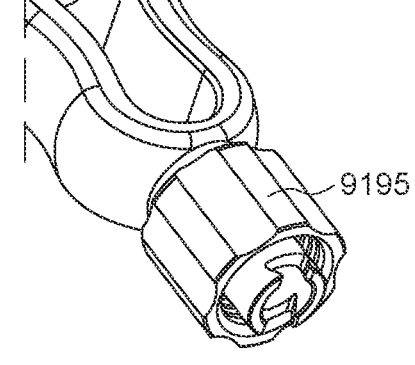

As with handle 8100, handle 9100 is provided as a multi-piece construct that is assembled together. Referring to FIGS. 35C-D, the distal end of the proximal handle portion includes a shaft 9196 that includes a plurality of recesses 9190 at a distal end thereof. In the illustrated example, the recesses 9190 are dovetail shaped recesses and a total of two are provided at opposite sides of the shaft 9196. However, it should be understood that other particular shapes, numbers, and spacing of recesses 9190 may be provided. As shown in FIG. 35C, an internally threaded locking nut 9195 may also be provided. In an initial step of assembly, the locking nut 9195 may be slipped over the shaft 9196, as shown in FIG. 35D.

Figure 35E:
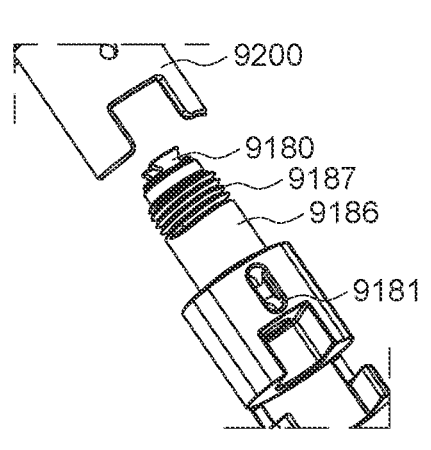
FIGS. 35E-F illustrate initial assembly steps of the distal handle portion and sleeve of FIGS. 35A-B.
Figure 35F:
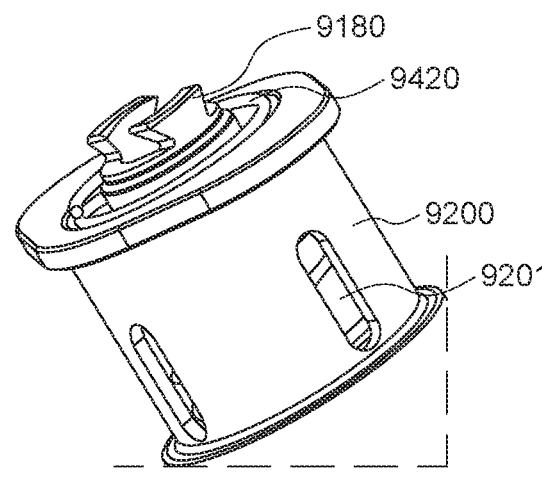

Referring to FIG. 35E, the distal portion of the handle 9100 is shown prior to an initial step of assembly with the sleeve 9200. As shown in FIG. 35E, the distal handle portion includes a proximally extending shaft 9186, which may include external threading 9187, and two proximally projecting protrusions 9180 that complement the recesses 9190. In other words, in this particular example, the two protrusions 9180 are dovetail-shaped protrusions at opposite diametric sides of the shaft 9186. In an initial step of assembly, the sleeve 9200 may be slipped over the shaft 9186 so that the protrusions 9180 extend above the top of the sleeve 9200. Also, as shown in FIG. 35F, the spring 9420 may be placed within the sleeve 9200 around the shaft 9186. It should be understood that the assembly steps shown in FIGS. 35D and 35F may be performed in any order, or simultaneously.

Figure 35G:
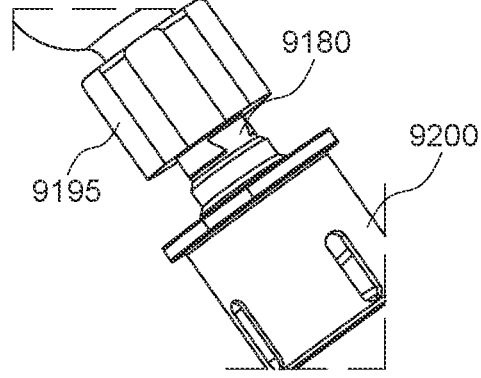
FIG. 35G illustrates an intermediate assembly step of the two handle portions of FIGS. 35A-B.
Figure 35H:
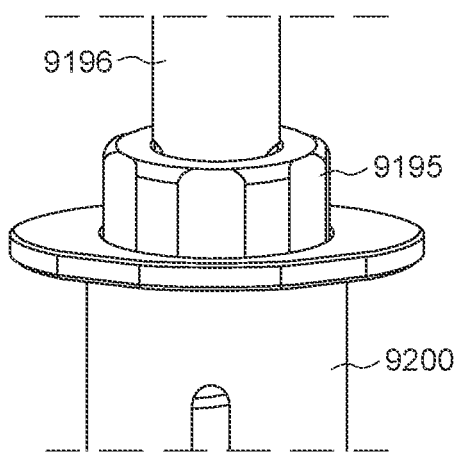
FIGS. 35H-I illustrate final assembly steps of the handle and sleeve of FIGS. 35A-B.
Figure 35I:
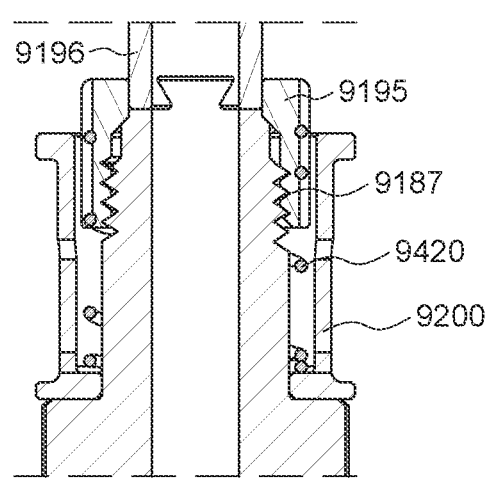

In a second stage of assembly, as shown in FIG. 35G, the shaft 9196 may be slid laterally relative to the shaft 9186 so that the dovetail protrusions 9180 are received within the dovetail recesses 9190. Then, in a final stage of assembly, as shown in FIGS. 35H-I, the locking nut 9195 may be slid downwardly until the internal threads of the locking nut 9195 are adjacent the external threads 9187 of the shaft 9186, and the locking nut 9195 may be rotated to drive the locking nut 9195 downwardly. As the locking nut 9195 rotates and translates downwardly, it enters an interior space of the sleeve 9200 and compresses the spring 9420, a top surface of which abuts a bottom rim of the locking nut 9195. Even when the locking nut 9195 is in the fully downward or rotated position, the locking nut 9195 still overlies the dovetail connection to ensure the shaft 9196 cannot slide laterally relative to the shaft 9186. In this position, the locking nut 9195 may be fixed (e.g. via laser welding) to the shaft 9196, for example laser welding at the circumferential gap between the top interior of the locking nut 9195 and the exterior circumference of the shaft 9196.

Referring to FIG. 35F, the sleeve 9200 may include a plurality of cleanout slots 9201 that allow access to the interior of the sleeve 9200 from the exterior of the sleeve 9200. Similarly, referring to FIG. 35E, the distal portion of the handle 9100 may include one or more cleanout holes 9181 that allow access from the exterior of the distal handle portion to an interior (e.g. a cannulated interior portion) of the distal handle portion. In conjunction, the cleanout slots 9201 and cleanout holes 9181 may align to allow for cleaning the interior space between the sleeve 9200 and the distal handle portion, as well as the interior of the distal handle portion.

Similar to handle 8100, handle 9100 is split into two pieces (proximal and distal handle portions) and later welded to complete the assembly. The dovetail and threaded connection described in connection with FIGS. 35A-I are provided to mechanically lock the two handle pieces prior to the welding. This configuration may increase the strength of the fixation and make the design more robust for sustaining the impaction (including reverse impaction) as described, for example, in connection with handle system 3000. Otherwise, the design principle remains the similar to handle 8100, and the use remains similar to handle system 3000.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A trial humeral prosthesis comprising:
   a trial stem configured for implantation into a humerus;
   a trial proximal body configured to couple to a trial articulating component of the trial humeral prosthesis; and
   a plurality of trial spacers configured to couple the trial stem to the trial proximal body, the plurality of trial spacers including a first trial spacer and a second trial spacer,
   wherein the first and second trial spacers each include a proximal post, a divot, a shoulder adjacent to the proximal post, and a distal body having a prong extending distally therefrom, the prong including an interior protrusion, and
   wherein the distal body of the first trial spacer is configured to receive the proximal post of the second trial spacer therein, and
   wherein the first trial spacer is configured to be axially pushed onto the second trial spacer such that, when the first trial spacer is axially pushed onto the second trial spacer, the shoulder of the second trial spacer forces the prong of the first trial spacer to flex outwardly and, when the interior protrusion of the prong of the first trial spacer clears the shoulder of the second trial spacer, the prong of the first trial spacer snaps back so that the interior protrusion of the prong of the first trial spacer is received within the divot of the second trial spacer and is in abutment with the shoulder of the second trial spacer.

2. The trial humeral prosthesis of claim 1, wherein the first trial spacer has a height that is different than a height of the second trial spacer.

3. The trial humeral prosthesis of claim 1, wherein the proximal post of the second trial spacer includes two opposing flats, and an interior surface of the distal body of the first trial spacer includes two opposing flats, the two opposing flats of the proximal post of the second trial spacer being in contact with corresponding ones of the two opposing flats of the distal body of the first trial spacer when the proximal post of the second trial spacer is received within the distal body of the first trial spacer.

4. The trial humeral prosthesis of claim 3, further comprising a trial stem adaptor configured to be fastened to a proximal end of the trial stem by at least one screw.

5. The trial humeral prosthesis of claim 4, wherein the trial stem adaptor includes a distally-extending protrusion configured to mate with a corresponding proximal recess in the trial stem to prevent rotational movement of the trial stem adaptor relative to the trial stem.

6. The trial humeral prosthesis of claim 4, wherein the trial stem adaptor includes a proximal post, a divot, and a shoulder adjacent to the proximal post.

7. The trial humeral prosthesis of claim 6, wherein the proximal post of the trial stem adaptor includes two opposing flats, and an interior surface of the distal body of the second trial spacer includes two opposing flats, the two opposing flats of the trial stem adaptor being in contact with corresponding ones of the two opposing flats of the distal body of the second trial spacer when the proximal post of the trial stem adaptor is received within the distal body of the second trial spacer.

8. The trial humeral prosthesis of claim 1, wherein the distal body of the first trial spacer includes an interior surface defining a cavity that has a shape that corresponds to the proximal post of the second trial spacer.

9. A humeral prosthesis system, comprising:
the trial humeral prosthesis of any of claims 1-7; and
a humeral prosthesis.

10. The humeral prosthesis system of claim 9, wherein the humeral prosthesis comprises:
a prosthetic humeral stem,
a prosthetic proximal body configured to couple to a prosthetic articulating component of the humeral prosthesis, and
a plurality of prosthetic spacers configured to couple the prosthetic humeral stem to the prosthetic proximal body, the plurality of prosthetic spacers including a first prosthetic spacer and a second prosthetic spacer.

11. The humeral prosthesis system of claim 10, wherein each of the trial spacers has a height that corresponds to a height of a corresponding one of the prosthetic spacers.

12. The trial humeral prosthesis of claim 1, wherein the shoulder is positioned distal relative to the proximal post such that the shoulder is positioned between the divot and the proximal post.

* * * * *